US012753189B2

(12) United States Patent
Ma et al.

(10) Patent No.: US 12,753,189 B2
(45) Date of Patent: Oct. 6, 2026

(54) AZAHETEROARYL COMPOUND, PREPARATION METHOD THEREFOR, AND APPLICATION THEREOF

(71) Applicant: SHANGHAI BLUERAY BIOPHARMA CO., LTD., Shanghai (CN)

(72) Inventors: Shichao Ma, Shanghai (CN); Zhongguo Zhang, Shanghai (CN); Song Zhang, Shanghai (CN); Wenjia Yuan, Shanghai (CN)

(73) Assignee: SHANGHAI AOLU BIOMEDICAL TECHNOLOGY CO., LTD., Shanghai (CN)

(*) Notice: Subject to any disclaimer, the term of this patent is extended or adjusted under 35 U.S.C. 154(b) by 378 days.

(21) Appl. No.: 18/264,073

(22) PCT Filed: Feb. 10, 2022

(86) PCT No.: PCT/CN2022/075822

§ 371 (c)(1), (2) Date: Aug. 2, 2023

(87) PCT Pub. No.: WO2022/171166

PCT Pub. Date: Aug. 18, 2022

(65) Prior Publication Data

US 2024/0182492 A1 Jun. 6, 2024

(30) Foreign Application Priority Data

Feb. 10, 2021 (CN) ........................ 202110188129.X

(51) Int. Cl.
*C07D 519/00* (2006.01)
*A61P 35/00* (2006.01)

(52) U.S. Cl.
CPC ............ *C07D 519/00* (2013.01); *A61P 35/00* (2018.01)

(58) Field of Classification Search
CPC .. C07D 519/00; C07D 213/79; C07D 239/42; C07D 471/04; C07D 487/04; A61P 35/00; A61P 35/02; A61K 31/519; A61K 31/5377; A61K 45/06
See application file for complete search history.

(56) References Cited

U.S. PATENT DOCUMENTS

| | | | | |
|---|---|---|---|---|
| 2016/0176882 | A1* | 6/2016 | Chan | A61K 31/5377 514/233.2 |
| 2020/0261459 | A1 | 8/2020 | Zhou et al. | |
| 2022/0274990 | A1 | 9/2022 | Marx et al. | |
| 2023/0002414 | A1 | 1/2023 | Ma et al. | |

FOREIGN PATENT DOCUMENTS

| | | | |
|---|---|---|---|
| CN | 109575013 | A | 4/2019 |
| CN | 110156787 | A | 8/2019 |
| CN | 110563722 | A | 12/2019 |
| CN | 110734436 | A | 1/2020 |
| CN | 111518100 | A | 8/2020 |
| CN | 112409385 | A | 2/2021 |
| CN | 114269748 | A | 4/2022 |
| JP | 2018500342 | A | 1/2018 |
| JP | 7357146 | B2 | 10/2023 |
| WO | 2017219948 | A1 | 12/2017 |
| WO | 2019062435 | A1 | 4/2019 |
| WO | 2019120276 | A1 | 6/2019 |
| WO | 2019152419 | A1 | 8/2019 |
| WO | 2019158025 | A1 | 8/2019 |
| WO | 2020156479 | A1 | 8/2020 |
| WO | 2020247475 | A1 | 12/2020 |

OTHER PUBLICATIONS

CAS Registry No. 2609036-85-1 (which entered the STN database on Mar. 12, 2021). (Year: 2021).*
Cecil Textbook of Medicine, 20th Ed., vol. 1 (Year: 1997).*
CAS Registry No. 1889793-92-3 (which entered the STN database on Apr. 14, 2016). (Year: 2016).*
May 9, 2022 International Search Report issued in International Patent Application No. PCT/CN2022/075822.
May 9, 2022 Written Opinion of the International Searching Authority issued in International Patent Application No. PCT/CN2022/075822.
ACS, "RN 1823490-44-3", STN Registry, Dec. 6, 2015.
First office action dated Dec. 19, 2024 issued in Japan Patent Application No. 2023-544550.

(Continued)

*Primary Examiner* — Kamal A Saeed
*Assistant Examiner* — Meghan C Heasley
(74) *Attorney, Agent, or Firm* — Houston Beshining Law Office PLLC; Liangang Ye

(57) ABSTRACT

The present invention provides an azaheteroaryl compound, a pharmaceutically acceptable salt thereof, and a solvate thereof. The present invention also provides a preparation method for such a compound, a composition containing such a compound, and a pharmaceutical use of such a compound in the preparation of a drug for treating a disease or disorder related to the mechanism of action of an EED protein and/or a PRC2 protein compound.

(I)

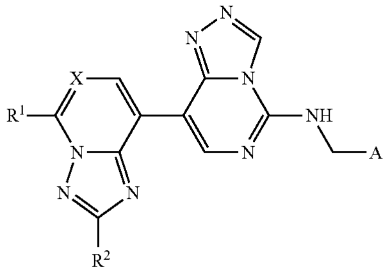

19 Claims, No Drawings

(56) References Cited

OTHER PUBLICATIONS

First office action dated Jun. 13, 2025 issued in Chinese Patent Application No. 2022100843882.

Feb. 29, 2024 Extended European Search Report issued in European application No. 22752326.3.

May 7, 2024 Japanese Second Office Action issued in Japanese application No. 2023-544550.

First office action dated Jan. 8, 2026 issued in Indian Patent Application No. 202317059826.

First office action dated Jan. 5, 2026 issued in Taiwan Patent Application No. 111104984.

Search report dated Jan. 2, 2026 issued in Taiwan Patent Application No. 111104984.

* cited by examiner

AZAHETEROARYL COMPOUND, PREPARATION METHOD THEREFOR, AND APPLICATION THEREOF

The present application is a National Stage of International Application No. PCT/CN2022/075822, filed on Feb. 10, 2022, which claims priority of the Chinese Patent Application No. CN202110188129.X filed on Feb. 10, 2021, the contents of which are incorporated herein by reference in their entireties.

TECHNICAL FIELD

The present disclosure relates to an azaheteroaryl compound, preparation method therefor, and application thereof.

BACKGROUND

PcG (Polycomb Group) proteins are an important class of chromatin modifying enzymes. It regulates the transcription of genes through chromatin modification and thereby plays an important role in the growth, differentiation and long-term cell memory of stem cells. In mammalian cells, PcG proteins are mainly divided into two types of transcriptional repressive complexes, namely PRC1 (Polycomb Repressive Complex 1) and PRC2 (Polycomb Repressive Complex 2), respectively. Wherein, PRC2 inhibits the expression of related genes by methylating the 27th lysine (H3K27) of histone 3 in chromatin. The PRC2 protein complex is mainly composed of core proteins such as EZH2 (Enhancer of Zeste Homolog 2) (or its very similar homologous protein EZH1), EED (Embryonic ectoderm Development) and SUZ12 (Suppressor of Zeste 12). Wherein, EZH2 has enzymatic activity and can transfer the methyl group of the substrate SAM (S-adenosyl-L-methionine) to H3K27 through the SET (Su (var), E(Z), and Trithorax) protein domain, thereby one-to three-methylation modification of H3K27 is achieved. The enzymatic activity of EZH2 also depends on other components of PRC2, such as EED proteins belonging to the WD40 repeat structural protein family. The combination effect of EED and trimethylated H3K27Me3 have great allosteric promoting effect on enzymatic function of EZH2 on the one hand, and on the other hand, it can also position the PCR2 complex on the chromatin that needs to be modified. Abnormal function of PRC2, such as EZH2 over-expression or gain-of-function mutation, is associated with many clinical tumor diseases, including lung cancer, breast cancer, rectal cancer, prostate cancer, bladder cancer, pancreatic cancer, sarcoma, and lymphoma, etc. PRC2 is also associated with a variety of cellular immune functions, for example, EZH2 is involved in the regulation of lymphocyte activation and can also cooperate with glycolysis to promote the response of T cells to tumor cells. Therefore, the development of PRC2 small molecule inhibitors has important and broad drug development value.

The research and development of PRC2 inhibitors mainly involves two strategies including the development of EZH2 inhibitors and EED inhibitors. EZH2 inhibitors currently entering the clinic include EPZ-6438 (Epizyme, clinical phase II), GSK2816126 (GSK, clinical phase I) and CPI-1205 (Constellation, clinical phase I), etc. Although several EZH2 inhibitors have entered the clinical research stage, these inhibitors all contain a common pharmacophore of 2-pyridone. Moreover, secondary mutations have begun to appear in clinical treatment with existing EZH2 inhibitors. EED inhibitors have an allosteric inhibitory effect on the enzyme function of EZH2, and can achieve the same or similar biological functions as EZH2. Moreover, on the one hand, EED inhibitors can overcome the drug resistance of EZH2 well, and on the other hand, EED inhibitors can be used in combination with EZH2 inhibitors to achieve better synergistic effects. Therefore, it's of very significant meaning to develop new EED inhibitors.

CONTENT OF THE PRESENT INVENTION

The technical problem to be solved by the present disclosure is that the EED inhibitors in the prior art have a single and simple structure. Therefore, the present disclosure provides an azaheteroaryl compound, preparation method therefor, and application thereof. The azaheteroaryl compound of the present disclosure exhibits good inhibitory activity on tumor cells and has broad prospects for drug development.

The present disclosure provides a compound represented by formula (I), a pharmaceutically acceptable salt thereof, a stereoisomer thereof, a solvate thereof or their isotope-labeled compound:

(I)

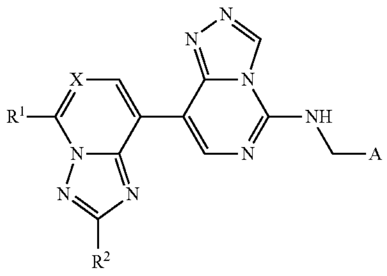

wherein,

A is

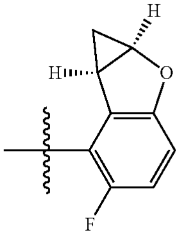

or

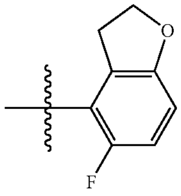

,

X is N or $CR^7$;

$R^1$ is H, halogen, $C_{1-4}$ alkoxy, unsubstituted $C_{1-6}$ alkyl or $C_{1-6}$ alkyl substituted by $R^3$, an unsubstituted amino group or an amino group substituted by $R^4$, unsubstituted $C_{1-4}$ haloalkyl or $C_{1-4}$ haloalkyl substituted by $R^3$, unsubstituted $C_{3-6}$ cycloalkyl or $C_{3-6}$ cycloalkyl substituted by hydroxyl, unsubstituted $C_{3-6}$ heterocycloalkyl or $C_{3-6}$ heterocycloalkyl substituted by $R^5$;

$R^2$ is H, $C_{1-4}$ alkyl, $C_{3-6}$ cycloalkyl, an unsubstituted amino group or an amino group substituted by $C_{1-4}$ alkyl;

$R^3$ is independently hydroxyl, carbonyl, —CN, halogen, $C_{3-6}$ heteroaryl, unsubstituted $C_{1-4}$ alkoxy or $C_{1-4}$ alkoxy substituted by hydroxyl, an unsubstituted amino group or an amino group substituted by $R^6$, $C_{1-4}$ alkyl, $C_{1-4}$ haloalkyl, $C_{3-6}$ cycloalkyl or unsubstituted $C_{3-6}$ heterocycloalkyl or heterocycloalkyl substituted by $C_{1-4}$ alkyl;

$R^4$ is independently carbonyl, $C_{1-4}$ alkyl, $C_{1-4}$ haloalkyl, $C_{3-6}$ cycloalkyl or $C_{3-6}$ heterocycloalkyl;

$R^5$ is $C_{1-4}$ alkyl or $C_{3-6}$ cycloalkyl; $R^6$ is independently unsubstituted $C_{1-4}$ alkyl or $C_{1-4}$ alkyl substituted by $R^{6-1}$;

$R^{6-1}$ is independently hydroxyl, an unsubstituted amino group or an amino group substituted by $C_{1-4}$ alkyl;

$R^7$ is independently H, hydroxyl, —CN, halogen, $C_{1-4}$ alkoxy or $C_{1-4}$ alkyl;

the number of $R^3$ is 1, 2, 3 or 4;

the number of $R^4$ is 1 or 2;

the number of $R^5$ is 1, 2, 3 or 4;

the number of $R^6$ is 1 or 2;

the heteroatom in said $C_{3-6}$ heterocycloalkyl and $C_{3-6}$ heteroaryl is selected from N, O and S, and the number of the heteroatom is 1, 2, 3 or 4;

said compound represented by formula (I) is not

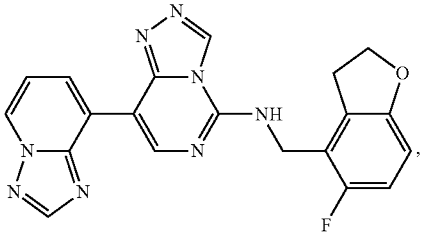,

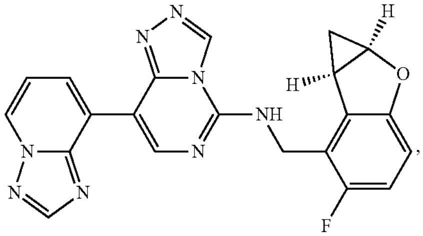,

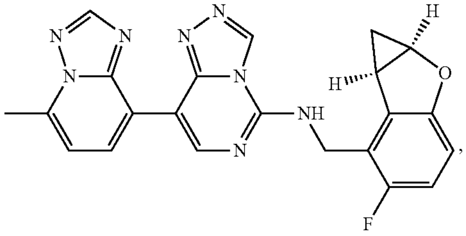,

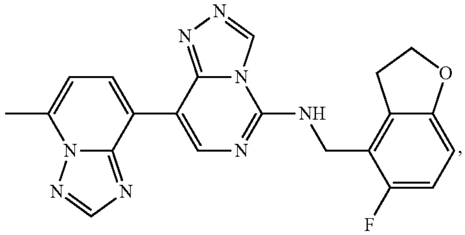,

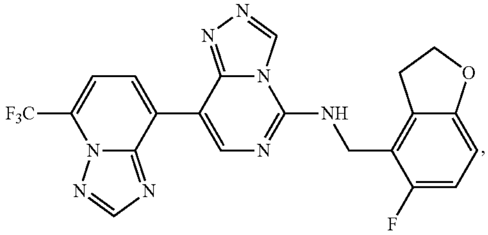,

-continued

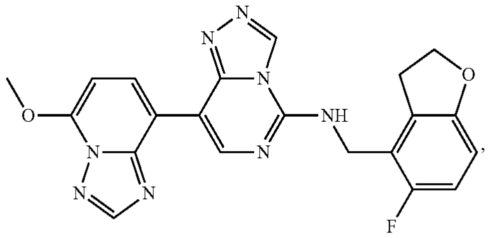,

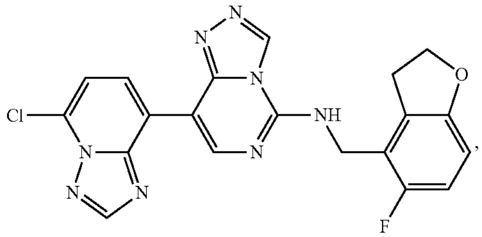,

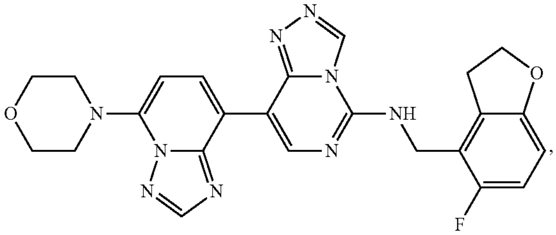,

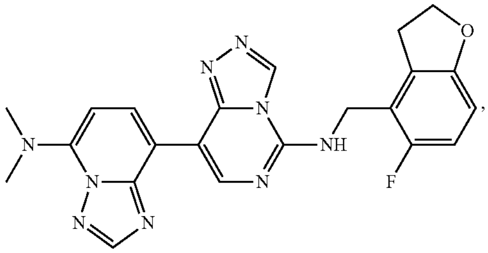,

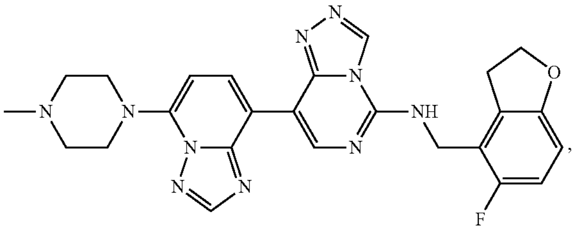,

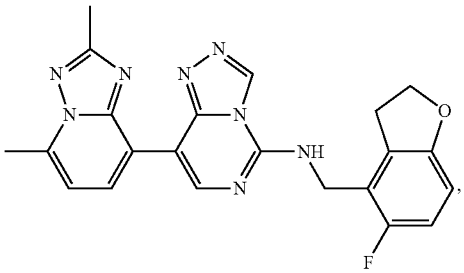,

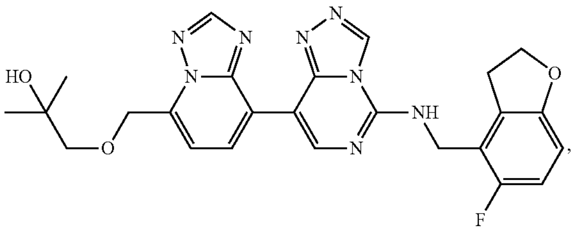,

-continued
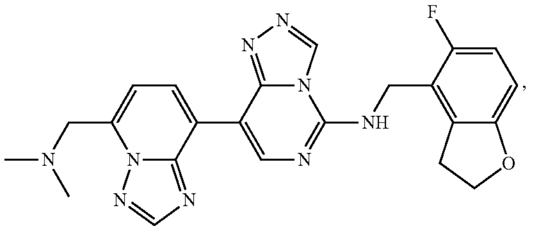
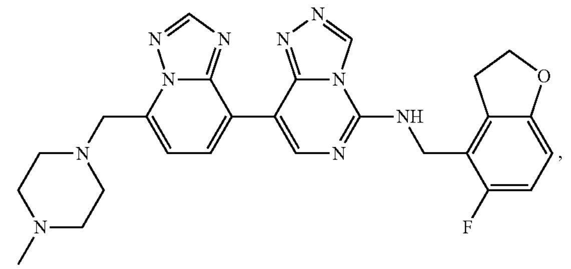
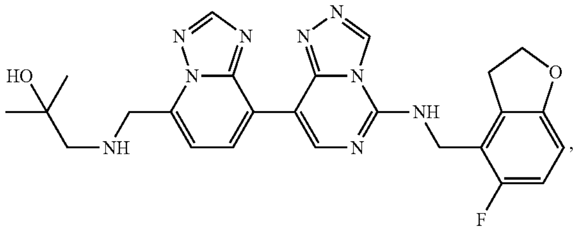
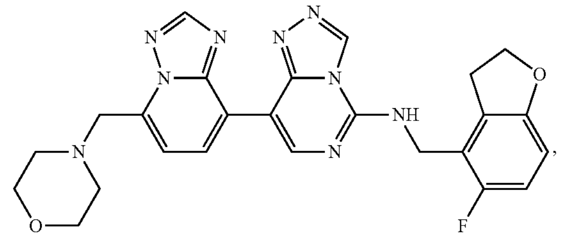
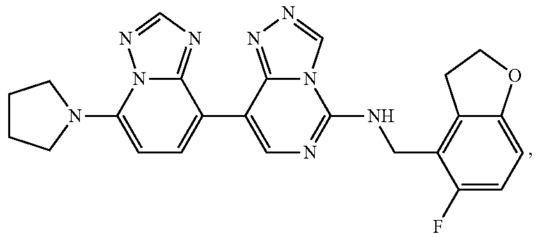
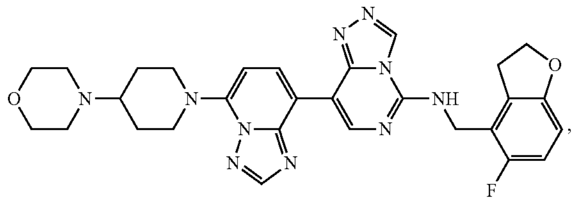
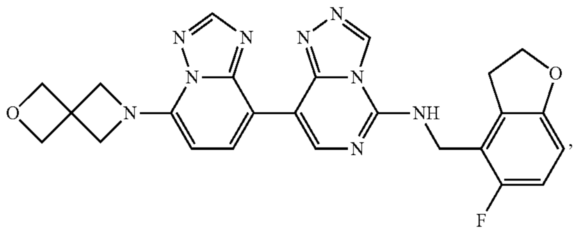
-continued
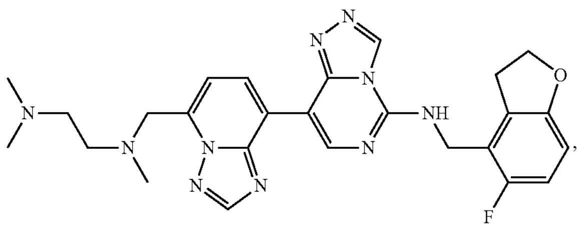
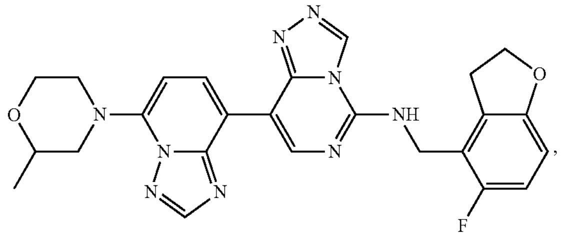
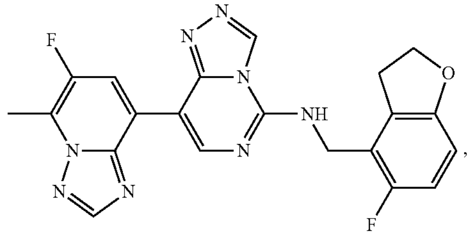
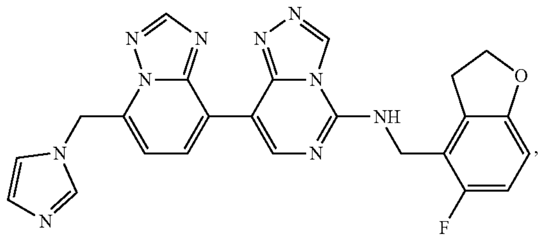
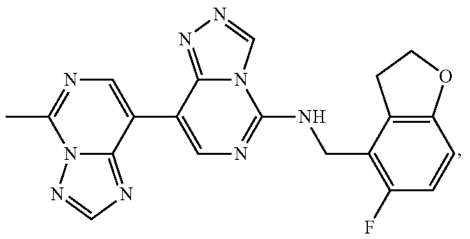
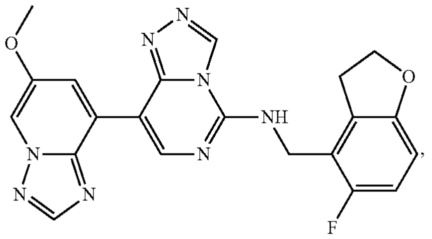
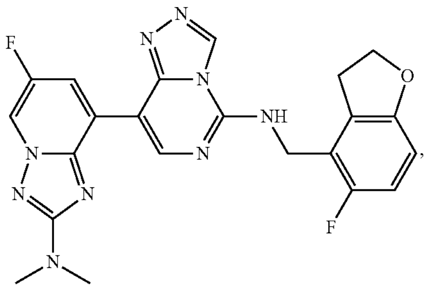

-continued

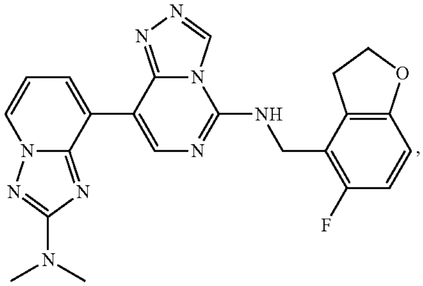

,

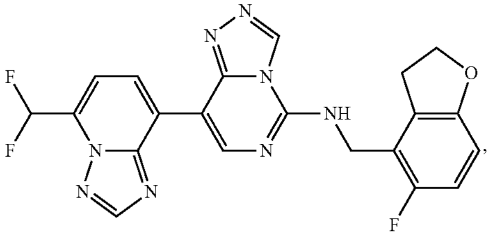

,

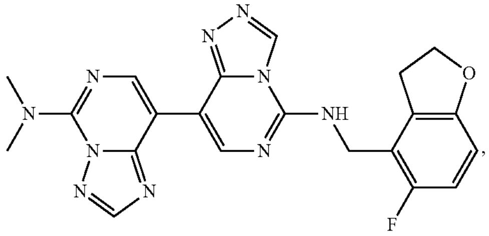

,

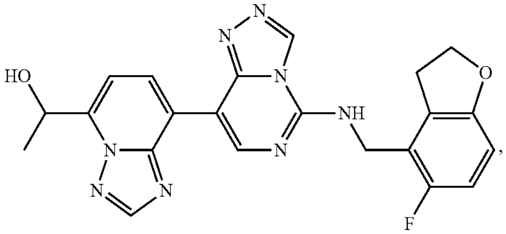

,

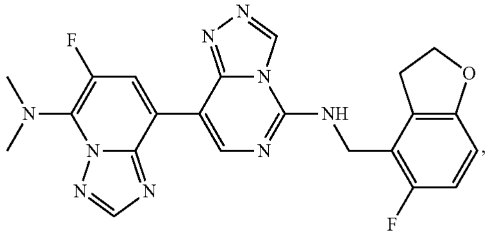

,

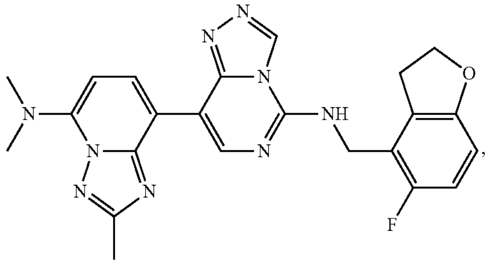

,

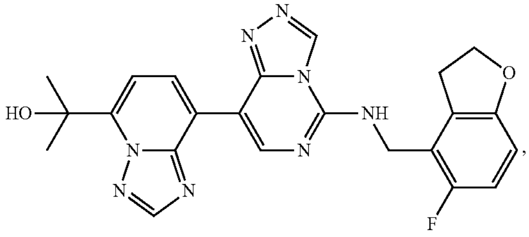

,

-continued

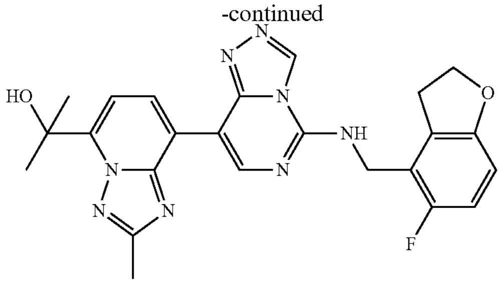

or

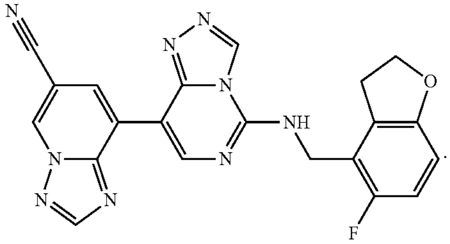

.

In some preferred embodiments of the present disclosure, certain groups in the compound represented by formula (I), the pharmaceutically acceptable salt thereof, stereoisomer thereof, the solvate thereof or their isotope-labeled compound are as defined below. The unmentioned groups are as described in any embodiment of the present application (referred to as "in some preferred embodiments of the present disclosure"):

When $R^1$ is halogen, said halogen is fluorine, chlorine, bromine or iodine, preferably chlorine.

In some preferred embodiments of the present disclosure: when $R^1$ is $C_{1-4}$ alkoxy, said $C_{1-4}$ alkoxy is methoxy, ethoxy, propoxy, isopropoxy, butoxy, isobutoxy or tert-butoxy, preferably methoxy.

In some preferred embodiments of the present disclosure: when $R^1$ is unsubstituted $C_{1-6}$ alkyl or $C_{1-6}$ alkyl substituted by $R^3$, said $C_{1-6}$ alkyl is methyl, ethyl, propyl, isopropyl, butyl, isobutyl, tert-butyl, 1-pentyl, 2-pentyl, 3-pentyl or isopentyl, preferably methyl, ethyl, propyl, isopropyl, isobutyl or 3-pentyl.

In some preferred embodiments of the present disclosure: when $R^3$ is halogen, said halogen is fluorine, chlorine, bromine or iodine, preferably fluorine.

In some preferred embodiments of the present disclosure: when $R^3$ is $C_{3-6}$ heteroaryl, said $C_{3-6}$ heteroaryl is imidazolyl, preferably

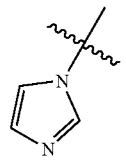

.

In some preferred embodiments of the present disclosure: when $R^3$ is unsubstituted $C_{1-4}$ alkoxy or $C_{1-4}$ alkoxy substituted by hydroxyl, said $C_{1-4}$ alkoxy is methoxy, ethoxy, propoxy, isopropoxy, butoxy, isobutoxy or tert-butoxy, preferably isobutoxy, and the number of the hydroxyl is preferably 1, 2 or 3.

In some preferred embodiments of the present disclosure: when $R^3$ is $C_{1-4}$ alkoxy substituted by hydroxyl, said $C_{1-4}$ alkoxy substituted by hydroxyl is

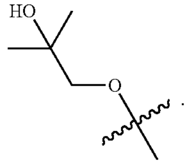 [SMILES: *OCC(C)(C)O]

In some preferred embodiments of the present disclosure: said $C_{1-4}$ alkyl group is methyl, ethyl, propyl, isopropyl, butyl, isobutyl or tert-butyl.

In some preferred embodiments of the present disclosure: when $R^3$ is $C_{1-4}$ haloalkyl, said $C_{1-4}$ haloalkyl is trifluoromethyl, trifluoroethyl, difluoromethyl, difluoroethyl.

In some preferred embodiments of the present disclosure: when $R^6$ is independently $C_{1-4}$ alkyl substituted by $R^{6-1}$, the number of $R^{6-1}$ is 1, 2 or 3.

In some preferred embodiments of the present disclosure: when $R^6$ is independently unsubstituted $C_{1-4}$ alkyl or $C_{1-4}$ alkyl substituted by $R^{6-1}$, said $C_{1-4}$ alkyl is methyl, ethyl, propyl, isopropyl, butyl, isobutyl or tert-butyl, preferably ethyl or isobutyl.

In some preferred embodiments of the present disclosure: when $R^{6-1}$ is independently an amino group substituted by a $C_{1-4}$ alkyl, the number of said $C_{1-4}$ alkyl is 1 or 2, and said $C_{1-4}$ alkyl is preferably methyl, ethyl, propyl, isopropyl, butyl, isobutyl or tert-butyl, more preferably methyl.

In some preferred embodiments of the present disclosure: when $R^{6-1}$ is independently an amino group substituted by $C_{1-4}$ alkyl, said amino group substituted by $C_{1-4}$ alkyl is

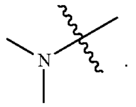 [SMILES: *N(C)C]

In some preferred embodiments of the present disclosure: when $R^6$ is independently $C_{1-4}$ alkyl substituted by $R^{6-1}$, said $C_{1-4}$ alkyl substituted by $R^{6-1}$ is

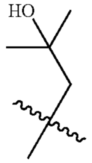 or 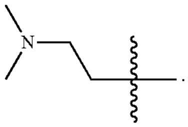

In some preferred embodiments of the present disclosure: when $R^1$ is $C_{1-4}$ alkyl, said $C_{1-4}$ alkyl is methyl.

In some preferred embodiments of the present disclosure: when $R^1$ is $C_{1-4}$ alkyl substituted by $R^3$, said $C_{1-4}$ alkyl substituted by $R^3$ is

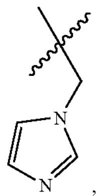, 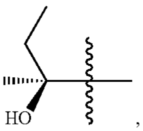, 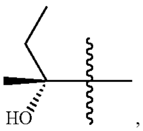, 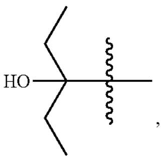,

-continued

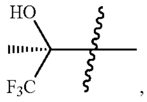, 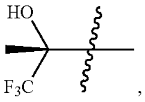, 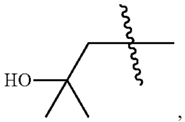,

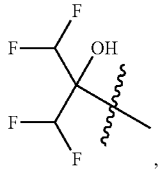, 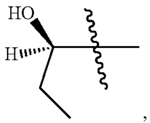, 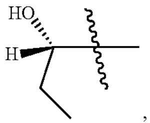,

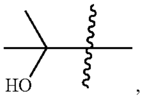, 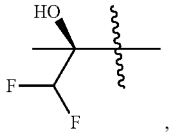, 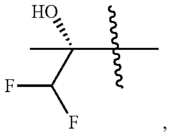,

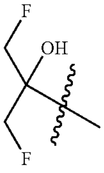, 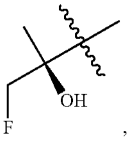, 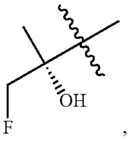, $CF_3$, 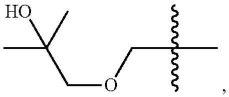, 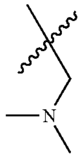,

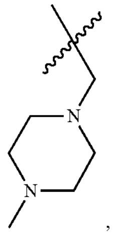, 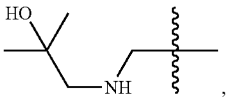, 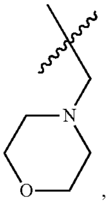,

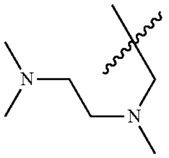 or 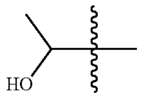;

In some preferred embodiments of the present disclosure: when $R^4$ is $C_{1-4}$ alkyl, said $C_{1-4}$ alkyl is methyl, ethyl, propyl, isopropyl, butyl, isobutyl or tert-butyl, preferably methyl.

In some preferred embodiments of the present disclosure: when $R^1$ is an amino group substituted by $R^4$, said amino group substituted by $R^4$ is

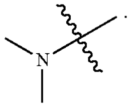 [SMILES: *N(C)C]

In some preferred embodiments of the present disclosure: when $R^1$ is a unsubstituted $C_{1-4}$ haloalkyl or $C_{1-4}$ haloalkyl substituted by $R^3$, the halogen in said haloalkyl is preferably fluorine, chlorine, bromine or iodine, more preferably fluorine, and the alkyl in said $C_{1-4}$ haloalkyl group is preferably methyl, ethyl, propyl, isopropyl, butyl, isobutyl or tert-butyl, more preferably methyl, and said $C_{1-4}$ haloalkyl is preferably monofluoromethyl, difluoromethyl or trifluoromethyl.

In some preferred embodiments of the present disclosure: when $R^1$ is unsubstituted $C_{3-6}$ cycloalkyl or $C_{3-6}$ cycloalkyl substituted by hydroxyl, the number of the hydroxyl is preferably 1, 2 or 3, and said $C_{3-6}$ alkyl is preferably cyclopropyl, cyclobutyl, cyclopentyl or cyclohexyl, more preferably cyclopropyl or cyclobutyl.

In some preferred embodiments of the present disclosure: when $R^1$ is $C_{3-6}$ cycloalkyl substituted by hydroxyl, said $C_{3-6}$ cycloalkyl substituted by hydroxyl is

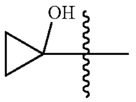 or 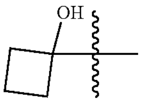 .

In some preferred embodiments of the present disclosure: when $R^1$ is unsubstituted $C_{3-6}$ heterocycloalkyl or $C_{3-6}$ heterocycloalkyl substituted by $R^5$, said $C_{3-6}$ heterocycloalkyl is tetrahydropyrrolyl, tetrahydrofuranyl, piperidinyl, piperazinyl, morpholinyl or 2-oxa-6-aza-spiro[3,3]heptyl, preferably

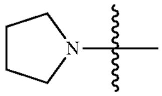 , 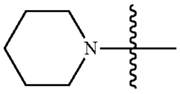 , 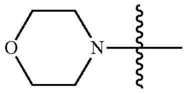 , 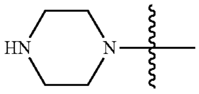 or 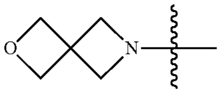 .

In some preferred embodiments of the present disclosure: when $R^5$ is $C_{1-4}$ alkyl, said $C_{1-4}$ alkyl is methyl, ethyl, propyl, isopropyl, butyl, isobutyl or tert-butyl, preferably methyl.

In some preferred embodiments of the present disclosure: when $R^5$ is $C_{3-6}$ heterocycloalkyl, said $C_{3-6}$ heterocycloalkyl is tetrahydropyrrolyl, tetrahydrofuranyl, piperidinyl, piperazinyl, morpholinyl or 2-oxa-6-aza-spiro[3,3]heptyl, preferably

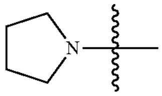 , 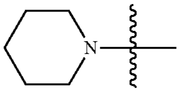 , 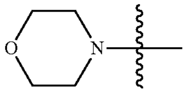 , 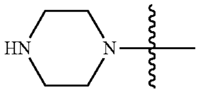 or 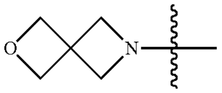 , more preferably

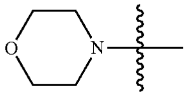 .

In some preferred embodiments of the present disclosure: when $R^1$ is a $C_{3-6}$ heterocycloalkyl substituted by $R^5$, said $C_{3-6}$ heterocycloalkyl substituted by $R^5$ is

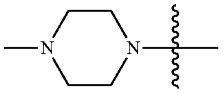 , 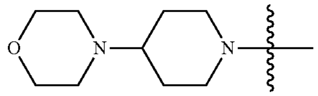 or 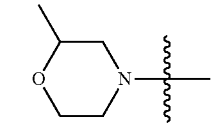 .

In some preferred embodiments of the present disclosure: when $R^1$ is $C_{3-6}$ heterocycloalkyl, said $C_{3-6}$ heterocycloalkyl is

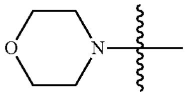 , 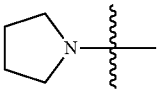 or 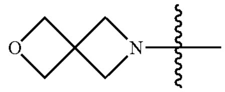 .

In some preferred embodiments of the present disclosure: $R^1$ is H, methyl, difluoromethyl, trifluoromethyl, methoxy,

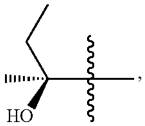 , 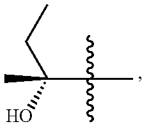 , 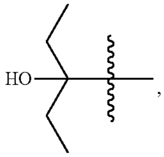 , 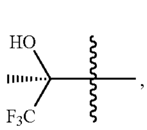 , 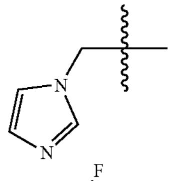 , 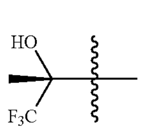 , 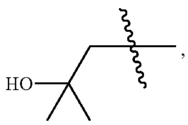 , 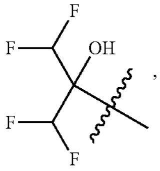 , 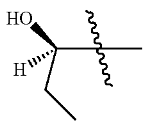 , 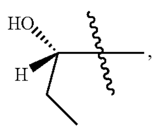 , 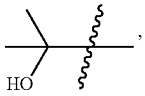 , 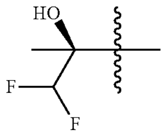 , -continued

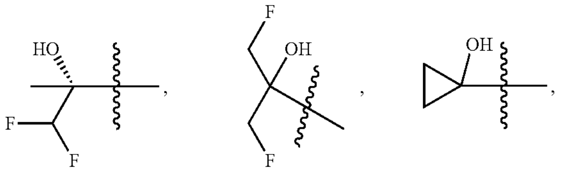
, , ,

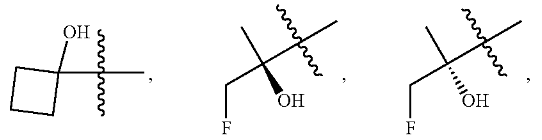
, , ,

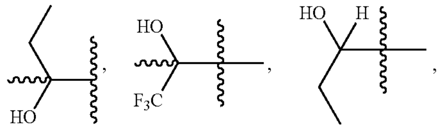
, , ,

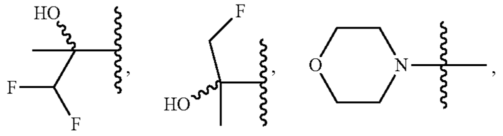
, , ,

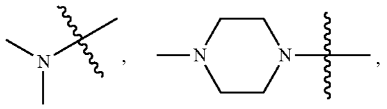
, ,

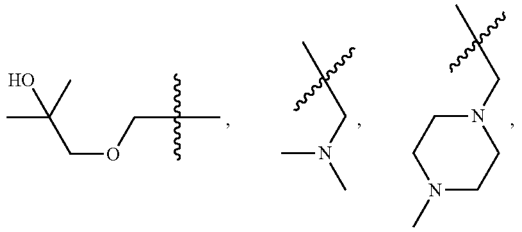
, , ,

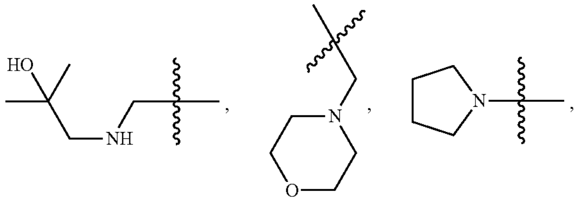
, , ,

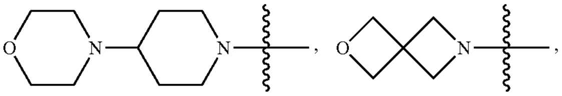
, ,

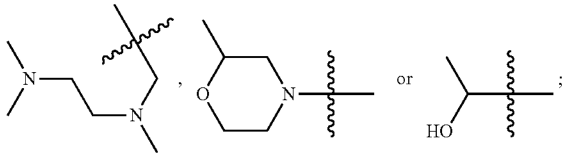
, or ;

more preferably, $R^1$ is

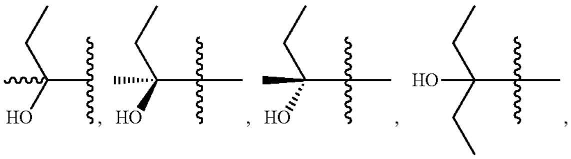
, , , ,

-continued

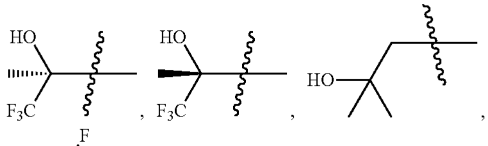
, , ,

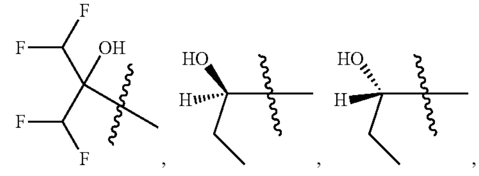
, , ,

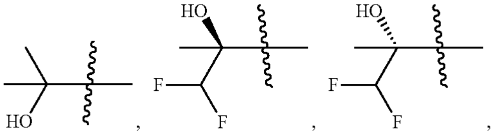
, , ,

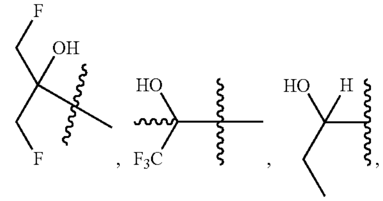
, , ,

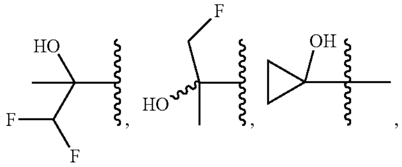
, , ,

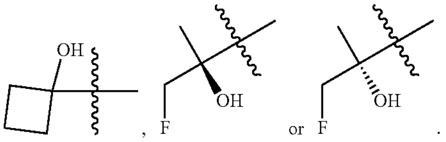
, or .

In some preferred embodiments of the present disclosure: when $R^2$ is $C_{1-4}$ alkyl, said $C_{1-4}$ alkyl is methyl, ethyl, propyl, isopropyl, butyl, isobutyl or tert-butyl, preferably methyl.

In some preferred embodiments of the present disclosure: when $R^2$ is $C_{3-6}$ cycloalkyl, said $C_{3-6}$ cycloalkyl is cyclopropyl, cyclobutyl, cyclopentyl or cyclohexyl.

In some preferred embodiments of the present disclosure: when $R^2$ is an unsubstituted amino group or an amino group substituted by $C_{1-4}$ alkyl, said $C_{1-4}$ alkyl is preferably methyl, ethyl, propyl, isopropyl, butyl, isobutyl or tert-butyl, more preferably methyl, the number of the $C_{1-4}$ alkyl is preferably 1 or 2, and the unsubstituted amino group or the amino group substituted by $C_{1-4}$ alkyl is preferably

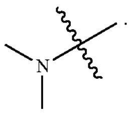 [SMILES: *N(C)C]
.

In some preferred embodiments of the present disclosure: when $R^7$ is halogen, said halogen is fluorine, chlorine, bromine or iodine, preferably fluorine.

In some preferred embodiments of the present disclosure: when $R^7$ is $C_{1-4}$ alkoxy, said $C_{1-4}$ alkoxy is methoxy, ethoxy, propoxy, isopropoxy, butoxy, isobutoxy or tert-butoxy, preferably methoxy.

In some preferred embodiments of the present disclosure: when $R^7$ is $C_{1-4}$ alkyl, said $C_{1-4}$ alkyl is methyl, ethyl, propyl, isopropyl, butyl, isobutyl or tert-butyl, preferably methyl.

In some preferred embodiments of the present disclosure: A is

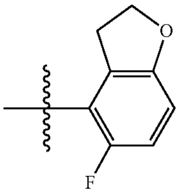.

In some preferred embodiments of the present disclosure: $R^1$ is preferably H, halogen, $C_{1-4}$ alkoxy, unsubstituted $C_{1-6}$ alkyl or $C_{1-6}$ alkyl substituted by $R^3$, an amino group substituted by $R^4$, $C_{1-4}$ haloalkyl, $C_{3-6}$ cycloalkyl substituted by hydroxyl, unsubstituted $C_{3-6}$ heterocycloalkyl or $C_{3-6}$ heterocycloalkyl substituted by $R^5$, more preferably H, $C_{1-4}$ alkoxy, unsubstituted $C_{1-6}$ alkyl or $C_{1-6}$ alkyl substituted by $R^3$, an amino group substituted by $R^4$, $C_{1-4}$ haloalkyl, $C_{3-6}$ cycloalkyl substituted by hydroxyl, unsubstituted $C_{3-6}$ heterocycloalkyl or $C_{3-6}$ heterocycloalkyl substituted by $R^5$, more preferably H, methyl, difluoromethyl, trifluoromethyl, methoxy,

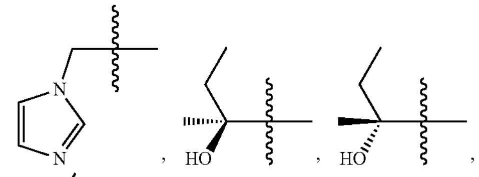,

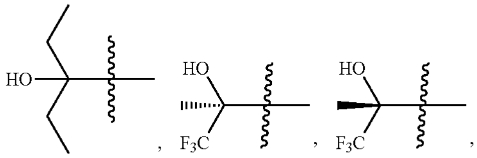,

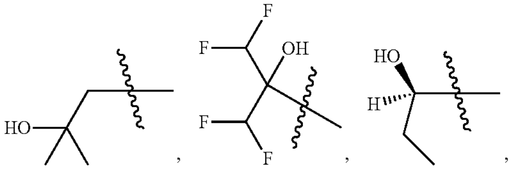,

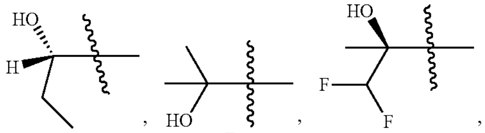,

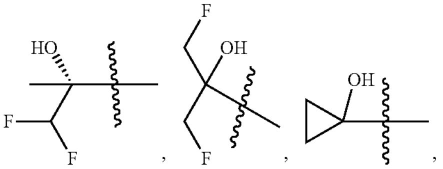,

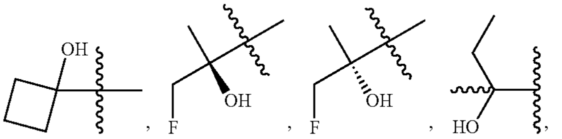,

-continued

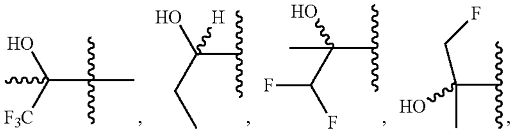,

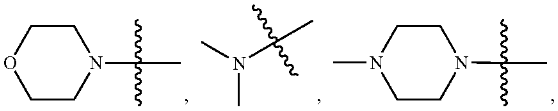,

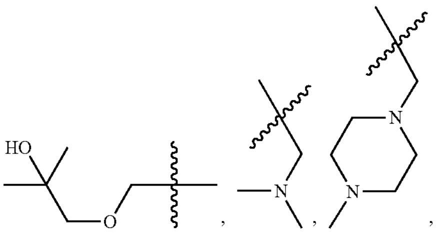,

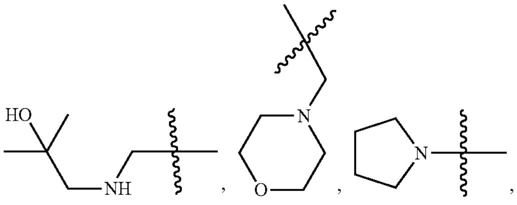,

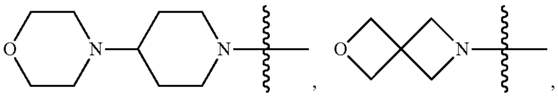,

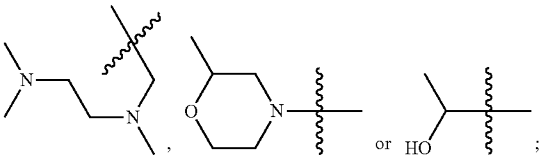;

preferably, $R^1$ is $C_{1-6}$ alkyl substituted by $R^3$ or $C_{3-6}$ cycloalkyl substituted by hydroxyl, preferably

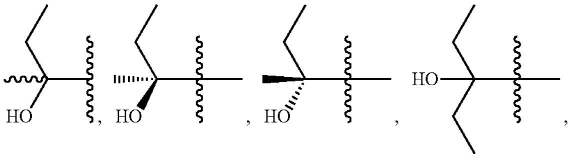,

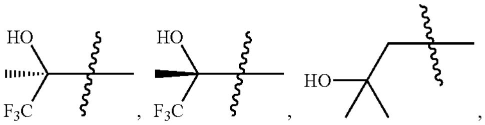,

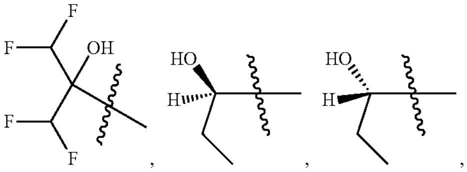,

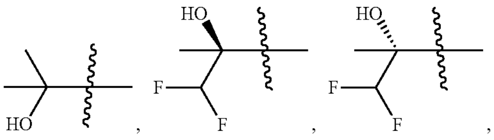,

-continued

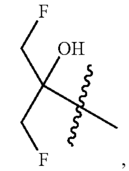, 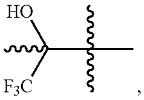, 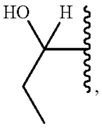

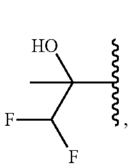 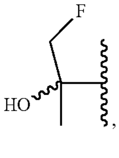 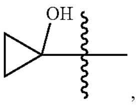,

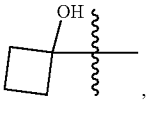, 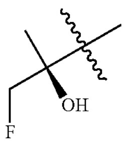 or 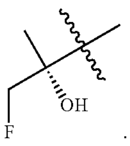.

In some preferred embodiments of the present disclosure: $R^2$ is preferably H, $C_{1-4}$ alkyl, or an amino group substituted by $C_{1-4}$ alkyl, more preferably H, methyl or

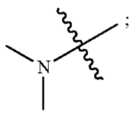 [SMILES: *N(C)C];

preferably, $R^2$ is H or $C_{1-4}$ alkyl, preferably H or methyl.

In some preferred embodiments of the present disclosure: when $R^1$ is unsubstituted $C_{1-6}$ alkyl or $C_{1-6}$ alkyl substituted by $R^3$, $R^3$ is preferably hydroxyl, halogen, $C_{3-6}$ heteroaryl, $C_{1-4}$ alkoxy substituted by hydroxyl, an amino group substituted by $R^6$, $C_{1-4}$ alkyl, $C_{1-4}$ haloalkyl, unsubstituted $C_{3-6}$ heterocycloalkyl or $C_{3-6}$ heterocycloalkyl substituted by $C_{1-4}$ alkyl, more preferably hydroxyl, fluorine,

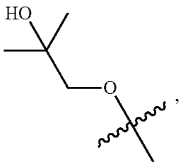, 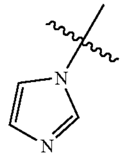,

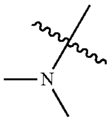, 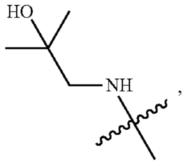,

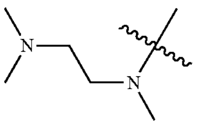, methyl, ethyl, difluoromethyl, trifluoromethyl,

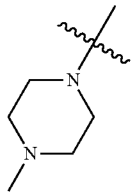 or 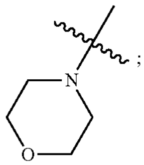 [SMILES: *N1CCOCC1];

preferably, $R^3$ is hydroxyl, halogen, $C_{1-4}$ alkyl or $C_{1-4}$ haloalkyl, preferably hydroxyl, fluorine, methyl, ethyl, monofluoromethyl, difluoromethyl or trifluoromethyl.

In some preferred embodiments of the present disclosure: when $R^1$ is an amino group substituted by $R^4$, $R^4$ is preferably $C_{1-4}$ alkyl, more preferably a methyl group.

In some preferred embodiments of the present disclosure: when $R^1$ is $C_{3-6}$ heterocycloalkyl substituted by $R^5$, $R^5$ is preferably methyl or

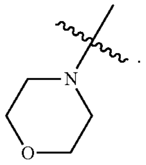.

In some preferred embodiments of the present disclosure: when $R^3$ is an amino group substituted by $R^6$, $R^6$ is preferably methyl,

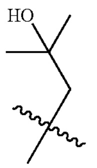 or 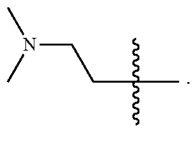.

In some preferred embodiments of the present disclosure: when $R^6$ is independently a $C_{1-4}$ alkyl group substituted by $R^{6-1}$, $R^{6-1}$ is preferably hydroxyl or an amino group substituted by $C_{1-4}$ alkyl, more preferably hydroxyl or

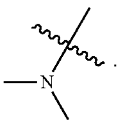.

In some preferred embodiments of the present disclosure: $R^7$ is preferably H, —CN, halogen, $C_{1-4}$ alkoxy or $C_{1-4}$ alkyl, more preferably H, halogen, $C_{1-4}$ alkoxy or $C_{1-4}$ alkyl, further preferably H, fluorine, methoxy or methyl; preferably, $R^7$ is H, halogen or $C_{1-4}$ alkyl, preferably H, methyl or fluorine.

In some preferred embodiments of the present disclosure:

$R^1$ is any of the following structures:

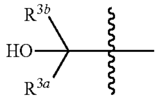 , 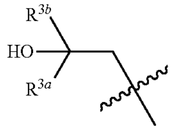 ,

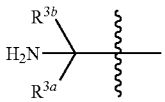 or 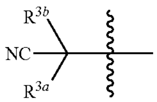 ; preferably

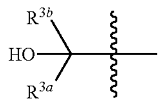 or 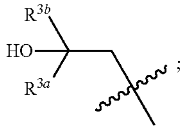 ;

$R^{3a}$, $R^{3b}$ are independently H, $C_{1-4}$ alkyl (preferably methyl or $C_{2-4}$ alkyl), $C_{1-4}$ haloalkyl (such as a monofluoromethyl, difluoromethyl or trifluoromethyl), $C_{3-6}$ cycloalkyl or $C_{3-6}$ heterocycloalkyl, preferably H, $C_{1-4}$ alkyl or $C_{1-4}$ haloalkyl; $R^{3a}$ and $R^{3b}$ are not methyl at the same time; when $R^{3a}$ is methyl, $R^{3b}$ is not H; when $R^{3a}$ is H, $R^{3b}$ is not methyl;

or $R^{3a}$ and $R^{3b}$ together with the connected atoms form $C_{3-6}$ cycloalkyl (such as cyclopropyl or cyclobutyl), $C_{3-6}$ heterocycloalkyl, preferably $C_{3-6}$ cycloalkyl;

the heteroatom in said $C_{3-6}$ heterocycloalkyl is selected from N, O and S, and the number of the heteroatom is 1, 2, 3 or 4.

In some preferred embodiments of the present disclosure: $R^2$ is H.

In some preferred embodiments of the present disclosure: $R^7$ is H, halogen (such as fluorine) or $C_{1-6}$ alkyl (such as methyl).

In some preferred embodiments of the present disclosure:

said compound represented by formula (I) is selected from the compounds shown below:

(I-1)

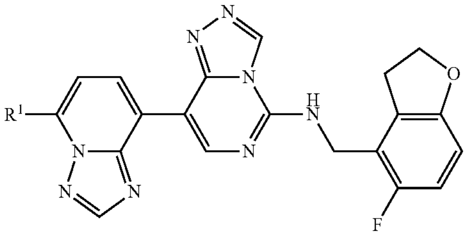

(I-2)

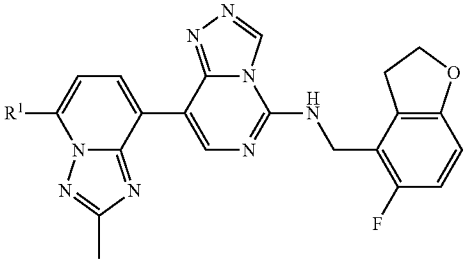

-continued (I-3)

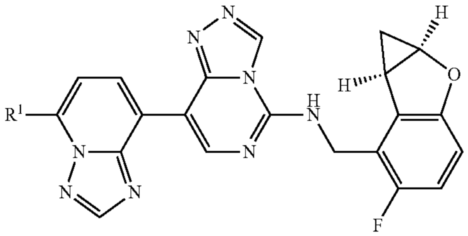

(I-4)

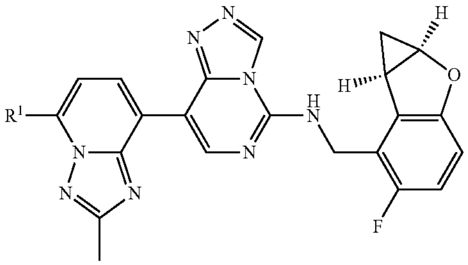

(I-5)

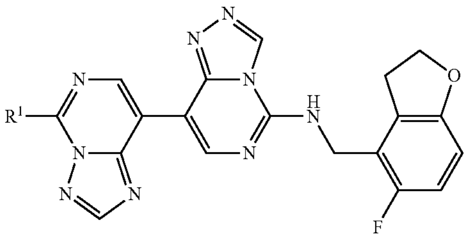

(I-6)

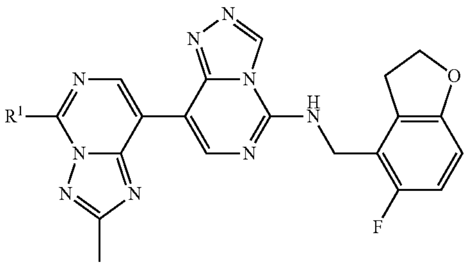

(I-7)

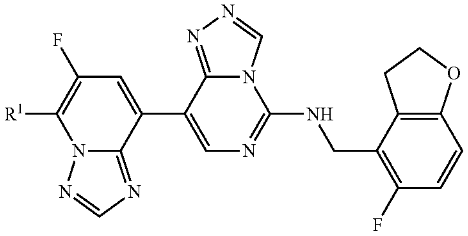

(I-8)

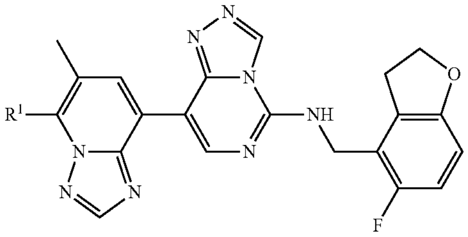

-continued
(I-9)
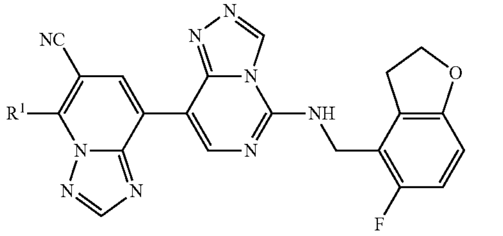
(I-10)
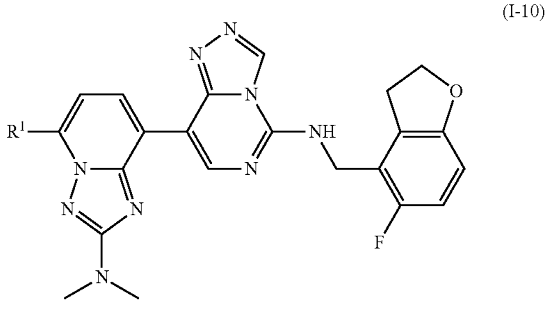
preferably,
(I-1)
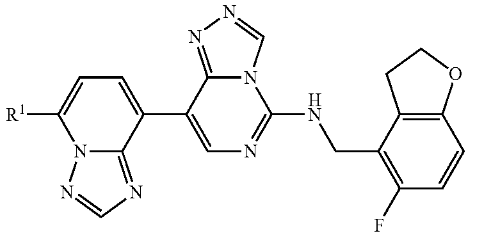
(I-2)
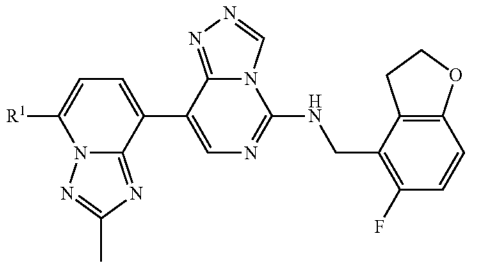
(I-5)
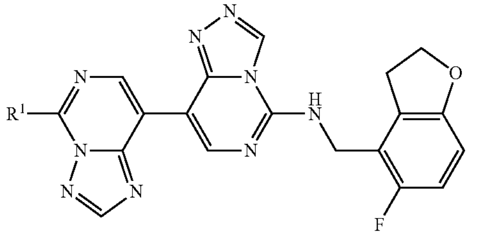
(I-6)
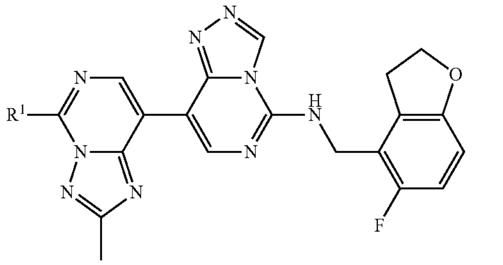
-continued
(I-7)
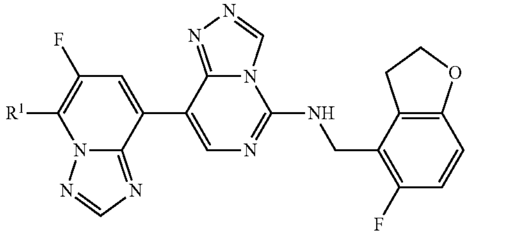
(I-8)
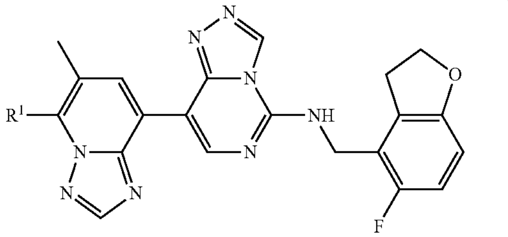
(I-8)
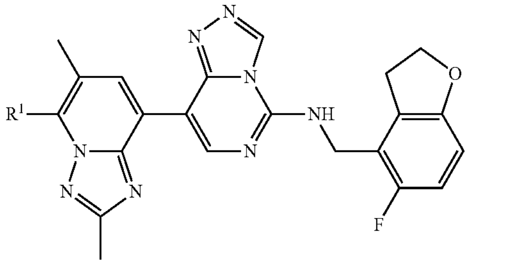
in the above compounds, $R^1$ is as defined above.
In some preferred embodiments of the present disclosure: the group
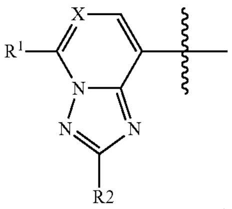
is preferably
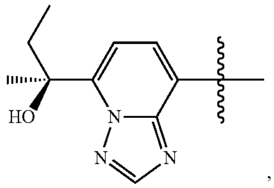
,
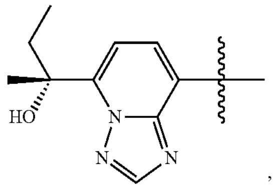
,
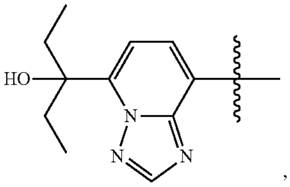
,
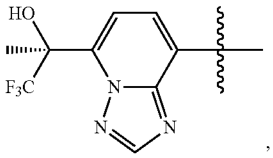
,
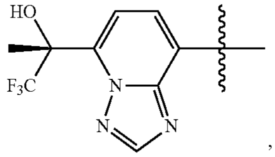
, -continued
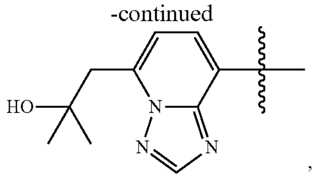,
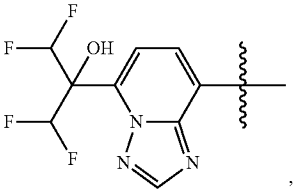, 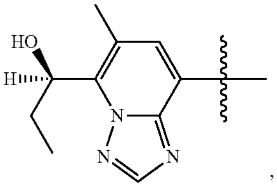,
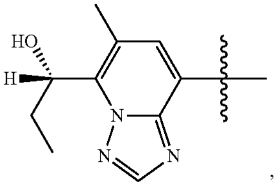, 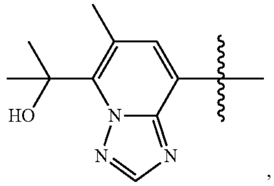,
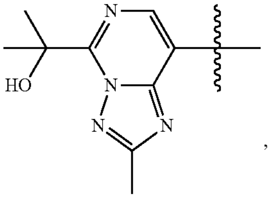, 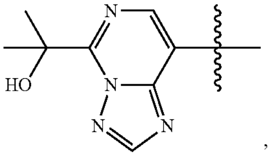,
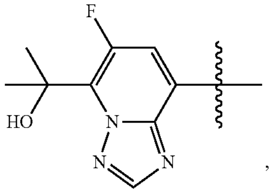, 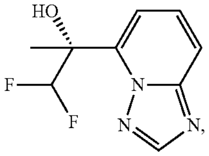
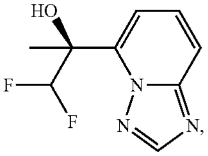 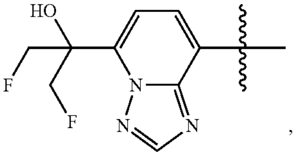,
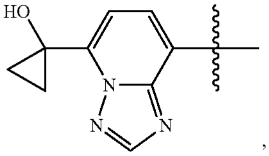, 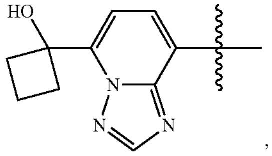,
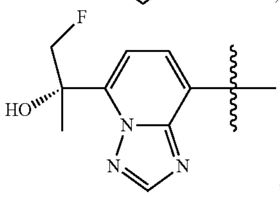, 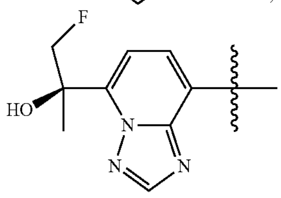,
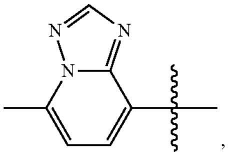, 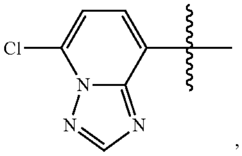,
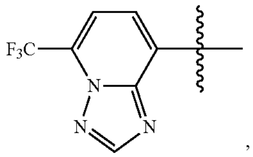, 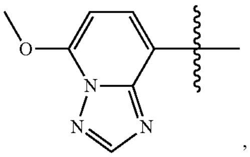,
-continued
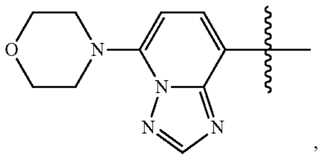, 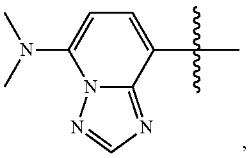,
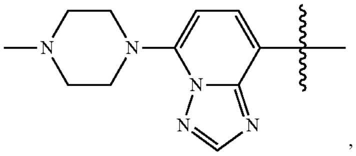,
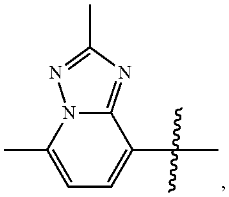,
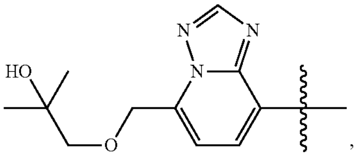,
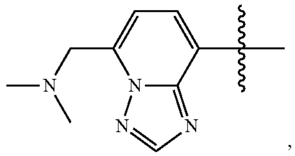,
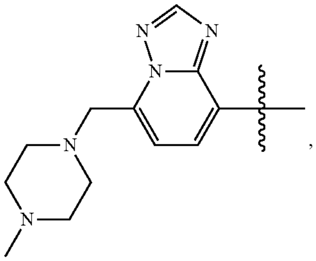,
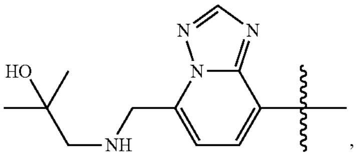,
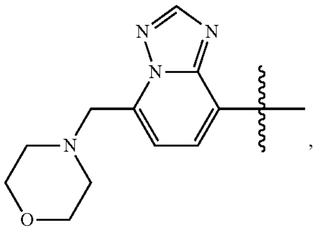,
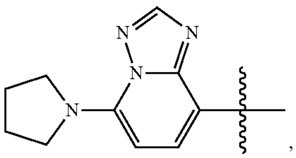, -continued

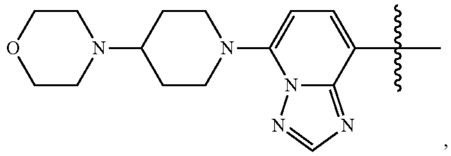

,

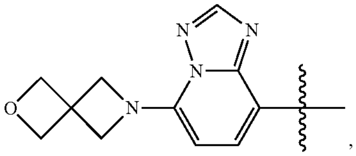

,

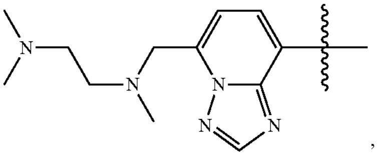

,

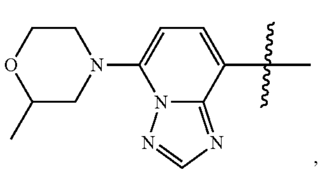

,

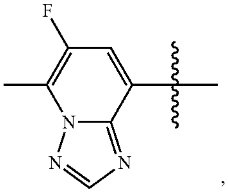

,

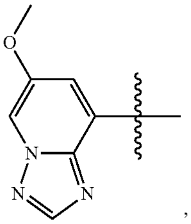

,

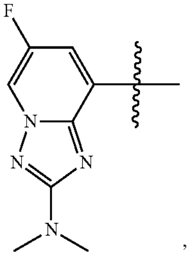

,

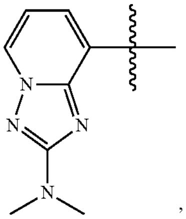

,

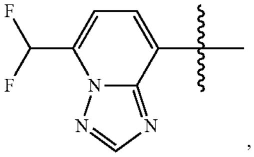

,

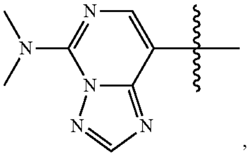

,

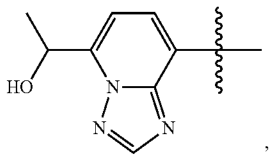

,

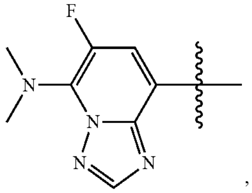

,

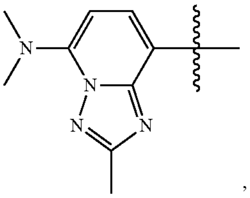

,

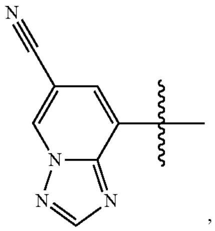

,

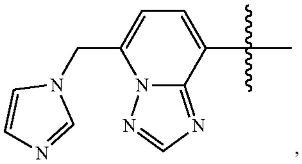

,

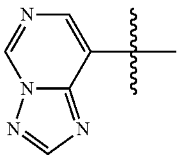

or

-continued

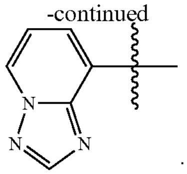

.

In some preferred embodiments of the present disclosure: the compound represented by formula (I) is any of the following schemes:

Scheme 1:

$R^1$ is H, halogen, $C_{1-4}$ alkoxy, unsubstituted $C_{1-6}$ alkyl or $C_{1-6}$ alkyl substituted by $R^3$, an amino group substituted by $R^4$, $C_{1-4}$ haloalkyl, $C_{3-6}$ cycloalkyl substituted by hydroxyl, unsubstituted $C_{3-6}$ heterocycloalkyl or $C_{3-6}$ heterocycloalkyl substituted by $R^5$;

$R^2$ is H, $C_{1-4}$ alkyl, $C_{1-4}$ cycloalkyl or an amino group substituted by $C_{1-4}$ alkyl;

$R^3$ is hydroxyl, halogen, $C_{3-6}$ heteroaryl, $C_{1-4}$ alkoxy substituted by hydroxyl, an amino group substituted by $R^6$, $C_{1-4}$ alkyl, $C_{1-4}$ haloalkyl, unsubstituted $C_{3-6}$ heterocycloalkyl or $C_{3-6}$ heterocycloalkyl substituted by $C_{1-4}$ alkyl;

$R^4$ is $C_{1-4}$ alkyl;

$R^7$ is independently H, —CN, halogen, $C_{1-4}$ alkoxy or $C_{1-4}$ alkyl;

Scheme 2:

$R^1$ is H, $C_{1-4}$ alkoxy, unsubstituted $C_{1-6}$ alkyl or $C_{1-6}$ alkyl substituted by $R^3$, an amino group substituted by $R^4$, $C_{1-4}$ haloalkyl, $C_{3-6}$ cycloalkyl substituted by hydroxyl, unsubstituted $C_{3-6}$ heterocycloalkyl or $C_{3-6}$ heterocycloalkyl substituted by $R^5$;

$R^2$ is H, $C_{1-4}$ alkyl or an amino group substituted by $C_{1-4}$ alkyl;

$R^3$ is hydroxyl, halogen, $C_{3-6}$ heteroaryl, $C_{1-4}$ alkoxy substituted by hydroxyl, an amino group substituted by $R^6$, $C_{1-4}$ alkyl, $C_{1-4}$ haloalkyl, unsubstituted $C_{3-6}$ heterocycloalkyl or $C_{3-6}$ heterocycloalkyl substituted by $C_{1-4}$ alkyl;

$R^4$ is $C_{1-4}$ alkyl;

$R^7$ is H, halogen, $C_{1-4}$ alkoxy or $C_{1-4}$ alkyl;

Scheme 3:

A is

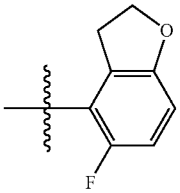

;

$R^1$ is H, $C_{1-4}$ alkoxy, unsubstituted $C_{1-6}$ alkyl or $C_{1-6}$ alkyl substituted by $R^3$, an amino group substituted by $R^4$, $C_{1-4}$ haloalkyl, $C_{3-6}$ cycloalkyl substituted by hydroxyl, or unsubstituted $C_{3-6}$ heterocycloalkyl or $C_{3-6}$ heterocycloalkyl substituted by $R^5$;

$R^2$ is H, methyl or

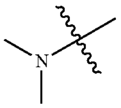

;

$R^3$ is hydroxyl, halogen, $C_{3-6}$ heteroaryl, $C_{1-4}$ alkoxy substituted by hydroxyl, an amino group substituted by $R^6$, $C_{1-4}$ alkyl, $C_{1-4}$ haloalkyl, unsubstituted $C_{3-6}$ heterocycloalkyl or $C_{3-6}$ heterocycloalkyl substituted by $C_{1-4}$ alkyl;

$R^4$ is $C_{1-4}$ alkyl;

$R^7$ is H, F, methoxy or methyl;

Scheme 4:

A is

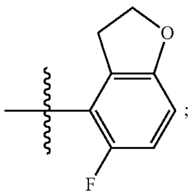 [SMILES: *c1c(F)ccc2c1CCO2];

$R^1$ is H, $C_{1-4}$ alkoxy, unsubstituted $C_{1-6}$ alkyl or $C_{1-6}$ alkyl substituted by $R^3$, an amino group substituted by $R^4$, $C_{1-4}$ haloalkyl, $C_{3-6}$ cycloalkyl substituted by hydroxyl, unsubstituted $C_{3-6}$ heterocycloalkyl or $C_{3-6}$ heterocycloalkyl substituted by R;

$R^2$ is H, methyl or

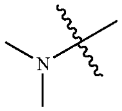;

$R^3$ is hydroxyl, fluorine,

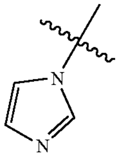, 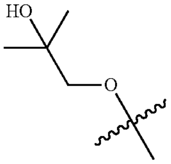, 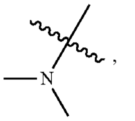, 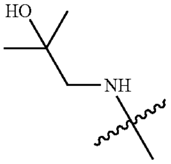, 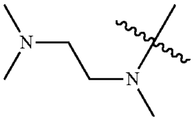, methyl, ethyl, difluoromethyl, trifluoromethyl,

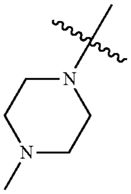 or 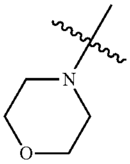;

$R^4$ is methyl;

$R^5$ is methyl or

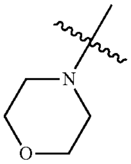;

$R^7$ is H, F, methoxy or methyl;

Scheme 5:

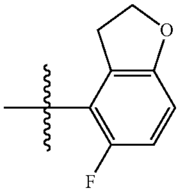;

$R^1$ is H, methyl, difluoromethyl, trifluoromethyl, methoxy,

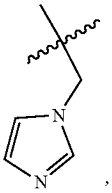, 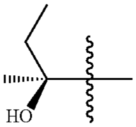, 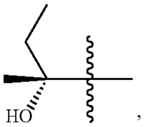, 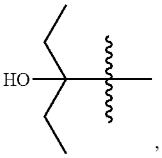, 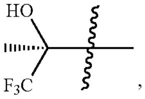, 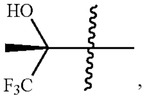, 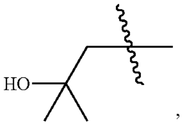, 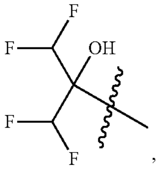, 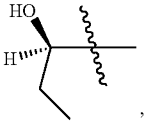, 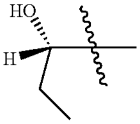, 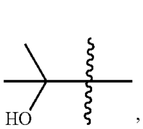, 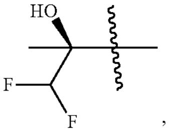, 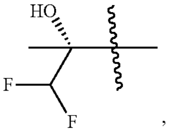, 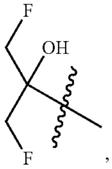, 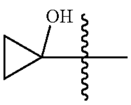, 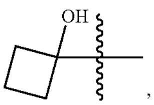, 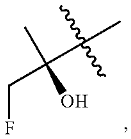, 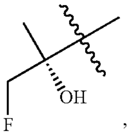, 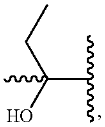, 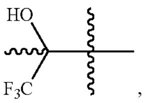, 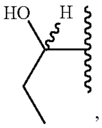, 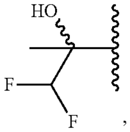, 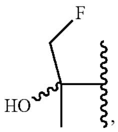, 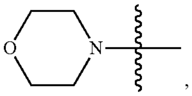, -continued

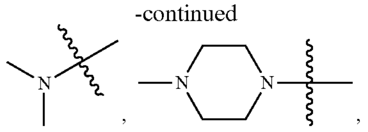

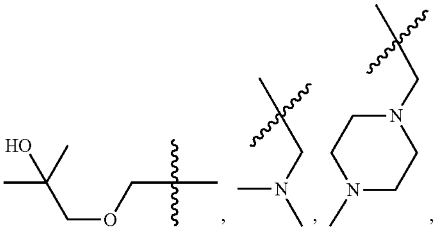

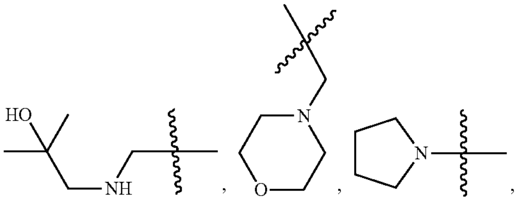

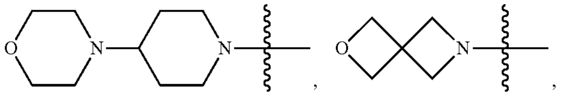

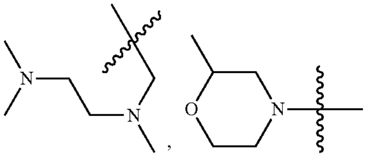

or

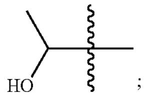

;

$R^2$ is H, methyl or

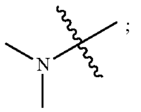 [SMILES: *N(C)C]

;

$R^7$ is H, F, methoxy or methyl;

Scheme 6:

A is

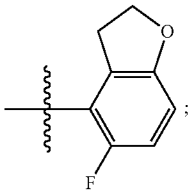 [SMILES: *c1c(F)ccc2c1CCO2]

;

$R_1$ is $C_{1-6}$ alkyl substituted by $R^3$ or $C_{3-6}$ cycloalkyl substituted by hydroxyl, preferably

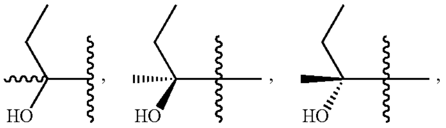

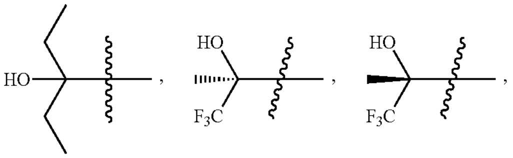

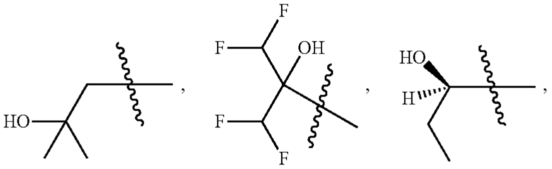

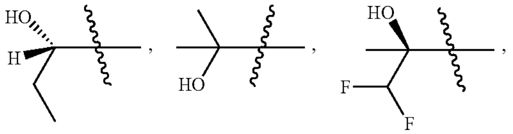

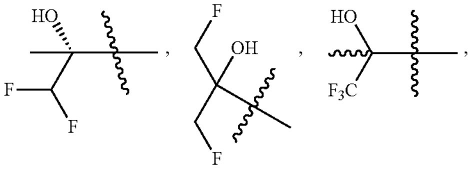

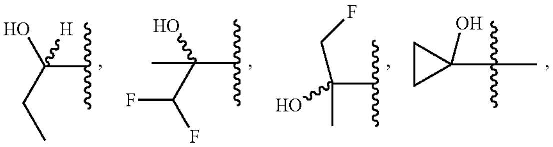

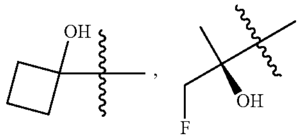

or

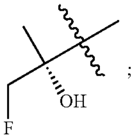

;

$R^2$ is H or $C_{1-4}$ alkyl, preferably H or methyl;

$R^3$ is hydroxyl, halogen, $C_{1-4}$ alkyl or $C_{1-4}$ haloalkyl, preferably hydroxyl, fluorine, methyl, ethyl, monofluoromethyl, difluoromethyl or trifluoromethyl;

$R^7$ is H, halogen or $C_{1-4}$ alkoxy, preferably H, methyl or fluorine.

In some preferred embodiments of the present disclosure: the compound represented by formula (I) is any of the following structures:

| Compound number | Compound structure | Name of compounds |
|---|---|---|
| E27-7 | 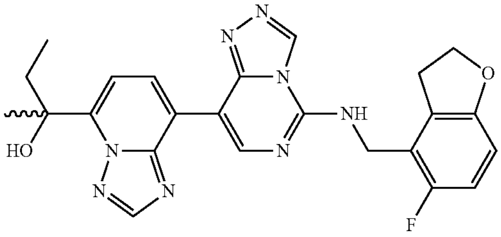 [SMILES: CCC(C)(O)c1ccc(-c2cnc(NCc3c(F)ccc4c3CCO4)n3cnnc23)c2ncnn12] | 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol |
| 1 | 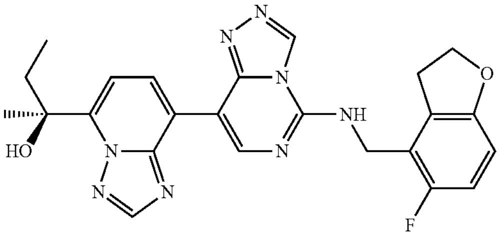 [SMILES: CC[C@](C)(O)c1ccc(-c2cnc(NCc3c(F)ccc4c3CCO4)n3cnnc23)c2ncnn12] | (S)-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol |
| 2 | 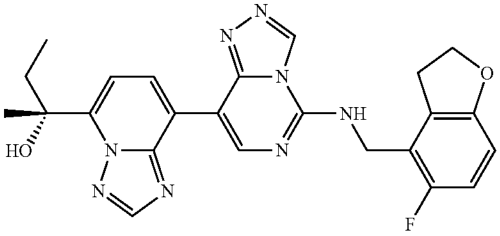 [SMILES: CC[C@@](C)(O)c1ccc(-c2cnc(NCc3c(F)ccc4c3CCO4)n3cnnc23)c2ncnn12] | (R)-2-(8-(5-(((5-fluoro-2,3-dihydrobenzofuran-4-yl)methyl)amino)-[1,2,4]triazolo[ 4,3-c]pyrimidin-8-yl)-[1,2,4]triazolo[1,5-a]pyridin-5-yl)butan-2-ol |
| 3 | 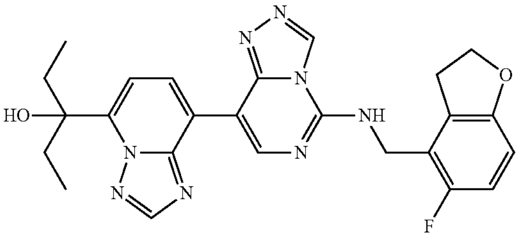 [SMILES: CCC(O)(CC)c1ccc(-c2cnc(NCc3c(F)ccc4c3CCO4)n3cnnc23)c2ncnn12] | 3-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)pentan-3-ol |
| E29-4 | 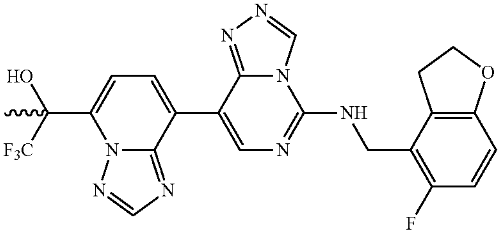 [SMILES: CC(O)(c1ccc(-c2cnc(NCc3c(F)ccc4c3CCO4)n3cnnc23)c2ncnn12)C(F)(F)F] | 1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol |
| 4 | 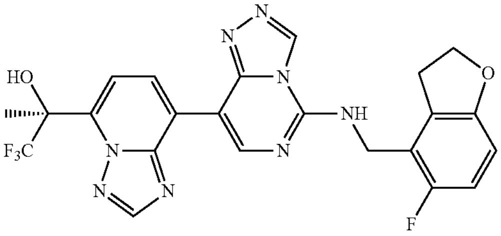 [SMILES: C[C@](O)(c1ccc(-c2cnc(NCc3c(F)ccc4c3CCO4)n3cnnc23)c2ncnn12)C(F)(F)F] | (S)-1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol |

-continued

| Compound number | Compound structure | Name of compounds |
| --- | --- | --- |
| 5 | 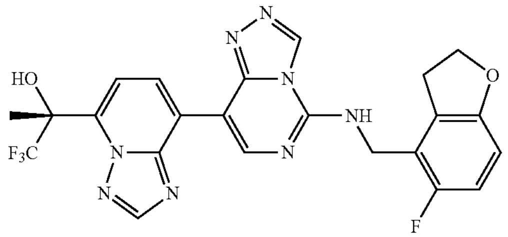 [SMILES: C[C@@](O)(c1ccc(-c2cnc(NCc3c(F)ccc4c3CCO4)n3cnnc23)c2ncnn12)C(F)(F)F] | (R)-1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol |
| 6 | 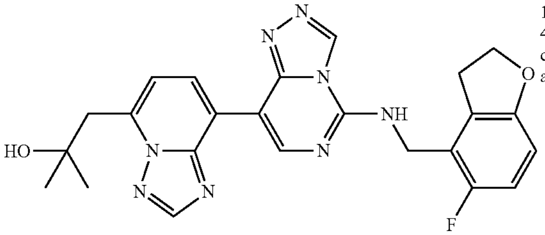 | 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)-2-methylpropan-2-ol |
| 7 | 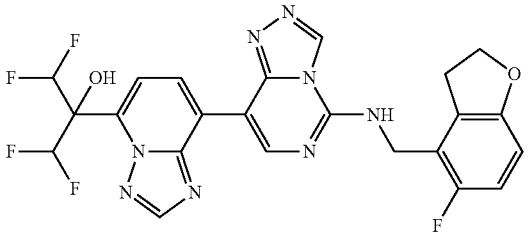 [SMILES: OC(c1ccc(-c2cnc(NCc3c(F)ccc4c3CCO4)n3cnnc23)c2ncnn12)(C(F)F)C(F)F] | 1,1,3,3-tetrafluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol |
| E32-4 | 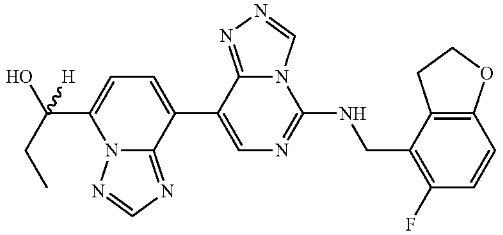 [SMILES: CCC(O)c1ccc(-c2cnc(NCc3c(F)ccc4c3CCO4)n3cnnc23)c2ncnn12] | 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-1-ol |
| 8 | 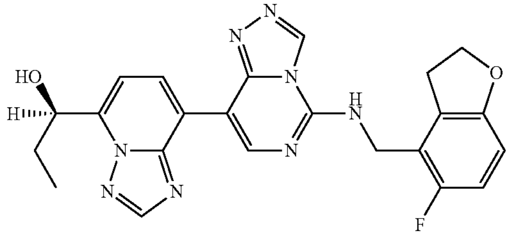 [SMILES: CC[C@@H](O)c1ccc(-c2cnc(NCc3c(F)ccc4c3CCO4)n3cnnc23)c2ncnn12] | (R)-1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-1-ol |
| 9 | 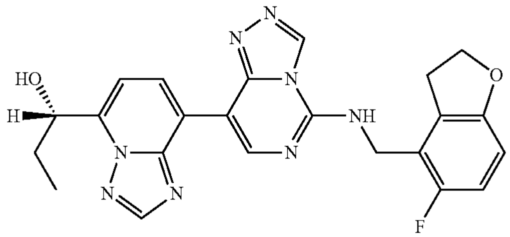 [SMILES: CC[C@H](O)c1ccc(-c2cnc(NCc3c(F)ccc4c3CCO4)n3cnnc23)c2ncnn12] | (S)-1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-1-ol |

-continued

| Compound number | Compound structure | Name of compounds |
|---|---|---|
| 10 | 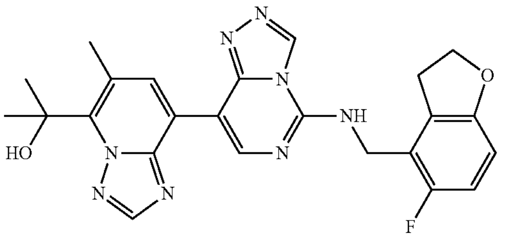 [SMILES: Cc1cc(-c2cnc(NCc3c(F)ccc4c3CCO4)n3cnnc23)c2ncnn2c1C(C)(C)O] | 2-(8-(5-(((5-fluoro-2,3-dihydrobenzofuran-4-yl)methyl)amino)-[1,2,4]triazolo[4,3-c]pyrimidin-8-yl)-6-methyl-[1,2,4]triazolo[1,5-a]pyridin-5-yl)propan-2-ol |
| 11 | 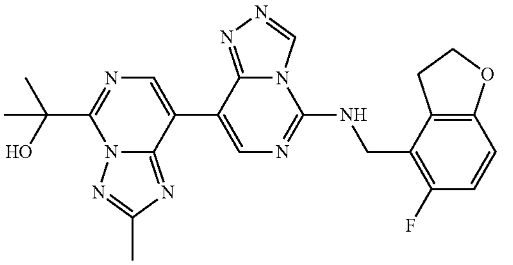 [SMILES: Cc1nc2c(-c3cnc(NCc4c(F)ccc5c4CCO5)n4cnnc34)cnc(C(C)(C)O)n2n1] | 2-(8-(5-(((5-fluoro-2,3-dihydrobenzofuran-4-yl)methyl)amino)-[1,2,4]triazolo[4,3-c]pyrimidin-8-yl)-2-methyl-[1,2,4]triazolo[1,5-c]pyrimidin-5-yl)propan-2-ol |
| 12 | 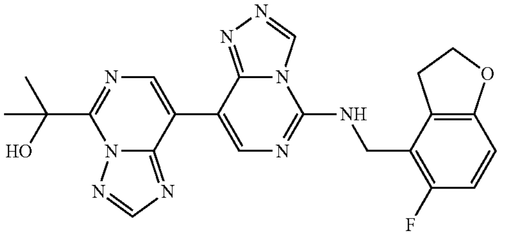 [SMILES: CC(C)(O)c1ncc(-c2cnc(NCc3c(F)ccc4c3CCO4)n3cnnc23)c2ncnn12] | 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-c]pyrimidin-5-yl)propan-2-ol |
| 13 | 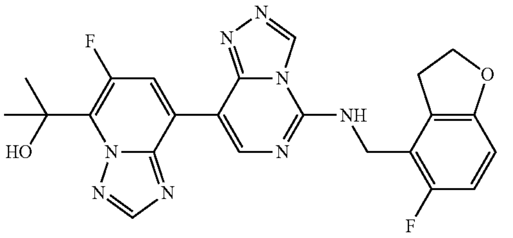 [SMILES: CC(C)(O)c1c(F)cc(-c2cnc(NCc3c(F)ccc4c3CCO4)n3cnnc23)c2ncnn12] | 2-(6-fluoro-8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol |
| 14 | 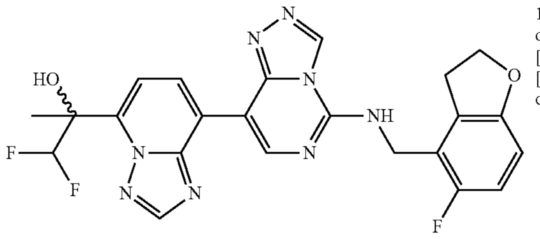 | 1,1-difluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol |
| 15 | 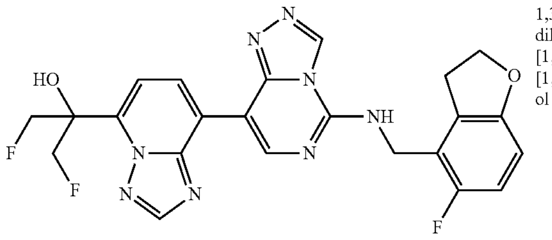 | 1,3-difluoro-2-[8-(5-{[(5-fluoro-2,3-dihydro-1-benzofuran-4-yl)methyl]amino}-[1,2,4]triazol[4,3-c]pyrimidin-8-yl)-[1,2,4]triazol[1,5-a]pyridin-5-yl]propan-2-ol |

-continued

| Compound number | Compound structure | Name of compounds |
|---|---|---|
| 16 | 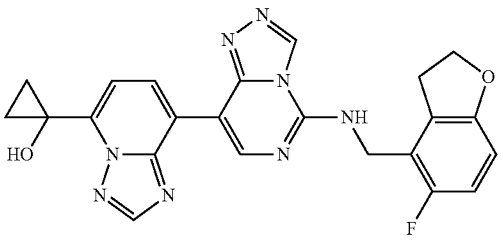 [SMILES: OC1(c2ccc(-c3cnc(NCc4c(F)ccc5c4CCO5)n4cnnc34)c3ncnn23)CC1] | 1-[8-(5-{[(5-fluoro-2,3-dihydro-1-benzofuran-4-yl)methyl]amino]-[1,2,4]triazolo[4,3-c]pyrimidin-8-yl)-[1,2,4]triazol[1,5-a]pyridin-5-yl]cyclopropan-1-ol |
| 17 | 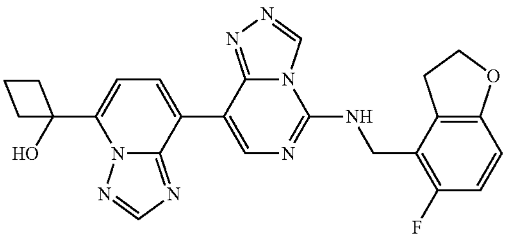 [SMILES: OC1(c2ccc(-c3cnc(NCc4c(F)ccc5c4CCO5)n4cnnc34)c3ncnn23)CCC1] | 1-[8-(5-{[(5-fluoro-2,3-dihydro-1-benzofuran-4-yl)methyl]amino]-[1,2,4]triazolo[4,3-c]pyrimidin-8-yl)-[1,2,4]triazolo [1,5-a]pyridin-5-yl]cyclobutan-1-ol |
| E40-3 | 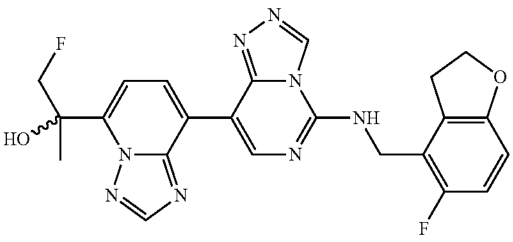 [SMILES: CC(O)(CF)c1ccc(-c2cnc(NCc3c(F)ccc4c3CCO4)n3cnnc23)c2ncnn12] | 1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol |
| 18 | 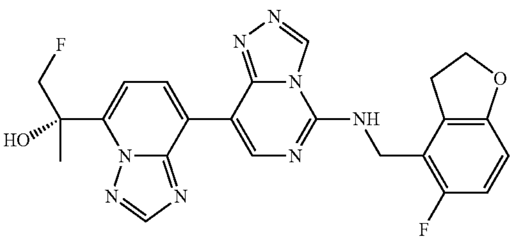 | (2S)-1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol |
| 19 | 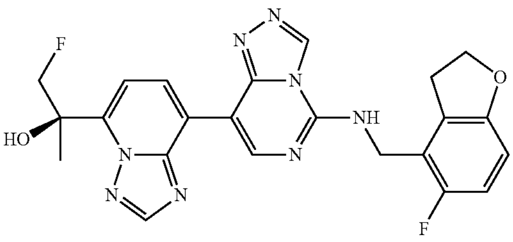 | (2R)-1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol |

In some preferred embodiments of the present disclosure: the compound represented by formula (I) is any of the following compounds:

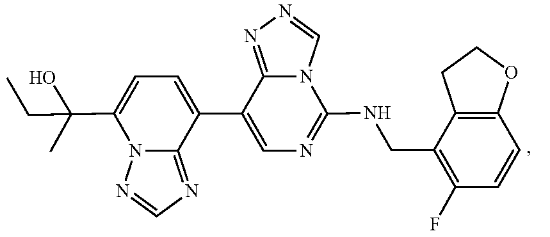 [SMILES: CCC(C)(O)c1ccc(-c2cnc(NCc3c(F)ccc4c3CCO4)n3cnnc23)c2ncnn12]

whose retention time is 3.134 min under the following conditions: chromatographic column is DAICEL CHIRALPAK IG, column length is 250 mm, column inner diameter is 30 mm, filler particle diameter is 10 m; mobile phase A is IPA containing 0.1% $NH_3H_2O$, and mobile phase B is ethanol; gradient: gradient elution with 5% mobile phase B→40% mobile phase B, flow rate is 4 mL/min;

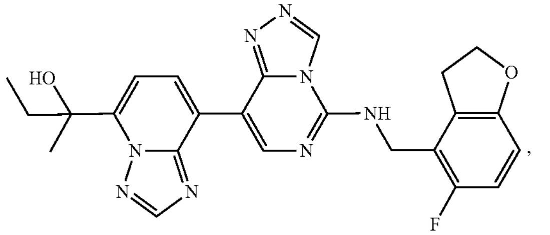 [SMILES: CCC(C)(O)c1ccc(-c2cnc(NCc3c(F)ccc4c3CCO4)n3cnnc23)c2ncnn12]

whose retention time is 3.547 min under the following conditions: chromatographic column is DAICEL CHIRALPAK IG, column length is 250 mm, column inner diameter is 30 mm, filler particle diameter is 10 m; mobile phase A is IPA containing 0.1% $NH_3H_2O$, and mobile phase B is ethanol; gradient: gradient elution with 5% mobile phase B→40% mobile phase B, flow rate is 4 mL/min;

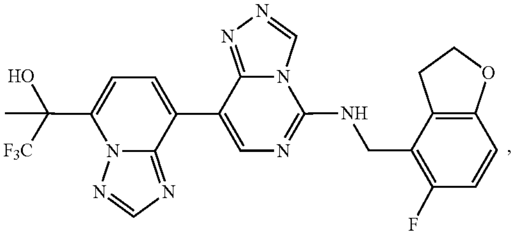 [SMILES: CC(O)(c1ccc(-c2cnc(NCc3c(F)ccc4c3CCO4)n3cnnc23)c2ncnn12)C(F)(F)F]

whose retention time is 4.974 min under the following conditions: chromatographic column is DAICEL CHIRALPAK IG, column length is 250 mm, column inner diameter is 30 mm, filler particle diameter is 10 m; mobile phase A is IPA containing 0.1% $NH_3H_2O$, and mobile phase B is ethanol; gradient: isocratic elution 45%, flow rate is 2.8 mL/min;

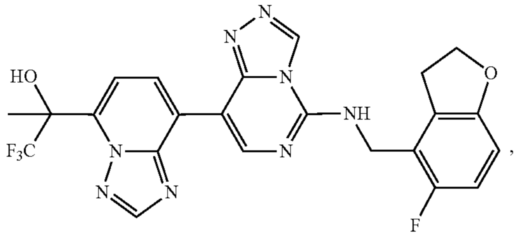 [SMILES: CC(O)(c1ccc(-c2cnc(NCc3c(F)ccc4c3CCO4)n3cnnc23)c2ncnn12)C(F)(F)F]

whose retention time is 5.440 min under the following conditions: chromatographic column is DAICEL CHIRALPAK IG, column length is 250 mm, column inner diameter is 30 mm, filler particle diameter is 10 m; mobile phase A is IPA containing 0.1% $NH_3H_2O$, and mobile phase B is ethanol; gradient: isocratic elution 45%, flow rate is 2.8 mL/min;

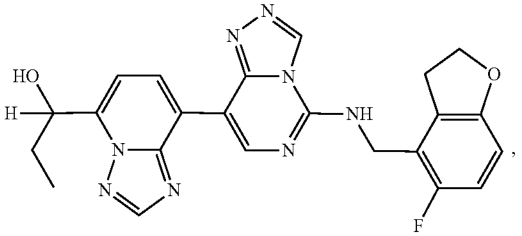 [SMILES: CCC(O)c1ccc(-c2cnc(NCc3c(F)ccc4c3CCO4)n3cnnc23)c2ncnn12]

whose retention time is 2.782 min under the following conditions: chromatographic column is DAICEL CHIRALPAK IG, column length is 250 mm, column inner diameter is 30 mm, filler particle diameter is 10 m; mobile phase A is IPA containing 0.1% $NH_3H_2O$, and mobile phase B is ethanol; gradient: gradient elution with 5% mobile phase B→40% mobile phase B, flow rate is 4 mL/min;

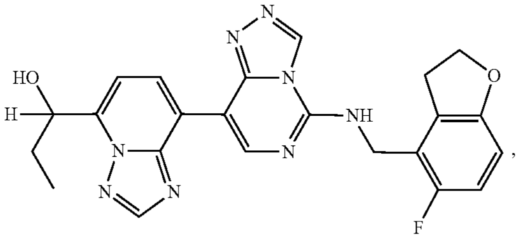 [SMILES: CCC(O)c1ccc(-c2cnc(NCc3c(F)ccc4c3CCO4)n3cnnc23)c2ncnn12]

whose retention time is 2.907 min under the following conditions: chromatographic column is DAICEL CHIRALPAK IG, column length is 250 mm, column inner diameter is 30 mm, filler particle diameter is 10 m; mobile phase A is IPA containing 0.1% $NH_3H_2O$, and mobile phase B is ethanol; gradient: gradient elution with 5% mobile phase B→40% mobile phase B, flow rate is 4 mL/min;

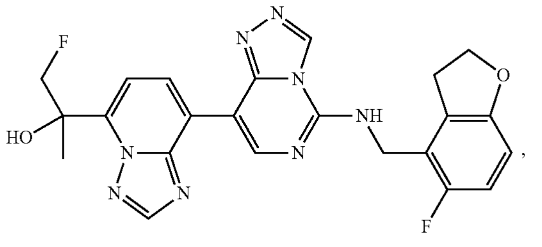 [SMILES: CC(O)(CF)c1ccc(-c2cnc(NCc3c(F)ccc4c3CCO4)n3cnnc23)c2ncnn12]

whose retention time is 0.971 min under the following conditions: chromatographic column is DAICEL CHIRALPAK IG, column length is 250 mm, column inner diameter is 30 mm, filler particle diameter is 10 m; mobile phase A is IPA containing 0.1% $NH_3H_2O$, and mobile phase B is isopropanol; gradient: isocratic elution with 45% mobile phase B, flow rate is 4 mL/min;

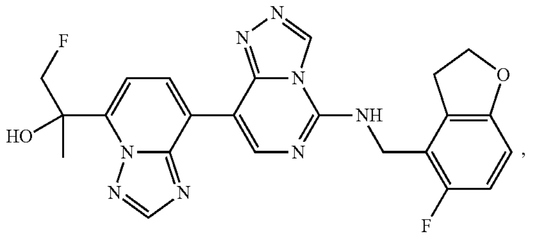 [SMILES: CC(O)(CF)c1ccc(-c2cnc(NCc3c(F)ccc4c3CCO4)n3cnnc23)c2ncnn12]

whose retention time is 1.134 min under the following conditions: chromatographic column is DAICEL CHIRALPAK IG, column length is 250 mm, column inner diameter is 30 mm, filler particle diameter is 10 m; mobile phase A is IPA containing 0.1% $NH_3H_2O$, and mobile phase B is isopropanol; gradient: isocratic elution with 45% mobile phase B, flow rate is 4 mL/min.

The present disclosure provides an isotope-labeled compound of the compound represented by formula (I), the pharmaceutically acceptable salt thereof, the stereoisomer thereof or the solvate thereof. The isotope in said isotope-labeled compound is selected from $^{2}H$, $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$ and $^{125}I$. The atoms that can be labeled with isotopes in the compound of formula (I) include but are not limited to hydrogen, carbon, nitrogen, oxygen, phosphorus, fluorine, chlorine and iodine, etc., which can be replaced by isotopes, such as $^{2}H$, $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$ and $^{125}I$, respectively.

In some preferred embodiments of the present disclosure: the solvate is a hydrate.

The present disclosure also provides a preparation method for the compound represented by formula (I), which comprises the following steps:

Coupling halogenated intermediate $B_0$ with intermediate $E_0$ to obtain the compound represented by formula (I);

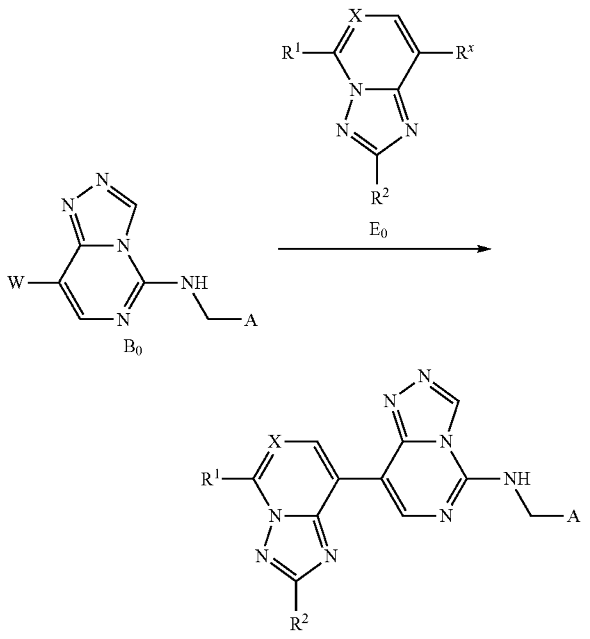

(I)

wherein W represents halogen; $R^X$ is —$B(OH)_2$ or

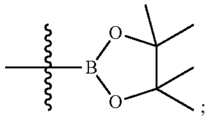 [SMILES: *B1OC(C)(C)C(C)(C)O1]

the definitions of A, $R^1$, $R^2$ and X are as defined above.

The preparation method for the compound represented by formula (I) may further comprise the following steps to prepare the intermediate $E_0$;

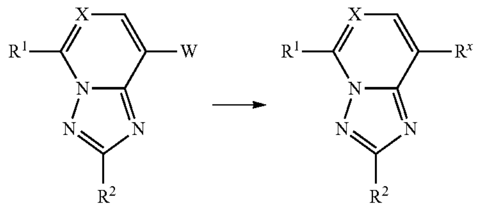

E-1 $E_0$ wherein W represents halogen, preferably Br; $R^X$ is —$B(OH)_2$ or

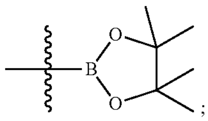 [SMILES: *B1OC(C)(C)C(C)(C)O1]

the definitions of $R^1$, X and $R^2$ are as defined in the present disclosure.

The present disclosure also provides a preparation method for intermediate compound C1-7, C1-a or C1-b, which comprises the following steps:

Compound C1-1 reacts with 1,2-dihaloethane (such as 1,2-dibromoethane) to obtain compound C1-2, and C1-2 undergoes elimination reaction to obtain compound C1-3, and the C1-3 is condensed with p-toluenesulfonhydrazide to obtain sulfonyl hydrazone C1-4, C1-4 closes the furan-fused three-membered ring to obtain compound C1-5, the bromine atom of C1-5 is substituted by a cyano group under catalytic condition to obtain compound C1-6. The cyano group is reduced to an amine group and in situ protected by Boc anhydride to obtain C1-7;

and/or, further, C1-7 is separated by chiral SFC to obtain C1-7a and C1-7b, and C1-7a and C1-7b are deprotected to obtain C1-a and C1-b respectively.

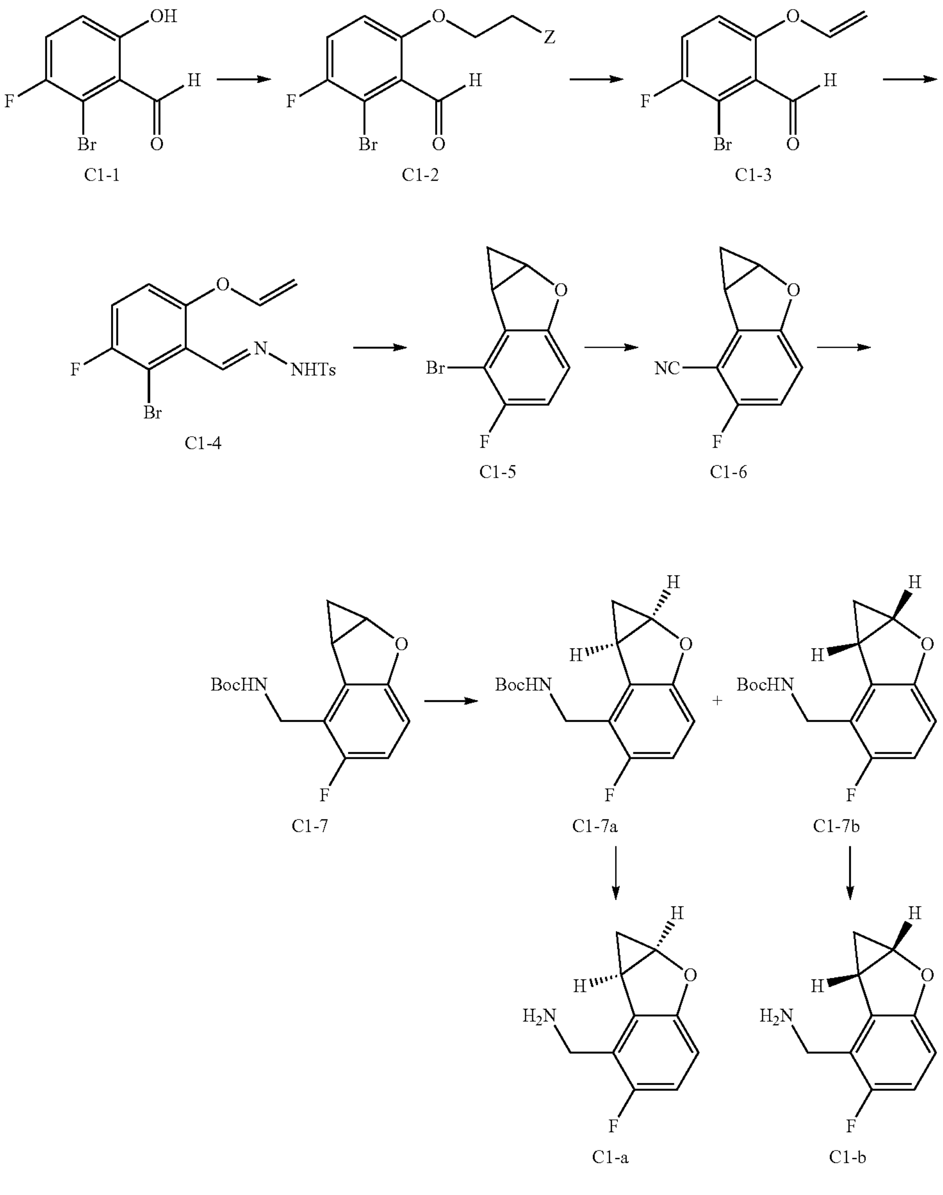

C1-1 C1-2 C1-3 C1-4 C1-5 C1-6 C1-7 C1-7a + C1-7b C1-a C1-b wherein Z is a halogen (such as Cl, Br or I), preferably Br.

The present disclosure also provides a preparation method for intermediate compound B, which comprises the following steps:

Compound D-1 reacts with hydrazine hydrate to obtain compound D-2, and compound D-2 and trimethyl orthoformate undergo ring closure reaction to obtain intermediate D in the presence of catalyst (such as trifluoroacetic acid), and D reacts with intermediate C to obtain intermediate B. The reaction equation is as follows:

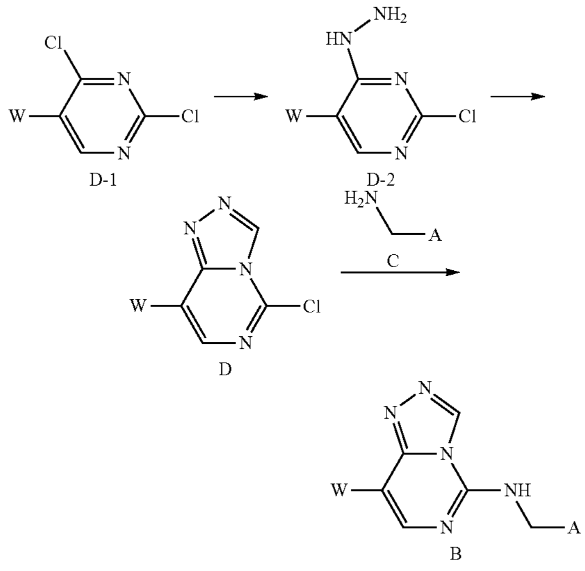

wherein the definitions of W and A are as above.

The present disclosure also provides intermediate compounds:

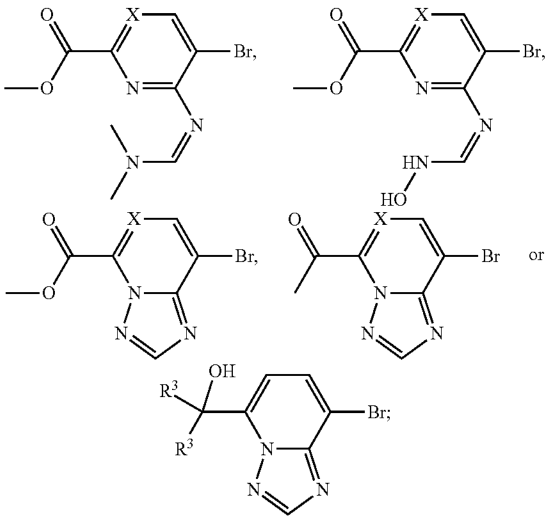

wherein the definitions of X and $R^3$ are as above.

The solvent involved in the present disclosure can be selected from, for example, methanol, ethanol, isopropanol, toluene, xylene, chlorobenzene, water, methylene chloride, chloroform, carbon tetrachloride, 1,2-dichloroethane, dioxane, DMF, acetonitrile, DMSO, NMP, THE or combinations thereof, for example, selected from dichloromethane, chloroform, 1,2-dichloroethane, dioxane, DMF, acetonitrile, DMSO, NMP, THF or a combination thereof.

The bases involved in the present disclosure may include organic bases and inorganic bases.

The organic bases involved in the present disclosure can be selected from, for example, TEA, DIPEA or a combination thereof.

The inorganic bases involved in the present disclosure can be selected from, for example, sodium hydride, sodium methoxide, potassium carbonate, sodium carbonate, cesium carbonate, potassium tert-butoxide, sodium tert-butoxide, lithium tert-butoxide, LiHMDS, LDA, butyllithium, potassium hydroxide, potassium acetate, lithium aluminum hydride or combinations thereof; for example, selected from sodium hydride, potassium carbonate, sodium carbonate, cesium carbonate, potassium tert-butoxide, sodium tert-butoxide, LiHMDS, LDA, butyllithium or combinations thereof.

The isotope-labeled compound of the compound represented by formula (I) according to the present disclosure can be prepared by a similar synthetic method to the unlabeled compound, except that the unlabeled starting materials and/or reagents are replaced by isotope-labeled starting materials and/or reagents.

The present disclosure also provides a pharmaceutical composition, which comprises the above-mentioned compounds represented by formula (I), the pharmaceutically acceptable salt thereof, the stereoisomer thereof, the solvate thereof, or their isotope-labeled compound and pharmaceutically acceptable excipients. The pharmaceutically acceptable excipients can be one or more than one diluent, absorbent, wetting agent, binder, disintegrant and lubricant. The amount of the compound represented by formula (I), the pharmaceutically acceptable salt thereof, the stereoisomer thereof, the solvate thereof, or their isotope-labeled compound can be therapeutically effective.

The present disclosure provides a use of the above-mentioned compound represented by formula (I), the pharmaceutically acceptable salt thereof, the stereoisomer thereof, the solvate thereof, or their isotope-labeled compound, or the above-mentioned pharmaceutical composition in preparation of a medicament. Said medicament is preferably a medicament for treating cancer. The amount of the compound represented by formula (I), the pharmaceutically acceptable salt thereof, the stereoisomer thereof, the solvate thereof, or their isotope-labeled compound can be therapeutically effective.

The present disclosure further provides a use of the above-mentioned compound represented by formula (I), the pharmaceutically acceptable salt thereof, the stereoisomer thereof, the solvate thereof, or their isotope-labeled compound, or the above-mentioned pharmaceutical composition in preparation of a medicament for treating cancers related to or mediated by the action mechanism of EED protein and/or PRC2 protein complex. The amount of the compound represented by formula (I), the pharmaceutically acceptable salt thereof, the stereoisomer thereof, the solvate thereof, or their isotope-labeled compound can be therapeutically effective.

Preferably, said cancers include but are not limited to diffuse large B-cell lymphoma, follicular lymphoma, non-Hodgkinson lymphoma and other lymphoma, leukemia, multiple myeloma, mesothelioma, gastric cancer, malignant rhabdoid tumor, liver cancer, prostate cancer, breast cancer, brain tumor including neuroblastoma, glioma, glioblastoma and astrocytoma, cervical cancer, colon cancer, melanoma, endometrial cancer, esophageal cancer, head and neck cancer, lung cancer, nasopharyngeal cancer, ovarian cancer, pancreatic cancer, kidney cancer, rectal cancer, thyroid cancer, parathyroid tumor, uterine tumor and soft tissue sarcoma, etc.

Preferably, the compound, the pharmaceutically acceptable salt thereof, the stereoisomer thereof, the solvate thereof, or their isotope-labeled compound is used in combination with other drugs; more preferably, the other drugs are selected from anticancer drugs, tumor immune drugs, antiallergic drugs, antiemetics, analgesics, or cytoprotective drugs.

The present disclosure further provides a pharmaceutical preparation, which comprises the above-mentioned compound represented by formula (I), the pharmaceutically acceptable salt thereof, the stereoisomer thereof, the solvate thereof, or their isotope-labeled compound, or the above-mentioned pharmaceutical composition. Said pharmaceutical preparation is preferably in a form of tablet, capsule (e.g. sustained release or timed release capsule), pellet, powder, granule (e.g. small granule), elixir, tincture, suspension (e.g. nanosuspension, microsuspension) and suspension in the form of spray-dried dispersion, etc., syrup, emulsion, solution and the like. The preferred administration method of said pharmaceutical preparation is oral administration, sublingual administration, injection including subcutaneous injection, intravenous injection, intramuscular injection, intrasternal injection, injection, etc., nasal administration (such as nasal membrane inhalation), topical surface administration (such as cream and ointment), rectal administration (such as suppository) and the like. The compound disclosed in the present disclosure can be administered alone or together with appropriate pharmaceutical carriers.

The present disclosure also provides the above-mentioned pharmaceutical preparation can be formulated into an appropriate drug dose to facilitate and control the administration of the drug. Dosage regimens of the compound disclosed in the present disclosure vary according to specific factors, such as pharmacodynamics and method of administration, subject, gender, age, health status and body weight of the subject, disease characteristic, other simultaneous administration conditions, the frequency of administration, liver and kidney function and desired effect. The compound disclosed in the present disclosure can be taken in a single dose every day or multiple times in total doses every day (such as two to four times a day).

The present disclosure also provides a method for treating cancer, which comprises administering to the subjects in need of the therapeutics a therapeutically effective amount of the above-mentioned compound represented by formula (I), the pharmaceutically acceptable salt thereof, the stereoisomer thereof or the solvate thereof, or their isotope-labeled compound, or the above-mentioned pharmaceutical compositions. Said cancers include but are not limited to diffuse large B-cell lymphoma, follicular lymphoma, non-Hodgkinson lymphoma and other lymphoma, leukemia, multiple myeloma, mesothelioma, gastric cancer, malignant rhabdoid tumor, liver cancer, prostate cancer, breast cancer, brain tumor including neuroblastoma, glioma, glioblastoma and astrocytoma, cervical cancer, colon cancer, melanoma, endometrial cancer, esophageal cancer, head and neck cancer, lung cancer, nasopharyngeal cancer, ovarian cancer, pancreatic cancer, kidney cancer, rectal cancer, thyroid cancer, parathyroid tumors, uterine tumors and soft tissue sarcomas, etc.

The present disclosure also provides the compound represented by formula (I), the pharmaceutically acceptable salt thereof, the stereoisomer thereof or the solvate thereof, or their isotope-labeled compounds for use in combination with other drugs; more preferably, the other drugs are selected from anticancer drugs, tumor immune drugs, antiallergic drugs, antiemetics, analgesics, cytoprotective drugs, etc., the combination has a better effect.

In the present disclosure, said cancer is preferably a cancer related to EED protein and/or PRC2 protein complex.

The present disclosure also provides a method for inhibiting the activity of EED protein and/or PRC2 protein complex, which comprises administering to the subject a therapeutically effective amount of the above-mentioned compounds represented by formula (I), the pharmaceutically acceptable salt thereof, the stereoisomer thereof or the solvate thereof, or their isotope-labeled compound, or the above-mentioned pharmaceutical compositions.

The present disclosure also provides a method for blocking the combination of EED and H3K27 (such as H3K27me3), which comprises administering to the subjects a therapeutically effective amount of the above-mentioned compound represented by formula (I), the pharmaceutically acceptable salt thereof, the stereoisomer thereof or the solvate thereof, or their isotope-labeled compound, or the above-mentioned pharmaceutical composition.

It should be understood that, within the scope of the present disclosure, the above-mentioned technical features of the present disclosure and the technical features specifically described in the following text (such as examples) can be combined with each other to form new or preferred technical solutions. Due to space limitations, they will not be repeated here.

Specification of Terms

Unless defined otherwise, all technical and scientific terms used herein have the same meaning as commonly understood by one skilled in the art to which this disclosure belongs.

As used herein, the term “about” used in specific examples of numerical values means that it may vary by no more than 1% from the exemplified value. For example, as used herein, the expression “about 100” comprises 99, 101 and all values between them (e.g., 99.1, 99.2, 99.3, 99.4, etc.).

As used herein, the term “comprises” or “includes (comprising)” can be open, semi-closed and closed. In other words, said term also includes “consisting essentially of”, or “consisting of”.

Group Definition

Definitions of standard chemical terms can be found in references, including Carey and Sundberg “ADVANCED ORGANIC CHEMISTRY 4TH ED.” Vols. A (2000) and B (2001), Plenum Press, New York. Unless otherwise specified, conventional methods within the skills of the art are employed, such as mass spectroscopy, NMR, IR and UV/VIS spectroscopy and pharmacological methods. Unless specific definitions are set forth, the terms employed herein in the relevant descriptions of analytical chemistry, synthetic organic chemistry, and pharmaceutical chemistry are those that are known in the art. Standard techniques can be used in chemosynthesis, chemical analyses, pharmaceutical preparation, formulation and delivery, and treatment of subjects. For example, reactions and purifications can be carried out using the manufacturer’s instructions for the kit, or by methods known in the art or as described herein. The above techniques and methods can generally be performed according to conventional methods well known in the art and the description in various general and more specific documents that are cited and discussed in this specification. In this specification, groups and substituents thereof can be selected by those skilled in the art to provide stable structural moieties and compounds.

When a substituent is described by a conventional chemical formula written from left to right, the substituent also includes a chemically equivalent substituent obtained when the structural formula is written from right to left. For example, $—CH_2O—$ is equivalent to $—OCH_2—$.

The section headings used herein are for the purpose of organizing the article only and should not be construed as limitations on the subject matter described. All documents or portions of documents cited in this application include but are not limited to patents, patent applications, articles, books, manuals, and treatises, which are hereby incorporated by reference in their entirety.

Certain chemical groups defined herein are preceded by abbreviated notations to indicate the total number of carbon atoms present in the group. For example, $C_{1-6}$ alkyl refers to an alkyl group as defined below having a total of 1 to 6 carbon atoms (e.g., 1, 2, 3, 4, 5, 6 carbon atoms). The total number of carbon atoms in the abbreviated notation does not include carbons that may be present in substituents of the group.

Unless otherwise specified, in addition to the above-mentioned terms, the following terms have the meanings shown below when they were used in the specification and the claims of the present application.

In the present application, the term "halogen" refers to fluorine, chlorine, bromine or iodine.

When "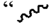" represents a single bond, it refers to a mixture of 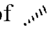 and 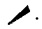.

"Hydroxyl" refers to an —OH group.

"Carbonyl" refers to a —C(═O)— group. When R

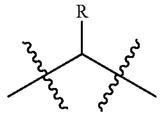

is a carbonyl group,

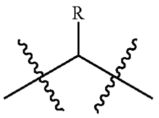

is

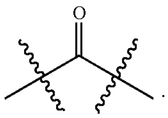

.

"Cyano" refers to —CN.

"Amino" refers to $—NH_2$.

"Substituted amino" refers to an amino group substituted by one or two alkyl, alkylcarbonyl, aryl alkyl, heteroaryl alkyl as defined below, for example, monoalkylamino, dialkylamino, alkylamido, aryl alkyl amino, heteroaryl alkyl amino.

"Carboxyl" refers to —COOH.

In the present application, as a group or a portion of other groups (e.g., used in groups such as halogen-substituted alkyl), the term "alkyl" refers to a fully saturated straight or branched hydrocarbon chain group, which consists solely of carbon and hydrogen atoms, having, for example, 1 to 12 (preferably 1 to 8, more preferably 1 to 6, more preferably 1 to 4) carbon atoms, and connected to the remainder of the molecule by a single bond. For example, the alkyl include but are not limited to methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl, decyl, etc.

In the present application, as a group or a portion of other groups, the term "haloalkyl" refers to that one or more than one hydrogen atoms in the alkyl (as defined in the present disclosure) are substituted by halogen (as defined in the present disclosure), the number of the halogen can be one or more than one; when there are multiple halogens, the halogens are the same or different. For example, fluoroalkyl refers to the alkyl substituted by one or more fluorines. Examples of haloalkyl include but are not limited to trifluoromethyl, difluoromethyl and monofluoromethyl.

In the present application, preferably, the number of the carbon atom in "heterocycloalkyl" is 3, 4, 5 or 6, the heteroatom is selected from N, O and S, and the number of the heteroatom is 1, 2, 3 or 4. Further preferably, the number of the carbon atom is 4 or 5, and the number of the heteroatom is selected from N and O, and the number of the heteroatom is 1 or 2; for example,

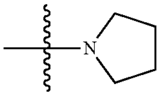

,

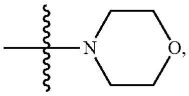

,

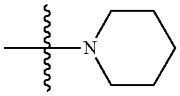

or

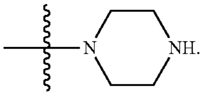

.

In the present application, preferably, the number of the carbon atom in "heterospirocycloalkyl" is 4, 5 or 6, the heteroatom is selected from N, O and S, and the number of the heteroatom is 1, 2, 3 or 4. Further preferably, the heteroatom is selected from N and O, and the number of the heteroatom is 1 or 2; for example,

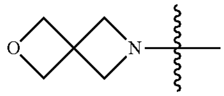

.

In the present application, as a group or a portion of other groups, the term "cyclohydrocarbyl" refers to a stable non-aromatic monocyclic or polycyclic hydrocarbon group consisting only of carbon and hydrogen atoms, which may include fused-ring system, bridged-ring system or spiro-ring system, having 3 to 15 carbon atoms, preferably having 3 to 10 carbon atoms, more preferably having 3 to 8 carbon atoms, and it is saturated or unsaturated and can be obtained by connecting to the remainder of the molecule by a single bond via any suitable carbon atom. Unless otherwise specified in this specification, the carbon atom in a cyclic hydrocarbon group may be optionally oxidized. Examples of cyclic hydrocarbon group include but are not limited to cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-indanyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-fused cyclopentadienyl, etc.

In the present application, as a group or a portion of other groups, the term "cycloalkyl" refers to a saturated cyclic hydrocarbon group.

In the present application, as a group or a portion of other groups, the term "cycloalkenyl" refers to a cyclic hydrocarbon group having at least one double bond (such as a carbon-carbon double bond). A cycloalkenyl group can be connected to the remainder of the molecule via an atom of its double bond.

In the present application, as a group or a portion of other groups, the term "heterocyclyl" refers to a stable 3- to 20-membered non-aromatic cyclic group consisting of 2 to 14 carbon atoms and 1 to 6 heteroatoms selected from nitrogen, phosphorus, oxygen and sulfur. Unless otherwise specified in this specification, the heterocyclyl may be a monocyclic, bicyclic, tricyclic or multicyclic ring system, which may include a fused-ring system, a bridged-ring system or a spiro-ring system; the nitrogen, carbon, or sulfur atom in the heterocyclyl can be optionally oxidized; the nitrogen atom can be optionally quaternized; and the heterocyclyl can be partially or fully saturated. The heterocyclyl can be connected to the remainder of the molecule by a single bond via a carbon atom or a heteroatom. In the heterocyclyl comprising fused rings, one or more rings may be aryl or heteroaryl as defined below, provided that the connection point with the remainder of the molecule is a non-aromatic ring atom. For the purposes of the present disclosure, heterocyclyl is preferably a stable 4- to 11-membered non-aromatic monocyclic, bicyclic, bridged or spirocyclic group comprising 1 to 3 heteroatoms selected from nitrogen, oxygen and sulfur, more preferably a stable 4- to 8-membered non-aromatic monocyclic, bicyclic, bridged or spirocyclic group comprising 1 to 3 heteroatoms selected from nitrogen, oxygen and sulfur. Examples of heterocyclyl include but are not limited to: pyrrolidinyl, morpholinyl, piperazinyl, homopiperazinyl, piperidinyl, thiomorpholinyl, 2,7-diaza-spiro[3.5]nonan-7-yl, 2-oxa-6-aza-spiro[3.3]heptan-6-yl, 2,5-diaza-bicyclo[2.2.1]heptan-2-yl, azetidinyl, pyranyl, tetrahydropyranyl, thiapyranyl, tetrahydrofuryl, oxazinyl, dioxolyl, tetrahydroisoquinolyl, decahydroisoquinolyl, imidazolinyl, imidazolidinyl, quinozinyl, thiazolidinyl, isothiazolidinyl, isoxazolidinyl, indolinyl, octahydroindolyl, octahydroisoindolyl, pyrrolidinyl, pyrazolidinyl, phthalimido, etc.

In the present application, as a group or a portion of other groups, the term "aryl" refers to a conjugated hydrocarbon ring system group having 6 to 18 carbon atoms, preferably having 6 to 10 carbon atoms. For the purposes of the present disclosure, aryl can be a monocyclic, bicyclic, tricyclic or polycyclic ring system and can also be fused to the cycloalkyl or the heterocyclyl as defined above, provided that the aryl is connected to the remainder of the molecule by a single bond via the atom on the aromatic ring. Examples of aryl include but are not limited to phenyl, naphthyl, anthryl, phenanthrenyl, fluorenyl, 2,3-dihydro-1H-isoindolyl, 2-benzoxazolinone, 2H-1,4-benzoxazin-3(4H)-one-7-yl, etc.

In the present application, the term "aryl alkyl" refers to the alkyl group as defined above substituted by the aryl group as defined above.

In the present application, as a group or a portion of other groups, the term "heteroaryl" refers to a 5- to 16-membered conjugated ring system group having 1 to 15 carbon atoms (preferably 1 to 10 carbon atoms) and 1 to 6 heteroatoms selected from nitrogen, oxygen and sulfur in the ring. Unless otherwise specified in this specification, the heteroaryl can be a monocyclic, bicyclic, tricyclic or polycyclic ring system, and can also be fused to the cycloalkyl or the heterocyclyl as defined above, provided that the heteroaryl is connected to the remainder of the molecule by a single bond via an atom on the aromatic ring. A nitrogen, carbon or sulfur atom in the heteroaryl can be optionally oxidized; the nitrogen atom can be optionally quaternized. For the purposes of the present disclosure, heteroaryl is preferably selected from a stable 5- to 12-membered aromatic group comprising 1 to 5 heteroatoms selected from nitrogen, oxygen and sulfur, more preferably a stable 5- to 10-membered aromatic group comprising 1 to 4 heteroatoms selected from nitrogen, oxygen, and sulfur, or a 5- to 6-membered aromatic group comprising 1 to 3 heteroatoms selected from nitrogen, oxygen, and sulfur (e.g., the heteroaryl is $C_1$-$C_5$ heteroaryl, wherein the heteroatoms are selected from N, O and S, and the number of heteroatoms is 1, 2, 3 or 4). Examples of heteroaryl groups include but are not limited to thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furyl, pyrrolyl, triazolyl, tetrazolyl, triazinyl, indolizinyl, isoindolyl, indazolyl, isoindazolyl, purinyl, quinolinyl, isoquinolinyl, naphthyridinyl, naphthyridinyl, quinoxalinyl, pteridinyl, carbazolyl, carbolinyl, phenanthridinyl, phenanthrolinyl, acridinyl, phenazinyl, isothiazolyl, benzothiazolyl, benzothienyl, oxatriazolyl, cinnolinyl, quinazolinyl, phenylthio, indolizyl, o-phenanthrolinyl, isoxazolyl, phenoxazinyl, phenothiazinyl, 4,5,6,7-tetrahydrobenzo[b]thienyl, naphthopyridinyl, [1,2,4]triazolo[4,3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine, etc.

In the present application, "optionally" refers to that the subsequently described event or circumstance may or may not occur, and this description includes both instances where the event or circumstance occurs and instances where it does not occur. For example, "optionally substituted aryl" means that the aryl is substituted or unsubstituted, and this description includes both substituted and unsubstituted aryl. The "optional" substituents described in the claims and specification of the present disclosure are selected from alkyl, alkenyl, alkynyl, halogen, haloalkyl, haloalkenyl, haloalkynyl, cyano, nitro, optionally substituted aryl, optionally substituted heteroaryl, optionally substituted cycloalkyl, optionally substituted heterocycloalkyl.

In the present disclosure, the term "substituted" or "substituent" means that one or more hydrogen atoms are substituted by the specified group. When the number of substituents is not specified, there may be one or more substituents; when the substitution position is not specified, the substitution may be at any position, but only when a stable or chemically feasible chemical compound is formed is considered allowed.

When any variable (such as R) occurs in the constitution or structure of the compound more than once, the definition of the variable at each occurrence is independent. Thus, for example, if a group is substituted with 0-2 R, said group may optionally be substituted by up to two R, and R has independent options under each circumstance. For example, in

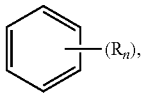

when n is 2, it means that the benzene ring is substituted by two R, and each R has an independent option, that is, the two R can be the same or different. In addition, combinations of the substituent and/or the variant thereof are allowed only when such combinations result in a stable compound.

As used herein, the terms "moiety", "structural moiety", "chemical moiety", "group", "chemical group" refer to a specific segment or functional group in a molecule. Chemical moieties are generally considered to be chemical entities embedded or attached to molecules.

When olefinic double bond are contained in the compound of the present disclosure, unless otherwise specified, the compound of the present disclosure is intended to include both E- and Z-geometric isomers.

"Tautomer" refers to isomers formed by the transfer of a proton from one atom of a molecule to another atom of the same molecule. All tautomeric forms of the compound of the present disclosure are also within the scope of the present disclosure.

The compound of the present disclosure or the pharmaceutically acceptable salt thereof may contain one or more chiral carbon atoms, and thus may give rise to enantiomers, diastereoisomers and other stereoisomeric forms. Each chiral carbon atom can be defined as (R)- or (S)-based on stereochemistry. The present disclosure is intended to include all possible isomers, as well as racemates thereof and optically pure forms. The racemate, diastereomer or enantiomer can be selected as raw material or intermediate in the preparation of the compound of the present disclosure. Optically active isomers can be prepared using chiral synthons or chiral reagents, or chiral separated by conventional techniques, such as crystallization and chiral chromatography. A stereoisomer of the compound of the present disclosure may exist as (R)- or (S)-isomer.

Conventional techniques for the preparation/separation of individual isomers include chiral synthesis from suitable optically pure precursors, or separation of racemates (or racemates of the salt or the derivative) using, for example, chiral high performance liquid chromatography, for example, referring to Gerald Gubitz and Martin G. Schmid (Eds.), Chiral Separations, Methods and Protocols, Methods in Molecular Biology, Vol. 243, 2004; A. M. Stalcup, Chiral Separations, Annu. Rev. Anal. Chem. 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem. Res. 1990, 23, 128.

In the present application, the term "pharmaceutically acceptable salt" includes pharmaceutically acceptable acid addition salts and pharmaceutically acceptable base addition salts.

"Pharmaceutically acceptable acid addition salt" refers to a salt formed with an inorganic or organic acid that can maintain the biological effectiveness of the free base without other side effects. Inorganic acid salts include but not limited to hydrochloride, hydrobromide, sulfate, nitrate, phosphate, etc.; organic acid salts include but not limited to formate, acetate, 2,2-dichloroacetate, trifluoroacetate, propionate, caproate, caprylate, caprate, undecylenate, glycolate, gluconate, lactate, sebacate, adipate, glutarate, malonate, oxalate, maleate, succinate, fumarate, tartrate, citrate, palmitate, stearate, oleate, cinnamate, laurate, malate, glutamate, pyroglutamate, aspartate, benzoate, mesylate, benzenesulfonate, p-toluenesulfonate, alginate, ascorbate, salicylate, 4-amino salicylate, naphthalene disulfonate, etc. These salts can be prepared by methods known in the art.

"Pharmaceutically acceptable base addition salt" refers to a salt formed with an inorganic or organic base that can maintain the biological effectiveness of the free acid without other side effects. Salts derived from inorganic bases include but are not limited to sodium, potassium, lithium, ammonium, calcium, magnesium, iron, zinc, copper, manganese, aluminum, etc. Inorganic salts are preferably ammonium, sodium, potassium, calcium and magnesium salts. Salts derived from organic bases include but are not limited to the following salts: primary, secondary and tertiary amines, substituted amines, including natural substituted amines, cyclic amines, and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucosamine, methylglucamine, theobromine, purine, piperazine, piperazine, pyridine, n-ethylpiperidine, polyamine resin, etc. Organic bases preferably include isopropylamine, diethylamine, ethanolamine, trimethylamine, dicyclohexylamine, choline and caffeine. These salts can be prepared by methods known in the art.

In the present application, a "pharmaceutical composition" refers to a preparation of the compound of the present disclosure with medium generally accepted in the art for the delivery of a biologically active compound to a mammal (e.g., a human). The medium includes a pharmaceutically acceptable carrier. The purpose of the pharmaceutical composition is to promote the administration of the organism, facilitate the absorption of the active ingredient and thus exert its biological activity.

The term "pharmaceutically acceptable" as used herein refers to a substance (such as a carrier or diluent) that does not affect the biological activity or properties of the compound of the present disclosure, and is relatively nontoxic, i.e., the substance can be administered to an individual without causing adverse biological reaction or interacting in an undesirable manner with any component contained in the composition.

In the present application, "pharmaceutically acceptable excipients" include but are not limited to any adjuvants, carriers, vehicles, glidants, sweeteners, diluent, preservative, dye/colorant, flavoring agent, surfactant, wetting agent, dispersing agent, suspending agent, stabilizing agent, isotonic agent, solvent or emulsifying agent approved by the relevant government regulatory agencies as acceptable for human or livestock use.

As used herein, the terms "preventative", "prevent" and "prevention" include reducing the likelihood of a disease or condition occurring or worsening in a subject.

As used herein, the term "treatment" and other similar synonyms include the following meanings:

(i) Preventing the occurrence of a disease or condition in a mammal, especially when such mammal is susceptible to the disease or condition but has not been diagnosed as having the same;

(ii) Inhibiting a disease or condition, i.e., arresting its development;

(iii) Ameliorating a disease or condition, i.e., causing regression of the state of the disease or condition; or (iv) Alleviating the symptoms caused by the disease or condition.

The term "effective amount", "therapeutically effective amount" or "pharmaceutically effective amount" as used herein refers to the amount of at least one medicament or compound which, when administered, is sufficient to relieve to some extent one or more symptoms of the disease or condition. The result may be a reduction and/or alleviation of a sign, symptom or cause, or any other desired change in a biological system. For example, a "effective amount" for treatment is the amount of the composition comprising the compound of the present disclosure required to provide a significant disease-ameliorating effect in clinical. The effective amount suitable for any individual case can be determined using techniques such as dose escalation trials.

As used herein, the terms "taking medicine", "application", "administration" and the like refer to methods capable of delivering a compound or composition to the desired site of biological function. These methods include but are not limited to oral route, duodenal route, parenteral injection (including intravenous, subcutaneous, intraperitoneal, intramuscular, intraarterial injection or infusion), topical administration and rectal administration. Administration techniques familiar to those skilled in the art and applicable to the compounds and methods of the present disclosure, such as those discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions discussed herein are administered orally.

As used herein, the terms "pharmaceutical combination", "drug combination", "combination", "administration of other treatments", "administration of other therapeutic agents" and the like refer to drug treatments obtained by mixing or combining more than one active ingredient, which includes fixed and non-fixed combinations of active ingredients. The term "fixed combination" refers to the simultaneous administration of at least one compound described herein and at least one synergistic preparation in the form of a single entity or single dosage form to a subject. The term "non-fixed combination" refers to simultaneous, concomitant or sequential administration at variable intervals of at least one compound described herein and at least one synergistic preparation as a single entity to a subject. These also apply to cocktail therapy, for example, the administration of three or more active ingredients.

Those skilled in the art will also understand that in the methods described below, the functional groups of intermediate compounds may need to be protected by appropriate protecting groups. Such functional groups include hydroxyl, amino, mercapto and carboxylic acid. Suitable hydroxy protecting groups include trialkylsilyl or diarylalkylsilyl (e.g., tert-butyldimethylsilyl, tert-butyldiphenylsilyl or trimethylsilyl), tetrahydropyranyl, benzyl, etc. Suitable protecting groups for amino, amidino and guanidino include tert-butoxycarbonyl, benzyloxycarbonyl and the like. Suitable mercapto protecting groups include "—C(O)—R" (where "R" is alkyl, aryl or aryl alkyl), p-methoxybenzyl, trityl and the like. Suitable carboxy protecting groups include alkyl, aryl or aryl aralkyl esters.

Protecting groups can be introduced and removed according to standard techniques known to those skilled in the art and as described herein. The use of protecting groups is described in detail in Greene, T. W. and P. G. M. Wuts, Protective Groups in Organi Synthesis, (1999), 4th Ed., Wiley. The protecting group can also be a polymeric resin.

On the basis of not violating common knowledge in the art, the above-mentioned preferred conditions can be combined arbitrarily to obtain preferred examples of the present disclosure.

The reagents and raw materials used in the present disclosure are all commercially available.

The positive progressive effect of the present disclosure is:

Compared with the compound N-((5-fluoro-2,3-dihydrobenzofuran-4-yl)methyl)-8-(2-methylpyridin-3-yl)-[1,2,4]triazolo[4,3-c]pyrimidin-5-amine in US20160176882A1 and WO2017219948A1, the anti-cell proliferation activity of the compound of the present disclosure increases by about 10 times. When the compound disclosed in the present disclosure is combined with the EED protein, the bicyclic structure outside the combined "pocket" can make the compound have better metabolic stability.

DETAILED DESCRIPTION OF THE PREFERRED EMBODIMENT

The present disclosure is further illustrated below by means of examples, but the present disclosure is not limited to the scope of the examples. The experimental methods that haven't illustrated specific conditions in the following examples are selected according to conventional methods and conditions, or according to the product instructions.

The starting materials used in the following examples can be purchased from chemical distributors such as Aldrich, TCI, Alfa Aesar, Bide Pharmatech, Energy Chemical, etc., or can be synthesized by known methods.

In the following examples, the ice bath refers to −5° C. to 0° C., the room temperature refers to 10° C. to 30° C., and the reflux temperature generally refers to the solvent reflux temperature under normal pressure. Reacting overnight means that the reaction time is 8-15 hours. In the following examples, those examples which do not illustrate the specific operating temperature are all carried out at room temperature.

In the following examples, the separation and purification of intermediates and final products are carried out by normal phase or reverse phase chromatographic column separation or other suitable methods. The normal-phase flash chromatography column uses ethyl acetate and n-hexane or methanol and methylene chloride and the like as mobile phases. Reversed-phase preparative high-pressure liquid chromatography (HPLC) uses a C18 column with UV 214 nm and 254 nm to detect, and its mobile phase is A (water and 0.1% formic acid), B (acetonitrile), or mobile phase A (water and 0.1% ammonium bicarbonate), B (acetonitrile).

In each example:

LCMS instrument: Pump Agilent 1260 UV Detector: Agilent 1260 DAD

Mass Spectrometer API 3000

Chromatographic column: Waters sunfire C18, 4.6×50 mm, Sum

Mobile phase: A-$H_2O$ (0.1% HCOOH); B-acetonitrile

NMR instrument: Bruker Ascend 400M (1H NMR: 400 MHz; $^{13}C$ NMR: 100 MHz).

Example 1: 8-bromo-5-chloro-[1,2,4]triazolo[4,3-c]pyrimidine (D)

Step 1: 5-Bromo-2-chloro-4-hydrazinopyrimidine (D-2)

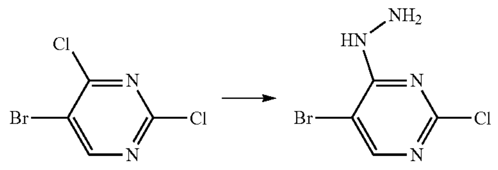

D-1 D-2

D-1 (2 g, 8.78 mmol) and ethanol (20 mL) were added to a 50 mL single-necked flask. Hydrazine hydrate (1.72 g, 53.65 mmol) was slowly added dropwise in an ice bath, and the suspension was stirred at 60° C. for 3 hours. After the reaction was completed, the temperature was lowered to room temperature. A pale yellow solid was precipitated, which was collected by filtration, and the filter cake was washed with ethanol (5 mL), and dried to obtain a pale yellow solid product D-2 (1.8 g, yield 92%).

$^1$H NMR (DMSO-$d_6$, 400 MHz) δ 8.06 (s, 1H), 7.85 (s, 1H), 4.34 (s, 2H) ppm.

Step 2: 8-bromo-5-chloro-[1,2,4]triazolo[4,3-c]pyrimidine (D)

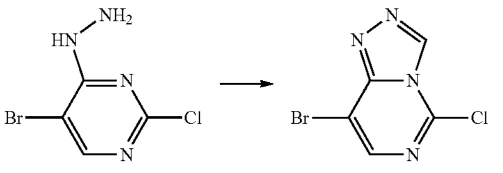

D-2 D

D-2 (1.2 g, 5.37 mmol), trimethyl orthoformate (12 mL) and trifluoroacetic acid (1 drop) were added into a 50 mL single-necked flask, and heat up to 100° C. for 10 h. After the reaction was completed, the temperature was lowered to room temperature. Trimethyl orthoformate was removed by rotary evaporation, and the concentrate was purified by a silica gel column (PE:EA=20:1) to obtain a yellow solid product D (960 mg, yield 77%).

$^1$H NMR (400 MHz, $CDCl_3$) δ 9.03 (s, 1H), 8.05 (s, 1H) ppm; LCMS: m/z 232.9 [M+H]$^+$.

Example 2: ((1aR,6bR)-5-fluoro-1a,6b-dihydro-1H-cyclopropeno[b]benzofuran-6-yl)methanamine (C1-a)

Step 1: intermediate 2-bromo-6-(2-bromoethoxy)-3-fluorobenzaldehyde (C1-2)

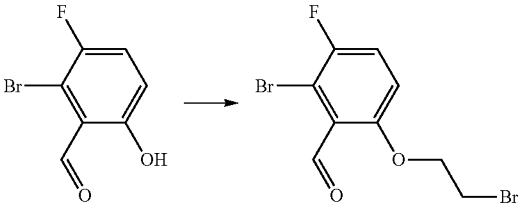

C1-1 C1-2

C1-1 (19 g, 86.7 mmol) was added into a 250 mL single-necked flask. Anhydrous DMF (90 mL) was added and stirred to dissolve C1-1. Potassium carbonate (24 g, 173.5 mmol) and 1,2-dibromoethane (24 g, 130.1 mmol) were added in sequence. The temperature was heated up to 64° C., and the reaction solution was stirred for 18 hours. After the reaction was completed, the temperature was lowered to room temperature. Ethyl acetate (400 mL) was added to dilute the solution, and the solution was stirred for 15 minutes and filtered to remove insoluble salts. The filter cake was wash once with ethyl acetate (100 mL), and the filtrate was washed twice with saturated sodium chloride (100 mL). The organic phase was dried over anhydrous sodium sulfate, filtered, and then concentrated under reduced pressure. The crude product was quickly purified through a short silica gel column (petroleum ether:ethyl acetate=50:1) to obtain intermediate C1-2 (25 g, 88% yield) as a yellow solid.

$^1$H NMR (400 MHz, $CDCl_3$) δ 10.52-10.27 (m, 1H), 7.40-7.09 (m, 1H), 7.02-6.78 (m, 1H), 4.53-4.05 (m, 2H), 3.68 (t, J=6.0 Hz, 2H) ppm.

Step 2: intermediate 2-bromo-3-fluoro-6-(ethyleneoxy)benzaldehyde (C1-3)

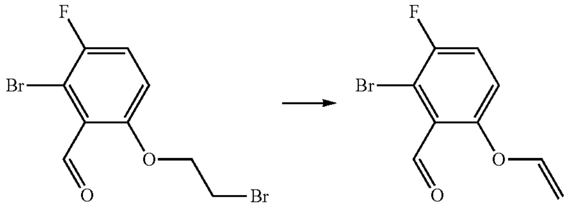

C1-2 C1-3

C1-2 (10 g, 30.7 mmol) was added into a 1 L single-necked flask. Anhydrous tetrahydrofuran (400 mL) was added and stirred to dissolve C1-2. The temperature was cool down to −20° C. Sodium tert-butoxide (4.4 g, 46.0 mmol) was slowly added in batches. After the addition was complete, the temperature was warmed to room temperature, and the reaction solution was stirred overnight. After the reaction was completed, the temperature was lowered to −10° C. Water (60 mL) was slowly added dropwise to quench the reaction. Ethyl acetate (100 mL) was added for extraction. The organic phase was dried over anhydrous sodium sulfate, filtered, and concentrated under reduced pressure. The crude product is purified by a silica gel column (petroleum ether:ethyl acetate=80:1 to 30:1) to obtain C1-3 (5 g, 66% yield) as a pale yellow solid.

$^1$H NMR (400 MHz, $CDCl_3$) δ 10.32 (d, J=9.8 Hz, 1H), 7.29 (dt, J=16.2, 8.3 Hz, 1H), 7.15-6.98 (m, 1H), 6.68-6.46 (m, 1H), 4.89-4.68 (m, 1H), 4.68-4.42 (m, 1H) ppm.

Step 3: Intermediate (E)-N'-(2-bromo-3-fluoro-6-(vinyloxy)benzylidene)-4-methylbenzenesulfonyl hydrazide (C1-4)

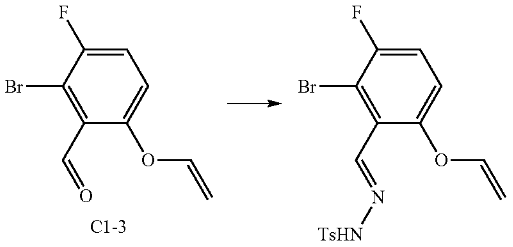

C1-3 C1-4

C1-3 (5 g, 20.4 mmol) was added into a 250 mL single-necked flask. Anhydrous methanol (100 mL) was added and stirred to dissolve C1-3, and p-toluenesulfonyl hydrazide (4.2 g, 22.4 mmol) was slowly added at room temperature, and the reaction solution was stirred at room temperature for 18 hours. After the reaction was completed, a large amount of white solids were precipitated. The temperature was lowered to 0° C. The solid product was filtered and collected. The mother liquor was concentrated. The crude solid product was slurried with a mixed solvent of petroleum ether and ethyl acetate (20:1). The solid product was collected and dried under reduced pressure to obtain C1-4 (7.5 g, 89% yield) as a white solid.

$^1H$ NMR (400 MHz, DMSO-$d_6$) δ 11.81 (s, 1H), 7.97 (s, 1H), 7.76 (d, J=7.6 Hz, 2H), 7.42 (t, J=9.0 Hz, 2H), 7.16 (dd, J=9.1, 4.3 Hz, 1H), 6.67 (dd, J=13.6, 6.2 Hz, 1H), 4.49 (dd, J=21.4, 9.8 Hz, 3H), 2.35 (s, 3H) ppm; LCMS: m/z 414.1 $[M+H]^+$.

Step 4: Intermediate 6-bromo-5-fluoro-1a,6b-dihydro-1H-cyclopropeno[b]benzofuran (C1-5)

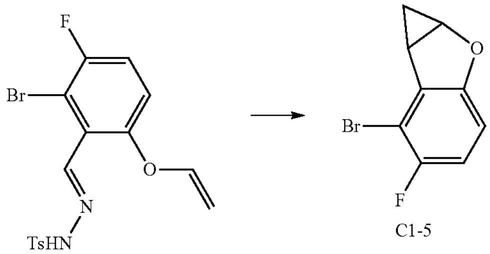

C1-4

C1-5

C1-4 (3 g, 7.3 mmol) was added into a 250 mL single-necked flask. Toluene (100 mL) was added and stirred to dissolve C1-4. Lithium tert-butoxide (639 mg, 7.9 mmol), rhodium (II) octanoate dimer (56 mg, 72.6 μmol) were slowly added at room temperature under nitrogen protection. The temperature was heated up to 100° C., and the reaction solution was stirred for 3 hours. After the reaction was completed, the temperature was lowered to room temperature. The reaction solution was filtered. The filter cake was washed with ethyl acetate (50 mL), and the filtrate was concentrated under reduced pressure to obtain C1-5 (1.67 g, 100% yield) as pale yellow oil, which was directly put into next reaction without further purification.

$^1H$ NMR (400 MHz, $CDCl_3$) δ 7.03-6.81 (m, 2H), 4.97 (t, J=5.2 Hz, 1H), 2.84 (dt, J 9.0, 4.4 Hz, 1H), 1.26 (dt, J=8.0, 6.1 Hz, 1H), 0.55-0.37 (m, 1H) ppm.

Step 5: intermediate 5-fluoro-1a,6b-dihydro-1H-cyclopropeno[b]benzofuran-6-carbonitrile (C1-6)

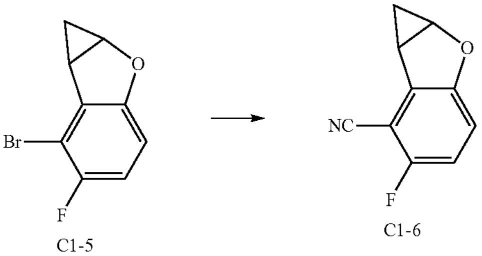 [SMILES: Fc1ccc2c(c1Br)C1CC1O2 ; N#Cc1c(F)ccc2c1C1CC1O2]

C1-5

C1-6

C1-5 (1.9 g, 8.30 mmol), zinc cyanide (1.46 g, 12.4 mmol), tetrakis(triphenylphosphine) palladium (1.44 g, 1.24 mmol), DMF (12 mL) were added into a 100 mL single-necked bottle under nitrogen protection. The temperature was heated up to 110° C., and the reaction solution was stirred for 18 hours. After the reaction was completed, the temperature was lowered to room temperature. Ethyl acetate (20 mL) was added to dilute the solution, and the solution was filtered. The filtrate was washed twice with saturated sodium chloride (10 mL). The organic phase was dried over anhydrous sodium sulfate, filtered, and then concentrated under reduced pressure. The crude product was purified through a silica gel column (petroleum ether:ethyl acetate=100:1 to 20:1) to obtain C1-6 (1.35 g, 92% yield) as a white solid.

$^1H$ NMR (400 MHz, $CDCl_3$) δ 7.03-6.84 (m, 2H), 4.97 (t, J=5.2 Hz, 1H), 2.84 (dt, J 9.0, 4.5 Hz, 1H), 1.33-1.20 (m, 1H), 0.52-0.40 (m, 1H) ppm.

Step 6: intermediate tert-butyl ((5-fluoro-1a,6b-dihydro-1H-cyclopropeno[b]benzofuran-6-yl) methyl)carbamate (C1-7)

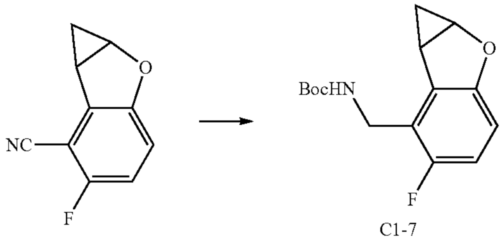

C1-6

C1-7

C1-6 (1.2 g, 6.8 mmol) was added to a 100 mL single-necked flask. Methanol (30 mL) was added to dissolve C1-6. Di-tert-butyl dicarbonate (2.2 g, 10.3 mmol) was added at room temperature, and the temperature was cooled to −5° C. Nickel chloride hexahydrate (1.95 g, 8.22 mmol) was slowly added. Sodium borohydride solid (778 mg, 20.5 mmol) was added in batches. The temperature was naturally raised to room temperature, and the reaction solution was stirred for 2 hours. After the reaction was completed, the solution was filtered with diatomaceous earth. The filter cake was washed with methanol (10 mL). The filtrate was cooled to 0° C., quenched with water (5 mL) and concentrated under reduced pressure. Ethyl acetate (80 mL) was added to the crude product. The organic phase was washed with saturated brine (10 mL), dried over anhydrous sodium sulfate, filtered and concentrated under reduced pressure. The crude product was separated and purified by a silica gel column (petroleum ether:ethyl acetate=100:1 to 40:1) to obtain C1-7 (1.2 g, 63% yield) as a white solid.

$^1H$ NMR (400 MHz, $CDCl_3$) δ 6.76 (t, J=9.3 Hz, 1H), 6.64 (dd, J=8.6, 3.7 Hz, 1H), 4.90 (s, 1H), 4.82 (t, J=5.3 Hz, 1H), 4.48 (d, J=6.1 Hz, 1H), 4.46-4.33 (m, 1H), 2.85 (d, J=3.8 Hz, 1H), 1.44 (s, 9H), 1.05 (dd, J=14.6, 6.0 Hz, 1H), 0.32 (s, 1H) ppm; LCMS: m/z 224.1 $[M-55]^+$.

Step 7: intermediate tert-butyl ((5-fluoro-1aR,6bR-dihydro-1H-cyclopropeno[b]benzofuran-6-yl) methyl)carbamate (C1-7a) and ((5-fluoro-1aS,6bS-dihydro-1H-cyclopropeno[b]benzofuran-6-yl) methyl)carbamate (C1-7b)

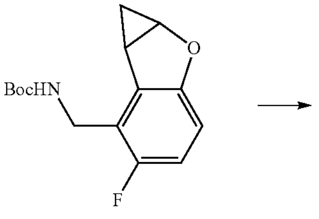

C1-7

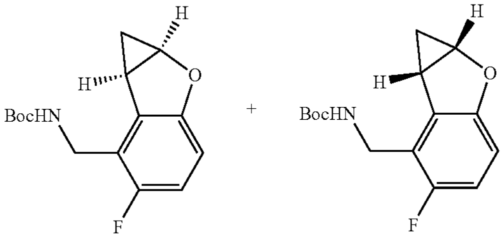

C1-7a C1-7b

C1-7 (1.2 g, 4.3 mmol) was further purified by chiral SFC as follows: column:AD-H 20×250 mm, 10 um (Daicel), flow rate: 80 g/min, mobile phase: 13% (0.2% ammonia in methanol/methanol) in $CO_2$, detection: 214 nM, and obtaining C1-7a (0.52 g, 43.3% yield), Rt: 0.99 min; and C1-7b (0.57 g, 47.5% yield), Rt: 0.71 min.

C1-7a: $^1$H NMR (400 MHz, $CDCl_3$) δ 6.76 (t, J=9.3 Hz, 1H), 6.64 (dd, J=8.6, 3.9 Hz, 1H), 4.98-4.73 (m, 2H), 4.45 (ddd, J=41.3, 14.0, 5.7 Hz, 2H), 2.84 (s, 1H), 1.45 (d, J=7.7 Hz, 9H), 1.05 (dd, J=14.8, 6.0 Hz, 1H), 0.31 (d, J=4.6 Hz, 1H) ppm; LCMS: m/z 224.1 $[M-55]^+$.

C1-7b: $^1$H NMR (400 MHz, $CDCl_3$) δ 6.76 (t, J=9.3 Hz, 1H), 6.64 (dd, J=8.6, 3.9 Hz, 1H), 4.98-4.73 (m, 2H), 4.45 (ddd, J=41.3, 14.0, 5.7 Hz, 2H), 2.84 (s, 1H), 1.45 (d, J=7.7 Hz, 9H), 1.05 (dd, J=14.8, 6.0 Hz, 1H), 0.31 (d, J=4.6 Hz, 1H) ppm; LCMS: m/z 224.1 $[M-55]^+$.

Step 8: intermediate ((1aR,6bR)-5-fluoro-1a,6b-dihydro-1H-cyclopropeno[b]benzofuran-6-yl)methanamine (C1-a)

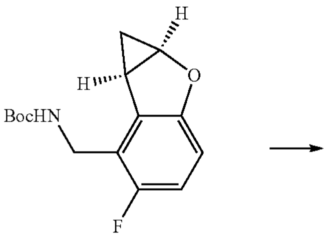

C1-7a

-continued

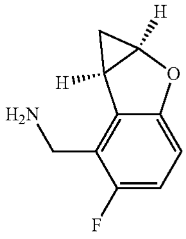

C1-a

Compound C1-7a (1.2 g, 4.30 mmol) was added into a 100 mL single-necked flask. Dichloromethane (20 mL) was added to dissolve C1-7a. Trifluoroacetic acid (4 mL, 52 mmol) was added at room temperature, and the reaction solution was stirred for 2 hours. After the reaction was completed, dichloromethane and trifluoroacetic acid were removed through vacuum concentration to obtain the trifluoroacetic acid salt of C1-a as a colorless solid, 1.26 g, yield 100%. The product was used directly in the next step.

$^1$H NMR (400 MHz, MeOD) δ 6.95 (t, J=9.5 Hz, 1H), 6.84 (dd, J=8.8, 4.0 Hz, 1H), 4.97 (t, J=5.4 Hz, 1H), 4.31 (q, J=13.7 Hz, 2H), 2.92-2.77 (m, 1H), 1.26-1.11 (m, 1H), 0.38-0.21 (m, 1H) ppm; LCMS: m/z 180.1 $[M+H]^+$.

Example 3: intermediate 4-(aminomethyl)-5-fluoro-2,3-dihydrobenzofuran-3-ol (C2)

Step 1: intermediate 2-bromo-3,6-difluorobenzaldehyde (C2-2)

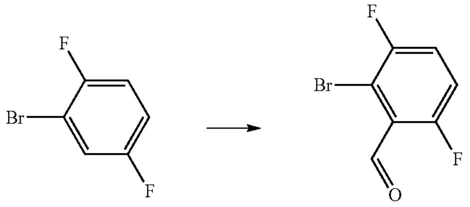

C2-1 C2-2

C2-1 (22 g, 114 mmol) and dry THE (200 mL) were added into a 500 mL dry three-necked flask, and the temperature was cooled to −70° C. Lithium diisopropylamide (2 M, 68.4 mL) was slowly added dropwise to the reaction solution. After the reaction solution was stirred at the same temperature for 45 minutes, DMF (17.8 mL, 228 mmol) was added. The reaction solution was stirred at the same temperature for two hours, and then was heated up to 0° C. Saturated ammonium chloride (200 mL) was added to the reaction solution. The reaction solution was extracted with EtOAc (200 mL×2). The combined organic phases were washed once with brine, dried over anhydrous sodium sulfate, filtered and concentrated under reduced pressure. The residue was purified on silica gel (petroleum ether:ethyl acetate=100:1) to obtain C2-2 (20 g, 79.4% yield) as a pale yellow solid.

$^1$H NMR (400 MHz, $CDCl_3$) δ 10.34 (s, 1H), 7.34 (ddd, J=9.2, 7.4, 4.5 Hz, 1H), 7.16 (td, J=9.3, 4.0 Hz, 1H) ppm.

Step 2: intermediate 2-bromo-3-fluoro-6-methoxybenzaldehyde (C2-3)

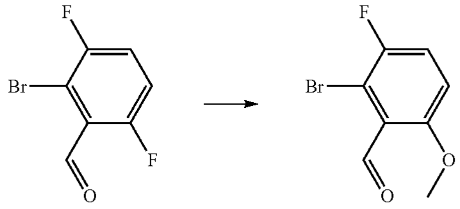

C2-2 C2-3

C2-2 (20 g, 90.5 mmol) was added into a 2 L three-necked flask, and stirred and dissolved with anhydrous THE (1000 mL) and MeOH (200 mL). Sodium methoxide (5.87 g, 108.6 mmol) was added, and the reaction solution was stirred at 60° C. for 18 hours. The reaction solution was concentrated under reduced pressure to remove most of the solvent, and 500 mL of water was added. The suspension was stirred for 30 minutes and filtered to collect the solid. The solid was slurried with a mixture of petroleum ether and ethyl acetate (5:1). The slurry was filtered to obtain a solid, which was dried under reduced pressure to obtain C2-3 (18 g, 85% yield) as a yellow solid.

LC-MS: m/z 233.1 $[M+H]^+$.

Step 3: intermediate 2-bromo-3-fluoro-6-hydroxybenzaldehyde (C2-4)

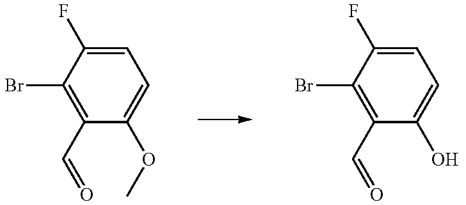

C2-3 C2-4

C2-3 (16.8 g, 72.1 mmol) and dichloromethane (300 mL) were added into a 1 L one-necked flask. Boron tribromide (21.7 g, 86.5 mmol) was slowly added dropwise at −78° C., and the reaction solution was raised to room temperature and stirred for 18 hours. The reaction solution was diluted with dichloromethane (300 mL), and saturated sodium bicarbonate (300 mL) was slowly added. The organic phases were washed twice with brine, dried over anhydrous sodium sulfate, filtered and concentrated under reduced pressure. The residue was purified on silica gel (petroleum ether:ethyl acetate=50:1) to obtain C2-4 (10 g, 63.3% yield) as a pale yellow solid.

$^1H$ NMR (400 MHz, $CDCl_3$) δ 11.77 (s, 1H), 10.34 (s, 1H), 7.29 (dt, J=12.7, 6.3 Hz, 1H), 6.94 (dd, J=9.3, 4.1 Hz, 1H) ppm.

Step 4: intermediate 4-bromo-5-fluoro-2,3-dihydrobenzofuran-3-ol (C2-5)

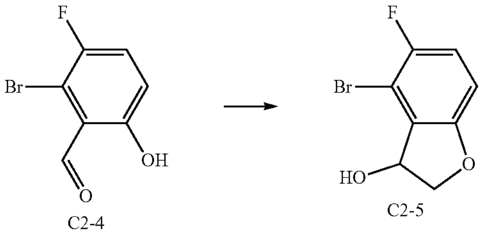

C2-4 C2-5

Trimethylsulfoxonium iodide (9.73 g, 44.2 mmol) and DMSO (50 ml) were added into a dry three-necked flask. Sodium tert-butoxide (4.25 g, 44.2 mmol) was added in an ice-water bath. The reaction solution was stirred at room temperature for 2 hours, and C2-4 (8.8 g, 40.2 mmol) was added. The reaction solution was stirred at room temperature for 18 hours, and then ethyl acetate (250 ml) and water (250 ml) were added. The solution was extracted with ethyl acetate (250 ml×2). The organic phase was washed once with water and brine respectively, dried over anhydrous sodium sulfate, filtered and concentrated under reduced pressure. The residue was purified on silica gel (petroleum ether:ethyl acetate=10:1) to obtain C2-5 (6.2 g, 66.2% yield) as a white solid.

$^1H$ NMR (400 MHz, $CDCl_3$) δ 7.03 (t, J=8.7 Hz, 1H), 6.76 (dd, J=8.8, 3.5 Hz, 1H), 5.51-5.40 (m, 1H), 4.58 (ddd, J=13.4, 10.8, 4.6 Hz, 2H), 2.33 (d, J=4.9 Hz, 1H) ppm.

Step 5: intermediate 5-fluoro-3-hydroxy-2,3-dihydrobenzofuran-4-carbonitrile (C2-6)

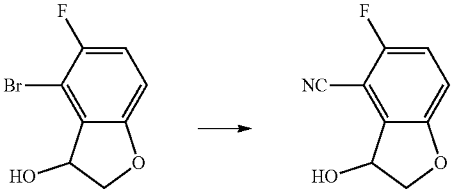

C2-5 C2-6

C2-5 (2.7 g, 11.6 mmol), zinc cyanide (2.04 g, 17.4 mmol), DMF (50 mL) and tetrakis(triphenylphosphine) palladium (1.34 g, 1.16 mmol) were added into a dry one-necked flask. The reaction solution was heated up to 120° C. under nitrogen protection and stirred for 18 hours. The reaction solution was cooled to room temperature, extracted with ethyl acetate (200 mL×3) and water (200 ml). The organic phase was washed once with water and brine respectively, dried over anhydrous sodium sulfate, filtered and concentrated under reduced pressure. The residue was purified on silica gel (petroleum ether:ethyl acetate=5:1) to obtain C2-6 (1.6 g, 77% yield) as a white solid.

$^1H$ NMR (400 MHz, $CDCl_3$) δ 7.20-6.99 (m, 2H), 5.63 (dd, J=6.9, 2.9 Hz, 1H), 4.69 (dd, J=10.8, 7.1 Hz, 1H), 4.55 (dd, J=10.8, 3.1 Hz, 1H), 2.74 (s, 1H) ppm.

Step 6: intermediate (5-fluoro-2,3-dihydrobenzofuran-4-yl)methanamine (C2)

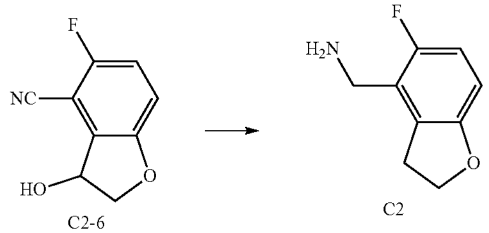

C2-6

C2

C2-6 (1.55 g, 8.65 mmol), trifluoroacetic acid (1.09 g, 8.65 mmol), methanol (20 mL) and 10% palladium on carbon (2 g, containing 50% water) were sequentially added into a 100 mL single-necked flask. The reaction mixture was blown with hydrogen for 5 minutes, the gas was replaced three times with a hydrogen balloon, and the reaction mixture was stirred at 60° C. for 48 hours under a hydrogen balloon. The mixture was filtered through diatomaceous earth and washed with methanol (50 mL×2). The filtrate was concentrated under reduced pressure. Dioxane (10 mL) and 10M sodium hydroxide aqueous solution (1 mL) were added and the mixture was extracted with dioxane (10 mL×2). The organic phase was dried over anhydrous sodium sulfate, filtered and concentrated under reduced pressure. Compound C2 (1.4 g, 90% purity, 87% yield) was obtained and used directly in the next step.

$^1$H NMR (400 MHz, $CD_3OD$) δ 3.27 (t, 2H), 3.77 (s, 2H), 4.56 (t, 2H), 6.59 (dd 1H), 6.81 (dd, 1H) ppm; LC-MS: m/z 168.1 $[M+H]^+$.

Example 4: 8-bromo-N-(((1aR,6bR)-5-fluoro-1a,6b-dihydro-1H-cyclopropeno[b]benzofuran-6-yl)methyl)-[1,2,4]triazolo[4,3-c]pyrimidin-5-amine (B1)

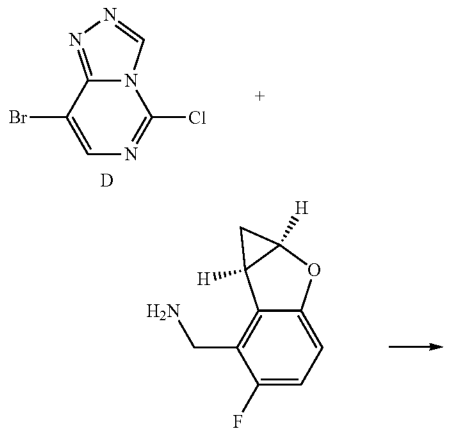

D

C1-a

-continued

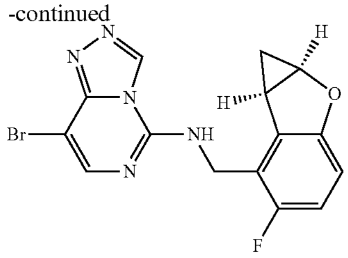

B1

The trifluoroacetic acid salt of compound C1-a (1.0 g, 3.41 mmol), compound D (0.95 g, 4.09 mmol), triethylamine (0.69 g, 6.82 mmol), acetonitrile (20 mL) were sequentially added into a 100 mL single-necked flask. The solution was stirred at room temperature for 3 hours. After the reaction was completed, ethyl acetate (80 mL) was added to dilute and dissolve. The organic phase was washed with saturated brine (10 mL*2), dried over anhydrous sodium sulfate, concentrated under reduced pressure, and purified by a silica gel column chromatography (mobile phase: PE:EA=30:1 to PE:EA=10:1) to obtain compound B1 (1.2 g, yield 94%).

$^1$H NMR (400 MHz, DMSO-$d_6$) δ 9.50 (s, 1H), 8.87 (d, J=4.5 Hz, 1H), 7.85 (s, 1H), 6.94 (t, J=9.5 Hz, 1H), 6.77 (dd, J=8.7, 3.7 Hz, 1H), 4.92 (t, J=5.2 Hz, 1H), 4.79 (p, J 9.7 Hz, 1H), 2.88 (dt, J=8.7, 4.5 Hz, 1H), 0.97 (dd, J=14.4, 5.7 Hz, 1H), 0.10 (s, 1H) ppm; LCMS: m/z 376.0 $[M+H]^+$.

Intermediate B2 was obtained through a reaction of the intermediates D and C2 using the method of example 4:

B2

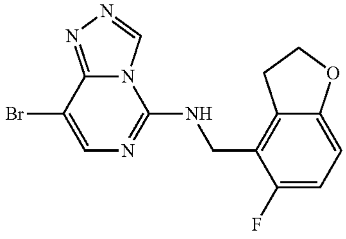

LCMS: m/z 364.0 $[M+H]^+$

Example 5: 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol Step 1: Methyl (E)-5-bromo-6-(((dimethylamino)methylene)amino)picolinate E27-1

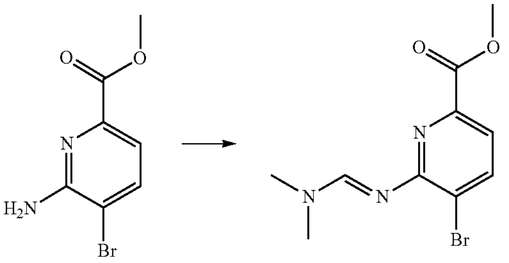

E27-1

Methyl (E)-5-bromo-6-(((dimethylamino)methylene)amino)picolinate (5.0 g, 21.6 mmol), 1,1-dimethoxy-N,N-dimethylmethylamine (5.16 g, 43.3 mmol) were dissolved in toluene (100 mL). The temperature of the reaction solution was raised to 110° C. and the reaction was carried out for 4 hours. No raw materials were detected by TLC. The reaction solution was concentrated to obtain the crude product E27-1 (6.00 g).

LCMS: m/z 285.7 $[M+H]^+$.

Step 2: Methyl (E)-5-bromo-6-(((hydroxylamino)methylene)amino)picolinate E27-2

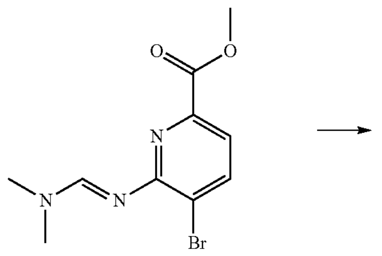

E27-1

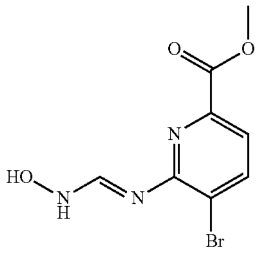

E27-2

E27-1 (6.0 g, 20.97 mmol), hydroxylamine hydrochloride (2.91 g, 41.94 mmol), sodium acetate (3.44 g, 41.9 mmol), ethanol (60 mL) were added in sequence to a reaction flask. The reaction solution was heated up to 50° C. and reacted for 4 hours under nitrogen atmosphere. LCMS monitored the completion of the reaction. The reaction solution was cooled to room temperature and filtered to obtain E27-2 (5.9 g, 85.0% yield).

$^1$H NMR (400 MHz, $CDCl_3$) δ 8.41-8.29 (m, 1H), 8.26-8.19 (m, 1H), 7.93 (d, J=7.9 Hz, 1H), 7.57 (d, J=7.9 Hz, 1H), 3.97 (s, 3H) ppm; LCMS: m/z 273.7 $[M+H]^+$.

Step 3: Methyl 8-bromo-[1,2,4]triazolo[1,5-a]pyridine-5-carboxylate E27-3

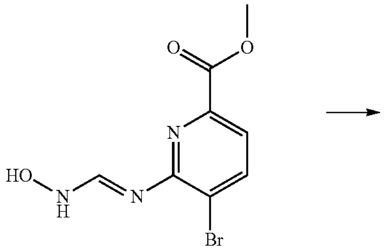

E27-2

-continued

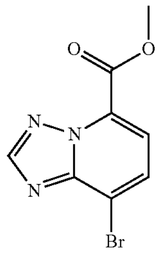

E27-3

Trifluoroacetic anhydride (23.0 g, 109 mmol) was added dropwise to a solution of E27-2 (10 g, 36.49 mmol) in tetrahydrofuran (100 mL) at room temperature. Then the mixture was slowly raised to 75° C., stirred and reacted for 3 hours. After the reaction was completed, the mixture was quenched by adding saturated sodium bicarbonate aqueous solution (100 mL) at 0° C. The mixture was extracted with ethyl acetate (100 mL*3), and the combined organic phases were dried and concentrated. The concentrate was purified by a silica gel column (petroleum ether:ethyl acetate=5:1 to 4:1) to obtain white solid E27-3 (5.00 g, yield 53.5%).

$^1$H NMR (400 MHz, $CDCl_3$) δ 8.52 (s, 1H), 7.85 (d, J=7.8 Hz, 1H), 7.68 (d, J=7.9 Hz, 1H), 4.08 (s, 3H) ppm; LCMS: m/z 256.0 $[M+H]^+$.

Step 4: 1-(8-bromo-[1,2,4]triazolo[1,5-a]pyridin-5-yl)ethanone E27-4

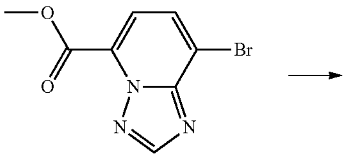

E27-3

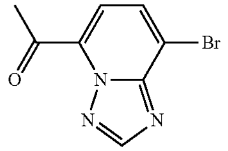

E27-4

Methyl 8-bromo-[1,2,4]triazolo[1,5-a]pyridine-5-carboxylate E27-3 (5.0 g, 19.3 mmoL) was dissolved in tetrahydrofuran (100 mL). The mixture was cooled to −30° C. Methylmagnesium bromide (3M, 32.5 mL) was added dropwise and the mixture was reacted for 3 hours under nitrogen atmosphere. The completion of the reaction was monitored by LCMS. The temperature was raised to 0° C. The mixture was quenched, extracted and concentrated under reduced pressure. The crude product was purified by a flash silica gel column to obtain 1-(8-bromo-[1,2,4]triazolo[1,5-a]pyridin-5-yl)ethanone E27-4 (0.3 g, 6.40% yield).

LCMS m/z 240.0 $[M+H]^+$.

Step 5: 2-(8-bromo-[1,2,4]triazolo[1,5-a]pyridin-5-yl)butan-2-ol E27-5

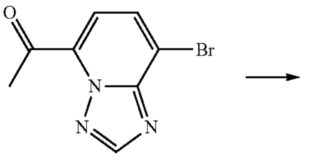

E27-4

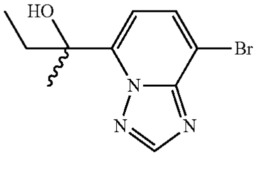

E27-5

Methyl 1-(8-bromo-[1,2,4]triazolo[1,5-a]pyridin-5-yl) ethanone E27-4 (150 mg, 0.6 mmoL) was dissolved in tetrahydrofuran (10 mL). The mixture was cooled to −30° C. Ethylmagnesium bromide (1M, 3.75 mL) was added dropwise and the mixture was reacted for 6 hours under nitrogen atmosphere. The completion of the reaction was monitored by LCMS. The temperature was raised to 0° C. The mixture was quenched, extracted and concentrated under reduced pressure. The crude product was purified by a flash silica gel column to obtain 2-(8-bromo-[1,2,4]triazolo[1,5-a]pyridin-5-yl)butan-2-ol E27-5 (100 mg, 59.3% yield).

$^1$H NMR (400 MHz, DMSO-$d_6$) δ 8.59 (s, 1H), 8.04 (d, J=8.0 Hz, 1H), 7.27 (d, J=8.0 Hz, 1H), 5.68 (s, 1H), 2.48-2.41 (m, 1H), 1.97-1.89 (m, 1H), 1.70 (s, 3H), 0.59 (t, J=7.4 Hz, 3H). LCMS m/z 270.0 $[M+H]^+$.

Step 6: (5-(2-hydroxybutan-2-yl)-[1,2,4]triazolo[1,5-a]pyridin-8-yl)boronic acid

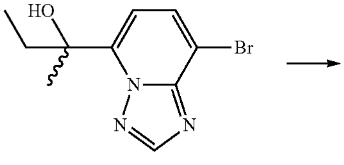

E27-5

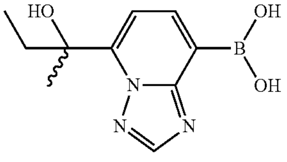

E27-6

2-(8-bromo-[1,2,4]triazolo[1,5-a]pyridin-5-yl)butan-2-ol E27-5 (100 mg, 0.37 mmol), bis(pinacolato)diboron (123 mg, 0.44 mmol), potassium acetate (109 mg, 1.11 mmol) and [1,1'-bis(diphenylphosphino)ferrocene]palladium dichloride dichloromethane complex (60.5 mg, 0.07 mmol) were dissolved in 1,4-dioxane (1.5 mL). The reaction temperature was raised to 120° C., and the mixture was reacted under nitrogen atmosphere for 5 hours. No raw materials were remained by TLC detection, and the reaction solution containing E27-6 was used directly in the next step without treatment.

Step 7: 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol E27-7

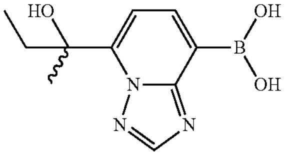

E27-6

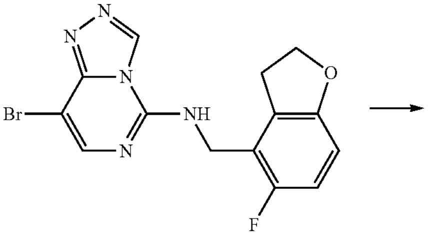

B2

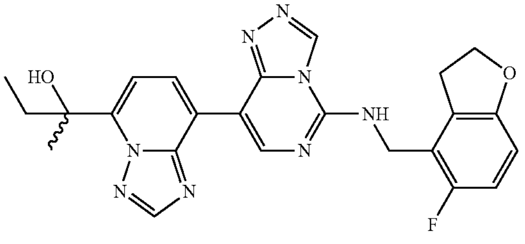

E27-7

8-bromo-N-((5-fluoro-2,3-dihydrobenzofuran-4-yl)methyl)-[1,2,4]triazolo[4,3-c]pyrimidin-5-amine (53.7 mg, 0.15 mmol), sodium carbonate (117 mg, 1.11 mmol), [1,1'-bis(diphenylphosphino)ferrocene]palladium dichloride dichloromethane complex (30.1 mg, 0.04 mmol), 1,4-dioxane (4 mL) and water (1 mL) were added to the reaction solution in the previous step. The reaction was raised to 100° C. and reacted for 2 hours under nitrogen atmosphere. The completion of the reaction was monitored by LCMS. The temperature was lowered to room temperature. The mixture was dried over anhydrous sodium sulfate, filtered, and concentrated under reduced pressure. The crude product was purified by a flash silica gel column and HPLC to obtain 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol E27-7 (43.0 mg, 23.3% yield).

$^1$H NMR (400 MHz, DMSO-$d_6$) δ 9.54 (s, 1H), 9.39 (s, 1H), 9.10 (d, J=8.0 Hz, 1H), 8.91 (br s, 1H), 8.62 (s, 1H), 7.50 (d, J=8.0 Hz, 1H), 7.00-6.93 (m, 1H), 6.71 (dd, J=3.9, 8.6 Hz, 1H), 5.67 (s, 1H), 4.78 (s, 2H), 4.55 (t, J=8.7 Hz, 2H), 3.33-3.30 (m, 2H), 2.55-2.51 (m, 1H), 1.99 (dd, J=7.4, 13.8 Hz, 1H), 1.75 (s, 3H), 0.64 (t, J=7.4 Hz, 3H). LCMS m/z 475.1 $[M+H]^+$.

Step 8: Separation of 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol E27-7

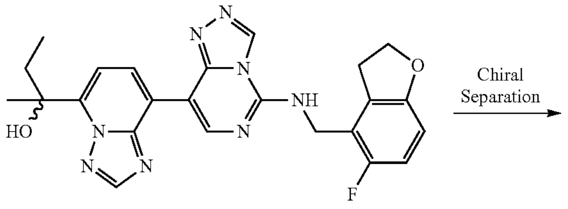

E27-7

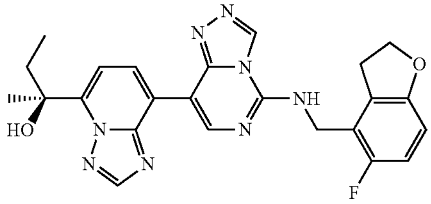

(S)-E27-7

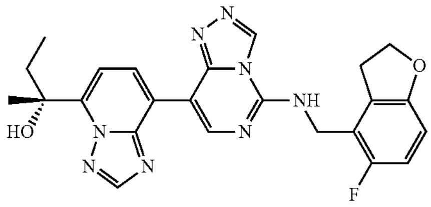

(R)-E27-7

2-(8-(5-(((5-fluoro-2,3-dihydrobenzofuran-4-yl)methyl)amino-[1,2,4]triazolo[4,3-c]pyrimidin-8-yl)-[1,2,4]triazolo[1,5-a]pyridin-5-yl)butan-2-ol E27-7 was chiral separated by SFC. Separation method: column: DAICEL CHIRALPAK IG (250 mm*30 mm, 10 m); mobile phase: A [0.1% $NH_3H_2O$ IPA]; B (ethanol): 5%-40% gradient, 4 mL/min, and (S)-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol ((S)-E27-7) or (R)-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol ((R)-E27-7) was obtained, one of which has a retention time of 3.134 min (compound a), and the other enantiomer has a retention time of 3.547 min (compound b).

Compound a: $^1H$ NMR (400 MHz, DMSO-d6) δ 9.54 (s, 1H), 9.39 (s, 1H), 9.10 (d, J=8.0 Hz, 1H), 8.91 (br s, 1H), 8.62 (s, 1H), 7.50 (d, J=8.0 Hz, 1H), 7.00-6.93 (m, 1H), 6.71 (dd, J=3.9, 8.6 Hz, 1H), 5.67 (s, 1H), 4.78 (s, 2H), 4.55 (t, J=8.7 Hz, 2H), 3.33-3.30 (m, 2H), 2.55-2.51 (m, 1H), 1.99 (dd, J=7.4, 13.8 Hz, 1H), 1.75 (s, 3H), 0.64 (t, J=7.4 Hz, 3H) ppm.

Compound b: $^1H$ NMR (400 MHz, DMSO-d6) δ 9.54 (s, 1H), 9.38 (s, 1H), 9.10 (d, J=8.0 Hz, 1H), 8.91 (br s, 1H), 8.62 (s, 1H), 7.50 (d, J=8.0 Hz, 1H), 6.99-6.93 (m, 1H), 6.71 (dd, J=3.9, 8.6 Hz, 1H), 5.67 (s, 1H), 4.78 (s, 2H), 4.55 (t, J=8.8 Hz, 2H), 3.33-3.30 (m, 2H), 2.54-2.51 (m, 1H), 2.04-1.94 (m, 1H), 1.75 (s, 3H), 0.64 (t, J=7.4 Hz, 3H) ppm.

Example 6: 3-(8-(5-(((5-fluoro-2,3-dihydrobenzofuran-4-yl)methyl)amino)-triazolo[4,3-c]pyrimidin-8-yl)-[1,2,4]triazolo[1,5-a]pyridin-5-yl)pentan-3-ol Step 1: 3-(8-bromo-[1,2,4]triazolo[1,5-a]pyridin-5-yl)pentan-3-ol E28-1

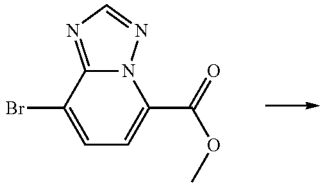

E27-3

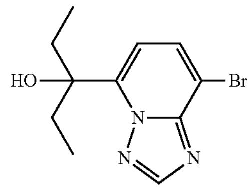

E28-1

Methyl 8-bromo-[1,2,4]triazolo[1,5-a]pyridine-5-carboxylate E27-3 (240 mg, 0.940 mmoL) was dissolved in tetrahydrofuran (5.00 mL). The mixture was cooled to −30° C. Ethylmagnesium bromide (1M, 2.83 mL) was added dropwise and the mixture was reacted for 3 hours under nitrogen atmosphere. The completion of the reaction was monitored by LCMS. The temperature was raised to 0° C. The mixture was quenched, extracted and concentrated under reduced pressure. The crude product was purified by a flash silica gel column to obtain 3-(8-bromo-[1,2,4]triazolo[1,5-a]pyridin-5-yl)pentan-3-ol E28-1 (80.0 mg, 29.8% yield).

$^1H$ NMR (400 MHz, DMSO-$d_6$) δ 8.58 (s, 1H), 8.04 (d, J=8.0 Hz, 1H), 7.25 (d, J=7.9 Hz, 1H), 5.37 (s, 1H), 2.60-2.51 (m, 2H), 1.91-1.80 (m, 2H), 0.54 (t, J=7.4 Hz, 6H) ppm; LCMS: m/z 286.0 $[M+H]^+$.

Step 2: (5-(3-hydroxypentan-3-yl)-[1,2,4]triazolo[1,5-a]pyridin-8-yl)boronic acid E28-2

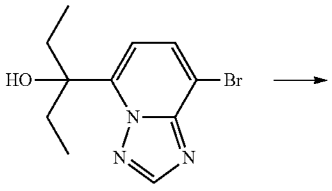

E28-1

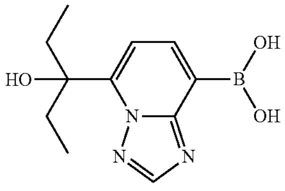

E28-2

3-(8-bromo-[1,2,4]triazolo[1,5-a]pyridin-5-yl)pentan-3-ol E28-1 (80.0 mg, 0.280 mmol), bis(pinacolato)diboron (79.0 mg, 0.310 mmol), potassium acetate (8.03 mg, 0.840 mmol) and [1,1'-bis(diphenylphosphino)ferrocene]palladium dichloride dichloromethane complex (46.0 mg, 0.056 mmol) were dissolved in 1,4-dioxane (1.00 mL). The reaction temperature was raised to 120° C., and the mixture was reacted under nitrogen atmosphere for 5 hours. No raw materials were remained by TLC detection, and the reaction solution containing E28-2 was used directly in the next step without treatment.

Step 3: 3-(8-(5-(((5-fluoro-2,3-dihydrobenzofuran-4-yl)methyl)amine)-[1,2,4]triazolo[4,3-c]pyrimidin-8-yl)-[1,2,4]triazolo[1,5-a]pyridin-5-yl)pentan-3-ol

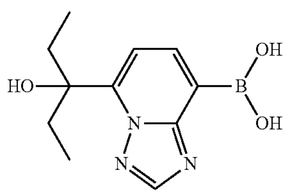

E28-2

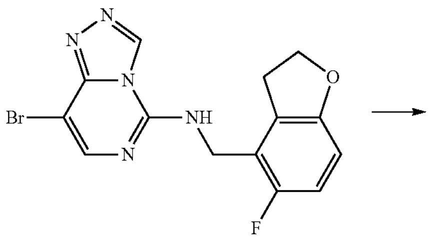

B2

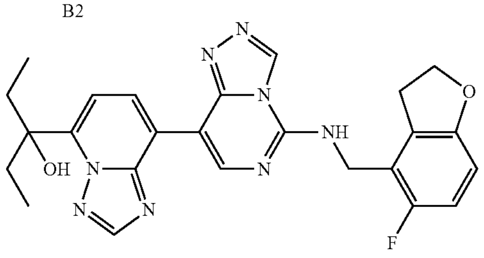

8-bromo-N-((5-fluoro-2,3-dihydrobenzofuran-4-yl)methyl)-[1,2,4]triazolo[[4,3-c]pyrimidin-5-amine B2 (41.0 mg, 0.110 mmol), sodium carbonate (89.0 mg, 0.800 mmol), [1,1'-bis(diphenylphosphino)ferrocene]palladium dichloride dichloromethane complex (46.0 mg, 0.056 mmol), 1,4-dioxane (1.00 mL) and water (0.500 mL) were added to the reaction solution in the previous step. The reaction was raised to 100° C. and reacted for 2 hours under nitrogen atmosphere. The completion of the reaction was monitored by LCMS. The temperature was lowered to room temperature. The mixture was dried over anhydrous sodium sulfate, filtered, and concentrated under reduced pressure. The crude product was purified by a flash silica gel column to obtain 3-(8-(5-(((5-fluoro-2,3-dihydrobenzofuran-4-yl)methyl)amine)-[1,2,4]triazolo[4,3-c]pyrimidin-8-yl)-[1,2,4]triazolo[1,5-a]pyridin-5-yl)pentan-3-ol (50.0 mg, 35.6% yield).

$^1$H NMR (400 MHz, DMSO-$d_6$) δ 9.54 (s, 1H), 9.40 (s, 1H), 9.11 (d, J=7.9 Hz, 1H), 8.95-8.86 (m, 1H), 8.61 (s, 1H), 7.49 (d, J=7.9 Hz, 1H), 7.00-6.93 (m, 1H), 6.75-6.67 (m, 1H), 5.36 (s, 1H), 4.78 (br d, J=4.8 Hz, 2H), 4.55 (t, J=8.8 Hz, 2H), 3.33-3.30 (m, 2H), 2.69-2.53 (m, 2H), 1.97-1.84 (m, 2H), 0.59 (t, J=7.4 Hz, 6H). LCMS m/z 489.3 [M+H]$^+$.

Example 7: 1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol Step 1: 8-bromo-5-(1,1,1-trifluoro-2-((trimethylsilyl)oxy)propan-2-yl)-[1,2,4]triazolo[1,5-a]pyridine E29-1

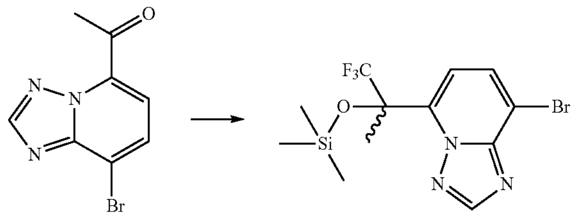

E27-4 E29-1

1-(8-bromo-[1,2,4]triazolo[1,5-a]pyridin-5-yl)ethanone E27-4 (500 mg, 2.08 mmol), cesium fluoride (55.0 mg, 0.362 mmol) was dissolved in N,N-dimethylformamide (5 mL), and (trifluoromethyl)trimethylsilane (326 mg, 2.29 mmol) was added under nitrogen atmosphere at 0° C. The reaction was carried out at 20° C. for 1 hour under nitrogen atmosphere. Trifluoromethyltrimethylsilane (296 mg, 2.08 mmol) was then added, and the reaction was continued at 20° C. for 1 hour. No raw material was remained by TLC and LCMS detection, and the reaction solution containing E29-1 was directly used in the next step without treatment.

LCMS: m/z 383.9 [M+H]$^+$.

Step 2: 2-(8-bromo-[1,2,4]triazolo[1,5-a]pyridin-5-yl)-1,1,1-trifluoropropan-2-ol E29-2

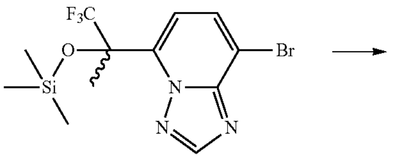

E29-1

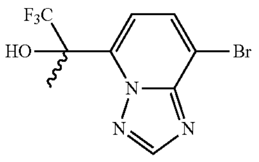

E29-2

Ethanol (5 mL) was added to the reaction solution in the previous step. The mixture was reacted at 20° C. for 2 hours. The completion of the reaction was monitored by TLC. After the reaction solution is concentrated, it is diluted with dichloromethane, washed with saturated sodium chloride solution, dried, filtered, and concentrated. The crude product was purified by column chromatography to obtain the white solid product 2-(8-bromo-[1,2,4]triazolo[1,5-a]pyridin-5-yl)-1,1,1-trifluoropropan-2-ol E29-2 (340 mg, 52.7% yield).

$^1$H NMR (400 MHz, $CDCl_3$) δ 8.46 (s, 1H), 7.85 (d, J=8.0 Hz, 1H), 7.70-7.66 (m, 1H), 7.05 (d, J=8.0 Hz, 1H), 1.93 (s, 3H) ppm.

Step 3: (5-(1,1,1-trifluoro-2-hydroxypropan-2-yl)-[1,2,4]triazolo[1,5-a]pyridin-8-yl)boronic acid E29-3

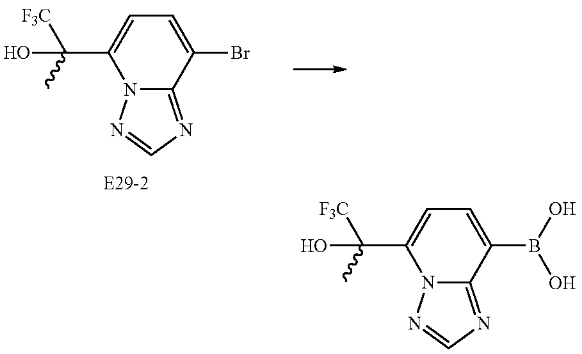

E29-2

E29-3

2-(8-bromo-[1,2,4]triazolo[1,5-a]pyridin-5-yl)-1,1,1-trifluoropropan-2-ol E29-2 (150 mg, 0.482 mmol), bis(pinacolato)diboron (135 mg, 0.530 mmol), potassium acetate (95.0 mg, 0.964 mmol), [1,1'-bis(diphenylphosphino)ferrocene] palladium dichloride dichloromethane complex (39.4 mg, 0.048 mmol) and dioxane (5 mL) were added in sequence to a bottle in a glove box. The reaction was carried out at 120° C. for 5 hours under nitrogen atmosphere, and no raw materials were remained by LCMS detection, and the reaction solution was directly used in the next step without treatment.

Step 4: 1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol E29-4

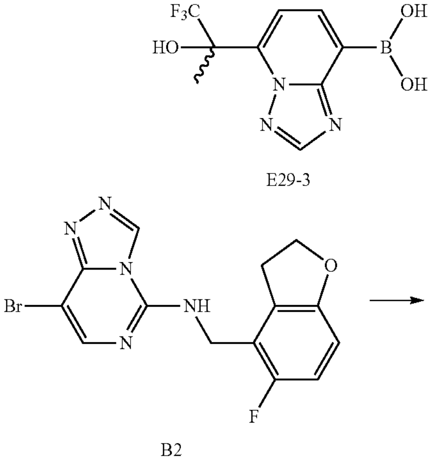

E29-3

B2

-continued

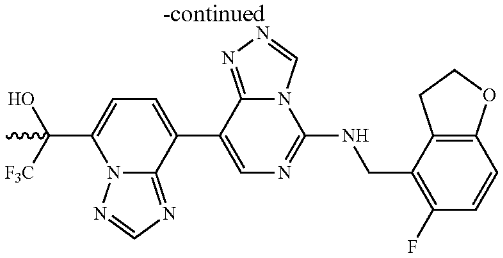

E29-4

8-bromo-N-((5-fluoro-2,3-dihydrobenzofuran-4-yl)methyl)-[1,2,4]triazolo[4,3-c]pyrimidin-5-amine (150 mg, 0.412 mmol), potassium carbonate (134 mg, 0.967 mmol), [1,1'-bis(diphenylphosphino)ferrocene]palladium dichloride dichloromethane complex (39.5 mg, 0.048 mmol) and water (1 mL) were added to the reaction solution in the previous step. The reaction solution was raised to 100° C. under nitrogen atmosphere and reactd for 2 hours. The completion of the reaction was monitored by LCMS. The reaction mixture was cooled to room temperature and concentrated, and the concentrate was purified by column chromatography to obtain a off-white solid product 1,1,1-trifluoro-2-(8-(5-(((5-fluoro-2,3-dihydrobenzofuran-4-yl)methyl)amino)-[1,2,4]triazolo[4,3-c]pyrimidine-8-yl)-[1,2,4]triazolo[1,5-a]pyridin-5-yl)propan-2-ol E29-4 (90.0 mg, 38.9% yield).

$^1$H NMR (400 MHz, DMSO-$d_6$) δ 9.55 (s, 1H), 9.44 (s, 1H), 9.17 (d, J=8.0 Hz, 1H), 9.00 (t, J=4.8 Hz, 1H), 8.70 (s, 1H), 7.76 (d, J=8.0 Hz, 1H), 7.53 (s, 1H), 7.01-6.92 (m, 1H), 6.75-6.68 (m, 1H), 4.78 (d, J=4.8 Hz, 2H), 4.55 (t, J=8.8 Hz, 2H), 3.36-3.34 (m, 2H), 2.16 (s, 3H) ppm; LCMS: m/z 515.3.0 $[M+H]^+$.

Step 5: separation of 1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol 1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol E29-4 was chiral separated by SFC. Separation method: column: DAICEL CHIRALPAK IG (250 mm*30 mm, 10 um); mobile phase: A [0.1% $NH_3H_2O$ IPA]; B (ethanol): 45% gradient, 2.8 mL/min, and (S)-1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol ((S)-E29-4) or (R)-1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol ((R)-E29-4) was obtained, one of which has a retention time of 4.974 min (compound c) and the other enantiomer has a retention time of 5.440 min (compound d).

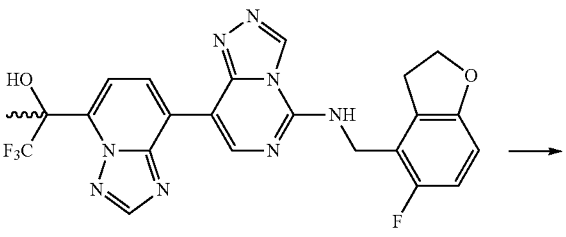

E29-4

-continued

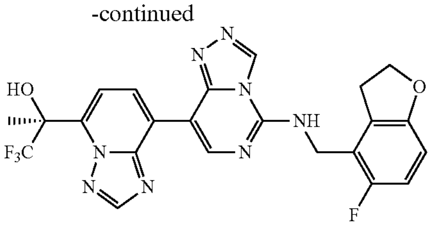

(S)-E29-4

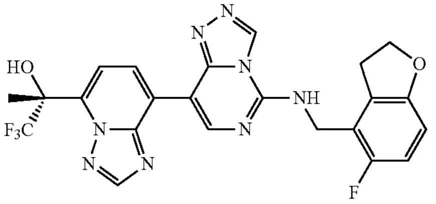

(R)-E29-4

Compound c: $^1H$ NMR (400 MHz, DMSO-$d_6$) δ 9.55 (s, 1H), 9.44 (s, 1H), 9.17 (d, J=8.0 Hz, 1H), 9.00 (t, J=4.8 Hz, 1H), 8.70 (s, 1H), 7.76 (d, J=8.0 Hz, 1H), 7.53 (s, 1H), 7.01-6.92 (m, 1H), 6.75-6.68 (m, 1H), 4.78 (d, J=4.8 Hz, 2H), 4.55 (t, J=8.8 Hz, 2H), 3.36-3.34 (m, 2H), 2.16 (s, 3H) ppm; LCMS: m/z 515.3.0 $[M+H]^+$.

Example 8 was Obtained Meanwhile: Compound d $^1H$ NMR (400 MHz, DMSO-$d_6$) δ 9.55 (s, 1H), 9.44 (s, 1H), 9.17 (d, J=8.0 Hz, 1H), 9.00 (t, J=4.8 Hz, 1H), 8.70 (s, 1H), 7.76 (d, J=8.0 Hz, 1H), 7.53 (s, 1H), 7.01-6.92 (m, 1H), 6.75-6.68 (m, 1H), 4.78 (d, J=4.8 Hz, 2H), 4.55 (t, J=8.8 Hz, 2H), 3.36-3.34 (m, 2H), 2.16 (s, 3H) ppm; LCMS: m/z 515.3.0 $[M+H]^+$.

Example 9: 1-(8-(5-(((5-fluoro-2,3-dihydrobenzofuran-4-yl)methyl)amino)-triazolo[4,3-c]pyrimidin-8-yl)-[1,2,4]triazolo[1,5-a]pyridin-5-yl)-2-methylpropan-2-ol Step 1: (E)-N'-(3-bromo-6-methyl-pyridin-2-yl)-N,N-dimethylformimidamide E30-2

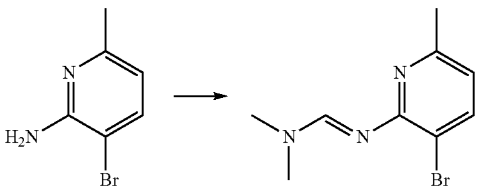

E30-1 E30-2

3-bromo-6-methylpyridin-2-amine E30-1 (4.50 g, 24.1 mmoL), N,N-dimethylformamide dimethyl acetal (14.3 g, 120 mmol) were dissolved in toluene (10.0 mL), and then the reaction mixture was raised to 100° C. and reacted for 2 hours under nitrogen atmosphere. After the reaction was completed, the reaction solution was cooled to room temperature and concentrated under reduced pressure to obtain (E)-N'-(3-bromo-6-methyl-pyridin-2-yl)-N,N-dimethylformimidamide (5.80 g, crude product).

$^1H$ NMR (400 MHz, $CDCl_3$) δ 8.34 (s, 1H), 7.66 (d, J=7.9 Hz, 1H), 6.60 (d, J=7.9 Hz, 1H), 3.14 (s, 3H), 3.10 (s, 3H), 2.40 (s, 3H) ppm; LCMS: m/z 242.1 $[M+H]^+$.

Step 2: (E)-N'-(3-bromo-6-methyl-pyridin-2-yl)-N-hydroxyformimidamide E30-3

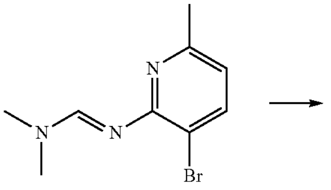

E30-2

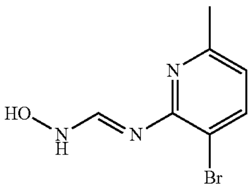

E30-3

(E)-N'-(3-bromo-6-methyl-pyridin-2-yl)-N,N-hydroxyformimidamide E30-2 (5.80 g, 24.0 mmoL), sodium acetate (4.32 g, 52.7 mmoL), hydroxylamine hydrochloride (3.33 g, 43.9 mmoL) were dissolved in ethanol (60.0 mL), and then the reaction mixture was raised to 50° C. and reacted for 2 hours under nitrogen atmosphere. The completion of the reaction was monitored by TLC. The mixture was cooled to room temperature, diluted with water and filtered. The filter cake was dried to obtain (E)-N'-(3-bromo-6-methyl-pyridin-2-yl)-N-hydroxyformimidamide E30-3 (5.50 g, 98.8% yield).

$^1H$ NMR (400 MHz, $CDCl_3$) δ 8.25-8.09 (m, 2H), 7.64 (d, J=8.0 Hz, 1H), 6.64 (d, J=8.0 Hz, 1H), 2.43 (s, 3H) ppm; LCMS: m/z 230.1 $[M+H]^+$.

Step 3: 8-bromo-5-methyl-[1,2,4]triazolo[1,5-a]pyridine E30-4

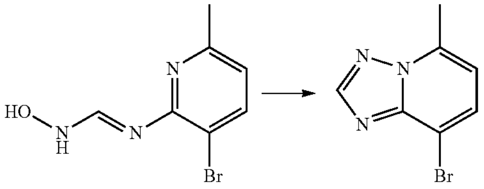

E30-3 E30-4

(E)-N'-(3-bromo-6-methyl-pyridin-2-yl)-N-hydroxyformimidamide E30-3 (5.50 g, 23.9 mmol) was dissolved in polyphosphoric acid (5.00 mL). The reaction mixture was raised to 90° C. and reacted for 2 hours under nitrogen atmosphere. No raw material was remained by TLC detection. The reaction mixture was cooled to room temperature, quenched with sodium bicarbonate, and extracted, filtered, washed and dried, and concentrated under reduced pressure. The crude product was purified by a flash silica gel column to obtain 8-bromo-5-methyl-[1,2,4]triazolo[1,5-a]pyridine E30-4 (1.70 g, 33.4% yield).

$^1$H NMR (400 MHz, DMSO-$d_6$) δ 8.58 (s, 1H), 7.95 (d, J=7.6 Hz, 1H), 7.06 (d, J=7.4 Hz, 1H), 2.72-2.69 (m, 3H) ppm; LCMS: m/z 212.1 $[M+H]^+$.

Step 4: 1-(8-bromo-[1,2,4]triazolo[1,5-a]pyridin-5-yl)-2-methyl-propan-2-ol E30-5

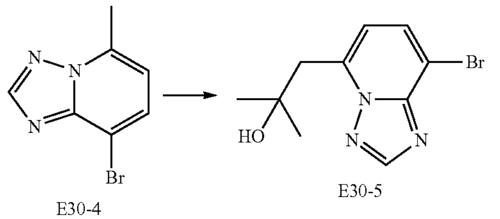

E30-4 E30-5

8-bromo-5-methyl-[1,2,4]triazolo[1,5-a]pyridine E30-4 (1.50 g, 7.07 mmoL) was dissolved in tetrahydrofuran (40.0 mL), and the mixture was cooled to −78° C. Lithium diisopropylamide (2.00 M, 7.07 mL) was added dropwise. The reaction mixture reacted for 2 hours at −78° C. under nitrogen atmosphere. Acetone (2.47 g, 42.4 mmol, 3.12 mL) was added, and the reaction mixture reacted for 3 hours at −78° C. under nitrogen atmosphere. The completion of the reaction was monitored by TLC and LCMS. The reaction mixture was quenched, extracted, filtered, washed and dried. The crude product was purified by HPLC to obtain 1-(8-bromo-[1,2,4]triazolo[1,5-a]pyridin-5-yl)-2-methyl-propan-2-ol E30-5 (450 mg, 21.9% yield).

$^1$H NMR (400 MHz, DMSO-$d_6$) δ 8.54 (s, 1H), 7.98 (d, J=7.8 Hz, 1H), 7.06 (d, J=7.8 Hz, 1H), 4.72 (s, 1H), 3.31 (s, 2H), 1.13 (s, 6H) ppm; LCMS: m/z 270.0 $[M+H]^+$.

Step 5: (5-(2-hydroxy-2-methyl-propyl)-[1,2,4]triazolo[1,5-a]pyridin-8-yl)boronic acid E30-6

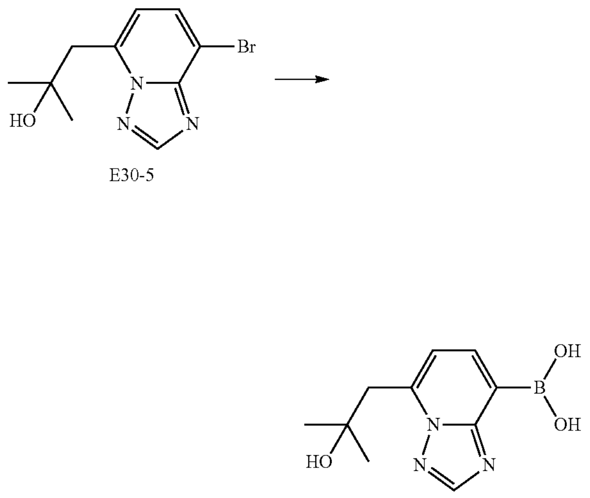

E30-5

E30-6

1-(8-bromo-[1,2,4]triazolo[1,5-a]pyridin-5-yl)-2-methyl-propan-2-ol E30-5 (150 mg, 0.56 mmol), bis(pinacolate) diboron (155 mg, 0.61 mmol), potassium acetate (163 mg, 1.67 mmol) and [1,1'-bis(diphenylphosphino)ferrocene]palladium dichloride dichloromethane complex (90.7 mg, 0.110 mmol) were dissolved in 1,4-dioxane (2.00 mL). The reaction mixture was raised to 120° C. and reacted under nitrogen atmosphere for 5 hours. No raw materials were remained by TLC detection, and the reaction solution was used directly in the next step.

Step 6: 1-(8-(5-(((5-fluoro-2,3-dihydrobenzofuran-4-yl)methyl)amino)-[1,2,4]triazol[4,3-c]pyrimidin-8-yl)-[1,2,4]triazolo[1,5-a]pyridin-5-yl)-2-methyl-propan-2-ol

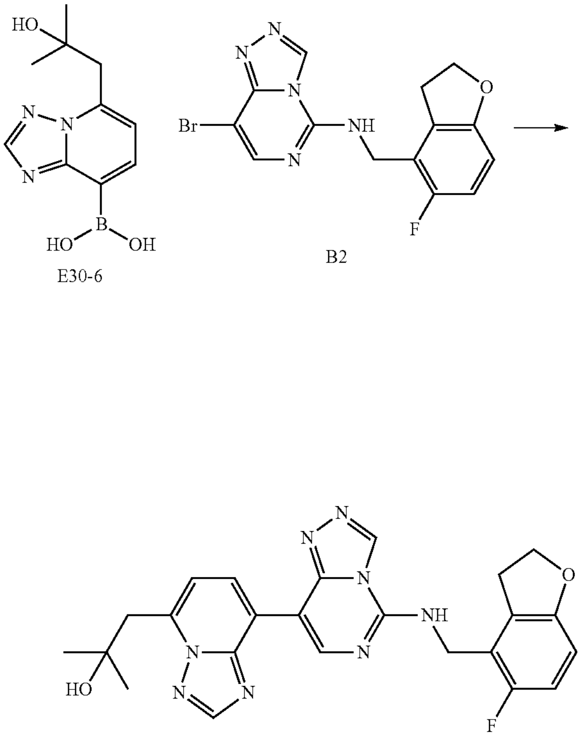

E30-6 B2

8-bromo-N-((5-fluoro-2,3-dihydrobenzofuran-4-yl) methyl)-[1,2,4]triazolo[4,3-c]pyrimidin-5-amine (80.6 mg, 0.220 mmol), sodium carbonate (176 mg, 1.66 mmol), [1,1'-bis(diphenylphosphino)ferrocene]palladium dichloride dichloromethane complex (45.2 mg, 0.055 mmol) 1,4-dioxane (1.00 mL) and water (0.500 mL) were added to the reaction solution in the previous step. The reaction mixture was raised to 100° C. and reacted for 2 hours under nitrogen atmosphere. The completion of the reaction was monitored by LCMS. The reaction mixture was cooled to room temperature, dried over anhydrous sodium sulfate, filtered, and concentrated under reduced pressure. The crude product was purified by a flash silica gel column, and then purified by HPLC to obtain 1-(8-(5-(((5-fluoro-2,3-dihydrobenzofuran-4-yl)methyl)amino)-[1,2,4]triazolo[4,3-c]pyrimidine-8-yl)-[1,2,4]triazolo[1,5-a]pyridin-5-yl)-2-methylpropan-2-ol (5.00 mg, 1.86% yield).

$^1$H NMR (400 MHz, DMSO-$d_6$) δ 9.55 (s, 1H), 9.43 (s, 1H), 9.10 (d, J=7.8 Hz, 1H), 8.94-8.87 (m, 1H), 8.59 (s, 1H), 7.30 (br d, J=7.8 Hz, 1H), 6.97 (br t, J=9.5 Hz, 1H), 6.72 (br dd, J=3.4, 8.5 Hz, 1H), 4.78 (br d, J=4.4 Hz, 2H), 4.76 (s, 1H), 4.55 (br t, J=8.6 Hz, 2H), 3.41 (br s, 2H), 3.27-3.18 (m, 2H), 1.17 (s, 6H) ppm; LCMS: m/z 475.3 $[M+H]^+$.

Example 10: 1,1,3,3-tetrafluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol Step 1: 8-bromo-[1,2,4]triazolo[1,5-a]pyridin-5-carboxylic acid E31-1

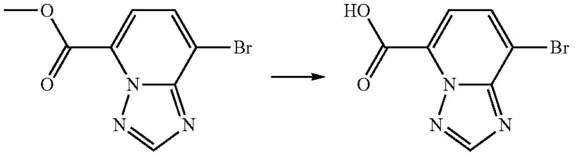

E27-3 E31-1

Methyl 8-bromo-[1,2,4]triazolo[1,5-a]pyridin-5-carboxylate E27-3 (2.50 g, 9.76 mmol), sodium hydroxide (1.17 g, 29.3 mmol) was dissolved in water (10.0 mL), methanol (20.0 mL) and tetrahydrofuran (20.0 mL). The mixture was reacted at 80° C. for 12 hours under nitrogen atmosphere. The completion of the reaction was monitored by TLC. The reaction solution was concentrated in vacuo, diluted with saturated sodium chloride solution, adjusted to pH 5 with 4M hydrochloric acid and filtered to collect the solid. The solid was washed with saturated sodium chloride solution to obtain the crude product 8-bromo-[1,2,4]triazolo[1,5-a]pyridine-5-carboxylic acid E31-1 (2.50 g, crude product) was used directly in the next step.

$^1$H NMR (400 MHz, DMSO-$d_6$) δ 8.67 (s, 1H), 8.11 (d, J=7.8 Hz, 1H), 7.67 (d, J=7.8 Hz, 1H) ppm.

Step 2: 8-bromo-[1,2,4]triazolo[1,5-a]pyridine-5-carbonyl chloride E31-2

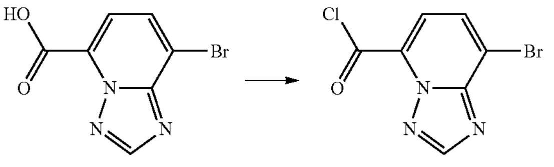

E31-1 E31-2

The mixture of 8-bromo-[1,2,4]triazolo[1,5-a]pyridine-5-carboxylic acid E31-1 (700 mg, 2.89 mmol), N,N-dimethylformamide (35 mg, 0.479 mmol) and thionyl chloride (10.0 mL) was reacted for 6 hours at 80° C. under nitrogen atmosphere. The completion of the reaction was monitored by LCMS. The reaction solution was concentrated to obtain the crude product 8-bromo-[1,2,4]triazolo[1,5-a]pyridine-5-carbonyl chloride E31-2 (770 mg, crude product).

Step 3: 2-(8-bromo-[1,2,4]triazolo[1,5-a]pyridine-5-yl)-1,1,3,3-tetrafluoropropan-2-ol E31-3

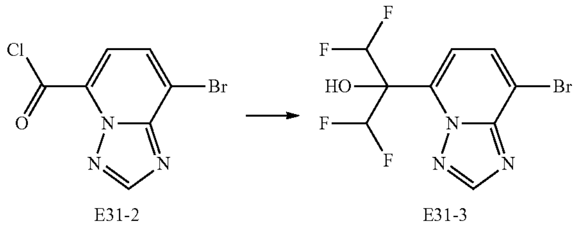 [SMILES: O=C(Cl)c1ccc(Br)c2ncnn12 ; OC(c1ccc(Br)c2ncnn12)(C(F)F)C(F)F]

E31-2 E31-3

8-bromo-[1,2,4]triazolo[1,5-a]pyridine-5-carbonyl chloride E31-2 (770 mg, 2.96 mmol), (bromodifluoromethyl) trimethylsilane (1.80 g, 8.87 mmol), triphenylphosphine (1.94 g, 7.39 mmol) and 1,3-dimethyl-3,4,5,6-tetrahydro-2-pyrimidinone (1.52 g, 11.8 mmol) in acetonitrile (10.0 mL) solution were reacted at 20° C. for 12 hours, then quenched with water (5.00 mL) and pyridine (0.935 g, 11.8 mmol). The mixture reacted for 1.5 hours at 80° C. The completion of the reaction was monitored by LCMS. The reaction solution was concentrated under reduced pressure, diluted with water and extracted with ethyl acetate. The organic phase was dried, filtered and concentrated. The crude product was separated by column chromatography to obtain a white solid product 2-(8-bromo-[1,2,4]triazolo[1,5-a]pyridin-5-yl)-1,1,3,3-tetrafluoropropan-2-ol E31-3 (300 mg, 30.6% yield).

$^1$H NMR (400 MHz, $CDCl_3$) 6.44 (s, 1H), 7.89 (d, J=8.0 Hz, 1H), 7.36 (d, J=7.6 Hz, 1H), 6.67-6.36 (m, 3H) ppm; LCMS: m/z 327.9 $[M+H]^+$.

Step 4: (5-(1,1,3,3-tetrafluoro-2-hydroxypropan-2-yl)-[1,2,4]triazolo[1,5-a]pyridin-8-yl)boric acid E31-4

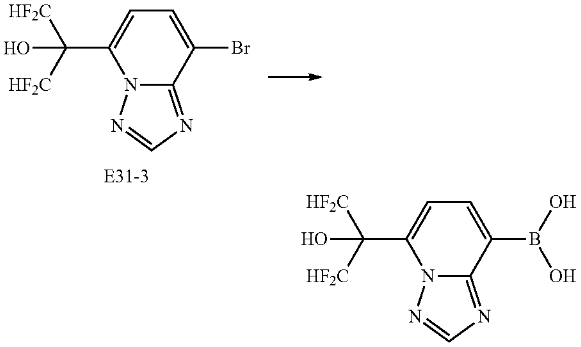

E31-3

E31-4

In a glove box, 2-(8-bromo-2-methyl-[1,2,4]triazolo[1,5-a]pyridin-5-yl)propan-2-ol E31-3 (250 mg, 0.762 mmol), bis(pinacolato)diboron (232 mg, 0.914 mmol), 1,1-bis(diphenylphosphino)ferrocene palladium chloride dichloromethane complex (62.2 mg, 0.0762 mmol), potassium acetate (150 mg, 1.52 mmol) and dioxane (5.00 mL) were added to the bottle in sequence. The reaction solution was reacted at 120° C. for 5 hours under nitrogen atmosphere. The completion of the reaction was monitored by TLC. The reaction solution was directly used in the next step.

Step 5: 1,1,3,3-tetrafluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol

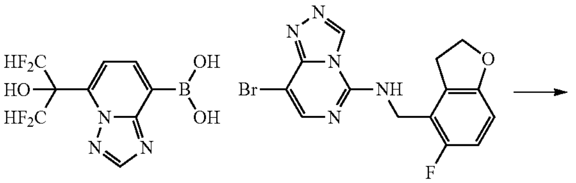

E31-4 B2

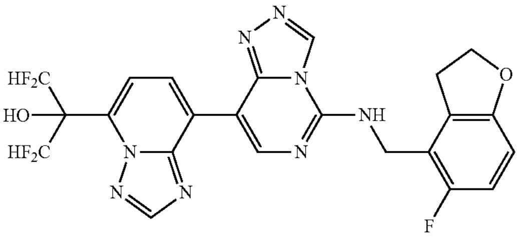

8-bromo-N-((5-fluoro-2,3-dihydrobenzofuran-4-yl)methyl)-[1,2,4]triazol[4,3-c]pyrimidin-5-amine B2 (222 mg, 0.609 mmol), potassium carbonate (211 mg, 1.52 mmol), water (1.00 mL), dioxane (5.00 mL) and 1,1-bis(diphenylphosphino)ferrocene palladium chloride dichloromethane complex (62.2 mg, 0.0761 mmol). The reaction solution was reacted at 100° C. for 2 hours under nitrogen atmosphere. The completion of the reaction was monitored by LCMS. The reaction solution was concentrated and purified by column chromatography. The crude product was then slurried with dichloromethane and methyl tert-butyl ether (10:1), then slurried with acetonitrile, and finally purified by pre-HPLC. The obtained product salt solution was adjusted to pH 8 with saturated sodium bicarbonate solution and concentrated. The solid was slurried with water, and filtered, washed, and freeze-dried to obtain the pure product 1,1,3,3-tetrafluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol (95.0 mg, 23.4% yield).

$^1$H NMR (400 MHz, DMSO-$d_6$) δ 9.55 (s, 1H), 9.45 (s, 1H), 9.23 (d, J=8.0 Hz, 1H), 9.04 (s, 1H), 8.74 (s, 1H), 7.86 (s, 1H), 7.74 (d, J=8.0 Hz, 1H), 7.17 (br t, J=53.8 Hz, 2H), 7.00-6.94 (m, 1H), 6.75-6.70 (m, 1H), 4.79 (s, 2H), 4.56 (t, J=8.8 Hz, 2H), 3.34-3.29 (m, 2H) ppm; LCMS m/z 533.3 [M+H]$^+$.

Example 11: 1-(8-(5-(((5-fluoro-2,3-dihydrobenzofuran-4-yl)methyl)amino)-triazolo[4,3-c]pyrimidin-8-yl)-[1,2,4]triazolo[1,5-a]pyridin-5-yl)propan-1-ol Step 1: 1-(8-bromo-[1,2,4]triazolo[1,5-a]pyridin-5-yl)propan-1-one E32-1

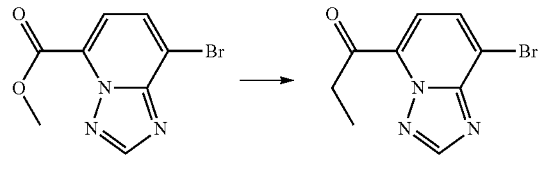

E27-3 E32-1

Methyl 8-bromo-[1,2,4]triazolo[1,5-a]pyridine-5-carboxylate E27-3 (1.50 g, 5.86 mmoL) was dissolved in tetrahydrofuran (20.0 mL). The reaction mixture was cooled to −30° C. Ethylmagnesium bromide was added dropwise. The temperature was kept and the mixture was reacted for 4 hours. The completion of the reaction was monitored by LCMS. The reaction mixture was quenched, extracted, washed, dried, concentrated, and purified by a silica gel column to obtain 1-(8-bromo-[1,2,4]benzotriazol[1,5-a]pyridin-5-yl)propan-1-one E32-1 (1.00 g, 67.2% yield).

$^1$H NMR (400 MHz, DMSO-$d_6$) δ 8.72 (s, 1H), 8.14 (d, J=7.9 Hz, 1H), 7.61 (d, J=7.9 Hz, 1H), 3.40-3.34 (m, 2H), 1.14 (t, J=7.1 Hz, 3H) ppm; LCMS: m/z 256.0 [M+3]$^+$.

Step 2: 1-(8-bromo-[1,2,4]benzotriazol[1,5-a]pyridin-5-yl)propan-1-ol E32-2

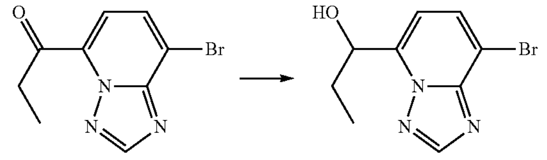

E32-1 E32-2

1-(8-bromo-[1,2,4]benzotriazol[1,5-a]pyridin-5-yl)propan-1-one E32-1 (1.00 g, 3.94 mmoL) was dissolved in methanol (20.0 mL). The reaction mixture was cooled to −5° C. Sodium borohydride (447 mg, 11.8 mmoL) was added. The reaction mixture was raised to 0° C. and reacted for 2 hours. The completion of the reaction was monitored by TLC. The reaction mixture was quenched, concentrated, extracted, washed, dried, and concentrated, and purified by a silica gel column to obtain 1-(8-bromo-[1,2,4]triazolo[1,5-a]pyridin-5-yl)propan-1-ol E32-2 (800 mg, 79.0% yield).

$^1$H NMR (400 MHz, DMSO-$d_6$) δ 8.60 (s, 1H), 8.05 (d, J=7.8 Hz, 1H), 7.17-7.15 (m, 1H), 5.88 (d, J=5.1 Hz, 1H), 5.19-5.13 (m, 1H), 2.02-1.90 (m, 1H), 1.74-1.62 (m, 1H), 0.92 (t, J=7.4 Hz, 3H) ppm; LCMS: m/z 258.0 [M+3]$^+$.

Step 3: (5-(1-hydroxypropyl)-[1,2,4]triazolo[1,5-a]pyridin-8-yl)boronic acid

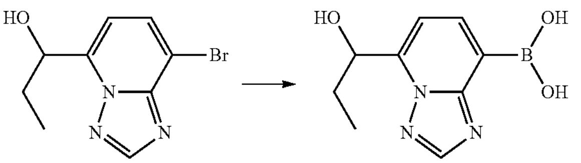

E32-2 E32-3

1-(8-bromo-[1,2,4]triazolo[1,5-a]pyridin-5-yl)propan-1-ol E32-2 (800 mg, 3.12 mmol), bis(pinacolato)diboron (872 mg, 3.44 mmol), potassium acetate (919 mg, 9.37 mmol) and [1,1'-bis(diphenylphosphino)ferrocene]palladium chloride dichloromethane complex (510 mg, 0.624 mmol) were dissolved in 1,4-dioxane (8.00 mL). The temperature was raised to 120° C., and the reaction mixture was reacted under nitrogen atmosphere for 5 hours. No raw materials were remained by TLC detection, and the reaction solution was directly used in the next step without treatment.

LCMS: m/z 222.0 $[M+3]^+$.

Step 4: 1-(8-(5-(((5-fluoro-2,3-benzodihydrofuran-4-yl)methyl)amino)-[1,2,4]triazolo[4,3-c]pyrimidin-8-yl)-[1,2,4]triazolo[1,5-a]pyridin-5-yl)propan-1-ol E32-4

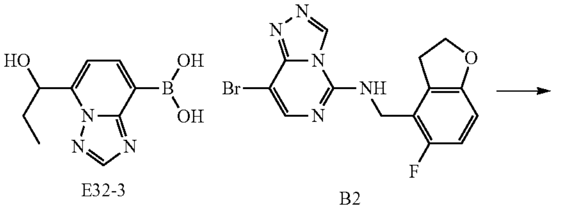

E32-3 B2

-continued

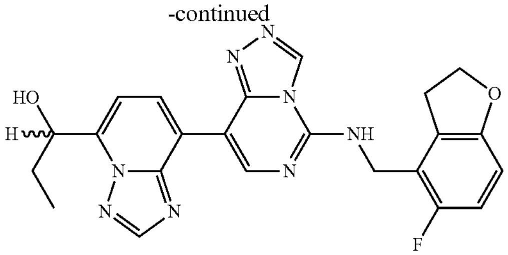

E32-4

8-bromo-N-((5-fluoro-2,3-benzodihydrofuran-4-yl)methyl)-[1,2,4]triazolo[4,3-c]pyrimidin-5-amine B2 (512 mg, 1.40 mmol), sodium carbonate (993 mg, 9.36 mmol), [1,1'-bis(diphenylphosphino)ferrocene]palladium dichloride dichloromethane complex (509 mg, 0.624 mmol), 1,4-dioxane (3.00 mL) and water (1.00 mL) were added to the reaction solution in the previous step. The reaction was raised to 100° C. and reacted for 2 hours under nitrogen atmosphere. The completion of the reaction was monitored by LCMS. The temperature was cooled to room temperature. The mixture was concentrated under reduced pressure. The crude product was purified by a flash silica gel column to obtain 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-1-ol E32-4 (product: 300 mg, 21.0% yield).

$^1H$ NMR (400 MHz, DMSO-$d_6$) δ 9.55 (s, 1H), 9.43 (s, 1H), 9.18 (d, J=7.8 Hz, 1H), 8.95-8.89 (m, 1H), 8.64 (s, 1H), 7.41 (d, J=7.8 Hz, 1H), 7.00-6.93 (m, 1H), 6.74-6.69 (m, 1H), 5.85 (d, J=5.0 Hz, 1H), 5.30-5.24 (m, 1H), 4.81-4.74 (m, 2H), 4.55 (t, J=8.7 Hz, 2H), 3.32-3.30 (m, 2H), 2.08-1.96 (m, 1H), 1.80-1.68 (m, 1H), 0.96 (t, J=7.3 Hz, 3H) ppm; LCMS: m/z 461.0 $[M+H]^+$.

Step 5: separation of 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-1-ol E32-4

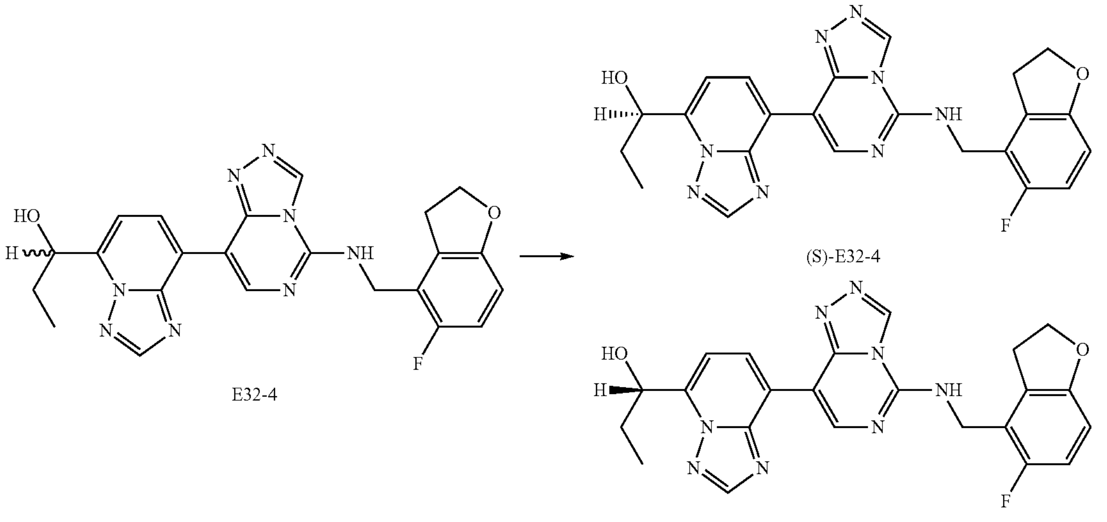

E32-4

(S)-E32-4

(R)-E32-4

1-(8-(5-(((5-fluoro-2,3-benzodihydrofuran-4-yl)methyl) amino)-[1,2,4]triazolo[4,3-c]pyrimidin-8-yl)-[1,2,4]triazolo [1,5-a]pyridin-5-yl)propan-1-ol E32-4 was chiral separated by SFC. Separation method: column: DAICEL CHIRALPAK IG (250 mm*30 m m, 10 m); mobile phase: A [0.10% $NH_3H_2O$ IPA]; B (ethanol): 5%-40% gradient, 4 mL/min) to obtain (S)-1-(8-(5-(((5-fluoro-2,3-benzodihydrofuran-4-yl) methyl)amino)-[1,2,4]triazolo[4,3-c]pyrimidin-8-yl)-[1,2,4] triazolo[1,5-a]pyridin-5-yl)propan-1-ol ((S)-E32-4) or (R)-1-(8-(5-(((5-fluoro-2,3-benzodihydrofuran-4-yl)methyl) amino)-[1,2,4]triazole[4,3-c]pyrimidin-8-yl)-[1,2,4]triazolo [1,5-a]pyridin-5-yl)propan-1-ol ((R)-E32-4, one of which has a retention time of 2.782 min (compound e), and the other enantiomer has a retention time of 2.907 min (compound f).

Compound e: $^1H$ NMR (400 MHz, DMSO-$d_6$) δ 9.55 (s, 1H), 9.43 (s, 1H), 9.18 (d, J=7.8 Hz, 1H), 8.95-8.89 (m, 1H), 8.63 (s, 1H), 7.41 (d, J=7.9 Hz, 1H), 7.01-6.93 (m, 1H), 6.75-6.69 (m, 1H), 5.84 (d, J=5.0 Hz, 1H), 5.30-5.24 (m, 1H), 4.78 (br d, J=4.5 Hz, 2H), 4.55 (t, J=8.7 Hz, 2H), 3.32-3.30 (m, 2H), 2.08-1.96 (m, 1H), 1.80-1.68 (m, 1H), 0.96 (t, J=7.3 Hz, 3H) ppm.

Compound f: $^1H$ NMR (400 MHz, DMSO-$d_6$) δ 9.55 (s, 1H), 9.43 (s, 1H), 9.18 (d, J=7.8 Hz, 1H), 8.95-8.89 (m, 1H), 8.64 (s, 1H), 7.41 (d, J=7.8 Hz, 1H), 7.00-6.93 (m, 1H), 6.74-6.69 (m, 1H), 5.85 (d, J=5.0 Hz, 1H), 5.30-5.24 (m, 1H), 4.81-4.74 (m, 2H), 4.55 (t, J=8.7 Hz, 2H), 3.32-3.30 (m, 2H), 2.08-1.96 (m, 1H), 1.80-1.68 (m, 1H), 0.96 (t, J=7.3 Hz, 3H) ppm.

Example 12: 2-(8-(5-(((5-fluoro-2,3-dihydrobenzofuran-4-yl)methyl)amino)-triazolo[4,3-c]pyrimidin-8-yl)-6-methyl-[1,2,4]triazolo[1,5-a]pyridin-5-yl) propan-2-ol

Step 1: methyl 6-amino-3-methylpyridine-2-carboxylate E33-2

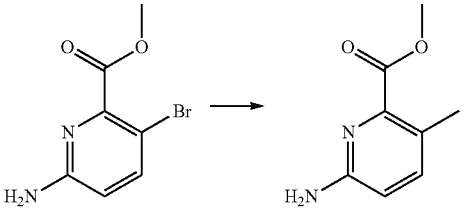

E33-1 E33-2

Methyl 6-amino-3-bromopyridine-2-carboxylate E33-1 (5 g, 21.6 mmol), methylboronic acid (3.24 g, 54.1 mmol), 2-dicyclohexylphosphino-2',6'-diisopropoxy-1,1'-biphenyl) [2-(2'-amino-1,1'-biphenyl)]palladium(II) methanesulfonate (904 mg, 1.08 mmol), potassium carbonate (4.49 g, 32.4 mmol) and 1,4-dioxane (50 mL) were mixed, and the gas was extracted and replaced by nitrogen for three times. The reaction solution was raised to 100° C. under nitrogen atmosphere and reacted for 12 hours. The completion of the reaction was monitored by LCMS. The reaction mixture was cooled to room temperature, and concentrated under reduced pressure. The concentrate was purified by a flash silica gel column to obtain methyl 6-amino-3-methylpyridine-2-carboxylate E33-2 (3.50 g, 21.06 mol, 97.3% yield).

$^1H$ NMR (400 MHz, $CDCl_3$) δ 7.15 (d, J=8.4 Hz, 1H), 6.42 (d, J=8.4 Hz, 1H), 4.54 (br s, 2H), 3.75 (s, 3H), 2.24 (s, 3H).

Step 2: methyl 6-amino-5-bromo-3-methylpyridine-2-carboxylate E33-3

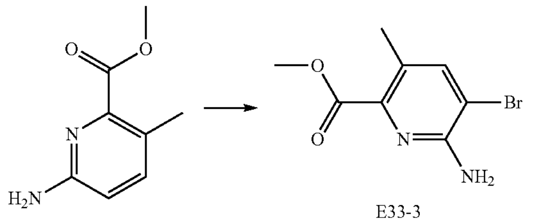

E33-2 E33-3

Methyl 6-amino-3-methylpyridine-2-carboxylate E33-2 (3.5 g, 21.1 mmol), tetrabutylammonium tribromide (15.2 g, 31.6 mmol) were dissolved in dichloromethane (42.0 mL). The reaction mixture was reacted at 25° C. for 12 hours, and no raw materials were remained by TLC detection. The reaction solution was quenched with sodium sulfite, extracted and dried, and concentrated under reduced pressure. The concentrate was purified by a flash silica gel column to obtain methyl 6-amino-5-bromo-3-methylpyridine-2-carboxylate E33-3 (2.10 g, 8.57 mmol, 40.7% yield).

$^1H$ NMR (400 MHz, $CDCl_3$) δ 7.63 (s, 1H), 5.05 (br s, 2H), 3.95 (s, 3H), 2.44 (s, 3H)

Step 3: methyl 5-bromo-6-(((dimethylamino)methylene)amino)-3-methylpyridine-2-carboxylate E33-4

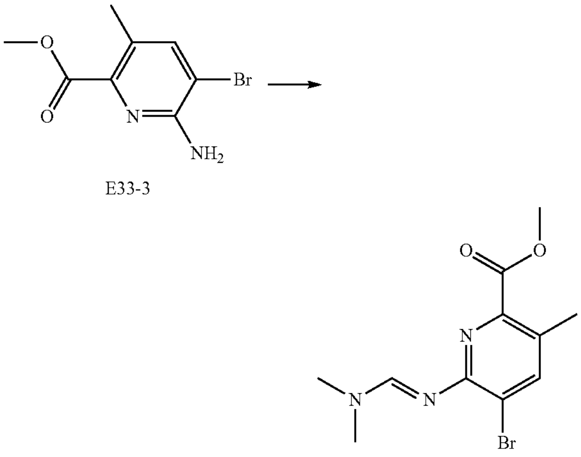

E33-3

E33-4

Methyl 6-amino-5-bromo-3-methylpyridine-2-carboxylate E33-3 (2.10 g, 8.57 mmol) and N,N-dimethylformamide dimethyl acetal (2.04 g, 17.1 mmol) were dissolved in toluene (20.0 mL). The reaction solution was raised to 110° C. and reacted for 4 hours. No raw materials were remianed by TLC detection, and the reaction solution was concentrated to obtain the crude product methyl 5-bromo-6-(((dimethylamino)methylene)amino)-3-methylpyridine-2-carboxylate E33-4 (2.30 g, 7.66 mmol, 89.4% yield).

$^1$H NMR (400 MHz, $CDCl_3$) δ 8.40 (s, 1H), 7.75 (s, 1H), 3.94 (s, 3H), 3.16 (s, 3H), 3.14 (s, 3H), 2.46 (s, 3H) ppm.

Step 4: Methyl (5-bromo-6-((((hydroxylamino) methylene)amino)-3-methylpyridine-2-carboxylate E33-5

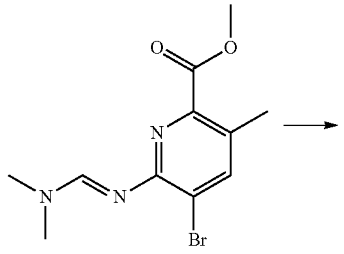

E33-4

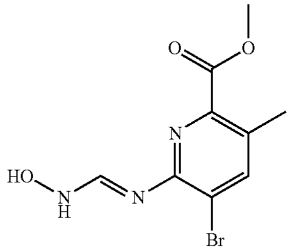

E33-5

Methyl (5-bromo-6-(((dimethylamino)methylene) amino)-3-methylpyridine-2-carboxylate E33-4 (2.30 g, 7.66 mmol), hydroxylamine hydrochloride (1.06 g, 15.3 mmol), sodium acetate (1.26 g, 15.3 mmol) and ethanol (23.0 mL) were added in a reaction flask in sequence. The reaction solution was raised to 50° C. under nitrogen atmosphere and reacted for 4 hours. The completion of the reaction was monitored by LCMS. The reaction solution was cooled to room temperature and filtered to obtain Methyl (5-bromo-6-(((hydroxylamino)methylene)amino)-3-methylpyridine-2-carboxylate E33-5 (1.12 g, 50.7% yield).

$^1$H NMR (400 MHz, $CDCl_3$) δ 8.23-8.20 (m, 2H), 7.75 (s, 1H), 3.95 (s, 3H), 2.48 (s, 3H) ppm.

Step 5: Methyl 8-bromo-6-methyl-[1,2,4]triazolo[1, 5-a]pyridine-5-carboxylate E33-6

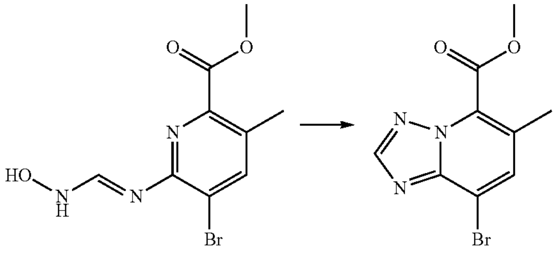

E33-5 E33-6

Polyphosphoric acid (3.89 mmol, 10.0 mL) was added to methyl (5-bromo-6-(((hydroxylamino)methylene)amino)-3-methylpyridine-2-carboxylate E33-5 (1.12 g, 3.89 mmol) at room temperature. Then the mixture was slowly raised to 95° C., stirred and reacted for 2 hours. After the reaction was completed, it was quenched by adding saturated sodium bicarbonate aqueous solution at 0° C. The reaction mixture was extracted with ethyl acetate, dried, concentrated and purified by column chromatography to obtain the white solid product methyl 8-bromo-6-methyl-[1,2,4]triazolo[1,5-a] pyridine-5-carboxylate E33-6 (1.01 g, 3.74 mmol, 96.2% yield)

$^1$H NMR (400 MHz, $CDCl_3$) δ 8.38 (s, 1H), 7.70 (s, 1H), 4.11 (s, 3H), 2.48 (s, 3H) ppm.

Step 6: 2-(8-bromo-6-methyl-[1,2,4]triazolo[1,5-a] pyridin-5-yl)propan-2-ol E33-7

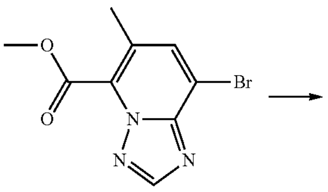

E33-6

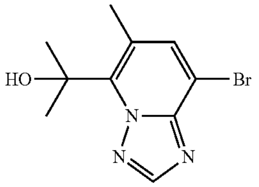

E33-7

Methylmagnesium bromide (3M, 12.4 mL) was added dropwise to a solution (10.0 mL) of methyl 8-bromo-6-methyl-[1,2,4]triazolo[1,5-a]pyridine-5-carboxylate E33-6 (1.01 g, 3.74 mmol) in THE at −30° C. and the mixture was stirred at this temperature for 3 hours. After the reaction was completed, water (30 mL) was added to the reaction solution to quench. The mixture was extracted with ethyl acetate, dried, concentrated and purified by a flash silica gel column to obtain 2-(8-bromo-6-methyl-[1,2,4]triazolo[1,5-a]pyridin-5-yl)propan-2-ol E33-7 (410 mg, 1.52 mmol, 40.6% yield).

$^1$H NMR (400 MHz, $CDCl_3$) δ 8.29 (s, 1H), 7.55 (s, 1H), 6.93 (s, 1H), 2.51 (s, 3H), 1.76 (s, 6H) ppm.

Step 7: (5-(2-hydroxypropyl-2-yl)-6-methyl-[1,2,4] triazolo[1,5-a]pyridin-8-yl)boronic acid E33-8

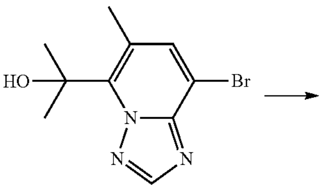

E33-7

-continued

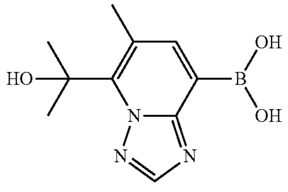

E33-8

Compound 2-(8-bromo-6-methyl-[1,2,4]triazolo[1,5-a]pyridin-5-yl)propan-2-ol E33-7 (310 mg, 1.15 mmol), bis(pinacolato)diboron (320 mg, 1.26 mmol), potassium acetate (225 mg, 2.30 mmol), [1,1'-bis(diphenylphosphino)ferrocene]palladium dichloride dichloromethane complex (187 mg, 0.229 mmol), 1,4-dioxane (3.00 mL) were added in sequence to a reaction flask in a glove box. The temperature of the reaction was raised to 120° C. The reaction was carried out under nitrogen atmosphere for 7 hours. No raw materials were remianed by LCMS detection, and the reaction solution was directly used in the next step without treatment.

Step 8: 2-(8-(5-(((5-fluoro-2,3-dihydrobenzofuran-4-yl)methyl)amino)-[1,2,4]triazolo[4,3-c] pyrimidin-8-yl)-6-pyrimidin-8-yl-[1,2,4]triazolo[1,5-a]pyridin-5-yl)propan-2-ol

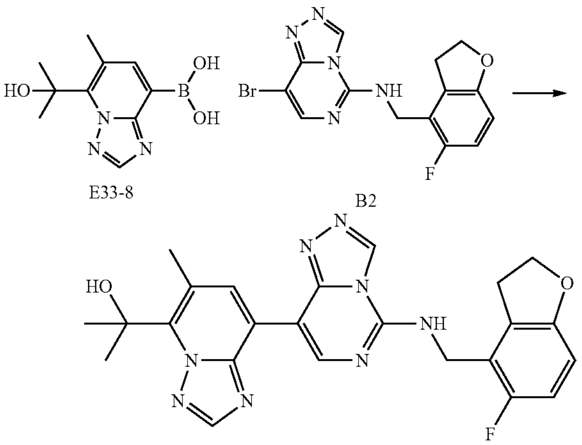

E33-8 B2

8-bromo-N-((5-fluoro-2,3-dihydrobenzofuran-4-yl)methyl)-[1,2,4]triazolo[4,3-c]pyrimidin-5-amine (433 mg, 1.19 mmol), potassium carbonate (470 mg, 3.40 mmol), [1,1'-bis(diphenyl)ferrocene]palladium dichloride dichloromethane (124 mg, 0.170 mmol), 1,4-dioxane (5 mL) and water (1 mL) were added to the reaction solution in the previous step. The reaction solution was raised to 100° C. under nitrogen atmosphere for 2 hours. The completion of the reaction was monitored by LCMS. The reaction mixture was cooled to room temperature and concentrated under reduced pressure. The concentrate was purified by a flash silica gel column to obtain the crude product, and then it was separated by HPLC and lyophilized to obtain 2-(8-(5-(((5-fluoro-2,3-dihydrobenzofuran-4-yl)methyl)amino)-[1,2,4]triazolo[4,3-c]pyrimidin-8-yl)-6-methyl-[1,2,4]triazolo[1,5-a]pyridin-5-yl)propan-2-ol (240 mg, 0.505 mmol, 29.7% yield).

$^1$H NMR (400 MHz, DMSO-$d_6$) δ 9.53 (s, 1H), 9.36 (s, 1H), 8.92 (s, 2H), 8.55 (s, 1H), 6.96 (t, J=9.4 Hz, 1H), 6.72 (dd, J=3.9, 8.6 Hz, 1H), 5.79 (s, 1H), 4.77 (s, 2H), 4.55 (t, J 8.8 Hz, 2H), 3.35-3.35 (m, 2H), 2.77 (s, 3H), 1.86 (s, 6H) ppm.

Example 13: 2-(8-(5-(((5-fluoro-2,3-dihydrobenzofuran-4-yl)methyl)amino)-triazolo[4,3-c]pyrimidin-8-yl)-2-methyl-[1,2,4]triazolo[1,5-c]pyrimidin-5-yl)propan-2-ol Step 1: 4-amino-5-bromopyrimidine-2-carbonitrile E34-2

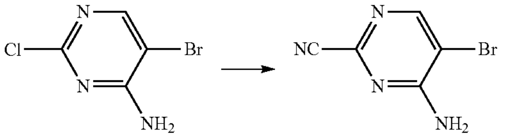

E34-1 E34-2

A solution of sodium cyanide (14.1 g, 287 mmol) in water (20 mL) was added to a solution of 5-bromo-2-chloropyrimidin-4-amine E34-1 (50 g, 239 mmol) and triethylenediamine (26.9 g, 239 mmol) in dimethylsulfoxide solution (450 mL) at 25° C. The temperature of the reaction solution was raised to 60° C., and the reaction was stirred for 18 hours at 60° C. The completion of the reaction was monitored by LCMS. The reaction solution is cooled to room temperature. Water and ethyl acetate were added to the mixture. The organic phase was dried and concentrated, and the concentrate is purified by a flash silica gel column to obtain 4-amino-5-bromopyrimidine-2-carbonitrile E34-2 (29.0 g, 59.5% yield).

$^1$H NMR (400 MHz, DMSO-$d_6$) δ 8.49 (s, 1H), 8.35 (br s, 1H), 7.55 (br s, 1H) ppm; LCMS: m/z 201.0 [M+3H]$^+$.

Step 2: methyl 4-amino-5-bromopyrimidine-2-carboxylate E34-3

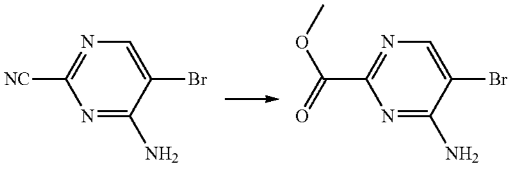

E34-2 E34-3

4-amino-5-bromopyrimidine-2-carbonitrile E34-2 (29.0 g, 145 mmol) was dissolved in methanol (290 mL). Then concentrated sulfuric acid (533 g, 5.33 mol) was added dropwise at 0° C., and the reaction solution was raised to 70° C. and reacted for 12 hours. No remaining raw material was remained by TLC detection. The pH of the reaction solution was adjusted to 7. The reaction mixture was extracted. The organic phase was washed with saline, then dried over sodium sulfate, filtered, concentrated and purified by a flash silica gel column to obtain methyl 4-amino-5-bromopyrimidine-2-carboxylate E34-3 (17.0 g, 49.2% yield).

$^{1}H$ NMR (400 MHz, DMSO-$d_6$) δ 8.46 (s, 1H), 8.05 (s, 1H), 7.28 (s, 1H), 3.82 (s, 3H) ppm; LCMS: m/z 234.0 $[M+3H]^+$.

Step 3: Methyl (E)-5-bromo-4-((1-(dimethylamino) ethylidene)amino)pyrimidine-2-carboxylate

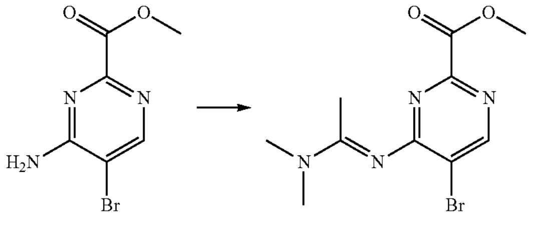

E34-3 E34-4

Methyl 4-amino-5-bromopyrimidine-2-carboxylate E34-3 (7.00 g, 30.2 mmoL), N,N-dimethylacetamide dimethyl acetal (12.1 g, 90.5 mmoL) were dissolved in toluene (70.0 mL). The reaction solution was raised to 100° C. and reacted for 1.5 hours under nitrogen atmosphere. The completion of the reaction was monitored by LCMS. The temperature was cooled to room temperature. The reaction solution was concentrated and dried to obtain methyl (E)-5-bromo-4-((1-(dimethylamino)ethylidene)amino)pyrimidine-2-carboxylate E34-4 (8.00 g, crude product).

$^{1}H$ NMR (400 MHz, DMSO-$d_6$) δ 8.67 (s, 1H), 3.85-3.81 (m, 3H), 3.16-3.11 (m, 6H), 2.16 (s, 3H) ppm; LCMS: m/z 302.9 $[M+3H]^+$.

Step 4: methyl (E)-5-bromo-4-((1-(hydroxylamino) ethylidene)amino)pyrimidine-2-carboxylate E34-5

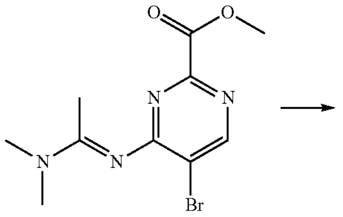

E34-4

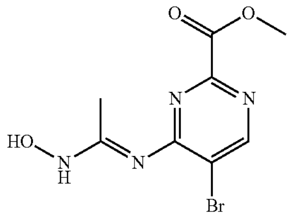

E34-5

Methyl (E)-5-bromo-4-((1-(dimethylamino)ethylidene) amino)pyrimidine-2-carboxylate E34-4 (8.00 g, 26.6 mmoL), hydroxylamine hydrochloride (3.69 g, 53.1 mmoL) were dissolved in methanol (80.0 mL). The reaction solution was reacted for 3 hours at 20° C. The completion of the reaction was monitored by LCMS. The reaction solution was concentrated under reduced pressure, slurried, and dried to obtain methyl (E)-5-bromo-4-((1-(hydroxylamino)ethylidene)amino)pyrimidine-2-carboxylate E34-5 (7.10 g, crude product).

$^{1}H$ NMR (400 MHz, DMSO-$d_6$) δ 10.93 (s, 1H), 8.84 (s, 1H), 8.77 (s, 1H), 3.87 (s, 3H), 2.40 (s, 3H) ppm; LCMS: m/z 289.0 $[M+H]^+$.

Step 5: methyl 8-bromo-2-methyl-[1,2,4]triazolo[1, 5-c]pyrimidine-5-carboxylate E34-6

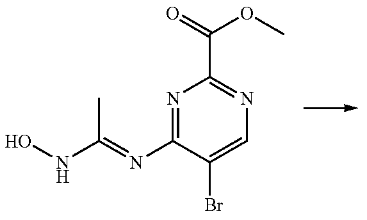

E34-5

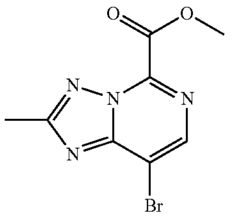

E34-6

Methyl (E)-5-bromo-4-((1-(hydroxylamino)ethylidene) amino)pyrimidine-2-carboxylate E34-5 (7.10 g, 24.5 mmoL) was dissolved in polyphosphoric acid (70.0 mL). The mixture solution reacted for 2.5 hours at 85° C. The completion of the reaction was monitored by LCMS. The pH of the reaction solution was adjusted to 7 with sodium bicarbonate. The reaction solution was extracted and concentrated to obtain methyl 8-bromo-2-methyl-[1,2,4]triazolo [1,5-c]pyrimidine-5-carboxylate E34-6 (2.60 g, 39.0% yield).

$^{1}H$ NMR (400 MHz, DMSO-$d_6$) δ 8.63 (s, 1H), 4.02 (s, 3H), 2.57 (s, 3H) ppm; LCMS: m/z 272.9 $[M+3H]^+$.

Step 6: 2-(8-bromo-2-methyl-[1,2,4]triazolo[1,5-c] pyrimidin-5-yl)propan-2-ol E34-7

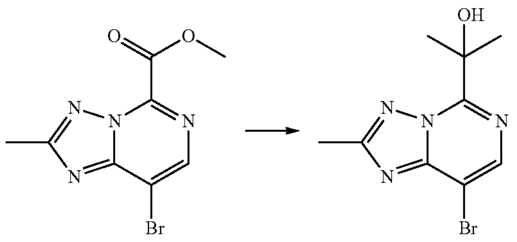

E34-6 E34-7

Methyl 8-bromo-2-methyl-[1,2,4]triazolo[1,5-c]pyrimidine-5-carboxylate E34-6 (1.60 g, 5.90 mmol) was dissolved in tetrahydrofuran (100 mL). The temperature of the mixture was cooled to −30° C. Methylmagnesium bromide (3M, 9.84 mL) was added dropwise. The temperature was kept for 0.5 hours. The completion of the reaction was monitored by TLC. The reaction solution was quenched, extracted, dried and concentrated. The crude product was separated by a flash silica gel column to obtain 2-(8-bromo-2-methyl-[1,2,4]triazolo[1,5-c]pyrimidin-5-yl)propan-2-ol E34-7 (180 mg, 20.2% yield).

$^1$H NMR (400 MHz, DMSO-$d_6$) δ 8.53 (s, 1H), 5.58 (s, 1H), 2.57 (s, 3H), 1.70 (s, 6H) ppm; LCMS: m/z 273.0 $[M+3H]^+$.

Step 7: (5-(2-hydroxypropyl-2-yl)-2-methyl-[1,2,4]triazolo[1,5-c]pyrimidin-8-yl)boronic acid

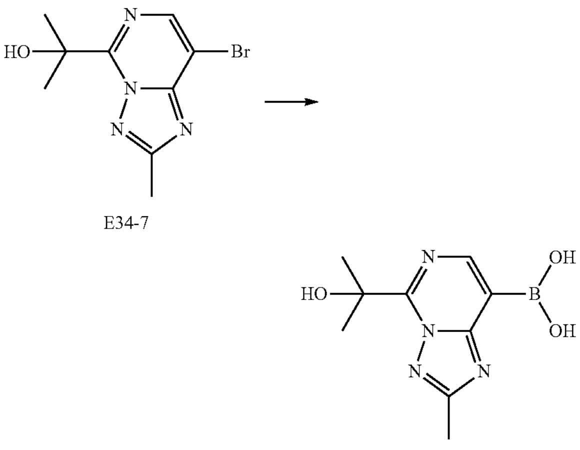
E34-7

E34-8

2-(8-bromo-[1,2,4]triazolo[1,5-c]pyrimidin-5-yl)propan-2-ol E34-7 (300 mg, 1.11 mmol), bis(pinacolato)diboron (309 mg, 1.22 mmol), potassium acetate (325 mg, 3.32 mmol), [1,1'-bis(diphenylphosphino)ferr°Cene]palladium dichloride dichloromethane complex (180 mg, 0.221 mmol) were dissolved in 1,4-dioxane (3.00 mL). The temperature was raised to 120° C., and the reaction mixture was reacted for 5 hours under nitrogen atmosphere. No raw materials were remained by TLC detection, and the reaction solution was directly used in the next step without treatment.

Step 8: 2-(8-(5-(((5-fluoro-2,3-dihydrobenzofuran-4-yl)methyl)amino)-[1,2,4]triazolo[4,3-c]pyrimidin-8-yl)-2-methyl-[1,2,4]triazolo[1,5-c]pyrimidin-5-yl)propan-2-ol

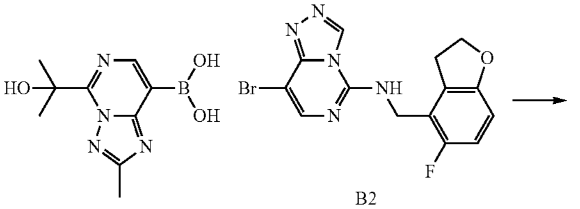
E34-8

B2

-continued

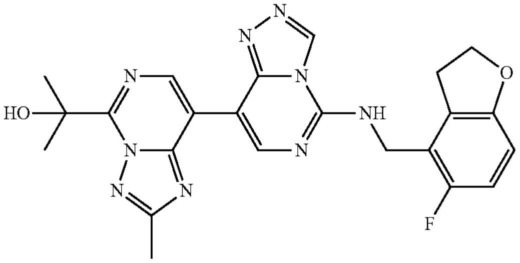

8-bromo-N-((5-fluoro-2,3-benzodihydrofuran-4-yl)methyl)-[1,2,4]triazolo[4,3-c]pyrimidine-5-amine E34-8 (260 mg, 1.10 mmol), sodium carbonate (350 mg, 3.30 mmol), [1,1'-bis(diphenylphosphino)ferrocene]palladium dichloride dichloromethane complex (179 mg, 0.220 mmol), 1,4-dioxane (3.00 mL) and water (1.00 mL) were added to the reaction solution in the previous step. The reaction was raised to 100° C. and reacted for 2 hours under nitrogen atmosphere. The completion of the reaction was monitored by LCMS. The temperature was cooled to room temperature. The mixture was concentrated under reduced pressure. The crude product was purified by a flash silica gel column to obtain 2-(8-(5-(((5-fluoro-2,3-dihydrobenzofuran-4-yl)methyl)amino)-[1,2,4]triazolo[4,3-c]pyrimidin-8-yl)-2-methyl-[1,2,4]triazolo[1,5-c]pyrimidin-5-yl)propan-2-ol (84.0 mg, 15.88% yield).

$^1$H NMR (400 MHz, DMSO-$d_6$) δ 9.66 (s, 1H), 9.55 (s, 1H), 9.35 (s, 1H), 9.07-8.99 (m, 1H), 7.01-6.93 (m, 1H), 6.75-6.69 (m, 1H), 5.63 (s, 1H), 4.82-4.76 (m, 2H), 4.55 (t, J 8.7 Hz, 2H), 3.31-3.28 (m, 2H), 2.64 (s, 3H), 1.76 (s, 6H) ppm; LCMS: m/z 476.4 $[M+H]^+$.

According to the method of Example 12, in step 3, N,N-dimethylacetamide dimethyl acetal was replaced by N,N-dimethylformamide dimethyl acetal, and other conditions remain unchanged. And the following compound can be obtained:

Example 14: 2-(8-(5-(((5-fluoro-2,3-dihydrobenzofuran-4-yl)methyl)amino)-triazolo[4,3-c]pyrimidin-8-yl)-[1,2,4]triazolo[1,5-c]pyrimidin-5-yl)propan-2-ol

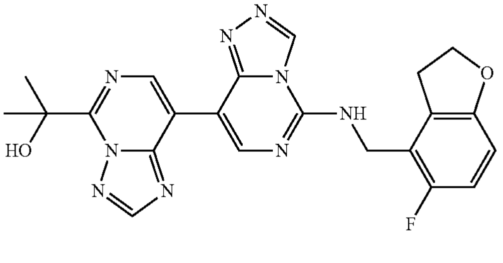 [SMILES: CC(C)(O)c1ncc(-c2cnc(NCc3c(F)ccc4c3CCO4)n3cnnc23)c2ncnn12]

$^1$H NMR (400 MHz, DMSO-$d_6$) δ 9.72 (s, 1H), 9.56 (s, 1H), 9.38 (s, 1H), 9.05 (br s, 1H), 8.84 (s, 1H), 6.97 (t, J=9.4 Hz, 1H), 6.72 (dd, J=3.8, 8.7 Hz, 1H), 5.66 (s, 1H), 4.79 (s, 2H), 4.55 (t, J=8.8 Hz, 2H), 3.36-3.34 (m, 2H), 1.78 (s, 6H) ppm; LCMS: m/z 462.0 $[M+H]^+$.

Example 15: 2-(6-fluoro-8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol Step 1: methyl 6-amino-5-bromo-3-fluoropyridine-2-carboxylate E35-2

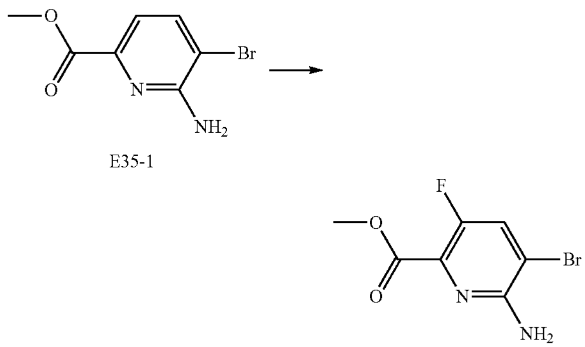

E35-1

E35-2

Methyl 6-amino-5-bromopyridine-2-carboxylate E35-1 (5.00 g, 21.6 mmol) and 1-chloromethyl-4-fluoro-1,4-diazabicyclo[2.2.2]octane bis(tetrafluoroborate) (9.97 g, 28.1 mmol) were dissolved in acetonitrile (25.0 mL). The reaction solution was stirred for 12 hours at 90° C. under nitrogen atmosphere. The remaining raw material was monitored by LCMS. The reaction solution was cooled to room temperature. Ethyl acetate was added to the reaction solution, and the reaction solution was washed with saturated brine. The organic phase was dried and concentrated, and the crude product was purified by a flash silica gel column to obtain methyl 6-amino-5-bromo-3-fluoropyridine-2-carboxylate E35-2 (620 mg, 9.20% yield).

$^1H$ NMR (400 MHz, DMSO-$d_6$) δ 8.05 (d, J=9.4 Hz, 1H), 6.55 (s, 2H), 3.82 (s, 3H), LCMS m/z 251.1 $[M+H]^+$.

Step 2: Methyl 5-bromo-6-(((dimethylamino)methylene)amino)-3-fluoropyridine-2-carboxylate E35-3

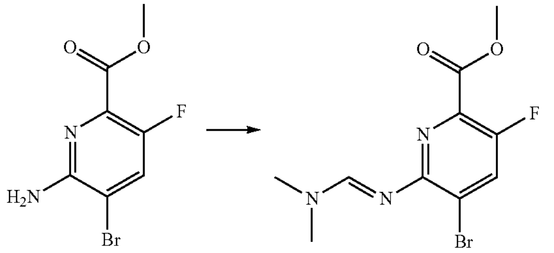

E35-2 E35-3

Methyl 6-amino-5-bromo-3-fluoropyridine-2-carboxylate E35-2 (1.50 g, 6.02 mmol) and N,N-dimethylformamide dimethyl acetal (2.87 g, 24.1 mmol) were dissolved in toluene (10.0 mL). The reaction solution was stirred for 3 hours at 100° C. under nitrogen atmosphere. The completion of the reaction was monitored by LCMS. The reaction solution was concentrated under reduced pressure, and the crude product was purified by a flash silica gel column to obtain methyl 5-bromo-6-(((dimethylamino)methylene)amino)-3-fluoropyridine-2-carboxylate E35-3 (1.40 g, 68.7% yield).

$^1H$ NMR (400 MHz, DMSO-$d_6$) δ 8.28 (s, 1H), 8.19 (d, J=9.3 Hz, 1H), 3.86 (s, 3H), 3.13 (s, 3H), 3.04 (s, 3H). LCMS m/z 306.1 $[M+H]^+$.

Step 3: Methyl 5-bromo-3-fluoro-6-(((hydroxylamino)methylene)amino)pyridine-2-carboxylate E35-4

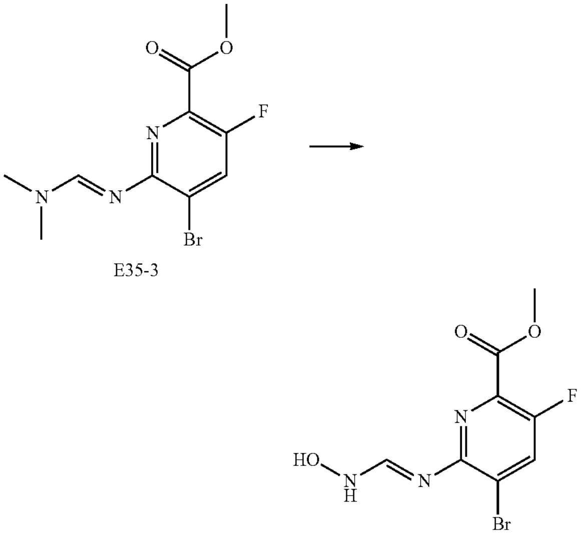

E35-3

E35-4

Methyl 5-bromo-6-(((dimethylamino)methylene)amino)-3-fluoropyridine-2-carboxylate E35-3 (1.40 g, 4.06 mmol) and hydroxylamine hydrochloride (639 mg, 9.21 mmol) were dissolved in ethanol (6.00 mL). The reaction solution was stirred at 50° C. for 5 hours under nitrogen atmosphere. The completion of the reaction was monitored by LCMS. The reaction solution was concentrated under reduced pressure, and the crude product was purified with a flash silica gel column to obtain methyl 5-bromo-3-fluoro-6-(((hydroxylamino)methylene)amino)pyridine-2-carboxylate E35-4 (1.30 g, 87.0% yield).

$^1H$ NMR (400 MHz, DMSO-$d_6$) δ 10.83 (s, 1H), 8.44 (d, J=9.3 Hz, 1H), 8.23 (d, J=9.8 Hz, 1H), 7.81 (d, J=9.5 Hz, 1H), 3.89 (s, 3H). LCMS m/z 292.1 $[M+H]^+$.

Step 4: Methyl 8-bromo-6-fluoro-[1,2,4]triazolo[1,5-a]pyridine-5-carboxylate E35-5

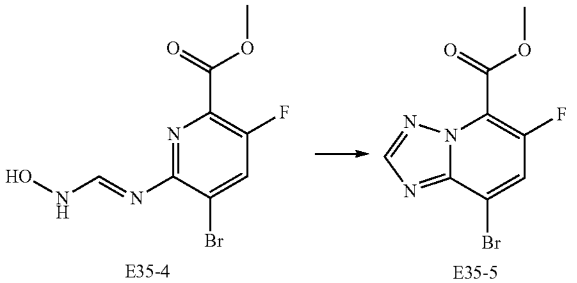 [SMILES: COC(=O)c1nc(/N=C/NO)c(Br)cc1F ; COC(=O)c1c(F)cc(Br)c2ncnn12]

E35-4 E35-5

Methyl 5-bromo-3-fluoro-6-(((hydroxylamino)methylene)amino)pyridine-2-carboxylate E35-4 (1.30 g, 4.45 mmol) was dissolved in polyphosphoric acid (6.00 mL). The reaction solution was stirred for 12 hours at 100° C. under nitrogen atmosphere. The completion of the reaction was monitored by LCMS. The reaction solution was quenched with saturated sodium bicarbonate aqueous solution and extracted three times with ethyl acetate. The organic phases were combined, dried, and concentrated, and the crude product is purified by a flash silica gel column to obtain methyl 8-bromo-6-fluoro-[1,2,4]triazolo[1,5-a]pyridine-5-carboxylate E35-5 (600 mg, 44.2% yield).

$^1$H NMR (400 MHz, DMSO-$d_6$) δ 8.70 (s, 1H), 8.48 (d, J=9.3 Hz, 1H), 4.03 (s, 3H) ppm; LCMS m/z 276.1 $[M+H]^+$.

Step 5: 2-(8-bromo-6-fluoro-[1,2,4]triazolo[1,5-a]pyridin-5-yl)propan-2-ol E35-6

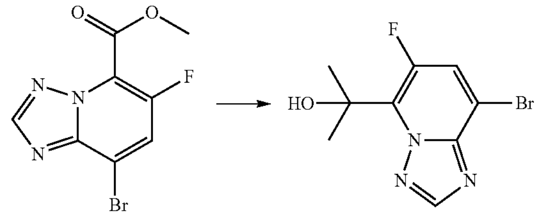

E35-5 E35-6

Methyl 8-bromo-6-fluoro-[1,2,4]triazolo[1,5-a]pyridine-5-carboxylate E35-5 (550 mg, 2.01 mmol) was dissolved in tetrahydrofuran (8.00 mL). The mixture was cooled to −50° C. Methylmagnesium bromide (3M, 4.5 mL) was added dropwise, and the mixture was reacted for 1.5 hours under nitrogen atmosphere. The completion of the reaction was monitored by LCMS. The reaction solution was quenched with saturated ammonium chloride aqueous solution, extracted with ethyl acetate, and concentrated under reduced pressure. The crude product was purified by a flash silica gel column to obtain 2-(8-bromo-6-fluoro-[1,2,4]triazolo[1,5-a]pyridin-5-yl)propan-2-ol E35-6 (370 mg, 63.2% yield).

$^1$H NMR (400 MHz, DMSO-$d_6$) δ 8.69 (s, 1H), 8.28 (d, J=11.4 Hz, 1H), 5.96 (s, 1H), 1.77 (s, 3H), 1.75 (s, 3H) ppm; LCMS m/z 274.0 $[M+H]^+$.

Step 6: (6-fluoro-5-(2-hydroxypropyl-2-yl)-[1,2,4]triazolo[1,5-a]pyridin-8-yl)boronic acid E35-7

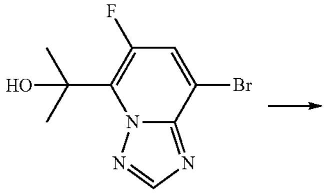

E35-6

-continued

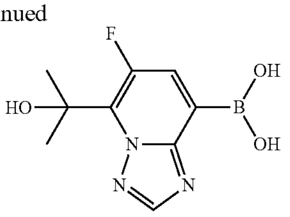

E35-7

2-(8-bromo-6-fluoro-[1,2,4]triazolo[1,5-a]pyridin-5-yl)propan-2-ol E35-6 (320 mg, 1.17 mmol), bis(pinacolate)diboron (355 mg, 1.40 mmol), potassium acetate (229 mg, 2.34 mmol), [1,1'-bis(diphenylphosphino)ferrocene]palladium dichloride dichloromethane complex (95.3 mg, 0.117 mmol) were dissolved in 1,4-dioxane (8.00 mL). The temperature of the reaction was raised to 120° C. and the mixture was reacted for 6.5 hours under nitrogen atmosphere. No raw material was remained by TLC detection, and the reaction solution was directly used in the next step without treatment.

Step 7: 2-(6-fluoro-8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol

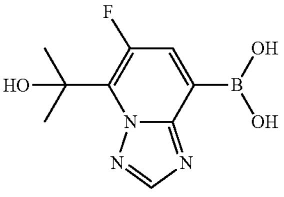

E35-7

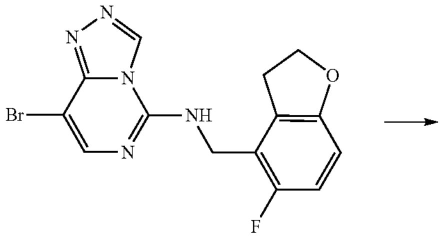

B2

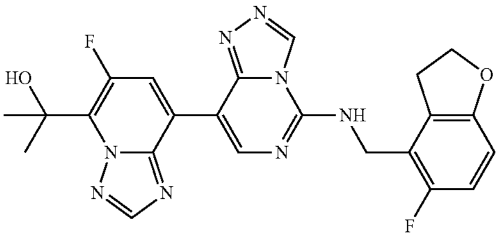

8-bromo-N-((5-fluoro-2,3-dihydrobenzofuran-4-yl)methyl)-[1,2,4]triazolo[[4,3-c]pyrimidin-5-amine B2 (298 mg, 0.819 mmol), sodium carbonate (372 mg, 3.51 mmol), [1,1'-bis(diphenylphosphino)ferrocene]palladium dichloride dichloromethane complex (95.5 mg, 0.117 mmol) were added to the reaction solution in the previous step. 1,4-dioxane (1.00 mL) and water (1.50 mL) were additionally added. The temperature of the reaction was raised to 100° C.

and the mixture was reacted for 2 hours under nitrogen atmosphere. The completion of the reaction was monitored by LCMS. The temperature of the reaction was cooled to room temperature, and the mixture was dried over anhydrous sodium sulfate, filtered, and concentrated under reduced pressure. The crude product was purified by a flash silica gel column, and then recrystallized to obtain 2-(6-fluoro-8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol (183 mg, 32.1% yield).

$^1$H NMR (400 MHz, DMSO-$d_6$) δ 9.61 (s, 1H), 9.57 (s, 1H), 9.24 (d, J=14.3 Hz, 1H), 9.14-9.06 (m, 1H), 8.77 (s, 1H), 6.97 (t, J=9.3 Hz, 1H), 6.72 (dd, J=3.9, 8.5 Hz, 1H), 6.10 (s, 1H), 4.80 (br d, J=4.3 Hz, 2H), 4.55 (t, J=8.8 Hz, 2H), 3.37-3.36 (m, 2H), 1.83 (s, 3H), 1.82 (s, 3H) ppm; LCMS m/z 479.4 $[M+H]^+$.

Example 16: 1,1-difluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol

Step 1: 2-(8-bromo-[1,2,4]triazolo[1,5-a]pyridin-5-yl)-1,1-difluoropropan-2-ol E36-2

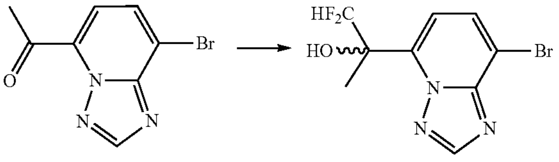

E27-4 E36-2

1,3-dimethyl-3,4,5,6-tetrahydro-2-pyrimidinone (1.07 g, 8.37 mmol) was added to a solution of 1-(8-bromo-[1,2,4]triazolo[1,5-a]pyridin-5-yl)ethan-1-one E27-4 (670 mg, 2.79 mmol), trimethyl(bromodifluoromethyl)silane (1.42 g, 6.98 mmol) and triphenylphosphine in acetonitrile (5 mL), and the reaction solution was reacted for 12 hours at 20° C. The completion of the reaction of the raw materials was monitored by TLC. Potassium hydroxide solution (400 mg potassium hydroxide was dissolved in 3 mL water) was added to the reaction solution, and the reaction solution was stirred for 2 hours at 20° C. Another 5 mL of 6M hydrochloric acid was added, and stirring was continued for 2 hours. The product was detected by LCMS. The reaction solution was adjusted to pH 8 with sodium bicarbonate, extracted with ethyl acetate, dried and concentrated, and purified by prep-HPLC to obtain the product 2-(8-bromo-[1,2,4]triazolo[1,5-a]pyridin-5-yl)-1,1-difluoropropan-2-ol E36-2 (570 mg, 1.91 mmol, 68.7% yield).

$^1$H NMR (400 MHz, DMSO-$d_6$) δ 8.66 (s, 1H), 8.12 (d, J=8.0 Hz, 1H), 7.39 (d, J=7.9 Hz, 1H), 6.92 (t, J=55.6 Hz, 1H), 6.77 (s, 1H), 1.78 (s, 3H) ppm; LCMS m/z 291.9/293.9 $[M+H]^+$.

Step 2: (5-(1,1-difluoro-2-hydroxypropyl-2-yl)-[1,2,4]triazolo[1,5-a]pyridin-8-yl)boronic acid E36-3

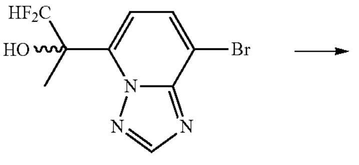

E36-2

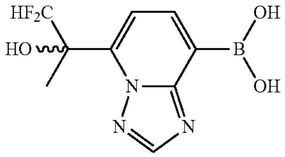

E36-3

2-(8-bromo-[1,2,4]triazolo[1,5-a]pyridin-5-yl)-1,1-difluoropropan-2-ol E36-2 (500 mg, 1.68 mmol), bis(pinacolate)diboron (511 mg, 2.01 mmol), potassium acetate (329 mg, 3.36 mmol) and [1,1'-bis(diphenylphosphino)ferrocene] palladium dichloride dichloromethane complex (137 mg, 0.167 mmol) were dissolved in 1,4-dioxane (10.0 mL). The reaction was raised to 120° C. and reacted for 6 hours under nitrogen atmosphere. No raw material remaining was remained by TLC detection, and the reaction solution was directly used in the next step without treatment.

Step 3: 1,1-difluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol

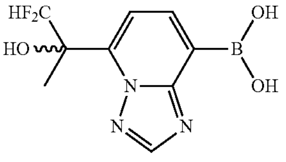

E36-3

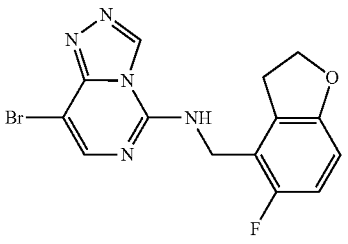

B2

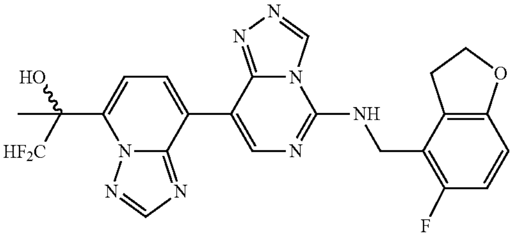

8-bromo-N-((5-fluoro-2,3-dihydrobenzofuran-4-yl) methyl)-[1,2,4]triazolo[[4,3-c]pyrimidin-5-amine B2 (488 mg, 1.68 mmol), sodium carbonate (533 mg, 5.03 mmol), [1,1'-bis(diphenylphosphino)ferrocene]palladium dichloride dichloromethane complex (137 mg, 0.167 mmol) were added to the reaction solution in the previous step. 1,4-dioxane (1.00 mL) and water (2.00 mL) were additionally added. The reaction was raised to 100° C. and reacted for 2 hours under nitrogen atmosphere. The completion of the reaction was monitored by LCMS. The temperature was cooled to room temperature. The mixture was dried over anhydrous sodium sulfate, filtered, and concentrated under reduced pressure. The crude product was purified by a flash silica gel column and preparative chromatography to obtain 1,1-difluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol (475 mg, 57.0% yield).

$^1$H NMR (400 MHz, DMSO-$d_6$) δ 9.55 (s, 1H), 9.42 (s, 1H), 9.18 (d, J=7.9 Hz, 1H), 9.01-8.95 (m, 1H), 8.70 (s, 1H), 7.64 (d, J=7.9 Hz, 1H), 7.17-6.83 (m, 2H), 6.77-6.68 (m, 2H), 4.79 (br d, J=3.8 Hz, 2H), 4.55 (t, J=8.8 Hz, 2H), 3.36-3.35 (m, 2H), 1.82 (s, 3H) ppm; LCMS m/z 497.3 $[M+H]^+$.

Example 17: 1,3-difluoro-2-[8-(5-{[(5-fluoro-2,3-dihydro-1-benzofuran-4-yl)methyl]amino]-[1,2,4]triazolo[4,3-c]pyrimidin-8-yl)-[1,2,4]triazol[1,5-a]pyridin-5-yl]propan-2-ol

Step 1: tert-butyl (8-bromo-[1,2,4]triazolo[1,5-a]pyridin-5-yl)carbamate E37-1

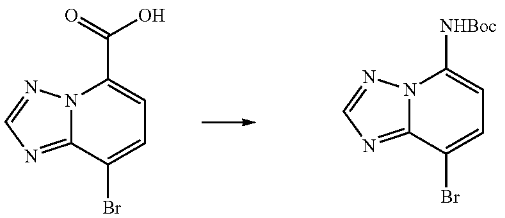

E31-1 E37-1

8-bromo-[1,2,4]triazolo[1,5-a]pyridine-5-carboxylic acid E31-1 (4.50 g, 18.5 mmol), 4 A molecular sieves (5.00 g), tert-butanol (13.7 g, 185 mmol), diisopropylethylamine (7.21 g, 55.7 mmol) were added to toluene (25.0 mL). The gas was replaced by Nitrogen three times. The reaction solution was stirred for 30 minutes at 25° C. Diphenylphosphoryl azide (7.68 g, 27.8 mmol) was added to the reaction solution, and the reaction solution was stirred for 8 hours at 85° C. The completion of the reaction was detected by TLC. The reaction solution was concentrated under reduced pressure, and the crude product was purified by a flash silica gel column to obtain tert-butyl (8-bromo-[1,2,4]triazolo[1,5-a]pyridin-5-yl)carbamate E37-1 (3.20 g, 54.4% yield).

$^1$H NMR (400 MHz, $CDCl_3$) δ 8.35 (s, 1H), 8.24 (brs, 1H), 7.77 (d, J=8.4 Hz, 1H), 7.57 (d, J=8.4 Hz, 1H), 1.57 (s, 9H) ppm. LCMS m/z 315.0 $[M+H]^+$.

Step 2: 8-bromo-[1,2,4]triazolo[1,5-a]pyridin-5-amine hydrochloride E37-2

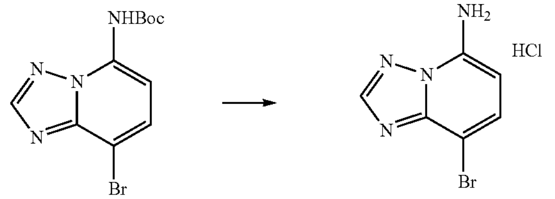

E37-1 E37-2

Tert-butyl (8-bromo-[1,2,4]triazolo[1,5-a]pyridin-5-yl) carbamate E37-1 (3.20 g, 9.83 mmol) was dissolved in ethanol (10.0 mL). Hydrochloric acid/1,4-dioxane solution (4M, 5.00 mL) was added dropwise. The reaction solution was stirred for 10 hours at 50° C. The completion of the reaction was detected by TLC. The reaction solution was concentrated under reduced pressure to obtain the crude product 8-bromo-[1,2,4]triazolo[1,5-a]pyridin-5-amine hydrochloride E37-2 (2.50 g, crude product).

$^1$H NMR (400 MHz, DMSO-$d_6$) δ 8.55 (s, 1H), 7.73 (d, J=8.4 Hz, 1H), 6.24 (d, J=8.4 Hz, 1H) ppm; LCMS m/z 213.1 $[M+H]^+$.

Step 3: 8-bromo-5-iodo-[1,2,4]triazolo[1,5-a]pyridine E37-3

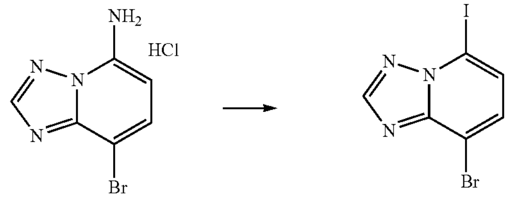

E37-2 E37-3

8-bromo-[1,2,4]triazolo[1,5-a]pyridin-5-amine hydrochloride E37-2 (450 mg, 1.80 mmol) and p-toluenesulfonic acid (931 mg, 5.41 mmol) were dissolved in acetonitrile (10.0 mL), and the mixture solution was stirred 30 minutes at 0° C. for. A solution of potassium iodide (748 mg, 4.51 mmol) and sodium nitrite (248 mg, 3.61 mmol) in water (2.00 mL) was slowly added dropwise, and the reaction was raised to 20° C. and stirred for 2.5 hours. The completion of the reaction was detected by TLC. The reaction solution was concentrated under reduced pressure, and the crude product was purified by a flash silica gel column to obtain 8-bromo-5-iodo-[1,2,4]triazolo[1,5-a]pyridine E37-3 (240 mg, 39.8% yield).

$^1$H NMR (400 MHz, $CDCl_3$) δ 8.44 (s, 1H), 7.54 (d, J=7.6 Hz, 1H), 7.42 (d, J=8.0 Hz, 1H) ppm. LCMS m/z 325.9 $[M+H]^+$.

Step 4: 2-(8-bromo-[1,2,4]triazolo[1,5-a]pyridin-5-yl)-1,3-difluoropropan-2-ol E37-4

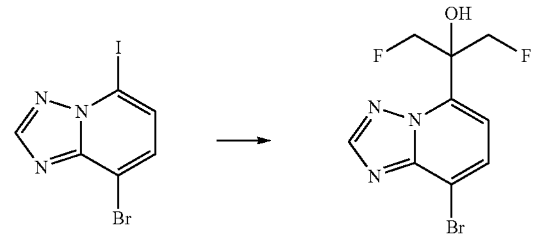

E37-3 E37-4

8-bromo-5-iodo-[1,2,4]triazolo[1,5-a]pyridine E37-3 (230 mg, 0.710 mmol) was dissolved in tetrahydrofuran (5.00 mL). The reaction solution was cooled to −65° C. A solution of n-butyllithium in tetrahydrofuran was slowly added dropwise (2.5M, 284 uL). After the reaction solution was stirred for 3 minutes, a solution of 1,3-difluoropropan-2-one (66.7 mg, 0.710 mmol) in tetrahydrofuran (2.00 mL) was slowly added. The reaction solution was continued to stir for 1 h at −65° C. The completion of the reaction was monitored by LCMS. The reaction solution was quenched with saturated ammonium chloride aqueous solution, extracted with ethyl acetate, dried, and concentrated under reduced pressure. The crude product was purified with a flash silica gel column to obtain 2-(8-bromo-[1,2,4]triazolo[1,5-a]pyridin-5-yl)-1,3-difluoropropan-2-ol E37-4 (170 mg, 60.6% yield).

$^1$H NMR (400 MHz, DMSO-$d_6$) δ 8.67 (s, 1H), 8.12 (d, J=7.9 Hz, 1H), 7.39 (d, J=8.0 Hz, 1H), 6.98 (s, 1H), 5.31-5.26 (m, 1H), 5.15 (d, J=9.6 Hz, 1H), 5.00 (d, J=9.6 Hz, 1H), 4.88 (d, J=9.6 Hz, 1H) ppm; LCMS m/z 294.0 $[M+H]^+$.

Step 5: (5-(1,3-difluoro-2-hydroxypropan-2-yl)-[1,2,4]triazolo[1,5-a]pyridin-8-yl)boronic acid E37-5

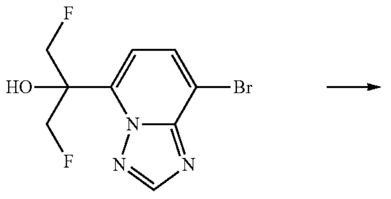

E37-4

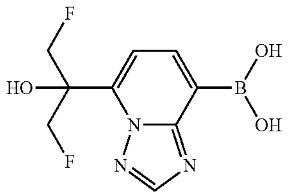

E37-5

2-(8-bromo-[1,2,4]triazolo[1,5-a]pyridin-5-yl)-1,3-difluoropropan-2-ol E37-4 (170 mg, 0.582 mmol), bis(pinacolate)diboron (177 mg, 0.698 mmol), potassium acetate (114 mg, 1.16 mmol), [1,1'-bis(diphenylphosphino)ferrocene] palladium dichloride dichloromethane complex (47.5 mg, 0.0582 mmol) were dissolved in 1,4-dioxane (6.00 mL). The reaction was raised to 120° C. and reacted for 6.5 hours under nitrogen atmosphere. No raw material remaining was remained by LCMS detection, and the reaction solution was directly used in the next step without treatment.

Step 6: 1,3-difluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol

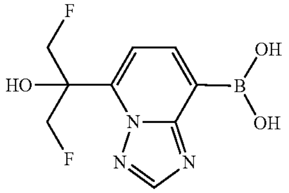

E37-5

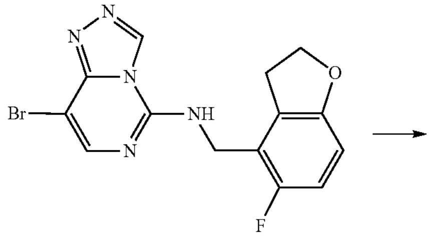

B2

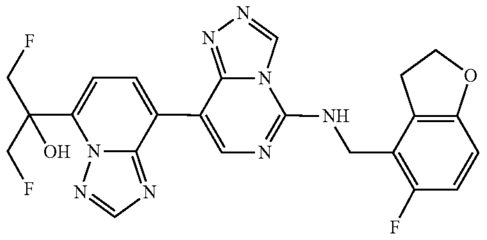

8-bromo-N-((5-fluoro-2,3-dihydrobenzofuran-4-yl)methyl)-[1,2,4]triazolo[4,3-c]pyrimidin-5-amine B2 (121 mg, 0.332 mmol), sodium carbonate (184 mg, 1.74 mmol), [1,1'-bis(diphenylphosphino)ferrocene]palladium dichloride dichloromethane complex (47.3 mg, 0.0579 mmol) were added to the reaction solution in the previous step. 1,4-dioxane (1.00 mL) and water (1.50 mL) were additionally added. The reaction was raised to 100° C. and reacted for 2 hours under nitrogen atmosphere. The completion of the reaction was monitored by LCMS. The temperature was cooled to room temperature. The mixture was dried over anhydrous sodium sulfate, filtered, and concentrated under reduced pressure. The crude product was purified by a flash silica gel column and preparative chromatography to obtain 1,3-difluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol (50.0 mg, 17.2% yield).

$^1$H NMR (400 MHz, DMSO-$d_6$) δ 9.53 (br s, 1H), 9.43 (s, 1H), 9.17 (d, J=8.0 Hz, 1H), 8.98 (br s, 1H), 8.70 (s, 1H), 7.64 (br d, J=7.4 Hz, 1H), 7.12-6.87 (m, 2H), 6.72 (dd, J=3.4, 8.4 Hz, 1H), 5.34 (br d, J=9.5 Hz, 1H), 5.22 (br d, J=9.6 Hz, 1H), 5.07 (d, J=9.5 Hz, 1H), 4.96 (d, J=9.4 Hz, 1H), 4.78 (s, 2H), 4.56 (t, J=8.8 Hz, 2H), 3.42-3.41 (m, 2H) ppm; LCMS m/z 497.4 $[M+H]^+$.

Example 18: 1-[8-(5-{[(5-fluoro-2,3-dihydro-1-benzofuran-4-yl)methyl]amino]-triazolo[4,3-c]pyrimidin-8-yl)-[1,2,4]triazolo[1,5-a]pyridin-5-yl]cyclopropan-1-ol Step 1: 8-bromo-5-(1-((tert-butyldimethylsilyl)oxy)vinyl)-[1,2,4]triazolo[1,5-a]pyridine E38-1

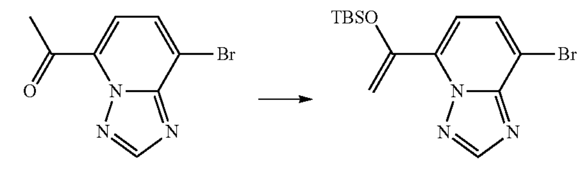

E27-4 E38-1

At −78° C., sodium bis(dimethylsilyl)amide (1M, 8.12 mL) was added dropwise to a solution of 1-(8-bromo-[1,2,4]triazolo[1,5-a]pyridin-5-yl)ethanone E27-4 (1.30 g, 5.42 mmol) in tetrahydrofuran solution (20 mL), and the reaction solution was stirred for 1 hour at 25° C. Tert-butyldimethylsilyl chloride (1.63 g, 10.8 mmol, 1.33 mL) was added dropwise to the reaction solution at 0° C. The reaction solution was stirred for 12 hours at 25° C. The completion of the reaction was monitored by LCMS. The reaction solution was quenched with ammonium chloride aqueous solution and extracted with ethyl acetate. The organic phase was dried and concentrated, and the concentrate was purified by a flash silica gel column to obtain a white solid 8-bromo-5-(1-((tert-butyldimethylsilyl)oxy)vinyl)-[1,2,4]triazolo[1,5-a]pyridine E38-1 (1.20 g, 3.39 mmol, 62.5% yield).

$^1$H NMR (400 MHz, DMSO-$d_6$) δ 8.69 (s, 1H), 8.13 (d, J=8.1 Hz, 1H), 7.38 (d, J=8.0 Hz, 1H), 6.49 (d, J=1.6 Hz, 1H), 5.18 (d, J=1.8 Hz, 1H), 0.98 (s, 9H), 0.24 (s, 6H).

Step 2: 8-bromo-5-(1-((tert-butyldimethylsilyl)oxy)cyclopropyl)-[1,2,4]triazolo[1,5-a]pyridine E38-2

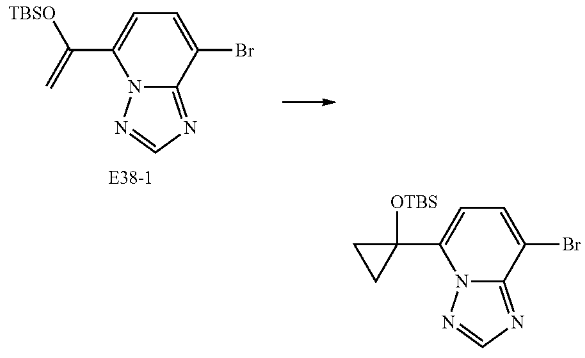

E38-1

E38-2

At 0° C., trimethylaluminum (2M, 10.1 mL) was added dropwise to a solution of 8-bromo-5-(1-((tert-butyldimethylsilyl)oxy)vinyl)-[1,2,4]triazolo[1,5-a]pyridine E38-1 (1.20 g, 3.39 mmol) in dichloromethane (150 mL), and then diiodomethane (7.26 g, 27.0 mmol, 2.19 mL) in dichloromethane solution (10 mL) was added dropwise. The reaction solution was stirred at 40° C. for 48 hours. After the reaction was complete, it was quenched with hydrochloric acid (1M) and extracted with dichloromethane. The organic phase was dried and concentrated, and the concentrate was purified with a flash silica gel column to obtain yellow oil: 8-bromo-5-(1-((tert-butyldimethylsilyl)oxy)cyclopropyl)-[1,2,4]triazolo[1,5-a]pyridine E38-2 (412 mg, 27.6% yield).

$^1$H NMR (400 MHz, DMSO-$d_6$) δ 8.62 (s, 1H), 8.00 (d, J=7.8 Hz, 1H), 7.23 (d, J=7.8 Hz, 1H), 1.28-1.16 (m, 4H), 0.67 (s, 9H), −0.17 (s, 6H) ppm; LCMS m/z 368.1 [M+H]$^+$.

Step 3: (5-(1-((tert-butyldimethylsilyl)oxy)cyclopropyl)-[1,2,4]triazolo[1,5-a]pyridin-8-yl)boronic acid E38-3

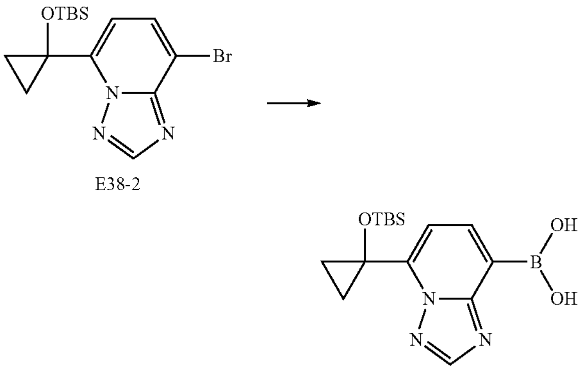

E38-2

E38-3

8-bromo-5-(1-((tert-butyldimethylsilyl)oxy)cyclopropyl)-[1,2,4]triazolo[1,5-a]pyridine E38-2 (412 mg, 1.12 mmol), bis(pinacolato)diboron (312 mg, 1.23 mmol), potassium acetate (329 mg, 3.36 mmol), [1,1'-bis(diphenylphosphino)ferrocene]palladium dichloride dichloromethane complex (182 mg, 223 μmol) were dissolved in 1,4-dioxane (6.00 mL). The temperature was raised to 120° C. and the mixture was reacted for 5 hours under nitrogen atmosphere. No remaining raw material was remained by TLC detection, and the reaction solution was used directly in the next step without treatment. LCMS: m/z 334.2 [M+H]$^+$.

Step 4: 8-(5-(1-((tert-butyldimethylsilyl)oxy)cyclopropyl)-[1,2,4]triazolo[1,5-a]pyridin-8-yl)-N-((5-fluoro-2,3-benzodihydrofuran-4-yl)methyl)-[1,2,4]triazolo[4,3-c]pyrimidine-5-amine E38-4

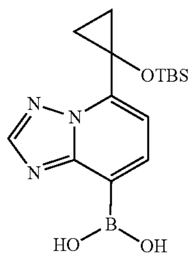

E38-3

-continued

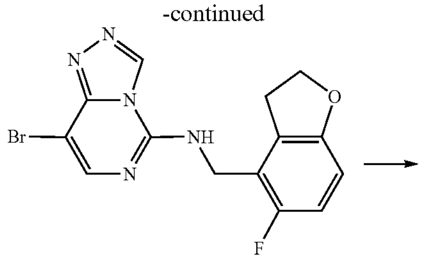

B2

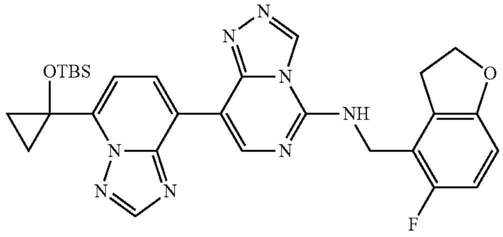

E38-4

8-bromo-N-((5-fluoro-2,3-benzodihydrofuran-4-yl)methyl)-[1,2,4]triazolo[4,3-c]pyrimidin-5-amine (244 mg, 0.671 mmol), sodium carbonate (355 mg, 3.36 mmol), [1,1'-bis(diphenylphosphino)ferrocene]palladium dichloride dichloromethane complex (182 mg, 0.223 mmol), 1,4-dioxane (5.00 mL) and water (1.00 mL) were added to the reaction solution in the previous step. The reaction was raised to 100° C. and reacted for 2 hours under nitrogen atmosphere. The completion of the reaction was monitored by LCMS. Then the reaction solution was cooled to room temperature and concentrated under reduced pressure. The crude product was purified by a flash silica gel column to obtain a brown solid 8-(5-(1-((tert-butyldimethylsilyl)oxy)cyclopropyl)-[1,2,4]triazolo[1,5-a]pyridin-8-yl)-N-((5-fluoro-2,3-benzodihydrofuran-4-yl)methyl)-[1,2,4]triazolo[4,3-c]pyrimidin-5-amine E38-4 (430 mg, 0.707 mmol, 63.2% yield).

$^1$H NMR (400 MHz, DMSO-$d_6$) δ 9.54 (d, J=1.4 Hz, 2H), 9.17 (d, J=7.8 Hz, 1H), 8.97 (t, J=5.1 Hz, 1H), 8.66 (s, 1H), 7.48 (d, J=7.9 Hz, 1H), 7.02-6.92 (m, 1H), 6.72 (dd, J=3.9, 8.6 Hz, 1H), 4.79 (d, J=4.9 Hz, 2H), 4.55 (t, J=8.8 Hz, 2H), 3.38-3.35 (m, 2H), 1.32-1.19 (m, 4H), 0.68 (s, 9H), −0.17 (s, 6H) ppm; LCMS: m/z 573.4 [M+H]$^+$.

Step 5: 1-(8-(5-(((5-fluoro-2,3-benzodihydrofuran-4-yl)methyl)amino)-[1,2,4]triazolo[4,3-c]pyrimidin-8-yl)-[1,2,4]triazolo[1,5-a]pyridin-5-yl)cyclopropanol

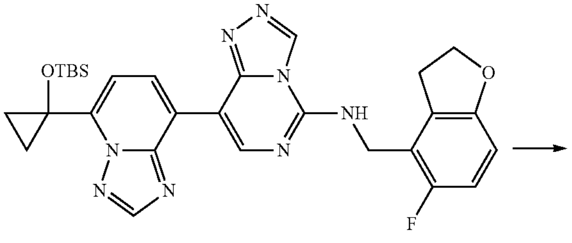

E38-4

-continued

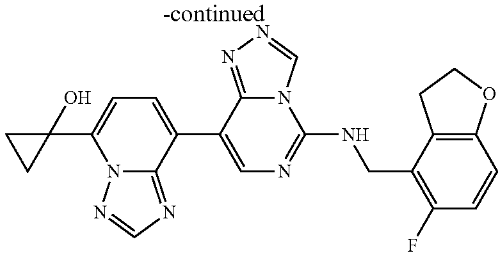

A mixture of 8-(5-(1-((tert-butyldimethylsilyl)oxy)cyclopropyl)-[1,2,4]triazolo[1,5-a]pyridin-8-yl)-N-((5-fluoro-2,3-benzodihydrofuran-4-yl)methyl)-[1,2,4]triazolo[4,3-c]pyrimidin-5-amine E38-4 (430 mg, 0.707 mmol, 94.2% purity) and tetrabutylammonium fluoride (1M in THF, 2.83 mL) was stirred for 2 hours at 25° C. The completion of the reaction was monitored by LCMS. The reaction solution was cooled to room temperature. Water and ethyl acetate were added to the mixture. The organic phase is dried and concentrated, and the concentrate is purified by a flash silica gel column to obtain 1-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]cyclopropan-1-ol (159 mg, 0.344 mmol, 48.6% yield).

$^1$H NMR (400 MHz, DMSO-$d_6$) δ 9.55 (s, 1H), 9.47 (s, 1H), 9.14 (d, J=7.9 Hz, 1H), 8.94 (br s, 1H), 8.64 (s, 1H), 7.48 (d, J=7.9 Hz, 1H), 7.01-6.93 (m, 1H), 6.75-6.70 (m, J=3.9 Hz, 1H), 6.39 (s, 1H), 4.79 (br d, J=3.3 Hz, 2H), 4.56 (t, J=8.8 Hz, 2H), 3.39-3.36 (m, 2H), 1.56-1.51 (m, 2H), 1.21-1.17 (m, 2H) ppm; LCMS: m/z 459.4 [M+1H]$^+$.

Example 19: 1-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]cyclobutan-1-ol Step 1: 1-(8-bromo-[1,2,4]triazolo[1,5-a]pyridin-5-yl)cyclobutanol E39-1

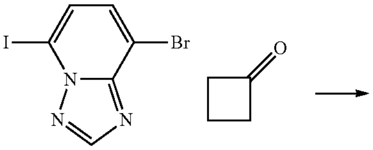

E37-3

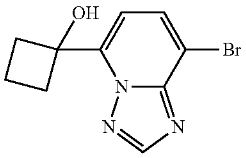

E39-1

8-bromo-5-iodo-[1,2,4]triazolo[1,5-a]pyridine E37-3 (800 mg, 2.47 mmol) was dissolved in tetrahydrofuran (15.0 mL). The temperature was lowered to −70° C. and n-butyl lithium (2.5 M, 988 uL) was added dropwise. The reaction was carried out for 5 min under nitrogen atmosphere. Then a solution of n-butyl ketone (173 mg, 2.47 mmol) in tetrahydrofuran (2.0 mL) was added dropwise at this temperature, and the reaction was carried out for 1 hour at −70° C. The completion of the reaction was monitored by TLC and LCMS. The reaction solution was quenched with saturated ammonium chloride aqueous solution, extracted with ethyl acetate, and concentrated under reduced pressure. The crude product was purified with a flash silica gel column to obtain 1-(8-bromo-[1,2,4]triazolo[1,5-a]pyridin-5-yl)cyclobutanol E39-1 (500 mg, 61.0% yield).

$^1$H NMR (400 MHz, $CDCl_3$) δ 8.43 (s, 1H), 7.82 (d, J=7.8 Hz, 1H), 6.99 (d, J=7.8 Hz, 1H), 2.71-2.56 (m, 4H), 2.27-2.13 (m, 1H), 1.91-1.74 (m, 1H) ppm; LCMS: m/z 270.0 $[M+H]^+$.

Step 2: (5-(1-hydroxycyclobutyl)-[1,2,4]triazolo[1,5-a]pyridin-8-yl)boronic acid E39-2

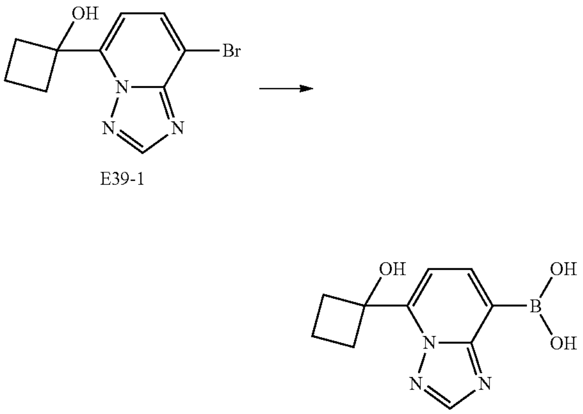

E39-1

E39-2

1-(8-bromo-[1,2,4]triazolo[1,5-a]pyridin-5-yl)cyclobutanol E39-1 (500 mg, 1.86 mmol), bis(pinacolate)diboron (568 mg, 2.24 mmol), potassium acetate (549 mg, 5.59 mmol), [1,1'-bis(diphenylphosphino)ferrocene]palladium dichloride dichloromethane complex (304 mg, 0.372 mmol) were dissolved in 1,4-dioxane (15.0 mL). The reaction solution was raised to 120° C. and reacted for 5 hours under nitrogen atmosphere. No raw materials was remained by TLC detection, and the reaction solution was directly used in the next step without treatment.

Step 3: 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)cyclobutanol

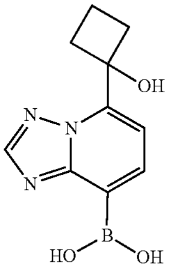

E39-2

-continued

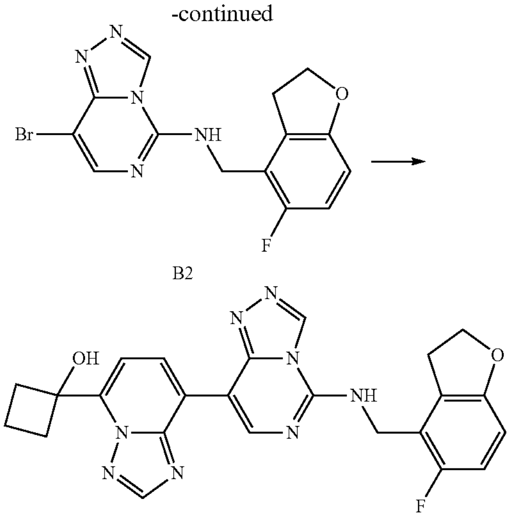

B2

8-bromo-N-((5-fluoro-2,3-dihydrobenzofuran-4-yl)methyl)-[1,2,4]triazolo[[4,3-c]pyrimidin-5-amine B2 (203 mg, 0.558 mmol), sodium carbonate (592 mg, 5.59 mmol), [1,1'-bis(diphenylphosphino)ferrocene]palladium dichloride dichloromethane complex (304 mg, 0.372 mmol), 1,4-dioxane (10.0 mL) and water (2.0 mL) were added to the reaction solution in the previous step. The reaction solution was raised to 100° C. and reacted for 1 hours under nitrogen atmosphere. The completion of the reaction was monitored by LCMS. The temperature was cooled to room temperature. The reaction solution was dried over anhydrous sodium sulfate, filtered, and concentrated under reduced pressure. The crude product was purified by a flash silica gel column to obtain 1-[8-(5-{[(5-fluoro-2,3-dihydro-1-benzofuran-4-yl)methyl]amino]-[1,2,4]triazolo[4,3-c]pyrimidin-8-yl)-[1,2,4]triazolo[1,5-a]pyridin-5-yl]cyclobutan-1-ol (90.0 mg, 0.189 mmol, 10.2% yield).

$^1$H NMR (400 MHz, DMSO-$d_6$) δ 9.54 (s, 1H), 9.47 (s, 1H), 9.15 (d, J=7.8 Hz, 1H), 8.94 (br s, 1H), 8.65 (s, 1H), 7.44 (d, J=7.8 Hz, 1H), 6.97 (t, J=9.4 Hz, 1H), 6.72 (dd, J=3.9, 8.6 Hz, 1H), 5.92 (s, 1H), 4.78 (s, 2H), 4.56 (t, J=8.6 Hz, 2H), 3.37-3.35 (m, 2H), 2.96-2.80 (m, 2H), 2.38 (ddd, J=6.9, 9.1, 12.1 Hz, 2H), 2.18-2.02 (m, 1H), 1.87-1.71 (m, 1H) ppm.

Example 20: 1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol Step 1: 2-(8-bromo-[1,2,4]triazolo[1,5-a]pyridin-5-yl)-1-fluoropropan-2-ol E40-1

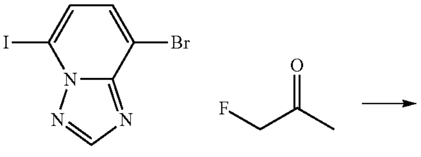

E37-3

-continued

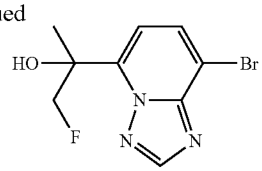

E40-1

8-bromo-5-iodo-[1,2,4]triazolo[1,5-a]pyridine E37-3 (1.50 g, 4.63 mmol) was dissolved in tetrahydrofuran (10.0 mL). The reaction solution was cooled to −65° C. and a solution of n-butyllithium in tetrahydrofuran was slowly added dropwise (2.5M, 1.85 mL). After the reaction solution was stirred for 3 minutes, a solution of 1-fluoropropan-2-one (352 mg, 4.63 mmol) in THF (1.00 mL) was slowly added dropwise. The reaction solution continues to be stirred for 0.5 h at −65° C. The completion of the reaction was monitored by LCMS. The reaction solution was quenched with saturated ammonium chloride aqueous solution, extracted with ethyl acetate, dried, and concentrated under reduced pressure. The crude product was purified with a flash silica gel column to obtain 2-(8-bromo-[1,2,4]triazolo[1,5-a]pyridin-5-yl)-1-fluoropropan-2-ol E40-1 (920 mg, 66.3% yield).

$^1$H NMR (400 MHz, DMSO-$d_6$) δ 8.64 (s, 1H), 8.09 (d, J=7.9 Hz, 1H), 7.34 (d, J=7.9 Hz, 1H), 6.39 (s, 1H), 5.32-5.13 (m, 1H), 4.82-4.62 (m, 1H), 1.66 (d, J=2.4 Hz, 3H) ppm; LCMS m/z 275.9 [M+H]$^+$.

Step 2: (5-(1-fluoro-2-hydroxypropan-2-yl)-[1,2,4]triazolo[1,5-a]pyridin-8-yl)boronic acid E40-2

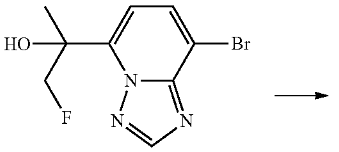

E40-1

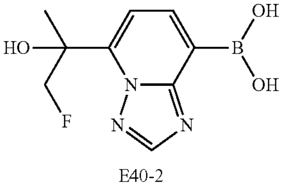

E40-2

2-(8-bromo-[1,2,4]triazolo[1,5-a]pyridin-5-yl)-1-fluoropropan-2-ol E40-1 (920 mg, 3.3 6 mmol), bis(pinacolate) diboron (1.02 g, 4.03 mmol), potassium acetate (1.15 g, 11.75 mmol), [1,1'-bis(diphenylphosphino)ferrocene]palladium dichloride dichloromethane complex (548 mg, 0.631 mmol) was dissolved in 1,4-dioxane (8.00 mL). The reaction was raised to 120° C. and reacted for 6.5 hours under nitrogen atmosphere. No raw materials were remained by LCMS detection, and the reaction solution was used directly in the next step without treatment.

Step 3: 1-fluoro-2-(8-(5-(((5-fluoro-2,3-dihydrobenzofuran-4-yl)methyl)amine)-[1,2,4]triazolo[4,3-c]pyrimidin-8-yl)-[1,2,4]triazolo[1,5-a]pyridin-5-yl)propan-2-ol E40-3

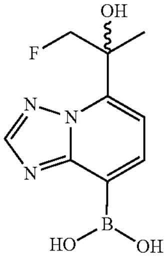

E40-2

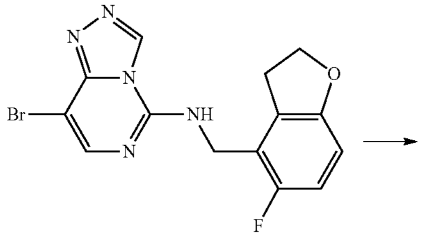

B2

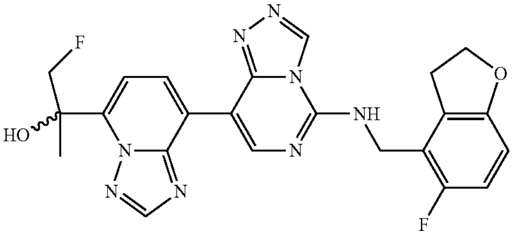

E40-3

8-bromo-N-((-5-fluoro-2,3-dihydrobenzofuran-4-yl)methyl)-[1,2,4]triazolo[4,3-c]pyrimidin-5-amine (855 mg, 2.35 mmol), sodium carbonate (1.07 g, 10.0 mmol), [1,1'-bis(diphenylphosphino)ferrocene]palladium dichloride dichloromethane complex (411 mg, 0.503 mmol) were added to the reaction solution in the previous step. 1,4-dioxane (1.00 mL) and water (2.00 mL) were additionally added. The reaction was raised to 100° C. and reacted for 2 hours under nitrogen atmosphere. The completion of the reaction was monitored by LCMS. The temperature was cooled to room temperature. The mixture was dried over anhydrous sodium sulfate, filtered, and concentrated under reduced pressure. The crude product was purified by a flash silica gel column and preparative chromatography to obtain 1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol E40-3 (816 mg, 50.7% yield).

$^1$H NMR (400 MHz, DMSO-$d_6$) δ 9.55 (s, 1H), 9.40 (s, 1H), 9.15 (d, J=7.9 Hz, 1H), 8.94 (t, J=4.9 Hz, 1H), 8.67 (s, 1H), 7.59 (d, J=7.9 Hz, 1H), 7.01-6.92 (m, 1H), 6.72 (dd, J=3.9, 8.6 Hz, 1H), 6.33 (s, 1H), 5.41-5.15 (m, 1H), 4.92-4.68 (m, 3H), 4.56 (t, J=8.8 Hz, 2H), 3.35-3.34 (m, 2H), 1.73 (d, J=2.1 Hz, 3H) ppm; LCMS m/z 479.4 [M+H]$^+$.

Step 4: separation of 1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol E40-3

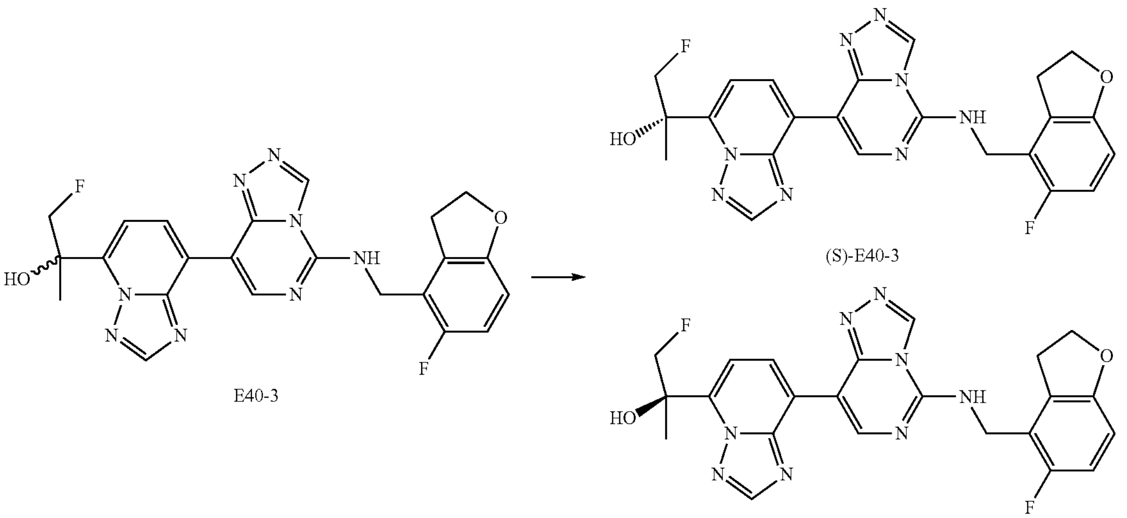

E40-3

(S)-E40-3

(R)-E40-3

1-fluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol (627 mg, 1.29 mmol) was chiral separated by SFC. Separation method: column: DAICEL CHIRALPAK IG (250 mm*30 mm, 10 um); mobile phase: A [0.1% $NH_3H_2O$ IPA]; B (isopropanol): 45% gradient, 4 mL/min, and (S)-1-fluoro-2-(8-(5-(((5-fluoro-2,3-dihydrobenzofuran-4-yl)methyl)amine)-[1,2,4]triazolo[4,3-c]pyrimidin-8-yl)-[1,2,4]triazolo[1,5-a]pyridin-5-yl)propan-2-ol ((S)-E40-3) or (R)-1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol ((R)-E40-3) was obtained, one of which has a retention time of 0.971 min (compound g) (210 mg, 34.1% yield, 98.6 ee %); and the other enantiomer as a retention time of 1.134 min (compound h) (206 mg, 33.1% yield, 98.4 ee %).

Compound g: $^1$H NMR (400 MHz, DMSO-$d_6$) δ 9.55 (s, 1H), 9.40 (s, 1H), 9.14 (d, J=8.0 Hz, 1H), 8.95 (br s, 1H), 8.67 (s, 1H), 7.59 (d, J=8.0 Hz, 1H), 7.02-6.92 (m, 1H), 6.72 (dd, J=3.9, 8.6 Hz, 1H), 6.35 (s, 1H), 5.44-5.15 (m, 1H), 4.90-4.68 (m, 3H), 4.55 (t, J=8.8 Hz, 2H), 3.39-3.38 (m, 2H), 1.72 (d, J=2.1 Hz, 3H) ppm; LCMS m/z 479.4 $[M+H]^+$.

Compound h of Example 21 was Obtained Simultaneously in the Chiral Separation:

$^1$H NMR (400 MHz, DMSO-$d_6$) δ 9.55 (s, 1H), 9.40 (s, 1H), 9.15 (d, J=7.9 Hz, 1H), 8.94 (br t, J=4.9 Hz, 1H), 8.67 (s, 1H), 7.59 (d, J=8.0 Hz, 1H), 7.03-6.91 (m, 1H), 6.72 (dd, J=3.9, 8.6 Hz, 1H), 6.33 (s, 1H), 5.46-5.14 (m, 1H), 4.89-4.69 (m, 3H), 4.55 (t, J=8.8 Hz, 2H), 3.36-3.35 (m, 2H), 1.73 (d, J=2.3 Hz, 3H) ppm; LCMS m/z 479.4 $[M+H]^+$.

Example 21 Using the Above Method, the Raw Materials were Replaced to Synthesize the Following Compound N-(((1aR,6bR)-5-fluoro-1a,6b-dihydro-]H-cyclopropa[b]benzofuran-6-yl)methyl)-8-(5-methyl-[1,2,4]triazolo[1,5-a]pyridin-8-yl)-[1,2,4]triazolo[4,3-c]pyrimidin-5-amine

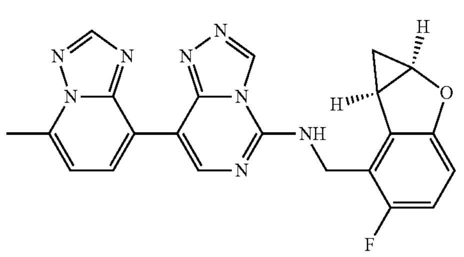 [SMILES: Cc1ccc(-c2cnc(NCc3c(F)ccc4c3[C@H]3C[C@H]3O4)n3cnnc23)c2ncnn12]

$^1$H NMR (400 MHz, DMSO-$d_6$) δ 9.57 (s, 1H), 9.45 (s, 1H), 9.11 (d, J=7.7 Hz, 1H), 9.04 (s, 1H), 8.63 (s, 1H), 7.29 (dd, J=7.7, 1.1 Hz, 1H), 6.96 (dd, J=10.3, 8.7 Hz, 1H), 6.78 (dd, J=8.7, 3.9 Hz, 1H), 5.00-4.85 (m, 3H), 2.97 (dt, J=9.1, 4.5 Hz, 1H), 2.79 (s, 3H), 1.02 (dt, J=9.0, 5.9 Hz, 1H), 0.14 (ddd, J=6.1, 4.0, 1.9 Hz, 1H) ppm; LCMS: m/z 429.0 $[M+H]^+$.

Example 22 Using the Above Method, the Raw Materials were Replaced to Synthesize the Following Compound N-((5-fluoro-2,3-dihydrobenzofuran-4-yl)methyl)-8-(5-methyl-[1,2,4]triazolo[1,5-a]pyridin-8-yl)-[1,2,4]triazolo[4,3-c]pyrimidin-5-amine

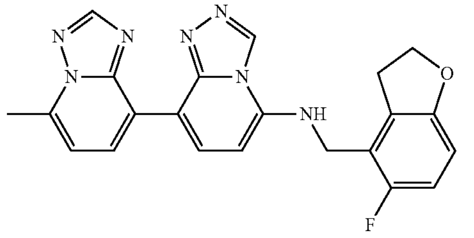 [SMILES: Cc1ccc(-c2ccc(NCc3c(F)ccc4c3CCO4)n3cnnc23)c2ncnn12]

$^1$H NMR (400 MHz, DMSO-$d_6$) δ 9.54 (s, 1H), 9.45 (s, 1H), 9.11 (d, J=7.7 Hz, 1H), 8.90 (t, J=5.0 Hz, 1H), 8.64 (d, J=9.7 Hz, 1H), 7.28 (d, J=7.8 Hz, 1H), 7.02-6.92 (m, 1H), 6.72 (dd, J=8.6, 3.9 Hz, 1H), 4.78 (d, J=4.9 Hz, 2H), 4.56 (t, J=8.7 Hz, 2H), 3.35 (s, 2H), 2.79 (s, 3H) ppm; LCMS: m/z 417.0 $[M+H]^+$.

Example 23 Using the Above Method, the Raw Materials were Replaced to Synthesize the Following Compound 8-(5-chloro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

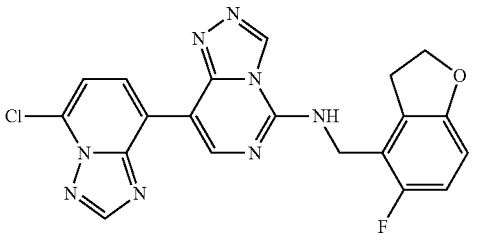 [SMILES: Fc1ccc2c(c1CNc1ncc(-c3ccc(Cl)n4ncnc34)c3nncn13)CCO2]

$^1$H NMR (400 MHz, MeOD) δ 9.40-9.30 (m, 1H), 9.25-9.19 (m, 1H), 8.88 (dd, J=9.3, 7.4 Hz, 1H), 8.53-8.47 (m, 1H), 7.38 (d, J=8.0 Hz, 2H), 6.84 (dd, J=17.3, 7.3 Hz, 1H), 6.70-6.64 (m, 1H), 4.82 (d, J=18.0 Hz, 1H), 4.63 (dd, J=20.5, 11.7 Hz, 1H), 3.45 (d, J=17.4 Hz, 2H) ppm; LCMS: m/z 437.0 $[M+H]^+$.

Example 24 Using the Above Method, the Raw Materials were Replaced to Synthesize the Following Compound N-((5-fluoro-2,3-dihydrobenzofuran-4-yl)methyl)-8-(5-(trifluoromethyl)-[1,2,4]triazolo[1,5-a]pyridin-8-yl)-[1,2,4]triazolo[4,3-c]pyrimidin-5-amine

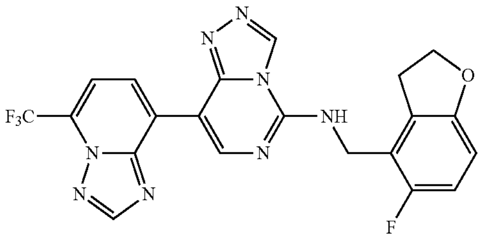

$^1$H NMR (400 MHz, DMSO-$d_6$) δ 9.66 (d, J=2.6 Hz, 1H), 9.58 (s, 1H), 9.36 (d, J=7.9 Hz, 1H), 9.18 (t, J=4.9 Hz, 1H), 8.82 (d, J=2.4 Hz, 1H), 8.03 (d, J=8.0 Hz, 1H), 6.97 (t, J=9.4 Hz, 1H), 6.72 (dd, J=8.6, 3.8 Hz, 1H), 4.81 (d, J=4.8 Hz, 2H), 4.56 (t, J=8.7 Hz, 2H), 3.32 (s, 2H) ppm; LCMS: m/z 471.1 $[M+H]^+$.

Example 25 Using the Above Method, the Raw Materials were Replaced to Synthesize the Following Compound N-((5-fluorodihydrobenzofuran-4-yl)methyl)-8-(5-methoxy-[1,2,4]triazolo[1,5-a]pyridin-8-yl)-[1,2,4]triazolo[4,3-c]pyrimidin-5-amine

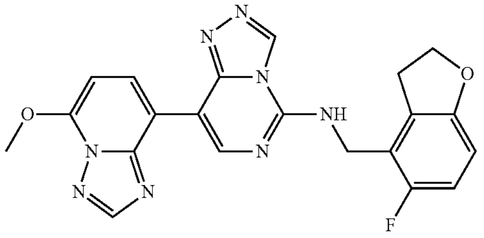 [SMILES: COc1ccc(-c2cnc(NCc3c(F)ccc4c3CCO4)n3cnnc23)c2ncnn12]

$^1$H NMR (400 MHz, DMSO-$d_6$) δ 9.54 (s, 1H), 9.33 (s, 1H), 9.17 (d, J=8.4 Hz, 1H), 8.83 (s, 1H), 8.59 (s, 1H), 6.99-6.93 (m, 1H), 6.91 (d, J=8.5 Hz, 1H), 6.72 (dd, J=8.6, 3.9 Hz, 1H), 4.77 (s, 2H), 4.55 (s, 2H), 4.20 (s, 3H), 3.30 (t, J=6.4 Hz, 2H) ppm; LCMS: m/z 433.1 $[M+H]^+$.

Example 26 Using the Above Method, the Raw Materials were Replaced to Synthesize the Following Compound N-((5-fluoro-2,3-dihydrobenzofuran-4-yl)methyl)-8-(5-morpholino-[1,2,4]triazolo[1,5-a]pyridin-8-yl)-[1,2,4]triazolo[4,3-c]pyrimidin-5-amine

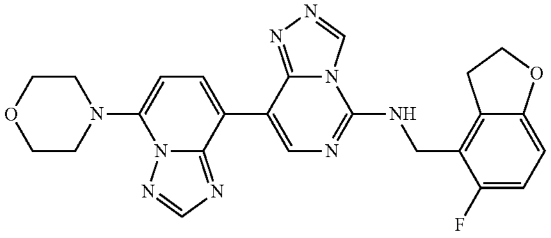 [SMILES: Fc1ccc2c(c1CNc1ncc(-c3ccc(N4CCOCC4)n4ncnc34)c3nncn13)CCO2]

$^1H$ NMR (400 MHz, DMSO-$d_6$) δ 9.53 (s, 1H), 9.32 (s, 1H), 9.10 (d, J=8.3 Hz, 1H), 8.81 (s, 1H), 8.59 (s, 1H), 6.99-6.94 (m, 1H), 6.81 (d, J=8.3 Hz, 1H), 6.72 (dd, J=8.7, 3.9 Hz, 1H), 4.77 (s, 2H), 4.55 (t, J=8.7 Hz, 2H), 3.92-3.81 (m, 4H), 3.56-3.46 (m, 4H), 3.35 (s, 2H) ppm; LCMS: m/z 488.1 $[M+H]^+$.

Example 27 Using the Above Method, the Raw Materials were Replaced to Synthesize the Following Compound 8-(5-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

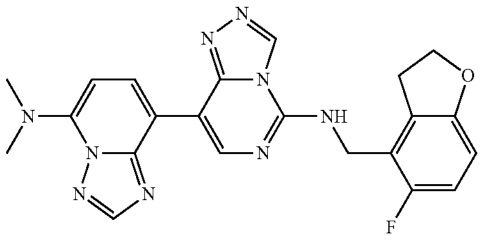 [SMILES: CN(C)c1ccc(-c2cnc(NCc3c(F)ccc4c3CCO4)n3cnnc23)c2ncnn12]

$^1H$ NMR (400 MHz, $CDCl_3$) δ 9.34 (s, 1H), 8.63 (s, 1H), 8.31 (d, J=8.4 Hz, 2H), 6.85-6.72 (m, 1H), 6.61 (dd, J=8.6, 3.9 Hz, 1H), 6.48 (d, J=8.1 Hz, 1H), 4.77 (s, 2H), 4.57 (t, J=8.7 Hz, 2H), 3.41 (t, J=8.7 Hz, 2H), 3.24 (s, 6H) ppm; LCMS: m/z 446.1 $[M+H]^+$.

Example 28 Using the Above Method, the Raw Materials were Replaced to Synthesize the Following Compound N-((5-fluoro-2,3-dihydrobenzofuran-4-yl)methyl)-8-(5-(4-methylpiperazin-1-yl)-[1,2,4]triazolo[1,5-a]pyridin-8-yl)-[1,2,4]triazolo[4,3-c]pyrimidin-5-amine

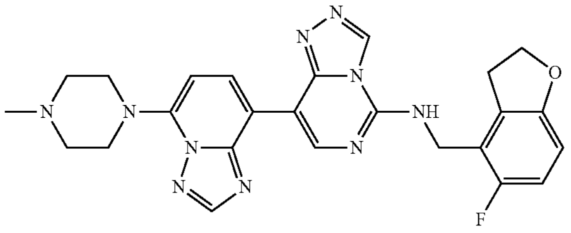 [SMILES: CN1CCN(c2ccc(-c3cnc(NCc4c(F)ccc5c4CCO5)n4cnnc34)c3ncnn23)CC1]

$^1H$ NMR (400 MHz, DMSO-$d_6$) δ 9.52 (s, 1H), 9.31 (s, 1H), 9.08 (d, J=8.3 Hz, 1H), 8.80 (d, J=4.7 Hz, 1H), 8.58 (s, 1H), 6.99-6.92 (m, 1H), 6.78 (d, J=8.3 Hz, 1H), 6.71 (dd, J=8.7, 3.9 Hz, 1H), 4.77 (d, J=4.3 Hz, 2H), 4.55 (t, J=8.7 Hz, 2H), 3.51 (s, 4H), 3.34 (d, J=7.4 Hz, 2H), 2.58 (s, 4H), 2.28 (s, 3H) ppm; LCMS: m/z 501.2 $[M+H]^+$.

Example 29 Using the Above Method, the Raw Materials were Replaced to Synthesize the Following Compound 8-(2,5-dimethyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

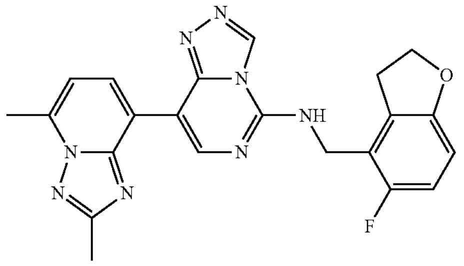 [SMILES: Cc1nc2c(-c3cnc(NCc4c(F)ccc5c4CCO5)n4cnnc34)ccc(C)n2n1]

$^1H$ NMR (400 MHz, DMSO-$d_6$) δ 9.53 (s, 1H), 9.44 (s, 1H), 9.05 (d, J=7.7 Hz, 1H), 8.88 (t, J=5.1 Hz, 1H), 7.19 (d, J=8.4 Hz, 1H), 7.03-6.92 (m, 1H), 6.72 (dd, J=8.7, 3.9 Hz, 1H), 4.79 (d, J=4.9 Hz, 2H), 4.55 (t, J=8.7 Hz, 2H), 3.30 (d, J=8.8 Hz, 2H), 2.74 (s, 3H), 2.58 (s, 3H) ppm; LCMS: m/z 431.1 $[M+H]^+$.

Example 30 Using the Above Method, the Raw Materials were Replaced to Synthesize the Following Compound 1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methoxy)-2-methylpropan-2-ol

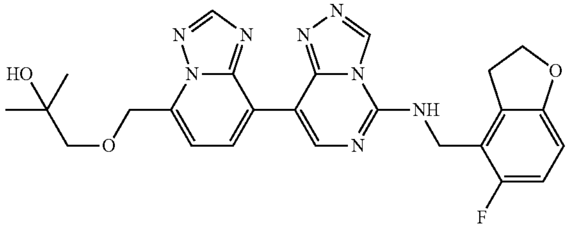 [SMILES: CC(C)(O)COCc1ccc(-c2cnc(NCc3c(F)ccc4c3CCO4)n3cnnc23)c2ncnn12]

$^1H$ NMR (400 MHz, MeOD) δ 9.35 (d, J=2.7 Hz, 1H), 9.08 (d, J=3.4 Hz, 1H), 8.78 (d, J=7.6 Hz, 1H), 8.44 (s, 1H), 7.44 (s, 1H), 7.40 (d, J=7.8 Hz, 1H), 6.89-6.81 (m, 1H), 6.67 (dd, J=8.6, 3.9 Hz, 1H), 5.35 (t, J=4.6 Hz, 1H), 5.13 (s, 2H), 4.84 (s, 2H), 4.64 (t, J=8.7 Hz, 2H), 3.93 (s, 2H), 3.22 (s, 2H), 1.28 (s, 6H) ppm; LCMS: m/z 460.2 $[M+H]^+$.

Example 31 Using the Above Method, the Raw Materials were Replaced to Synthesize the Following Compound 8-(5-((dimethylamino)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

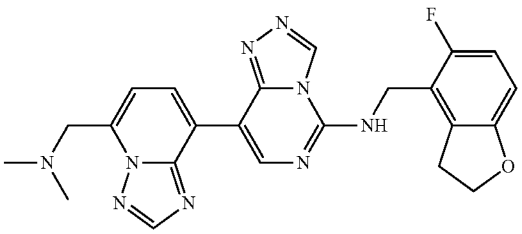 [SMILES: CN(C)Cc1ccc(-c2cnc(NCc3c(F)ccc4c3CCO4)n3cnnc23)c2ncnn12]

$^1H$ NMR (400 MHz, DMSO-$d_6$) δ 9.55 (s, 1H), 9.46 (s, 1H), 9.18 (d, J=7.7 Hz, 1H), 8.93 (s, 1H), 8.63 (s, 1H), 7.38 (d, J=7.7 Hz, 1H), 6.97 (dd, J=10.3, 8.7 Hz, 1H), 6.72 (dd, J=8.6, 3.9 Hz, 1H), 4.78 (d, J=4.9 Hz, 2H), 4.56 (t, J=8.7 Hz, 2H), 4.01 (s, 2H), 3.36 (t, 2H), 2.35 (s, 6H) ppm; LCMS: m/z 460.2 $[M+H]^+$.

Example 32 Using the Above Method, the Raw Materials were Replaced to Synthesize the Following Compound N-((5-fluoro-2,3-dihydrobenzofuran-4-yl)methyl)-8-(5-((4-methylpiperazin-1-yl)methyl)-[1,2,4]triazolo[1,5-a]pyridin-8-yl)-[1,2,4]triazolo[4,3-c]pyrimidin-5-amine

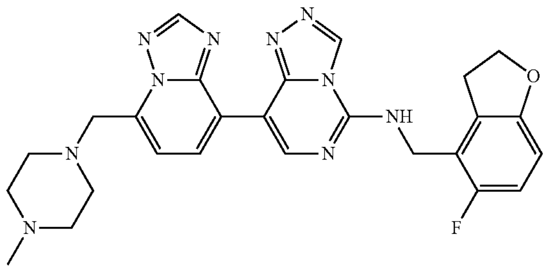 [SMILES: CN1CCN(Cc2ccc(-c3cnc(NCc4c(F)ccc5c4CCO5)n4cnnc34)c3ncnn23)CC1]

$^1H$ NMR (400 MHz, DMSO-$d_6$) δ 9.55 (s, 1H), 9.45 (s, 1H), 9.16 (d, J=7.7 Hz, 1H), 8.93 (s, 1H), 8.63 (s, 1H), 7.38 (d, J=7.8 Hz, 1H), 7.02-6.92 (m, 1H), 6.72 (dd, J=8.7, 3.9 Hz, 1H), 4.78 (d, J=4.7 Hz, 2H), 4.56 (t, J=8.7 Hz, 2H), 4.07 (s, 2H), 3.30 (s, 2H), 2.61 (s, 4H), 2.40 (s, 4H), 2.19 (s, 3H) ppm; LCMS: m/z 515.2 $[M+H]^+$.

Example 33 Using the Above Method, the Raw Materials were Replaced to Synthesize the Following Compound 1-(((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)amino)-2-methylpropan-2-ol

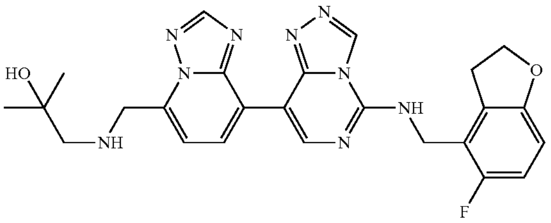

$^1H$ NMR (400 MHz, DMSO-$d_6$) δ 9.55 (s, 1H), 9.45 (s, 1H), 9.16 (d, J=7.7 Hz, 1H), 8.92 (s, 1H), 8.65 (s, 1H), 7.42 (d, J=7.7 Hz, 1H), 6.96 (d, J=10.1 Hz, 1H), 6.72 (dd, J=8.6, 4.0 Hz, 1H), 4.79 (d, J=4.9 Hz, 2H), 4.56 (s, 2H), 4.28 (s, 3H), 3.37 (s, 1H), 3.30 (s, 2H), 2.07 (s, 2H), 1.12 (s, 6H) ppm; LCMS: m/z 504.1 $[M+H]^+$.

Example 34 Using the Above Method, the Raw Materials were Replaced to Synthesize the Following Compound N-((5-fluoro-2,3-dihydrobenzofuran-4-yl)methyl)-8-(5-(morpholinomethyl)-[1,2,4]triazolo[1,5-a]pyridin-8-yl)-[1,2,4]triazolo[4,3-c]pyrimidin-5-amine

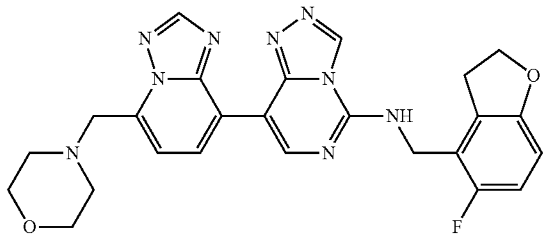 [SMILES: Fc1ccc2c(c1CNc1ncc(-c3ccc(CN4CCOCC4)n4ncnc34)c3nncn13)CCO2]

$^1$H NMR (400 MHz, DMSO-$d_6$) δ 9.55 (s, 1H), 9.45 (s, 1H), 9.17 (d, J=7.7 Hz, 1H), 8.94 (s, 1H), 8.64 (s, 1H), 7.42 (d, J=7.8 Hz, 1H), 6.97 (t, J=9.4 Hz, 1H), 6.72 (dd, J=8.4, 3.6 Hz, 1H), 4.79 (s, 2H), 4.56 (t, J=8.7 Hz, 2H), 4.08 (s, 2H), 3.65 (s, 4H), 3.33 (s, 2H), 2.60 (s, 4H) ppm; LCMS: m/z 502.1 [M+H]$^+$.

Example 35 Using the Above Method, the Raw Materials were Replaced to Synthesize the Following Compound N-((5-fluoro-2,3-dihydrobenzofuran-4-yl)methyl)-8-(5-(pyrrolidin-1-yl)-[1,2,4]triazolo[1,5-a]pyridin-8-yl)-[1,2,4]triazolo[4,3-c]pyrimidin-5-amine

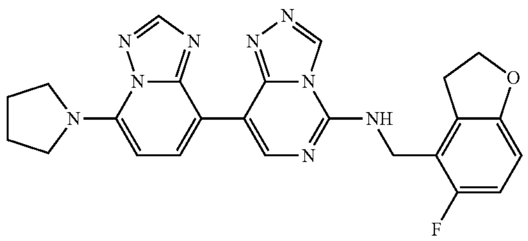 [SMILES: Fc1ccc2c(c1CNc1ncc(-c3ccc(N4CCCC4)n4ncnc34)c3nncn13)CCO2]

$^1$H NMR (400 MHz, DMSO-$d_6$) δ 9.51 (s, 1H), 9.24 (s, 1H), 9.02 (d, J=8.4 Hz, 1H), 8.68 (s, 1H), 8.46 (s, 1H), 7.00-6.91 (m, 1H), 6.71 (dd, J=8.6, 3.8 Hz, 1H), 6.41 (d, J=8.5 Hz, 1H), 4.75 (s, 2H), 4.55 (t, J=8.7 Hz, 2H), 3.82 (s, 4H), 3.31 (s, 2H), 2.00 (s, 4H) ppm; LCMS: m/z 472.1 [M+H]$^+$.

Example 36 Using the Above Method, the Raw Materials were Replaced to Synthesize the Following Compound N-((5-fluoro-2,3-dihydrobenzofuran-4-yl)methyl)-8-(5-(4-morpholinopiperidin-1-yl)-[1,2,4]triazolo[1,5-a]pyridin-8-yl)-[1,2,4]triazolo[4,3-c]pyrimidin-5-amine

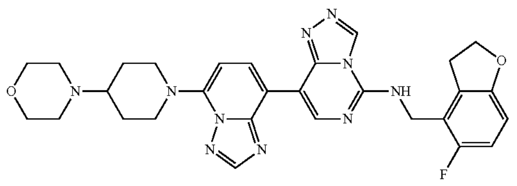

$^1$H NMR (400 MHz, DMSO-$d_6$) δ 9.52 (s, 1H), 9.31 (s, 1H), 9.07 (d, J=8.3 Hz, 1H), 8.78 (s, 1H), 8.58 (s, 1H), 7.01-6.92 (m, 1H), 6.78 (d, J=8.3 Hz, 1H), 6.71 (dd, J=8.7, 3.9 Hz, 1H), 4.76 (s, 2H), 4.55 (t, J=8.7 Hz, 2H), 4.12 (d, J=11.9 Hz, 2H), 3.72-3.50 (m, 4H), 3.32-3.28 (m, 2H), 2.91 (t, J=11.1 Hz, 2H), 2.58-2.51 (m, 4H), 2.43 (d, J=9.8 Hz, 1H), 1.96 (d, J=12.3 Hz, 2H), 1.66 (dd, J=20.5, 11.4 Hz, 2H) ppm; LCMS: m/z 571.2 [M+H]$^+$.

Example 37 Using the Above Method, the Raw Materials were Replaced to Synthesize the Following Compound 8-(5-(2-oxa-6-azaspiro[3.3]heptan-6-yl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

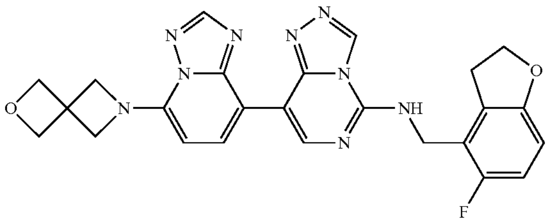 [SMILES: Fc1ccc2c(c1CNc1ncc(-c3ccc(N4CC5(COC5)C4)n4ncnc34)c3nncn13)CCO2]

$^1$H NMR (400 MHz, DMSO-$d_6$) δ 9.51 (s, 1H), 9.25 (s, 1H), 9.05 (d, J=8.3 Hz, 1H), 8.70 (s, 1H), 8.50 (s, 1H), 7.02-6.91 (m, 1H), 6.71 (dd, J=8.6, 3.9 Hz, 1H), 6.26 (d, J=8.4 Hz, 1H), 4.76 (d, J=11.0 Hz, 6H), 4.62-4.44 (m, 6H), 3.31 (d, J=8.8 Hz, 2H) ppm; LCMS: m/z 500.2 [M+H]$^+$.

Example 38 Using the Above Method, the Raw Materials were Replaced to Synthesize the Following Compound N1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)-N1,N2,N2-trimethylethane-1,2-diamine

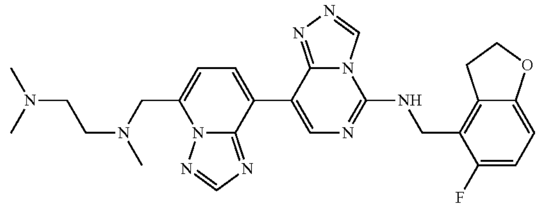 [SMILES: CN(C)CCN(C)Cc1ccc(-c2cnc(NCc3c(F)ccc4c3CCO4)n3cnnc23)c2ncnn12]

$^1$H NMR (400 MHz, DMSO-$d_6$) δ 9.54 (s, 1H), 9.43 (s, 1H), 9.14 (d, J=7.7 Hz, 1H), 8.94 (s, 1H), 8.62 (s, 1H), 7.40 (d, J=7.7 Hz, 1H), 6.97 (t, J=9.5 Hz, 1H), 6.72 (dd, J=8.5, 3.7 Hz, 1H), 4.78 (s, 2H), 4.56 (s, 2H), 4.11 (s, 2H), 3.35 (d, J=8.6 Hz, 2H), 2.64 (d, J=7.0 Hz, 2H), 2.46 (d, J=6.9 Hz, 2H), 2.36 (s, 3H), 2.15 (s, 6H) ppm; LCMS: m/z 517.2 $[M+H]^+$.

Example 39 Using the Above Method, the Raw Materials were Replaced to Synthesize the Following Compound N-((5-fluoro-2,3-dihydrobenzofuran-4-yl)methyl)-8-(5-(2-methylmorpholino)-[1,2,4]triazolo[1,5-a]pyridin-8-yl)-[1,2,4]triazolo[4,3-c]pyrimidin-5-amine

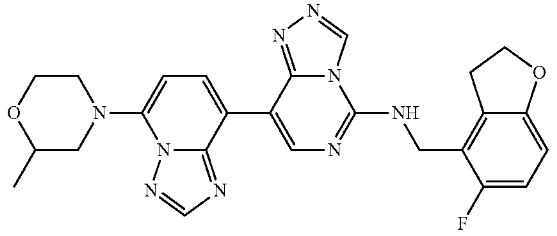 [SMILES: CC1CN(c2ccc(-c3cnc(NCc4c(F)ccc5c4CCO5)n4cnnc34)c3ncnn23)CCO1]

$^1$H NMR (400 MHz, DMSO-$d_6$) δ 9.53 (s, 1H), 9.32 (s, 1H), 9.09 (d, J=8.2 Hz, 1H), 8.81 (s, 1H), 8.60 (s, 1H), 6.97 (s, 1H), 6.80 (d, J=8.3 Hz, 1H), 6.76-6.67 (m, 1H), 4.77 (d, J=4.0 Hz, 2H), 4.55 (t, J=8.7 Hz, 2H), 3.99 (d, J=11.3 Hz, 3H), 3.82 (dd, J=19.0, 9.7 Hz, 2H), 3.31 (s, 2H), 2.96 (dd, J=11.6, 8.7 Hz, 1H), 2.70 (d, J=10.6 Hz, 1H), 1.19 (d, J=6.2 Hz, 3H) ppm; LCMS: m/z 502.2 $[M+H]^+$.

Example 40 Using the Above Method, the Raw Materials were Replaced to Synthesize the Following Compound N-((5-fluoro-2,3-dihydrobenzofuran-4-yl)methyl)-8-(6-fluoro-5-methyl-[1,2,4]triazolo[1,5-a]pyridin-8-yl)-[1,2,4]triazolo[4,3-c]pyrimidin-5-amine

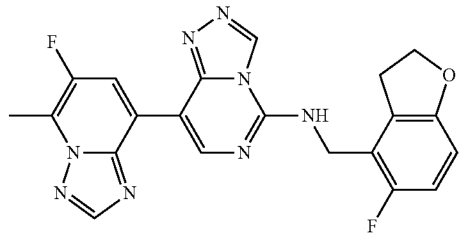 [SMILES: Cc1c(F)cc(-c2cnc(NCc3c(F)ccc4c3CCO4)n3cnnc23)c2ncnn12]

$^1$H NMR (400 MHz, DMSO-$d_6$) δ 9.62 (s, 1H), 9.57 (s, 1H), 9.32 (d, J=11.5 Hz, 1H), 9.09-9.04 (m, 1H), 8.70 (s, 1H), 6.98 (t, J=9.5 Hz, 1H), 6.73 (dd, J=3.9, 8.6 Hz, 1H), 4.80 (d, J=3.4 Hz, 2H), 4.56 (t, J=8.7 Hz, 2H), 3.64-3.58 (m, 1H), 3.32-3.30 (m, 2H), 2.76 (d, J=2.5 Hz, 3H) ppm; LCMS: m/z 435.1 $[M+H]^+$.

Example 41 Using the Above Method, the Raw Materials were Replaced to Synthesize the Following Compound N-((5-fluoro-2,3-dihydrobenzofuran-4-yl)methyl)-8-(6-methoxy-[1,2,4]triazolo[1,5-a]pyridin-8-yl)-[1,2,4]triazolo[4,3-c]pyrimidin-5-amine

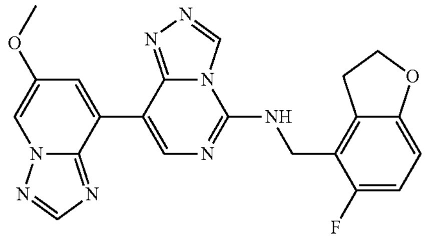 [SMILES: COc1cc(-c2cnc(NCc3c(F)ccc4c3CCO4)n3cnnc23)c2ncnn2c1]

$^1$H NMR (400 MHz, DMSO-$d_6$) δ 9.59 (s, 1H), 9.55 (s, 1H), 9.05 (d, J=2.3 Hz, 1H), 9.01 (s, 1H), 8.65 (d, J=2.3 Hz, 1H), 8.53 (s, 1H), 7.00-6.94 (m, 1H), 6.72 (dd, J=8.7, 3.9 Hz, 1H), 4.79 (s, 2H), 4.55 (t, J=8.7 Hz, 2H), 3.93 (s, 3H), 3.31 (s, 2H) ppm; LCMS: m/z 433.1 $[M+H]^+$.

Example 42 Using the Above Method, the Raw Materials were Replaced to Synthesize the Following Compound 8-(2-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

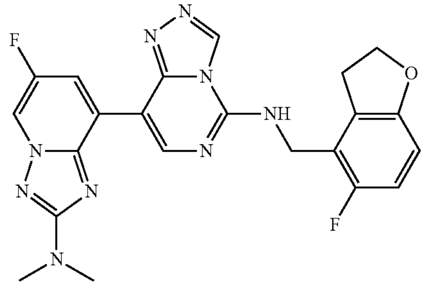 [SMILES: CN(C)c1nc2c(-c3cnc(NCc4c(F)ccc5c4CCO5)n4cnnc34)cc(F)cn2n1]

$^1$H NMR (400 MHz, DMSO-$d_6$) δ 9.62 (s, 1H), 9.55 (s, 1H), 9.18 (dd, J=2.3, 11.3 Hz, 1H), 8.98-8.90 (m, 2H), 6.98 (t, J=9.5 Hz, 1H), 6.73 (dd, J=3.9, 8.6 Hz, 1H), 4.80 (d, J=4.8 Hz, 2H), 4.55 (t, J=8.7 Hz, 2H), 3.31-3.28 (m, 2H), 3.10 (s, 6H) ppm; LCMS: m/z 464.3 $[M+H]^+$.

Example 43 Using the Above Method, the Raw Materials were Replaced to Synthesize the Following Compound 8-(2-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

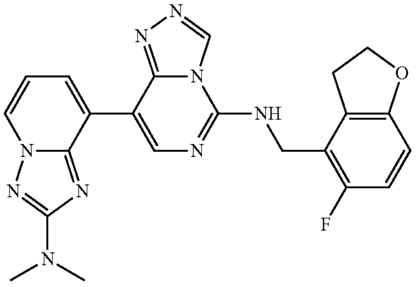 [SMILES: CN(C)c1nc2c(-c3cnc(NCc4c(F)ccc5c4CCO5)n4cnnc34)cccn2n1]

$^1$H NMR (400 MHz, DMSO-$d_6$) δ 9.53 (s, 1H), 9.50 (s, 1H), 9.07 (dd, J=7.7, 1.2 Hz, 1H), 8.82 (s, 1H), 8.61 (dd, J=6.6, 1.2 Hz, 1H), 7.10 (dd, J=7.7, 6.6 Hz, 1H), 6.98 (dd, J=10.3, 8.7 Hz, 1H), 6.73 (dd, J=8.7, 3.9 Hz, 1H), 4.79 (s, 2H), 4.55 (t, J=8.7 Hz, 2H), 3.30 (d, J=8.8 Hz, 2H), 3.10 (s, 6H) ppm; LCMS: m/z 446.1 $[M+H]^+$.

Example 44 Using the Above Method, the Raw Materials were Replaced to Synthesize the Following Compound 8-(5-(difluoromethyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

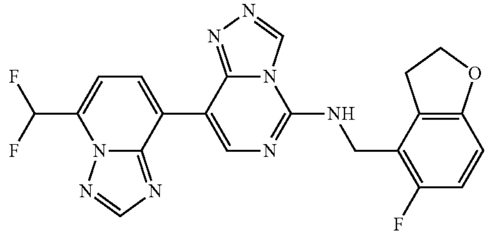 [SMILES: Fc1ccc2c(c1CNc1ncc(-c3ccc(C(F)F)n4ncnc34)c3nncn13)CCO2]

$^1$H NMR (400 MHz, DMSO-$d_6$) δ 9.60 (s, 1H), 9.57 (s, 1H), 9.33 (br d, J=7.6 Hz, 1H), 9.09 (br s, 1H), 8.77 (s, 1H), 7.78 (br s, 1H), 7.65 (t, J=52.8 Hz, 1H), 6.98 (br t, J=9.5 Hz, 1H), 6.73 (br dd, J=3.4, 8.5 Hz, 1H), 4.81 (br d, J=3.4 Hz, 2H), 4.56 (t, J=8.5 Hz, 2H), 3.31-3.23 (m, 2H) ppm; LCMS: m/z 453.3 $[M+H]^+$.

Example 45 Using the Above Method, the Raw Materials were Replaced to Synthesize the Following Compound 8-(5-(dimethylamino)-[1,2,4]triazolo[1,5-c]pyrimidin-8-yl)-N-((5-fluoro-2,3-dihydrobenzofuran-4-yl)methyl)-[1,2,4]triazolo[4,3-c]pyrimidin-5-amine

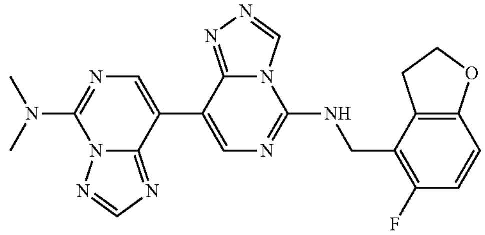 [SMILES: CN(C)c1ncc(-c2cnc(NCc3c(F)ccc4c3CCO4)n3cnnc23)c2ncnn12]

$^1$H NMR (400 MHz, DMSO-$d_6$) δ 9.46 (br s, 1H), 9.35 (s, 1H), 9.07 (s, 1H), 8.59 (s, 1H), 6.93 (t, J=9.2 Hz, 1H), 6.68 (dd, J=4.0, 8.8 Hz, 1H), 4.73 (s, 2H), 4.53 (t, J=8.8 Hz, 2H), 3.44 (s, 6H), 3.32-3.28 (m, 2H) ppm; LCMS: m/z 447.3 $[M+H]^+$.

Example 46 Using the Above Method, the Raw Materials were Replaced to Synthesize the Following Compound 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)ethan-1-ol

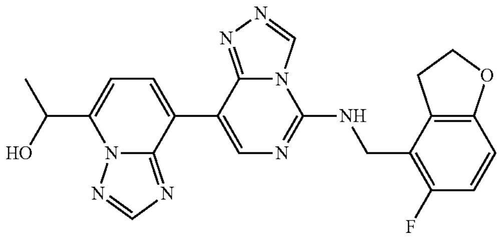 [SMILES: CC(O)c1ccc(-c2cnc(NCc3c(F)ccc4c3CCO4)n3cnnc23)c2ncnn12]

$^1$H NMR (400 MHz, DMSO-$d_6$) δ 9.55 (s, 1H), 9.43 (s, 1H), 9.19-9.17 (d, J=8.0 Hz, 1H), 8.93 (s, 1H), 8.64 (s, 1H), 7.44-7.42 (d, J=8.0 Hz, 1H), 6.99-6.94 (m, 1H), 6.73-6.70 (m, 1H), 5.90-5.89 (d, J=4.0 Hz, 1H), 5.43-5.40 (m, 1H), 4.78 (s, 2H), 4.55 (t, J=8.8 Hz, 2H), 3.34-3.27 (m, 2H), 1.56-1.54 (d, J=8.0 Hz, 3H) ppm; LCMS: 447.3 m/z $[M+H]^+$.

Example 47 Using the Above Method, the Raw Materials were Replaced to Synthesize the Following Compound 8-(5-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

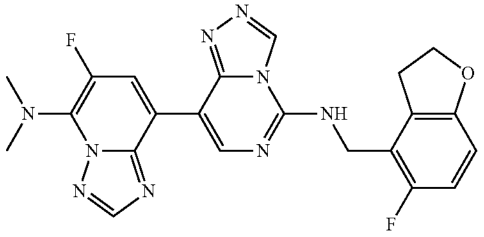 [SMILES: CN(C)c1c(F)cc(-c2cnc(NCc3c(F)ccc4c3CCO4)n3cnnc23)c2ncnn12]

$^1$H NMR (400 MHz, DMSO-$d_6$) δ 9.54 (s, 1H), 9.49 (s, 1H), 9.25 (d, J=14.4 Hz, 1H), 8.95-8.90 (m, 1H), 8.62 (s, 1H), 6.97 (t, J=9.5 Hz, 1H), 6.72 (dd, J=4.1, 8.7 Hz, 1H), 4.77 (br d, J=4.0 Hz, 2H), 4.55 (t, J=8.7 Hz, 2H), 3.27 (br d, J=5.1 Hz, 2H), 3.15 (d, J=2.8 Hz, 6H) ppm; LCMS m/z 464.1 [M+H]$^+$.

Example 48 Using the Above Method, the Raw Materials were Replaced to Synthesize the Following Compound 8-(5-(dimethylamino)-2-methyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

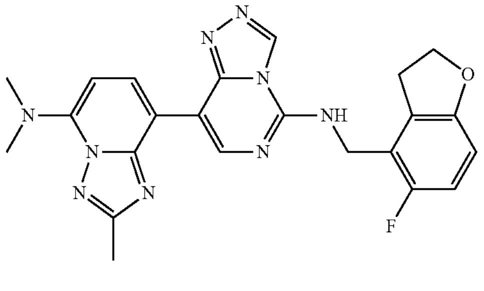 [SMILES: Cc1nc2c(-c3cnc(NCc4c(F)ccc5c4CCO5)n4cnnc34)ccc(N(C)C)n2n1]

$^1$H NMR (400 MHz, DMSO-$d_6$) δ 9.50 (s, 1H), 9.28 (s, 1H), 9.00 (d, J=8.4 Hz, 1H), 8.74 (d, J=1.2 Hz, 1H), 6.96 (t, J=9.6 Hz, 1H), 6.71 (dd, J=3.9, 8.8 Hz, 1H), 6.61 (d, J=8.4 Hz, 1H), 4.76 (s, 2H), 4.54 (t, J=8.8 Hz, 2H), 3.31-3.27 (m, 2H), 3.13 (s, 6H), 2.55 (s, 3H) ppm; LCMS: m/z 460.3 [M+H]$^+$.

Example 49 Using the Above Method, the Raw Materials were Replaced to Synthesize the Following Compound 8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridine-6-carbonitrile

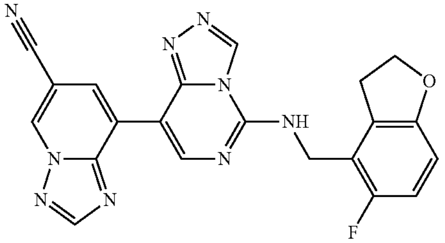 [SMILES: N#Cc1cc(-c2cnc(NCc3c(F)ccc4c3CCO4)n3cnnc23)c2ncnn2c1]

$^1$H NMR (400 MHz, DMSO-$d_6$) δ 9.81 (s, 1H), 9.59 (s, 1H), 9.57 (br s, 1H), 9.40 (s, 1H), 9.14 (br d, J=1.1 Hz, 1H), 8.86 (s, 1H), 6.97 (t, J=9.6 Hz, 1H), 6.72 (dd, J=3.9, 8.6 Hz, 1H), 4.80 (s, 2H), 4.55 (t, J=8.7 Hz, 2H), 3.25-3.22 (m, 2H) ppm; LCMS: m/z 428.0 [M+H]$^+$.

Example 49 Using the Above Method, the Raw Materials were Replaced to Synthesize the Following Compound 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

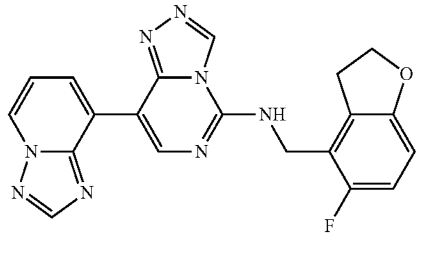 [SMILES: Fc1ccc2c(c1CNc1ncc(-c3cccn4ncnc34)c3nncn13)CCO2]

$^1$H NMR (400 MHz, DMSO-$d_6$) δ 9.56 (s, 1H), 9.51 (s, 1H), 9.19 (dd, J=7.6, 0.9 Hz, 1H), 8.98 (s, 1H), 8.93 (dd, J=6.7, 1.0 Hz, 1H), 8.63 (s, 1H), 7.43-7.38 (m, 1H), 7.01-6.95 (m, 1H), 6.73 (dd, J=8.6, 3.9 Hz, 1H), 4.79 (s, 2H), 4.56 (t, J=8.7 Hz, 2H), 3.33 (d, J=8.8 Hz, 2H) ppm; LCMS: m/z 403.1 [M+H]$^+$.

Example 50 Using the Above Method, the Raw Materials were Replaced to Synthesize the Following Compound 8-([1,2,4]triazolo[1,5-a]pyridin-8-yl)-N-(((1aR,6bR)-5-fluoro-1a,6b-dihydro-1H-cyclopropeno[b]benzofuran-6-yl)methyl)-[1,2,4]triazolo[4,3-c]pyrimidin-5-amine

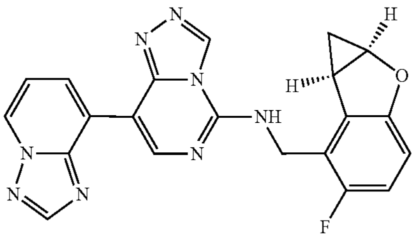 [SMILES: Fc1ccc2c(c1CNc1ncc(-c3cccn4ncnc34)c3nncn13)[C@H]1C[C@H]1O2]

$^1$H NMR (400 MHz, DMSO-$d_6$) δ 9.56 (s, 1H), 9.51 (s, 1H), 9.19 (dd, J=7.6, 0.9 Hz, 1H), 8.98 (s, 1H), 8.93 (dd, J=6.7, 1.0 Hz, 1H), 8.63 (s, 1H), 7.43-7.38 (m, 1H), 7.01-6.95 (m, 1H), 6.73 (dd, J=8.6, 3.9 Hz, 1H), 4.79 (s, 2H), 4.56 (t, J=8.7 Hz, 2H), 3.33 (d, J=8.8 Hz, 2H) ppm; LCMS: m/z 403.1 $[M+H]^+$.

Example 51 Using the Above Method, the Raw Materials were Replaced to Synthesize the Following Compound 8-(5-((1H-imidazol-1-yl)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

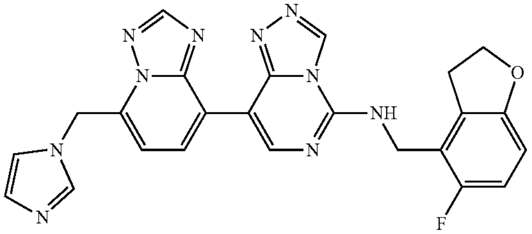 [SMILES: Fc1ccc2c(c1CNc1ncc(-c3ccc(Cn4ccnc4)n4ncnc34)c3nncn13)CCO2]

$^1$H NMR (400 MHz, DMSO-$d_6$) δ 9.54-9.51 (m, 1H), 9.44 (s, 1H), 9.12 (d, J=7.8 Hz, 1H), 8.72 (s, 1H), 7.90 (s, 1H), 7.35 (s, 1H), 7.07 (d, J=7.9 Hz, 1H), 6.96 (s, 1H), 6.72 (s, 1H), 5.81 (s, 2H), 4.78 (s, 2H), 4.55 (s, 2H), 3.17-3.15 (m, 2H) ppm; LCMS: m/z 483.1 $[M+H]^+$.

Example 52 Using the Above Method, the Raw Materials were Replaced to Synthesize the Following Compound N-((5-fluoro-2,3-dihydrobenzofuran-4-yl)methyl)-8-(5-methyl-[1,2,4]triazolo[1,5-c]pyrimidin-8-yl)-[1,2,4]triazolo[4,3-c]pyrimidin-5-amine

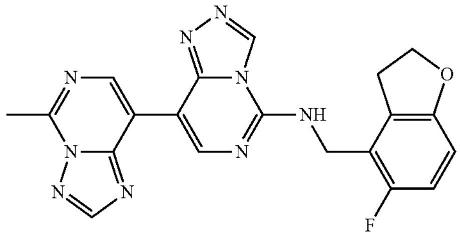 [SMILES: Cc1ncc(-c2cnc(NCc3c(F)ccc4c3CCO4)n3cnnc23)c2ncnn12]

$^1$H NMR (400 MHz, DMSO-$d_6$) δ 9.68 (s, 1H), 9.55 (s, 1H), 9.38 (s, 1H), 9.02 (br t, J=5.1 Hz, 1H), 8.78 (s, 1H), 7.00-6.93 (m, 1H), 6.72 (dd, J=3.9, 8.6 Hz, 1H), 4.78 (d, J=4.9 Hz, 2H), 4.55 (t, J=8.8 Hz, 2H), 3.32-3.30 (m, 2H), 2.96 (s, 3H) ppm; LCMS: m/z 418.0 $[M+H]^+$.

Pharmacology and Application

As one of the main components of the PRC2 protein complex, EED does not have enzymatic activity, but it plays an important role in the overall function of PRC2. The effect of EED on PRC2 is manifested in two aspects: 1) EED directly binds to trimethylated H3K27Me3, which can localize the PCR2 complex on the chromatin that needs to be modified; 2) EED have great allosteric promoting effect on enzymatic function of EZH2. Therefore, the development of compounds targeting an allosteric protein EED provides a new strategy for producing inhibition of EZH2 enzymatic activity. Moreover, such inhibitors have better or complementary advantages compared with EZH2 enzyme catalytic site inhibitors. For example, when subjects develop resistance to EZH2 enzyme inhibitors, EED inhibitors can also inhibit EZH2 enzyme activity. The invention discloses that the compound can be used as an EED target inhibitor, and has a therapeutic effect on diseases related to the action mechanism of EED and/or PRC2.

The biological functions of the compound disclosed in the present disclosure have been demonstrated in biochemical and cell level tests. For example, in a biochemical test, the compound disclosed in the present disclosure can have a strong competitive binding effect with the H3K27Me3 polypeptide binding to the EED protein ($IC_{50}$ can reach <1 nM). At the cellular level, the compounds disclosed in the present disclosure can not only inhibit the methylation level of histone H3K27 but also inhibit the proliferation of cancer cells through this effect ($IC_{50}$ can reach <5 nM). When the compound disclosed in the present disclosure is combined with the EED protein, the bicyclic structure outside the combined "pocket" can make the compound have better metabolic stability.

Example 53: Evaluation of the Effect of the Compound in Blocking the Binding of EED to H3K27Me3 by AlphaScreen (a-Screening) Method First, compound solutions with different concentration gradients are prepared. Compound powder is dissolved in DMSO to form mother liquor. 1.5 μL of the compound mother liquor is taken to 198.5 μL reaction buffer (25 mM HEPES (pH 8.0), 50 mM NaCl, 0.015% Tween 20, 0.5% BSA) and the solution is mix uniformly, and then 3-fold gradient dilution is performed with the above buffer containing 0.75% DMSO. 9 different test concentrations are set for the same compound. 5 μL of compounds with different concentration gradients was taken to ProxiPlate-384 Plus, White detection plate (PerkinElmer, 6008280), and 2 parallel replicates are set for each concentration gradient.

Next, a binding blocking reaction is performed. The full-length EED protein (441 amino acids) with His6 tag is diluted to 60 nM with the above buffer, and the biotinylated polypeptide fragment H3K27me3 (amino acids 19-33) (Biotinylated-H3K27me3) is diluted to 75 nM with the same buffer. 5 μL of 75 nM peptide fragments and 5 μL of 60 nM protein are transferred to the testing wells containing the compound respectively. The testing plate is sealed with a film, and is incubated for 30 minutes at room temperature.

Finally, AlphaScreen method is used for detection. Before use, nickel chelate acceptor beads and streptavidin donor beads (Perkin Elmer, product number 6760619M) are mixed into the above reaction buffer at a ratio of 1:1, and then 5 μL of the above pre-mixed testing solution is added to each testing well. The final concentration of the donor beads and acceptor beads is 5 μg/mL. The testing plate is covered with tin foil and placed at room temperature in the dark for 1 hour. Signals are read using an AlphaScreen detector on a Spectra max i3. The AlphaScreen signal is normalized according to the readings obtained from the positive control (maximum signal control) and negative control (minimum signal control) to give the inhibition rate of different concentrations of the compound. After that, non-linear regression analysis was performed with GraphPad Prism 5, and dose-response equation Y=Bottom+(Top−Bottom)/(1+10^((Log IC50−X)*HillSlope)) is used to make an inhibition curve, obtaining the $IC_{50}$ value of each compound.

In order to exclude false positives caused by compound interference with the AlphaScreen detection system, the compound is diluted in the same way, and the EED and peptide H3K27me3 in the detection system are replaced with biotinylated polypeptide Biotinylated-$(His)_6$. After incubation for the same time, the signal value is read on Spectra max i3. The data is processed in the same way.

Table 3 below shows the $IC_{50}$ values of some compounds.

TABLE 3

| Name of compounds | $IC_{50}$ (μM), AlphaScreen |
|---|---|
| 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol | 0.0075 |
| Compound a | 0.0054 |
| Compound b | 0.0089 |
| 3-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)pentan-3-ol | 0.0035 |
| 1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo]1,5-a]pyridin-5-yl)propan-2-ol | 0.0048 |
| Compound c | 0.0025 |
| Compound d | 0.0055 |
| 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)-2-methylpropan-2-ol | 0.0113 |
| 1,1,3,3-tetrafluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0030 |
| 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-1-ol | 0.0065 |
| Compound e | 0.0064 |
| Compound f | 0.0066 |
| 2-(8-(5-(((5-fluoro-2,3-dihydrobenzofuran-4-yl)methyl)amino)-[1,2,4]triazolo[4,3-c]pyrimidin-8-yl)-6-methyl-[1,2,4]triazolo[1,5-a]pyridin-5-yl)propan-2-ol | 0.0075 |
| 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-c]pyrimidin-5-yl)propan-2-ol | 0.0062 |
| 2-(8-(5-(((5-fluoro-2,3-dihydrobenzofuran-4-yl)methyl)amino)-[1,2,4]triazolo[4,3-c]pyrimidin-8-yl)-2-methyl-[1,2,4]triazolo[1,5-c]pyrimidin-5-yl)propan-2-ol | 0.0084 |
| 2-(6-fluoro-8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0057 |
| 1,1-difluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0051 |
| 1,3-difluoro-2-[8-(5-{[(5-fluoro-2,3-dihydro-1-benzofuran-4-yl)methyl]amino]-[1,2,4]triazolo[4,3-c]pyrimidin-8-yl)-[1,2,4]triazol[1,5-a]pyridin-5-yl]propan-2-ol | 0.0069 |
| 1-[8-(5-{[(5-fluoro-2,3-dihydro-1-benzofuran-4-yl)methyl]amino]-[1,2,4]triazolo[4,3-c]pyrimidin-8-yl)-[1,2,4]triazol[1,5-a]pyridin-5-yl]cyclopropan-1-ol | 0.0047 |
| 1-[8-(5-{[(5-fluoro-2,3-dihydro-1-benzofuran-4-yl)methyl]amino]-[1,2,4]triazolo[4,3-c]pyrimidin-8-yl)-[1,2,4]triazolo[1,5-a]pyridin-5-yl]cyclobutan-1-ol | 0.0055 |
| 1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol | 0.0043 |
| Compound g | 0.0040 |
| Compound h | 0.0048 |
| N-(((1aR,6bR)-5-fluoro-1a,6b-dihydro-1H-cyclopropeno[b]benzofuran-6-yl)methyl)-8-(5-methyl-[1,2,4]triazolo[1,5-a]pyridin-8-yl)-[1,2,4]triazolo[4,3-c]pyrimidin-5-amine | 0.0035 |
| N-((5-fluoro-2,3-dihydrobenzofuran-4-yl)methyl)-8-(5-methyl-[1,2,4]triazolo[1,5-a]pyridin-8-yl)-[1,2,4]triazolo[4,3-c]pyrimidin-5-amine | 0.0089 |
| 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0047 |

Example 54: ELISA (H3K27 Trimethylation) Analysis

Representative compounds of the present disclosure are diluted in DMSO with 3-fold gradient, and 10 concentration gradients are tested per compound. The maximum testing concentration is 10 μM. The compound is diluted 200-fold into G401 cells cultured in 96-well plates (the final concentration of DMSO is 0.5%). After the cells are cultured for 72 hours, the trimethylation level of histone H3K27 is detected by ELISA method.

Histone extraction: compound-treated cells in a 96-well plate are washed 3 times with 1×PBS (10×PBS buffer (80 g NaCl (Sigma, Product No. S3014), 2 g KCl (Sigma, Product No. 60128), 14.4 g $Na_2HAPO_4$ (Sigma, Product No. S5136) and 2.4 g $KH_2PO_4$ (Sigma, Product No. P9791) are added to 1 L water, pH to 7.4), and 100 μL of 0.4N HCl is added to each well. The 96-well plate is placed at 4° C. and gently shaken for 2 hours to lyse the cells. The cell lysate is then neutralized with 80 μL of neutralization buffer (0.5M disodium hydrogen phosphate, pH 12.5, 2.5 mM DTT; 1% cocktail (Sigma, Product No. P8340) (mixing the cell lysate and neutralization buffer thoroughly).

ELISA detection method: the cell lysates are transferred in parallel to two 384-well assay plates (PerkinElmer, OptiPlate-384HB, Product No. 6007290). One plate is used to detect the trimethylation level of H3K27, and the other plate is used to measure the level of H3. PBS is adjusted to a final volume of 50 μL/well. The wells are coated overnight at 4° C. On the next day, the solution in the wells was discarded. TBST buffer (1 xTBS (10×TBS: 24.2 g Tris (Sigma, Product No. T6066) and 80 g NaCl (Sigma, Product No. S3014) are added to 1 L water, and pH is adjusted to 7.6 with HCl) and 0.1% Tween-20) is used to wash it 5 times, and the water is dried on absorbent papers. 70 μL of blocking buffer (TBST, 5% BSA) is added to the coated reaction wells, and the wells are incubated for 1 hour at room temperature. The blocking buffer was discarded, and the primary antibody is added (30 μL/well). The required primary antibodies are diluted with blocking buffer, and the dilution ratios were as follows: anti-H3K27me3 antibody (Cell Signaling Technology, Product No. 9733), 1:2000 dilution; anti-H3 antibody (Cell Signaling Technology, Product No. 4499), 1:10000 dilution. After adding the primary antibody, the wells are incubated at room temperature for 1 hour. After washing with TBST for 5 times, the water are dried. The secondary antibody (30 μL/well) is added to each reaction well, and the wells are incubated at room temperature for 1 hour. Secondary antibody (anti-rabbit antibody (Jackson ImmunoResearch, Product No. 111-035-003)) is used after dilution 2000-fold in blocking buffer. After 1 hour, it is washed with TBST and dried. 30 μL of ECL substrate (Pierce, Product No. 34080) is added to each well and centrifuged for 30 seconds at 2000 rpm. Signal of each sample is detected using Molecular Devices, SpectraMax. Data processing: H3K27 methylation readings are first normalized by H3 signal. 0.500 DM8)-treated sample is used as a control, and the inhibition percentage of the compound is calculated. The data is fitted to a dose-response curve using the GraphPad prisim5 program, obtaining the $IC_{50}$ values of the test compounds.

Table 4 below shows the IC50 values of some compounds.

TABLE 4

| Name of compounds | $IC_{50}$ (μM), ELISA, G401 |
|---|---|
| 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol | 0.0021 |
| Compound a | 0.0012 |
| Compound b | 0.0017 |
| 3-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)pentan-3-ol | 0.0024 |
| 1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0019 |
| Compound c | 0.0017 |
| Compound d | 0.0047 |
| 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)-2-methylpropan-2-ol | 0.0032 |
| 1,1,3,3-tetrafluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0012 |
| 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-1-ol | 0.0026 |
| Compound e | 0.0004 |
| Compound f | 0.0013 |
| 2-(8-(5-(((5-fluoro-2,3-dihydrobenzofuran-4-yl)methyl)amino)-[1,2,4]triazolo[4,3-c]pyrimidin-8-yl)-6-methyl-[1,2,4]triazolo[1,5-a]pyridin-5-yl)propan-2-ol | 0.0024 |
| 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-c]pyrimidin-5-yl)propan-2-ol | 0.0028 |
| 2-(8-(5-(((5-fluoro-2,3-dihydrobenzofuran-4-yl)methyl)amino)-[1,2,4]triazolo[4,3-c]pyrimidin-8-yl)-2-methyl-[1,2,4]triazolo[1,5-c]pyrimidin-5-yl)propan-2-ol | 0.0006 |
| 2-(6-fluoro-8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0059 |
| 1,1-difluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0015 |
| 1,3-difluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazol[1,5-a]pyridin-5-yl]propan-2-ol | 0.0011 |
| 1-[8-(5-{[(5-fluoro-2,3-dihydro-1-benzofuran-4-yl)methyl]amino}-[1,2,4]triazolo[4,3-c]pyrimidin-8-yl)-[1,2,4]triazol[1,5-a]pyridin-5-yl]cyclopropan-1-ol | 0.0009 |

TABLE 4-continued

| Name of compounds | $IC_{50}$ (μM), ELISA, G401 |
|---|---|
| 1-[8-(5-{[(5-fluoro-2,3-dihydro-1-benzofuran-4-yl)methyl]amino]-[1,2,4]triazolo[4,3-c]pyrimidin-8-yl)-[1,2,4]triazolo[1,5-a]pyridin-5-yl]cyclobutan-1-ol | 0.0003 |
| 1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol | 0.0011 |
| Compound g | 0.0006 |
| Compound h | 0.0012 |
| N-(((1aR,6bR)-5-fluoro-1a,6b-dihydro-1H-cyclopropeno[b]benzofuran-6-yl)methyl)-8-(5-methyl-[1,2,4]triazolo[1,5-a]pyridin-8-yl)-[1,2,4]triazolo[4,3-c]pyrimidin-5-amine | 0.0024 |
| N-((5-fluoro-2,3-dihydrobenzofuran-4-yl)methyl)-8-(5-methyl-[1,2,4]triazolo[1,5-a]pyridin-8-yl)-[1,2,4]triazolo[4,3-c]pyrimidin-5-amine | 0.0017 |
| 8-(5-chloro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0330 |
| N-((5-fluoro-2,3-dihydrobenzofuran-4-yl)methyl)-8-(5-(trifluoromethyl)-[1,2,4]triazolo[1,5-a]pyridin-8-yl)-[1,2,4]triazolo[4,3-c]pyrimidin-5-amine | 0.0069 |
| N-((5-fluoro-2,3-dihydrobenzofuran-4-yl)methyl)-8-(5-methoxy-[1,2,4]triazolo[1,5-a]pyridin-8-yl)-[1,2,4]triazolo[4,3-c]pyrimidin-5-amine | 0.0032 |
| N-((5-fluoro-2,3-dihydrobenzofuran-4-yl)methyl)-8-(5-morpholino-[1,2,4]triazolo[1,5-a]pyridin-8-yl)-[1,2,4]triazolo[4,3-c]pyrimidin-5-amine | 0.0011 |
| 8-(5-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0010 |
| N-((5-fluoro-2,3-dihydrobenzofuran-4-yl)methyl)-8-(5-(4-methylpiperazin-1-yl)-[1,2,4]triazolo[1,5-a]pyridin-8-yl)-[1,2,4]triazolo[4,3-c]pyrimidin-5-amine | 0.0041 |
| 8-(2,5-dimethyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0013 |
| 1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methoxy)-2-methylpropan-2-ol | 0.0064 |
| 8-(5-((dimethylamino)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0006 |
| N-((5-fluoro-2,3-dihydrobenzofuran-4-yl)methyl)-8-(5-((4-methylpiperazin-1-yl)methyl)-[1,2,4]triazolo[1,5-a]pyridin-8-yl)-[1,2,4]triazolo[4,3-c]pyrimidin-5-amine | 0.0011 |
| 1-(((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)amino)-2-methylpropan-2-ol | 0.0022 |
| N-((5-fluoro-2,3-dihydrobenzofuran-4-yl)methyl)-8-(5-(morpholinomethyl)-[1,2,4]triazolo[1,5-a]pyridin-8-yl)-[1,2,4]triazolo[4,3-c]pyrimidin-5-amine | 0.0011 |
| N-((5-fluoro-2,3-dihydrobenzofuran-4-yl)methyl)-8-(5-(pyrrolidin-1-yl)-[1,2,4]triazolo[1,5-a]pyridin-8-yl)-[1,2,4]triazolo[4,3-c]pyrimidin-5-amine | 0.0027 |
| N-((5-fluoro-2,3-dihydrobenzofuran-4-yl)methyl)-8-(5-(4-morpholinopiperidin-1-yl)-[1,2,4]triazolo[1,5-a]pyridin-8-yl)-[1,2,4]triazolo[4,3-c]pyrimidin-5-amine | 0.0011 |
| 8-(5-(2-oxa-6-azaspiro[3.3]heptan-6-yl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0017 |
| N1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)-N1,N2,N2-trimethylethane-1,2-diamine | 0.0112 |
| N-((5-fluoro-2,3-dihydrobenzofuran-4-yl)methyl)-8-(5-(2-methylmorpholino)-[1,2,4]triazolo[1,5-a]pyridin-8-yl)-[1,2,4]triazolo[4,3-c]pyrimidin-5-amine | 0.0008 |
| N-((5-fluoro-2,3-dihydrobenzofuran-4-yl)methyl)-8-(6-fluoro-5-methyl-[1,2,4]triazolo[1,5-a]pyridin-8-yl)-[1,2,4]triazolo[4,3-c]pyrimidin-5-amine | 0.0036 |
| N-((5-fluoro-2,3-dihydrobenzofuran-4-yl)methyl)-8-(6-methoxy-[1,2,4]triazolo[1,5-a]pyridin-8-yl)-[1,2,4]triazolo[4,3-c]pyrimidin-5-amine | 0.0012 |
| 8-(2-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0018 |
| 8-(2-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0084 |
| 8-(5-(difluoromethyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0055 |
| 8-(5-(dimethylamino)-[1,2,4]triazolo[1,5-c]pyrimidin-8-yl)-N-((5-fluoro-2,3-dihydrobenzofuran-4-yl)methyl)-[1,2,4]triazolo[4,3-c]pyrimidin-5-amine | 0.0018 |
| 8-(5-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0028 |
| 8-(5-(dimethylamino)-2-methyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0006 |
| 8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridine-6-carbonitrile | 0.0143 |
| 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0009 |
| 8-(5-((1H-imidazol-1-yl)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0006 |
| N-((5-fluoro-2,3-dihydrobenzofuran-4-yl)methyl)-8-(5-methyl-[1,2,4]triazolo[1,5-c]pyrimidin-8-yl)-[1,2,4]triazolo[4,3-c]pyrimidin-5-amine | 0.0045 |

Example 55: Cell Proliferation Analysis

Human B-cell non-Hodgkin lymphoma cells KARPAS-422 S were cultured in culture flasks using standard cell culture conditions. The culture medium contains 15% fetal bovine serum (FBS, Invitrogen, product number 10099-141), 1% penicillin/streptomycin solution (P/S) RPMI-1640 (Invitrogen, product number 11875), and the culture flask is placed and cultured in a sterile incubator at 37° C., 95% relative humidity, and 5% $CO_2$. In order to detect the effect of PRC2 inhibitors on cell proliferation, cells in the exponential growth phase were seeded into 96-well plates (Corning, product number 3904) at a density of $1\times10^4$ cells/well, and 100 μL of medium was added to each well. Subsequently, the compounds disclosed herein at different concentrations were added to the wells seeded with cells (9 concentration gradients were set for each compound, and the highest detection concentration was 10 μM, 3-fold gradient dilution), and 2 repeats in parallel were set for each treatment concentration. The final concentration of DMSO is 0.5%. Then the number of surviving cells was counted with Vi-CELL (Beckman Coulter) every 3-4 days. The cells counted each time were seeded into a new 96-well plate at the same density ($1\times10^4$ cells/well). The wells were supplemented with fresh medium to 100 μL, and different concentrations of the compound were added at the same time. The cells were cultured until the 13th day, on which 100 μL of CellTiter-Glo (CellTiter-GloCellTiter-GloCellTiter-GloCTG) (Promega, Product No. G7573) was added to each well. The plate was placed for 10-20 minutes in the dark at room temperature, and Molecular Devices and SpectraMax i3X were used to read the luminous signal. The data were fitted to a dose-response curve using GraphPad prisim5 and the $IC_{50}$ values of the tested compounds were obtained.

Table 5 below shows the $IC_{50}$ values of some compounds.

TABLE 5

| Name of compounds | $IC_{50}$ (μM), Karpas-422, 13 days |
|---|---|
| 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)butan-2-ol | 0.0052 |
| Compound a | 0.0041 |
| Compound b | 0.0079 |
| 3-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)pentan-3-ol | 0.0077 |
| 1,1,1-trifluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0088 |
| Compound c | 0.0095 |
| Compound d | 0.0087 |
| 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)-2-methylpropan-2-ol | 0.0102 |
| 1,1,3,3-tetrafluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0049 |
| 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-1-ol | 0.0032 |
| Compound e | 0.0020 |
| Compound f | 0.0054 |
| 2-(8-(5-(((5-fluoro-2,3-dihydrobenzofuran-4-yl)methyl)amino)-[1,2,4]triazolo[4,3-c]pyrimidin-8-yl)-6-methyl-[1,2,4]triazolo[1,5-a]pyridin-5-yl)propan-2-ol | 0.0087 |
| 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-c]pyrimidin-5-yl)propan-2-ol | 0.0066 |
| 2-(8-(5-(((5-fluoro-2,3-dihydrobenzofuran-4-yl)methyl)amino)-[1,2,4]triazolo[4,3-c]pyrimidin-8-yl)-2-methyl-[1,2,4]triazolo[1,5-c]pyrimidin-5-yl)propan-2-ol | 0.0065 |
| 2-(6-fluoro-8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0146 |
| 1,1-difluoro-2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0048 |
| 1,3-difluoro-2-[8-(5-{[(5-fluoro-2,3-dihydro-1-benzofuran-4-yl)methyl]amino]-[1,2,4]triazolo[4,3-c]pyrimidin-8-yl)-[1,2,4]triazol[1,5-a]pyridin-5-yl]propan-2-ol | 0.0041 |
| 1-[8-(5-{[(5-fluoro-2,3-dihydro-1-benzofuran-4-yl)methyl]amino]-[1,2,4]triazolo[4,3-c]pyrimidin-8-yl)-[1,2,4]triazol[1,5-a]pyridin-5-yl]cyclopropan-1-ol | 0.0033 |
| 1-[8-(5-{[(5-fluoro-2,3-dihydro-1-benzofuran-4-yl)methyl]amino]-[1,2,4]triazolo[4,3-c]pyrimidin-8-yl)-[1,2,4]triazolo[1,5-a]pyridin-5-yl]cyclobutan-1-ol | 0.0016 |
| 1-fluoro-2-[8-(5-{[(5-fluoro-2,3-dihydro-1-benzofuran-4-yl)methyl]amino}-[1,2,4]triazolo[4,3-c]pyrimidin-8-yl)-[1,2,4]triazolo[1,5-a]pyridin-5-yl]propan-2-ol | 0.0022 |
| Compound g | 0.0015 |
| Compound h | 0.0025 |
| N-(((1aR,6bR)-5-fluoro-1a,6b-dihydro-1H-cyclopropeno[b]benzofuran-6-yl)methyl)-8-(5-methyl-[1,2,4]triazolo[1,5-a]pyridin-8-yl)-[1,2,4]triazolo[4,3-c]pyrimidin-5-amine | 0.0044 |
| N-((5-fluoro-2,3-dihydrobenzofuran-4-yl)methyl)-8-(5-methyl-[1,2,4]triazolo[1,5-a]pyridin-8-yl)-[1,2,4]triazolo[4,3-c]pyrimidin-5-amine | 0.0018 |
| 8-(5-chloro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0180 |
| N-((5-fluoro-2,3-dihydrobenzofuran-4-yl)methyl)-8-(5-(trifluoromethyl)-[1,2,4]triazolo[1,5-a]pyridin-8-yl)-[1,2,4]triazolo[4,3-c]pyrimidin-5-amine | 0.0360 |
| N-((5-fluoro-2,3-dihydrobenzofuran-4-yl)methyl)-8-(5-methoxy-[1,2,4]triazolo[1,5-a]pyridin-8-yl)-[1,2,4]triazolo[4,3-c]pyrimidin-5-amine | 0.0011 |
| N-((5-fluoro-2,3-dihydrobenzofuran-4-yl)methyl)-8-(5-morpholino-[1,2,4]triazolo[1,5-a]pyridin-8-yl)-[1,2,4]triazolo[4,3-c]pyrimidin-5-amine | 0.0007 |
| 8-(5-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0014 |

TABLE 5-continued

| Name of compounds | $IC_{50}$ (μM), Karpas-422, 13 days |
|---|---|
| N-((5-fluoro-2,3-dihydrobenzofuran-4-yl)methyl)-8-(5-(4-methylpiperazin-1-yl)-[1,2,4]triazolo[1,5-a]pyridin-8-yl)-[1,2,4]triazolo[4,3-c]pyrimidin-5-amine | 0.0007 |
| 8-(2,5-dimethyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0013 |
| 1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methoxy)-2-methylpropan-2-ol | 0.0012 |
| 8-(5-((dimethylamino)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0005 |
| N-((5-fluoro-2,3-dihydrobenzofuran-4-yl)methyl)-8-(5-((4-methylpiperazin-1-yl)methyl)-[1,2,4]triazolo[1,5-a]pyridin-8-yl)-[1,2,4]triazolo[4,3-c]pyrimidin-5-amine | 0.0007 |
| 1-(((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)amino)-2-methylpropan-2-ol | 0.0021 |
| N-((5-fluoro-2,3-dihydrobenzofuran-4-yl)methyl)-8-(5-(morpholinomethyl)-[1,2,4]triazolo[1,5-a]pyridin-8-yl)-[1,2,4]triazolo[4,3-c]pyrimidin-5-amine | 0.0011 |
| N-((5-fluoro-2,3-dihydrobenzofuran-4-yl)methyl)-8-(5-(pyrrolidin-1-yl)-[1,2,4]triazolo[1,5-a]pyridin-8-yl)-[1,2,4]triazolo[4,3-c]pyrimidin-5-amine | 0.0032 |
| N-((5-fluoro-2,3-dihydrobenzofuran-4-yl)methyl)-8-(5-(4-morpholinopiperidin-1-yl)-[1,2,4]triazolo[1,5-a]pyridin-8-yl)-[1,2,4]triazolo[4,3-c]pyrimidin-5-amine | 0.0008 |
| 8-(5-(2-oxa-6-azaspiro[3.3]heptan-6-yl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0018 |
| N1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)-N1,N2,N2-trimethylethane-1,2-diamine | 0.0035 |
| N-((5-fluoro-2,3-dihydrobenzofuran-4-yl)methyl)-8-(5-(2-methylmorpholino)-[1,2,4]triazolo[1,5-a]pyridin-8-yl)-[1,2,4]triazolo[4,3-c]pyrimidin-5-amine | 0.0005 |
| N-((5-fluoro-2,3-dihydrobenzofuran-4-yl)methyl)-8-(6-fluoro-5-methyl-[1,2,4]triazolo[1,5-a]pyridin-8-yl)-[1,2,4]triazolo[4,3-c]pyrimidin-5-amine | 0.0047 |
| N-((5-fluoro-2,3-dihydrobenzofuran-4-yl)methyl)-8-(6-methoxy-[1,2,4]triazolo[1,5-a]pyridin-8-yl)-[1,2,4]triazolo[4,3-c]pyrimidin-5-amine | 0.0017 |
| 8-(2-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0244 |
| 8-(2-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0054 |
| 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0014 |
| 8-(5-((1H-imidazol-1-yl)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0009 |
| N-((5-fluoro-2,3-dihydrobenzofuran-4-yl)methyl)-8-(5-methyl-[1,2,4]triazolo[1,5-c]pyrimidin-8-yl)-[1,2,4]triazolo[4,3-c]pyrimidin-5-amine | 0.0025 |

The compounds disclosed in the present invention above can be used to treat cancers related to the action mechanism of EED protein and/or PRC2 protein complex, including but not limited to diffuse large B-cell lymphoma, follicular lymphoma, non-Hodgkinson lymphoma and other lymphoma, leukemia, multiple myeloma, mesothelioma, gastric cancer, malignant rhabdoid tumors, liver cancer, prostate cancer, breast cancer, brain tumors including neuroblastoma, glioma, glioblastoma and astrocytoma, cervical cancer, colon cancer, melanoma, endometrial cancer, esophageal cancer, head and neck cancer, lung cancer, nasopharyngeal cancer, ovarian cancer, pancreatic cancer, kidney cancer, rectal cancer, thyroid cancer, parathyroid tumors, uterine tumors and soft tissue sarcomas, etc.

What is claimed is:

1. A compound represented by formula (I), a pharmaceutically acceptable salt thereof, a stereoisomer thereof, a solvate thereof or an isotope-labeled compound thereof:

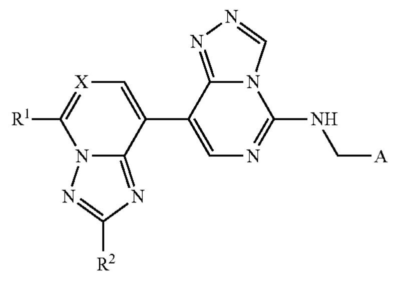

(I)

wherein

A is

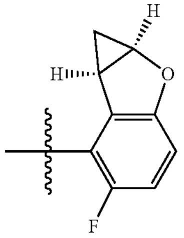

or

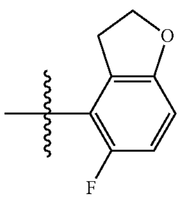

,

X is N or $CR^7$;
$R^1$ is
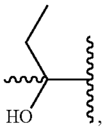 , 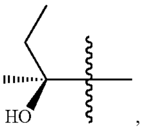 , 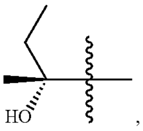 , 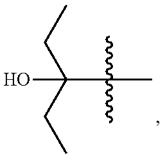 ,
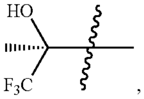 , 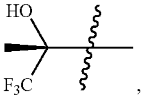 , 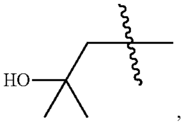 ,
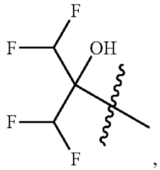 , 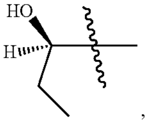 , 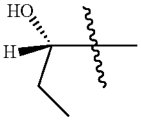 ,
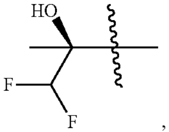 , 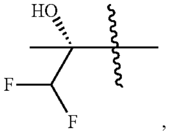 ,
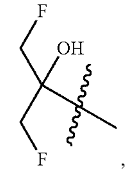 , 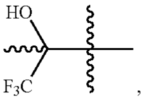 , 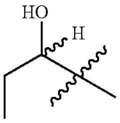 ,
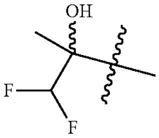 , 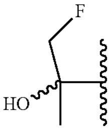 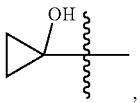 ,
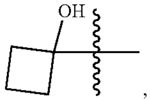 , 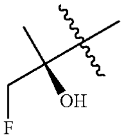 or 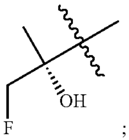 ;
$R^2$ is H, $C_{1-4}$ alkyl, $C_{3-6}$ cycloalkyl or an unsubstituted amino group or an amino group substituted by $C_{1-4}$ alkyl;
or, the group
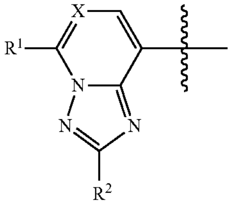
is
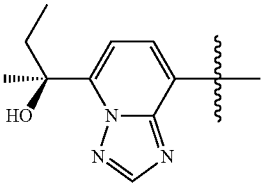 ,
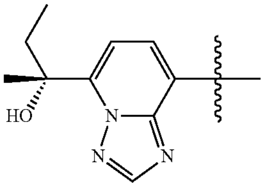 ,
-continued
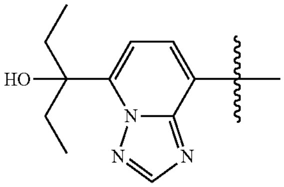 ,
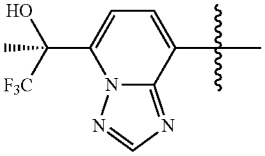 , 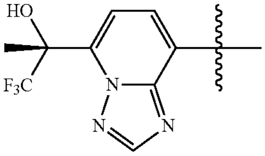 ,
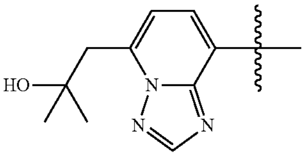 ,
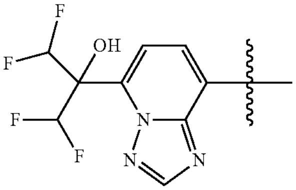 ,
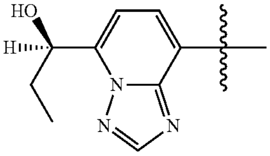 , 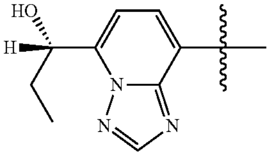 ,
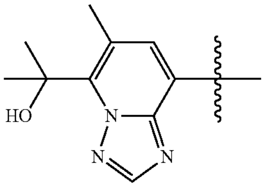 , 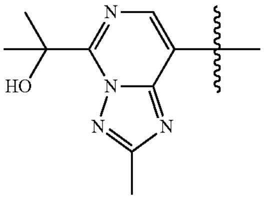 ,
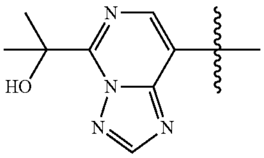 , 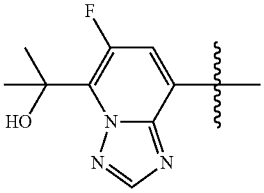 ,
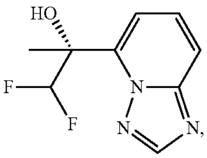 , 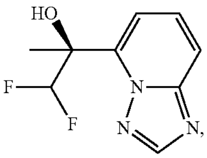 ,
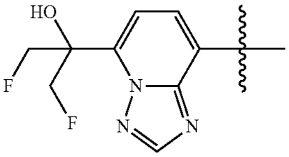 ,
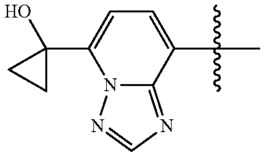 , 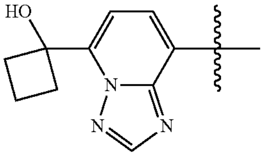 , -continued

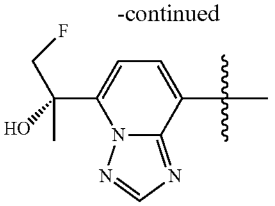

, or

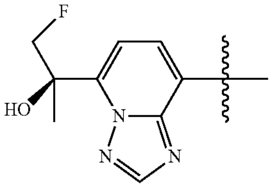

;

$R^7$ is independently H, hydroxyl, —CN, halogen, $C_{1-4}$ alkoxy or $C_{1-4}$ alkyl.

2. The compound represented by formula (I), the pharmaceutically acceptable salt thereof, the stereoisomer thereof, the solvate thereof, or the isotope-labeled compound thereof according to claim 1, wherein, the solvate is a hydrate;

or, when $R^2$ is $C_{1-4}$ alkyl, the $C_{1-4}$ alkyl is methyl, ethyl, propyl, isopropyl, butyl, isobutyl or tert-butyl;

or, when $R^2$ is $C_{3-6}$ cycloalkyl, the $C_{3-6}$ cycloalkyl is cyclopropyl, cyclobutyl, cyclopentyl or cyclohexyl;

or, when $R^2$ is an unsubstituted amino group or an amino group substituted by $C_{1-4}$ alkyl, the $C_{1-4}$ alkyl is methyl, ethyl, propyl, isopropyl, butyl, isobutyl or tert-butyl;

or, when $R^2$ is an amino group substituted by $C_{1-4}$ alkyl, the number of the $C_{1-4}$ alkyl substituent on the amino group is 1 or 2;

or, when $R^7$ is halogen, the halogen is fluorine, chlorine, bromine or iodine;

or, when $R^7$ is $C_{1-4}$ alkoxy, the $C_{1-4}$ alkoxy is methoxy, ethoxy, propoxy, isopropoxy, butoxy, isobutoxy or tert-butoxy;

or, when $R^7$ is $C_{1-4}$ alkyl, the $C_{1-4}$ alkyl is methyl, ethyl, propyl, isopropyl, butyl, isobutyl or tert-butyl.

3. The compound represented by formula (I), the pharmaceutically acceptable salt thereof, the stereoisomer thereof, the solvate thereof, or the isotope-labeled compound thereof according to claim 1, wherein A is

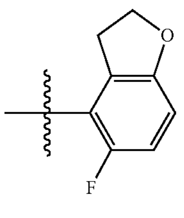

;

or, $R^7$ is H, —CN, halogen, $C_{1-4}$ alkoxy or $C_{1-4}$ alkyl.

4. The compound represented by formula (I), the pharmaceutically acceptable salt thereof, the stereoisomer thereof, the solvate thereof, or the isotope-labeled compound thereof according to claim 1, wherein the compound represented by formula (I) is selected from the compounds shown below:

(I-1)

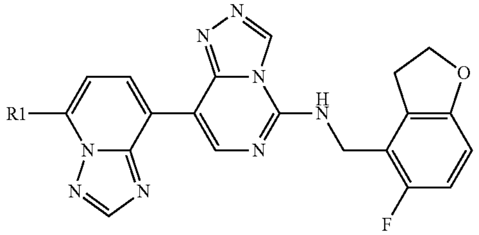

, (I-2)

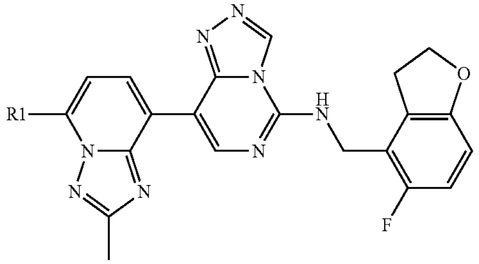

, (I-3)

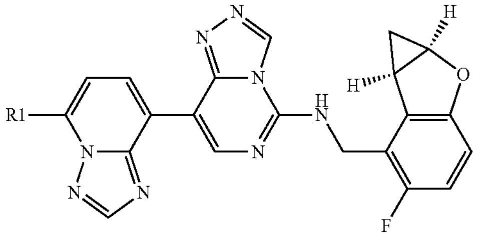

, (I-4)

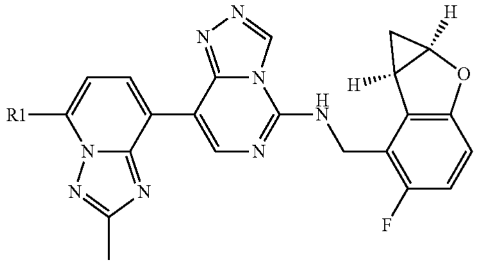

, (I-5)

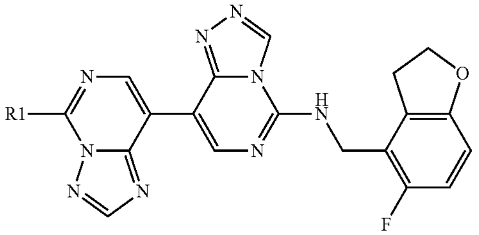

, (I-6)

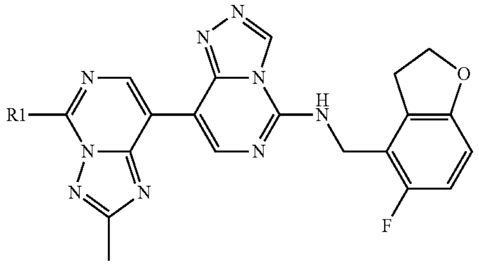

,

-continued
(I-7)
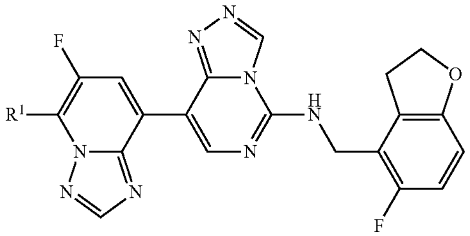
,
(I-8)
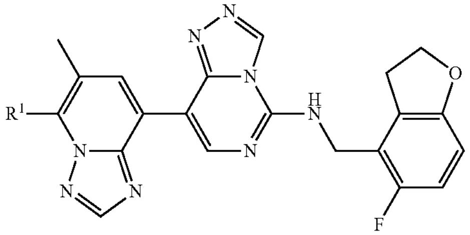
,
(I-9)
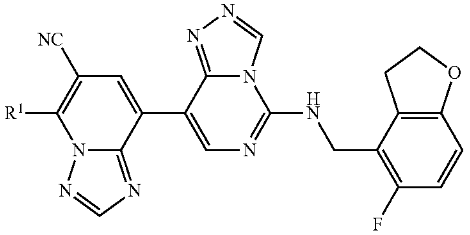
and
(I-10)
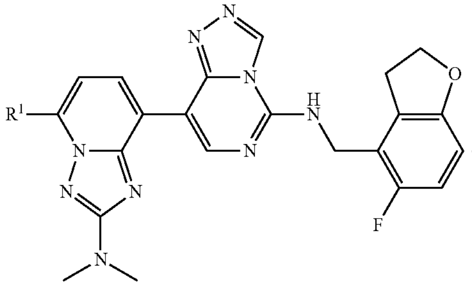
.
5. The compound represented by formula (I), the pharmaceutically acceptable salt thereof, the stereoisomer thereof, the solvate thereof, or the isotope-labeled compound thereof according to claim 1, wherein the compound represented by formula (I) is selected from the group consisting of:
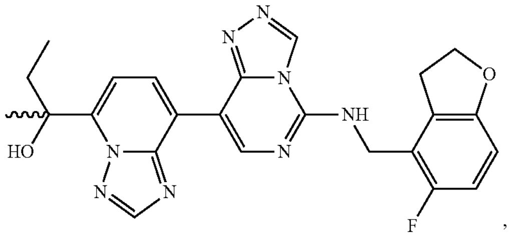
,
-continued
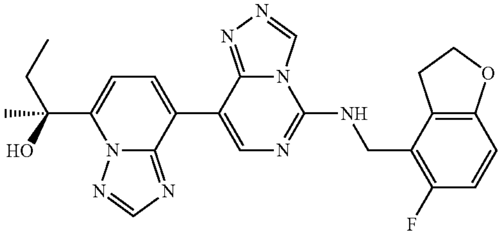
,
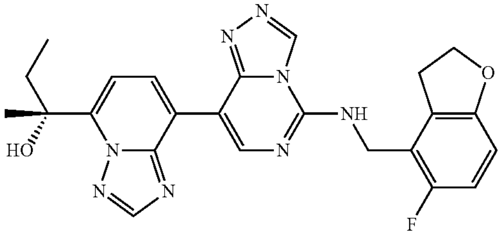
,
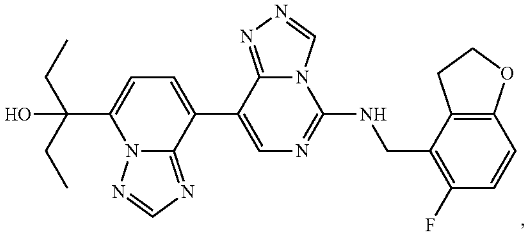
,
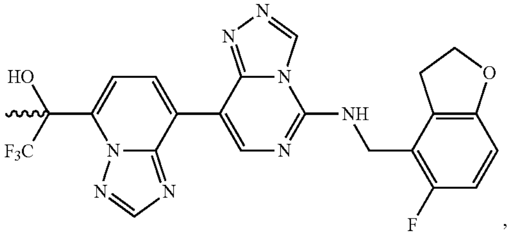
,
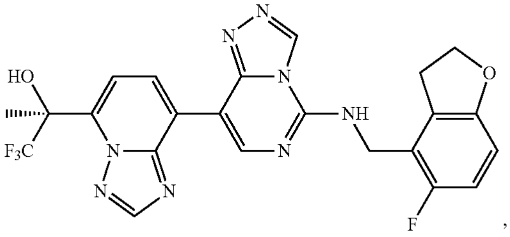
,
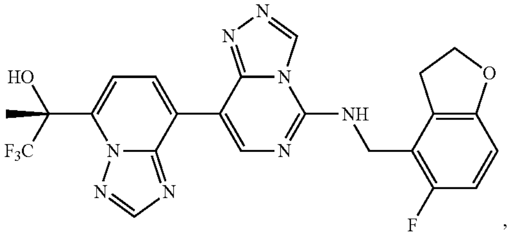
,
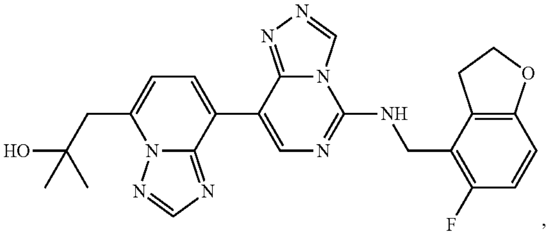
, -continued
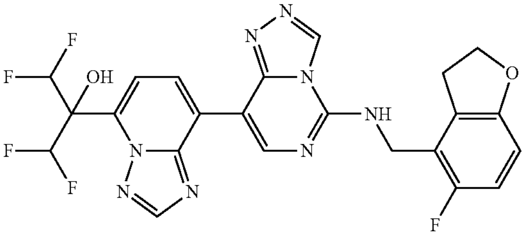
,
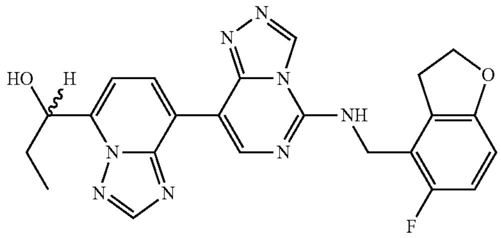
,
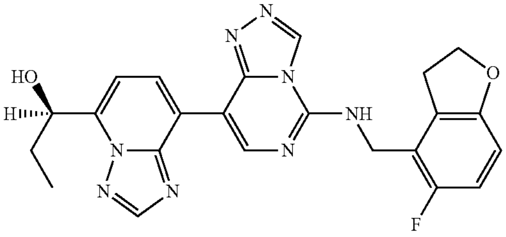
,
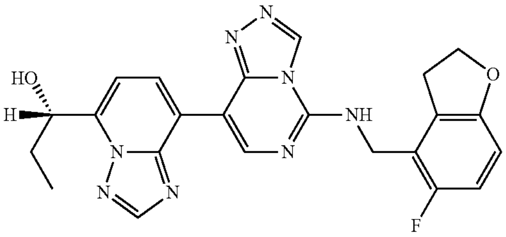
,
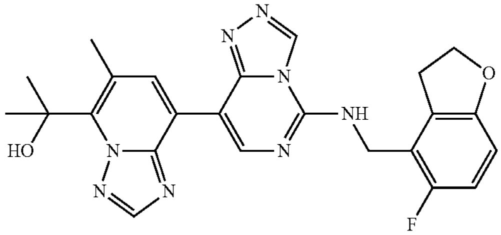
,
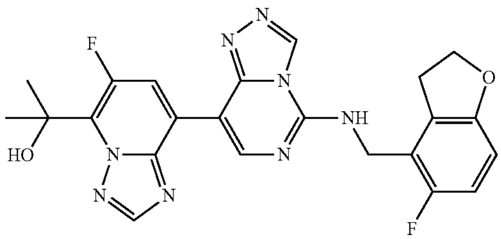
,
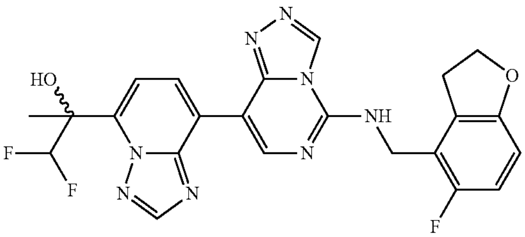
,
-continued
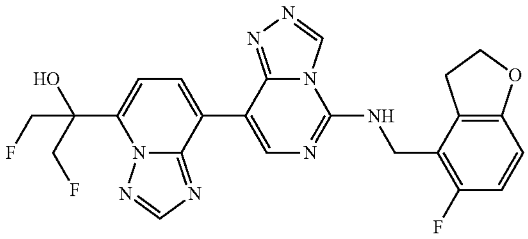
,
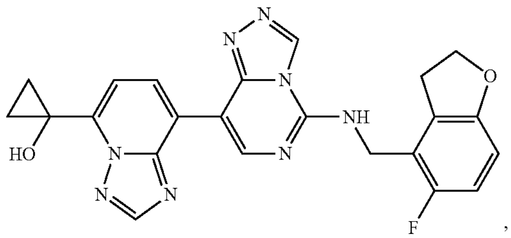
,
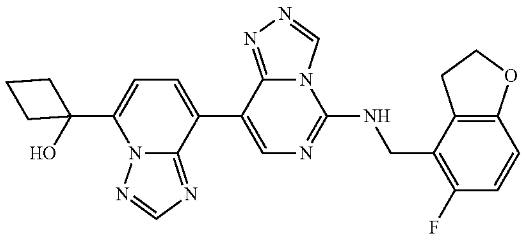
,
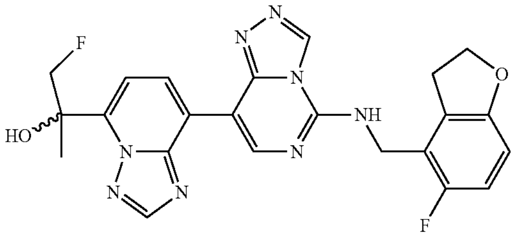
,
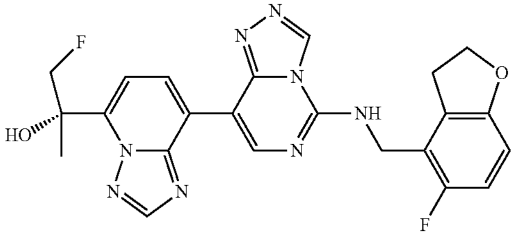
,
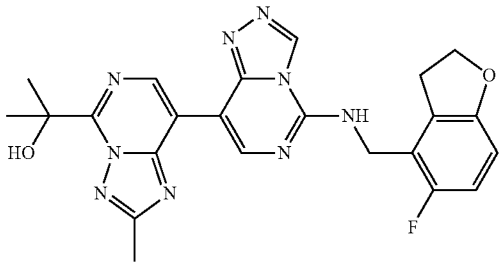
,
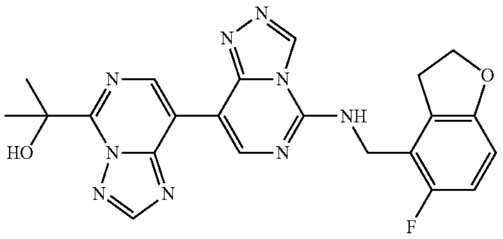
and -continued

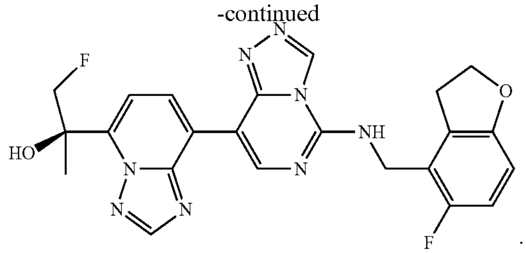
.

6. The compound represented by formula (I), the pharmaceutically acceptable salt thereof, the stereoisomer thereof, the solvate thereof, or the isotope-labeled compound thereof according to claim 1, wherein the compound represented by formula (I) is selected from the group consisting of:

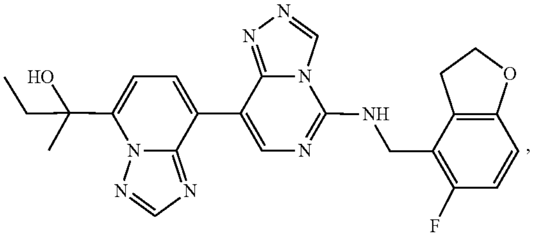 [SMILES: CCC(C)(O)c1ccc(-c2cnc(NCc3c(F)ccc4c3CCO4)n3cnnc23)c2ncnn12]
, whose retention time is 3.134 min under the following conditions: chromatographic column length is 250 mm, chromatographic column inner diameter is 30 mm, filler particle diameter is 10 μm; mobile phase A is IPA containing 0.1% $NH_3H_2O$, and mobile phase B is ethanol; gradient: gradient elution with 5% mobile phase B→40% mobile phase B, flow rate is 4 mL/min;

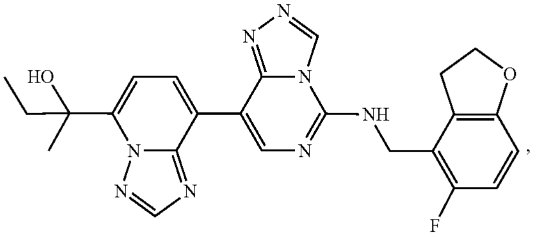 [SMILES: CCC(C)(O)c1ccc(-c2cnc(NCc3c(F)ccc4c3CCO4)n3cnnc23)c2ncnn12]
, whose retention time is 3.547 min under the following conditions: chromatographic column length is 250 mm, chromatographic column inner diameter is 30 mm, filler particle diameter is 10 μm; mobile phase A is IPA containing 0.1% $NH_3H_2O$, and mobile phase B is ethanol; gradient: gradient elution with 5% mobile phase B→40% mobile phase B, flow rate is 4 mL/min;

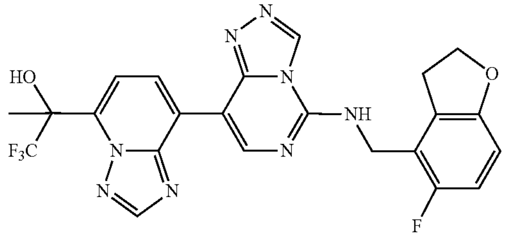
, whose retention time is 4.974 min under the following conditions: chromatographic column length is 250 mm, chromatographic column inner diameter is 30 mm, filler particle diameter is 10 μm; mobile phase A is IPA containing 0.1% $NH_3H_2O$, and mobile phase B is ethanol; gradient: isocratic elution 45%, flow rate is 2.8 mL/min;

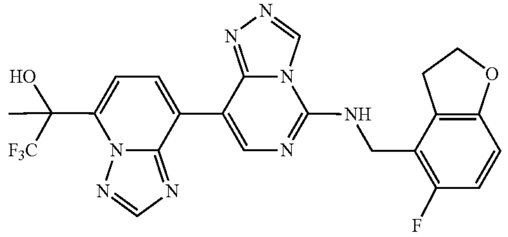
, whose retention time is 5.440 min under the following conditions: chromatographic column length is 250 mm, chromatographic column inner diameter is 30 mm, filler particle diameter is 10 μm; mobile phase A is IPA containing 0.1% $NH_3H_2O$, and mobile phase B is ethanol; gradient: isocratic elution 45%, flow rate is 2.8 mL/min;

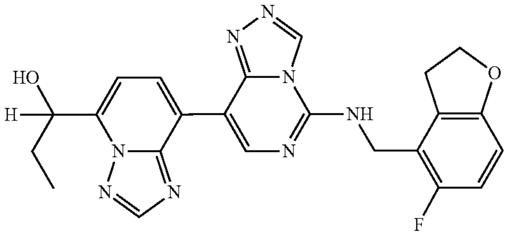
, whose retention time is 2.782 min under the following conditions: chromatographic column length is 250 mm, chromatographic column inner diameter is 30 mm, filler particle diameter is 10 μm; mobile phase A is IPA containing 0.1% $NH_3H_2O$, and mobile phase B is ethanol; gradient: gradient elution with 5% mobile phase B→40% mobile phase B, flow rate is 4 mL/min;

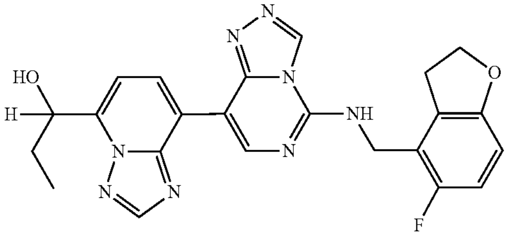
, whose retention time is 2.907 min under the following conditions: chromatographic column length is 250 mm, chromatographic column inner diameter is 30 mm, filler particle diameter is 10 μm; mobile phase A is IPA containing 0.1% $NH_3H_2O$, and mobile phase B is ethanol; gradient: gradient elution with 5% mobile phase B→40% mobile phase B, flow rate is 4 mL/min;

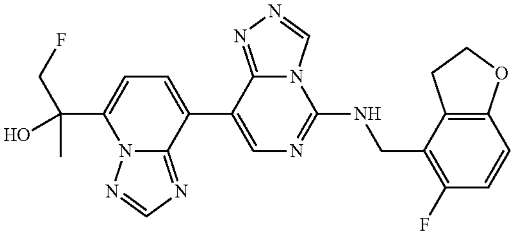
, whose retention time is 0.971 min under the following conditions: chromatographic column length is 250 mm, chromatographic column inner diameter is 30 mm, filler particle diameter is 10 μm; mobile phase A is IPA containing 0.1% $NH_3H_2O$, and mobile phase B is isopropanol; gradient: isocratic elution with 45% mobile phase B, flow rate is 4 mL/min;

and

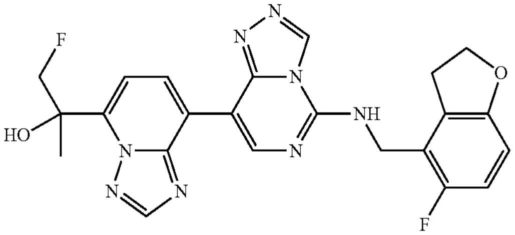
, and whose retention time is 1.134 min under the following conditions: chromatographic column length is 250 mm, chromatographic column inner diameter is 30 mm, filler particle diameter is 10 μm; mobile phase A is IPA containing 0.1% $NH_3H_2O$, and mobile phase B is isopropanol; gradient: isocratic elution with 45% mobile phase B, flow rate is 4 mL/min.

7. A preparation method for the compound represented by formula (I) according to claim 1, which comprises the following steps:

Coupling halogenated intermediate $B_0$ with intermediate $E_0$ to obtain the compound represented by formula (I);

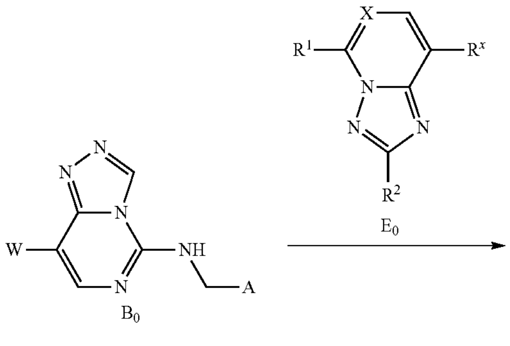

-continued

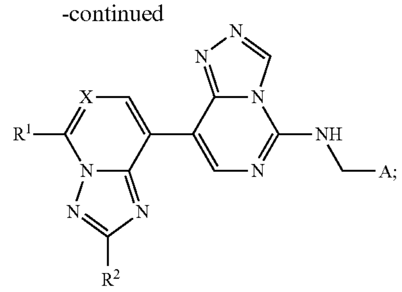

(I)

wherein W represents halogen; $R^x$ is —$B(OH)_2$ or

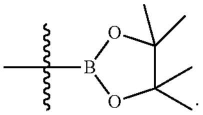 [SMILES: *B1OC(C)(C)C(C)(C)O1]
.

8. A compound as follows:

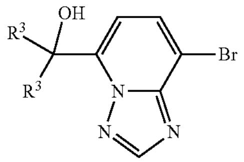

wherein $R^3$ is independently ethyl, monofluoromethyl, difluoromethyl or trifluoromethyl.

9. A method for treating cancer in a subject in need thereof, comprising: administering the compound represented by formula (I), the pharmaceutically acceptable salt thereof, the stereoisomer thereof, the solvate thereof, or the isotope-labeled compound thereof according to claim 1 to the subject, the cancer is selected from rhabdoid tumor, B-cell non-Hodgkin's lymphoma, lymphoma, leukemia, multiple myeloma, prostate cancer, lung cancer, colon cancer, pancreatic cancer, breast cancer and ovarian cancer.

10. The method according to claim 9, wherein the cancer is selected from rhabdoid tumor and B-cell non-Hodgkin's lymphoma.

11. A pharmaceutical composition, which comprises the compound represented by formula (I), the pharmaceutically acceptable salt thereof, the stereoisomer thereof, the solvate thereof, or the isotope-labeled compound thereof according to claim 1 and pharmaceutically acceptable excipients.

12. A pharmaceutical preparation, which comprises the compound represented by formula (I), the pharmaceutically acceptable salt thereof, the stereoisomer thereof, the solvate thereof, or the isotope-labeled compound thereof according to claim 1.

13. The compound represented by formula (I), the pharmaceutically acceptable salt thereof, the stereoisomer thereof, the solvate thereof, or the isotope-labeled compound thereof according to claim 2, wherein, the solvate is a hydrate;

or, when $R^2$ is $C_{1-4}$ alkyl, the $C_{1-4}$ alkyl is methyl;

or, when $R^2$ is an unsubstituted amino group or an amino group substituted by $C_{1-4}$ alkyl, the $C_{1-4}$ alkyl is methyl;

or, when $R^7$ is halogen, the halogen is fluorine;

or, when $R^7$ is $C_{1-4}$ alkoxy, the $C_{1-4}$ alkoxy is methoxy;

or, when $R^7$ is $C_{1-4}$ alkyl, the $C_{1-4}$ alkyl is methyl.

14. The compound represented by formula (I), the pharmaceutically acceptable salt thereof, the stereoisomer thereof, the solvate thereof, or the isotope-labeled compound thereof according to claim 3, wherein $R^2$ is H, methyl or

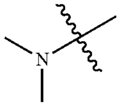

;

or, $R^7$ is H, halogen, $C_{1-4}$ alkoxy or $C_{1-4}$ alkyl.

15. The compound represented by formula (I), the pharmaceutically acceptable salt thereof, the stereoisomer thereof, the solvate thereof, or the isotope-labeled compound thereof according to claim 1, wherein $R^2$ is H or $C_{1-4}$ alkyl;

or, $R^7$ is H, halogen or $C_{1-4}$ alkyl.

16. The compound represented by formula (I), the pharmaceutically acceptable salt thereof, the stereoisomer thereof, the solvate thereof, or the isotope-labeled compound thereof according to claim 4, wherein the compound represented by formula (I) is selected from the compounds shown below:

(I-1)

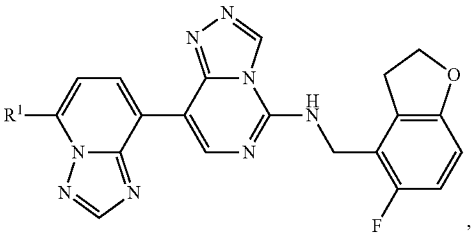

, (I-2)

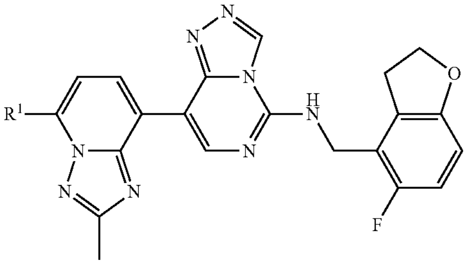

, (I-5)

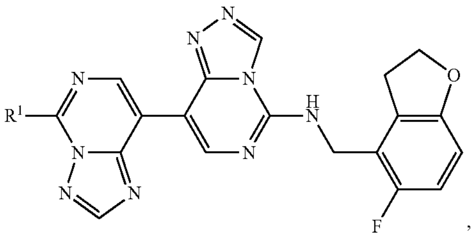

,

-continued (I-6)

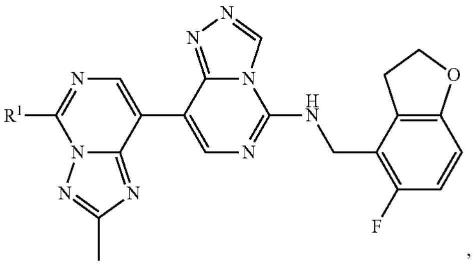

, (I-7)

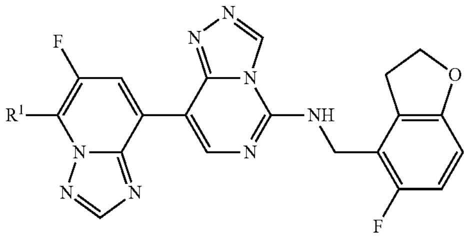

and (I-8)

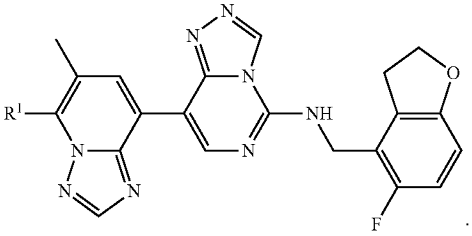

.

17. The pharmaceutical preparation according to claim 12, wherein the pharmaceutical preparation is a tablet, a capsule, a pellet, a powder, a granule, an elixir, a tincture, a suspension, a syrup, an emulsion or a solution;

or, the administration method of the pharmaceutical preparation is oral administration, bilingual administration, subcutaneous injection, intravenous injection, intramuscular injection, intrasternal injection, nasal administration, topical surface administration or rectal administration.

18. The compound represented by formula (I), the pharmaceutically acceptable salt thereof, the stereoisomer thereof, the solvate thereof, or the isotope-labeled compound thereof according to claim 1, wherein $R^1$ is

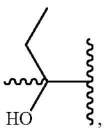, 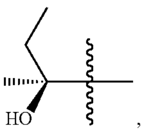, 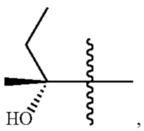, 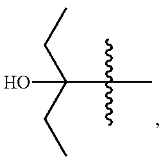,

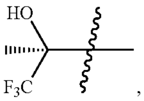, 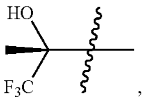, 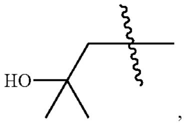,

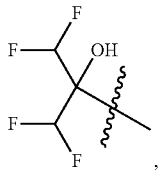, 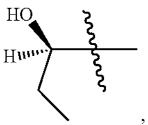, 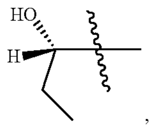,

-continued
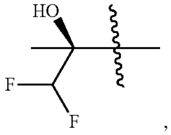,
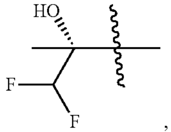,
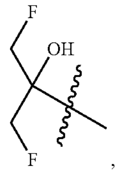,
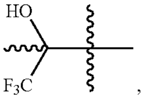,
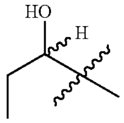,
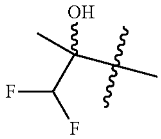,
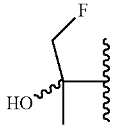,
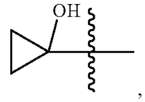,
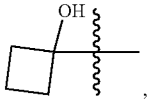,
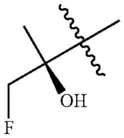
or
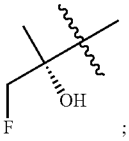;
and
$R^2$ is H, $C_{1-4}$ alkyl, $C_{3-6}$ cycloalkyl or an unsubstituted amino group or an amino group substituted by $C_{1-4}$ alkyl.
19. The compound represented by formula (I), the pharmaceutically acceptable salt thereof, the stereoisomer thereof, the solvate thereof, or the isotope-labeled compound thereof according to claim 1, wherein the group
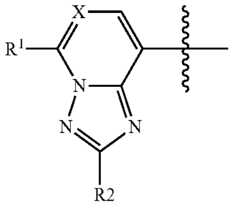
is
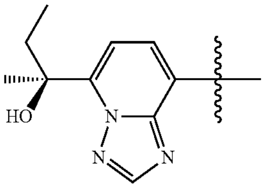,
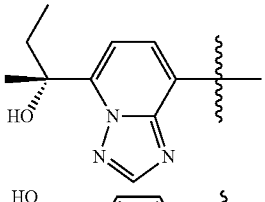,
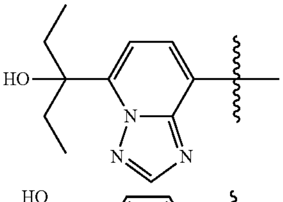,
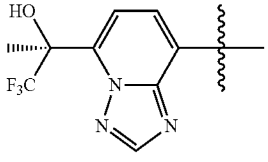,
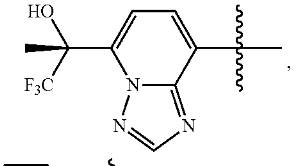,
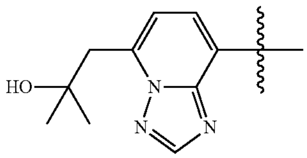,
-continued
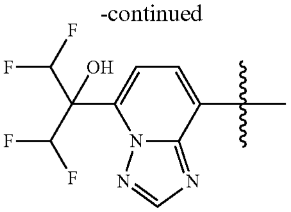,
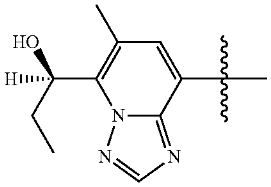,
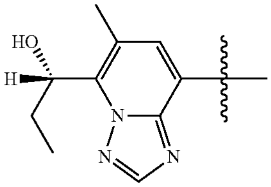,
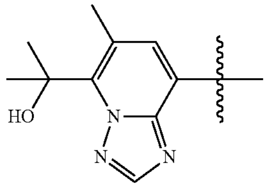,
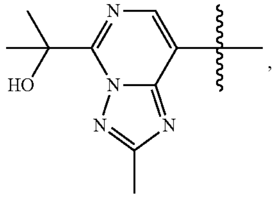,
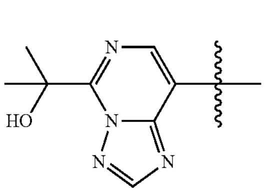,
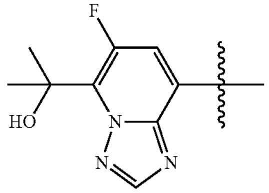,
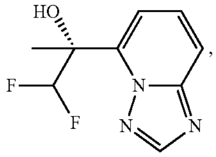,
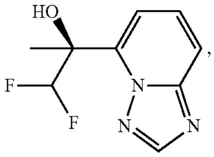,
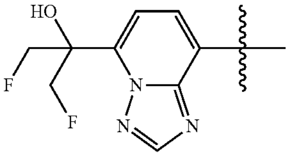,
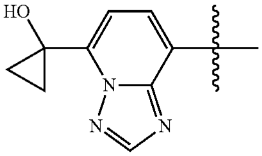,
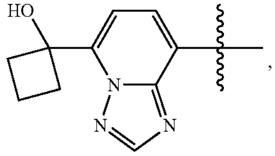,
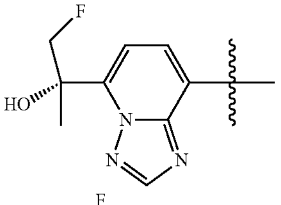, or
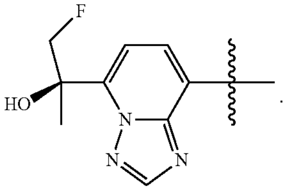.
* * * * *